US008912343B2

(12) United States Patent
Gruss et al.

(10) Patent No.: US 8,912,343 B2
(45) Date of Patent: *Dec. 16, 2014

(54) SOLID FORMS OF (1R,4R)-6'-FLUORO-(N, N-DIMETHYL)-4-PHENYL-4',9'-DIHYDRO-3'H-SPIRO[CYCLOHEXANE-1,1'-PYRANO-[3,4,B]INDOL]-4-AMINE AND SULFURIC ACID

(71) Applicant: Gruenenthal GmbH, Aachen (DE)

(72) Inventors: Michael Gruss, Aachen (DE); Stefan Kluge, Riehen (CH); Stefan Pruehs, Neuss (DE)

(73) Assignee: Gruenenthal GmbH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/711,375

(22) Filed: Dec. 11, 2012

(65) Prior Publication Data

US 2013/0150589 A1    Jun. 13, 2013

Related U.S. Application Data

(60) Provisional application No. 61/569,461, filed on Dec. 12, 2011.

(30) Foreign Application Priority Data

Dec. 12, 2011    (EP) .................................... 11009774

(51) Int. Cl.
C07D 491/107    (2006.01)
(52) U.S. Cl.
CPC ................................. *C07D 491/107* (2013.01)
USPC ....................................................... 548/407
(58) Field of Classification Search
CPC .................................................. C07D 491/052
USPC ....................................................... 548/807
See application file for complete search history.

(56) References Cited

U.S. PATENT DOCUMENTS 7,951,948 B2 *    5/2011    Hinze et al. ...................... 546/18
2011/0015220 A1    1/2011    Linz et al.
2011/0319440 A1   12/2011    Hinze et al.

FOREIGN PATENT DOCUMENTS

WO    WO 2004/043967 A1    5/2004
WO    WO 2008/040481 A1    4/2008
WO    WO2012016695 A2 *    2/2012

OTHER PUBLICATIONS

Kratochvil, B. "Solid forms of pharmaceutical molecules" Prague Institute of Chemical Technology, published online Feb. 7, 2010, retrieved online Nov. 26, 2013 from the internet at http://www.imc.cas.cz/nmr/projekt/ws/springer.pdf.*

Shumaila et al. Arkivoc 2011 (ii) 41-46, published Dec. 4, 2010.*
International Search Report including Written Opinion (PCT/ISA/237) dated Jan. 31, 2013 {Nine (9) Pages}.
Hilfiker, Rolf, "Physical Characterization of Hygroscopicity in Pharmaceutical Solids", Polymorphism in the Pharmaceutical Industry, 2006, pp. 235-242, Wiley VCH Verlag GmbH & Co., Weinheim, Germany.
Chou, Shan-Yen, "A Novel Substitution Reaction of Tetrahydropyrano[3,4-*b*]Indole Derivative—Chain Extension and Structural Correlation Study", Heterocycles, Mar. 2003, pp. 1095-1110, vol. 60, No. 5.
Zott, Matthias et al., "Tricyclic Benzomorphan Analogues by Intramolecular Oxa-Pictet-Spengler Reaction", Tetrahedron: Asymmetry, 1993, pp. 2307-2310, vol. 4, No. 11, Pergamon Press Ltd., Great Britain.
Ravin, L. PhD., "Preformulation", Remington Chapter 76, pp. 1409-1423, 1985 (fifteen (15) sheets).
Disanto, A., "Bioavailability and Bioequivalency Testing", Remington Chapter 77, pp. 1424-1431, 1985 (eight (8) sheets).
Knevel, A. PhD., "Separation", Remington Chapter 78, pp. 1432-1442, 1985 (eleven (11) sheets).
Phillips, G Briggs, PhD., "Sterilization", Remington Chapter 79, pp. 1443-1454, 1985 (twelve (12) sheets).
Siegel, F. PhD., "Tonicity, Osmoticity, Osmolality and Osmolarity", Remington Chapter 80, pp. 1455-1472, 1985 (eighteen (18) sheets).
Giles et al., "Plastic Packaging Materials", Remington Chapter 81, pp. 1473-1477, 1985 (five (5) sheets).
Lintner, C. PhD., "Stability of Pharmaceutical Products", Remington Chapter 82, pp. 1478-1486, 1985 (nine (9) sheets).
Erskine, C., Jr., "Quality Assurance and Control" Remington Chapter 83, pp. 1487-1491, 1985 (five (5) sheets).
Nairn, J.G. PhD., "Solutions, Emulsions, Suspensions and Extractives", Remington Chapter 84, pp. 1492-1517, 1985 (twenty-six (26) sheets).
Avis, K. DSc., "Parenteral Preparations", Remington Chapter 85, pp. 1518-1541, 1985 (twenty-four (24) sheets).
Turco et al., "Intravenous Admixtures", Remington Chapter 86, pp. 1542-1552, 1985 (eleven (11) sheets).
Mullins, J. PhD., "Ophthalmic Preparations", Remington Chapter 87, pp. 1553-1566, 1985 (fourteen (14) sheets).
Block, L. PhD., "Medicated Applications", Remington Chapter 88, pp. 1567-1584, 1985 (eighteen (18) sheets).
Rippie, E. PhD., "Powders", Remington Chapter 89, pp. 1585-1602 (eighteen, 1985 (18) sheets).
King et al., "Oral Solid Dosage Forms", Remington Chapter 90, pp. 1603-1632, 1985 (thirty (30) sheets).

(Continued)

*Primary Examiner* — Samantha Shterengarts
*Assistant Examiner* — Amanda L Aguirre
(74) *Attorney, Agent, or Firm* — Crowell & Moring LLP

(57) ABSTRACT

Solid forms of (1r,4r)-6'-fluoro-N,N-dimethyl-4-phenyl-4', 9'-dihydro-3'H-spiro[cyclohexane-1,1'-pyrano[3,4b]indol]-4-amine and sulfuric acid such as (1r,4r)-6'-fluoro-N,N-dimethyl-4-phenyl-4',9'-dihydro-3'H-spiro[cyclohexane-1,1'-pyrano[3,4b]indol]-4-amine sulfate or hemi-sulfate, particularly crystalline forms and/or amorphous forms thereof, pharmaceutical compositions and medicaments containing these solid forms, the use of these solid forms, and a process for obtaining such solid forms.

24 Claims, 13 Drawing Sheets

(56) References Cited

OTHER PUBLICATIONS

Porter, S. PhD., "Coating of Pharmaceutical Dosage Forms", Remington Chapter 91, pp. 1633-1643, 1985 (eleven (11) sheets).
Longer et al., "Sustained-Release Drug Delivery Systems", Remington Chapter 92, pp. 1644-1661, 1985 (eighteen (18) sheets).
Sclarra et al., "Aerosols", Remington Chapter 93, 1985, pp. 1662-1677, 1985 (sixteen (16) sheets).
Reutzel-Edens et al., "Physical Characterization of Hygroscopicity in Pharmaceutical Solids", Polymorphism in the Pharmaceutical Industry, 2006, pp. 235-242 (ten (10) sheets).
Extended European Search Report dated Mar. 23, 2012 (five (5) sheets).

* cited by examiner

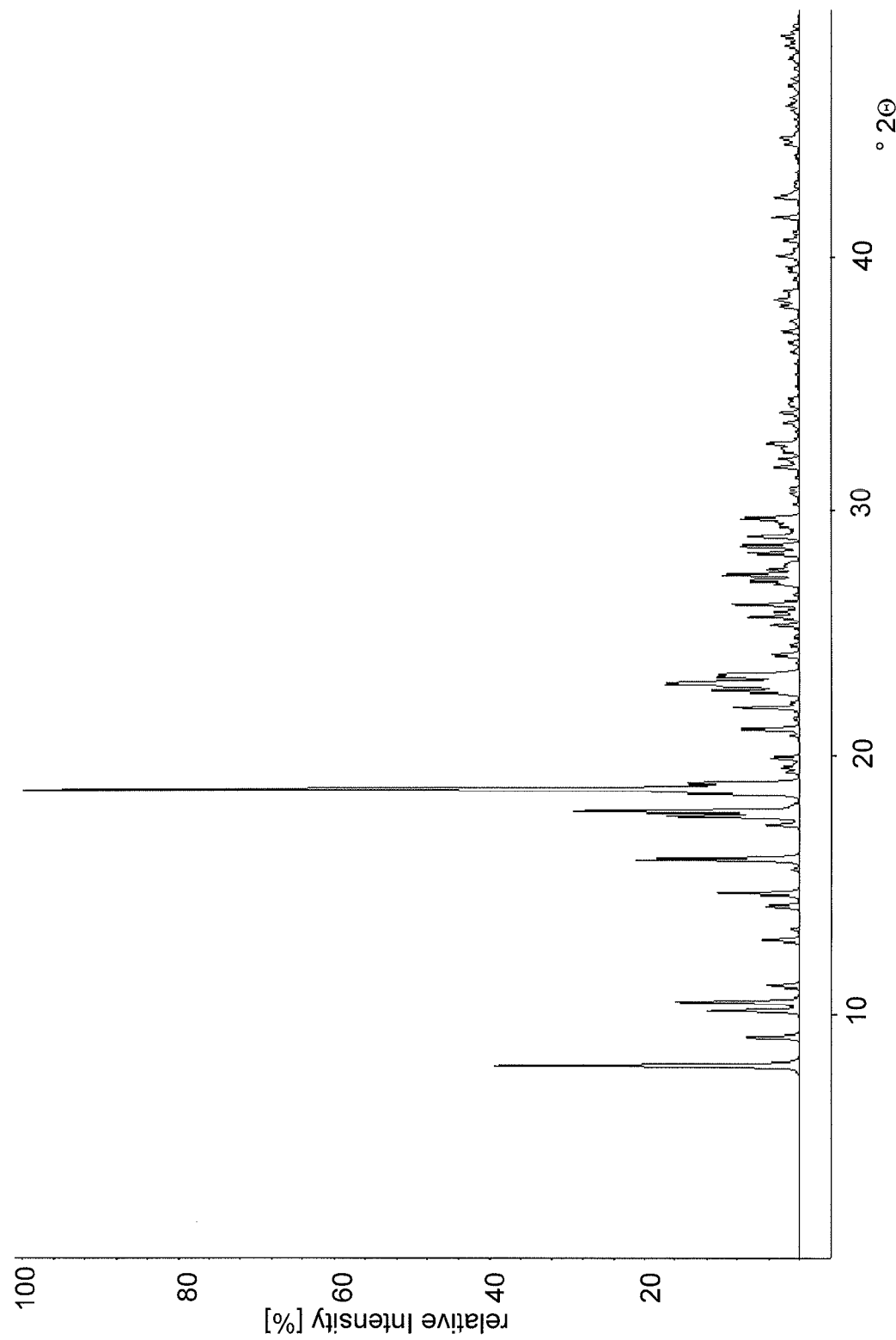

SOLID FORMS OF (1R,4R)-6'-FLUORO-(N, N-DIMETHYL)-4-PHENYL-4',9'-DIHYDRO-3'H-SPIRO[CYCLOHEXANE-1,1'-PYRANO-[3,4,B]INDOL]-4-AMINE AND SULFURIC ACID

CROSS-REFERENCE TO RELATED APPLICATIONS

This application claimed priority based on U.S. provisional patent application No. 61/569,461, filed Dec. 12, 2011, the entire disclosure of which is incorporated herein by reference. Priority is also claimed based on European patent application no. EP 11 009 774.8, filed Dec. 12, 2011, the entire disclosure of which is likewise incorporated herein by reference.

FIELD OF THE INVENTION

The invention relates to solid forms of (1r,4r)-6'-fluoro-N,N-dimethyl-4-phenyl-4',9'-dihydro-3'H-spiro[cyclohexane-1,1'-pyrano[3,4b]indol]-4-amine and sulfuric acid such as (1r,4r)-6'-fluoro-N,N-dimethyl-4-phenyl-4',9'-dihydro-3'H-spiro[cyclohexane-1,1'-pyrano[3,4b]-indol]-4-amine sulfate or hemi-sulfate, in particular crystalline forms and/or amorphous forms thereof, pharmaceutical compositions and medicaments comprising these solid forms, the use of these solid forms as well as to a process for obtaining them.

BACKGROUND OF THE INVENTION

Pharmaceutically active drugs can exist in different solid forms. For example, a drug may exist in different crystalline forms which have different physical and chemical properties. Different physical properties can cause different crystalline forms of the same drug to have largely different processing and storage performance. Such physical properties include, for example, thermodynamic stability, crystal morphology [form, shape, structure, particle size, particle size distribution, degree of crystallinity, color], ripple behavior, flowability, density, bulk density, powder density, apparent density, vibrated density, depletability, emptyability, hardness, deformability, grindability, compressability, compactability, brittleness, elasticity, caloric properties [particularly melting point], solubility [particularly equilibrium solubility, pH dependence of solubility], dissolution [particularly dissolution rate, intrinsic dissolution rate], reconstitutability, hygroscopicity, tackiness, adhesiveness, tendency to electrostatic charging, and the like.

In addition, different chemical properties can cause different crystalline forms of the same drug to have largely different performance properties. For example, a crystalline form having a low hygroscopicity (relative to other crystalline forms) can have superior chemical stability and longer shelf-life stability (cf. R. Hilfiker, Polymorphism, 2006 Wiley VCH, pp 235-242). Further, different stereoisomers of one compound can form different crystalline forms. In some cases this difference can be exploited to allow separation of the stereoisomers from one another.

One particular compound that is of great interest for use in the treatment of pain such as acute, visceral, neuropathic, cancer and chronic pain is (1r,4r)-6'-fluoro-N,N-dimethyl-4-phenyl-4',9'-dihydro-3'H-spiro[cyclohexane-1,1'-pyrano[3,4b]indol]-4-amine as depicted below in formula (I) (in the following also referred to as (1r,4r)-1)

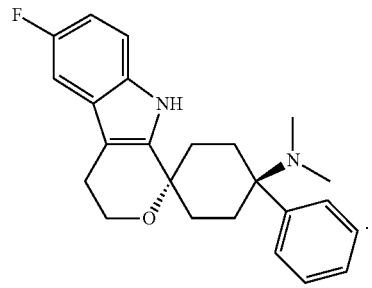

(I)

The solid forms of (1r,4r)-6'-fluoro-N,N-dimethyl-4-phenyl-4',9'-dihydro-3'H-spiro[cyclohexane-1,1'-pyrano[3,4b]indol]-4-amine that are known so far are not satisfactory in every respect and there is a demand for advantageous solid forms.

SUMMARY OF THE INVENTION

It is an object of the invention to provide forms or modifications of (1r,4r)-6'-fluoro-N,N-dimethyl-4-phenyl-4',9'-dihydro-3'H-spiro[cyclohexane-1,1'-pyrano[3,4,b]indol]-4-amine that have advantages compared to the forms or modifications of the prior art.

This and other objects have been achieved by the present invention, i.e. by a solid form of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid.

It has been found that by converting (1r,4r)-6'-fluoro-N,N-dimethyl-4-phenyl-4',9'-dihydro-3'H-spiro[cyclohexane-1,1'-pyrano[3,4b]indol]-4-amine into a solid form of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid such as a sulfate or hemi-sulfate salt of (1r,4r)-6'-fluoro-N,N-dimethyl-4-phenyl-4',9'-dihydro-3'H-spiro[cyclohexane-1,1'-pyrano[3,4b]indol]-4-amine, optionally in the form of a solvate thereof, the aqueous solubility of the compound may be improved.

It has surprisingly been found that converting (1r,4r)-6'-fluoro-N,N-dimethyl-4-phenyl-4',9'-dihydro-3'H-spiro[cyclohexane-1,1'-pyrano[3,4b]indol]-4-amine into a solid form of (1r,4r)-6'-fluoro-N,N-dimethyl-4-phenyl-4',9'-dihydro-3'H-spiro[cyclohexane-1,1'-pyrano-[3,4,b]indol]-4-amine and sulfuric acid such as a sulfate or hemi-sulfate salt of (1r,4r)-6'-fluoro-N,N-dimethyl-4-phenyl-4',9'-dihydro-3'H-spiro[cyclohexane-1,1'-pyrano[3,4b]indol]-4-amine, optionally in the form of a solvate thereof, and subsequent crystallization purifies the compound.

Moreover, it has surprisingly been found that different crystalline forms of (1r,4r)-6'-fluoro-N,N-dimethyl-4-phenyl-4',9'-dihydro-3'H-spiro[cyclohexane-1,1'-pyrano[3,4b]indol]-4-amine and sulfuric acid such as (1r,4r)-6'-fluoro-N,N-dimethyl-4-phenyl-4',9'-dihydro-3'H-spiro[cyclohexane-1,1'-pyrano[3,4b]indol]-4-amine sulfate or (1r,4r)-6'-fluoro-N,N-dimethyl-4-phenyl-4',9'-dihydro-3'H-spiro[cyclohexane-1,1'-pyrano[3,4b]indol]-4-amine hemi-sulfate, optionally in the form of solvates thereof, can be prepared which have fundamentally different properties. These inventive crystalline forms are described herein.

BRIEF DESCRIPTION OF THE DRAWINGS

FIG. 3a-c (FIG. 3a-c) show PXRD patterns of crystalline forms E, F and G, respectively, in each case calculated based on the parameters determined from a corresponding SCXRD experiment.

DETAILED DESCRIPTION

Figure 1A:
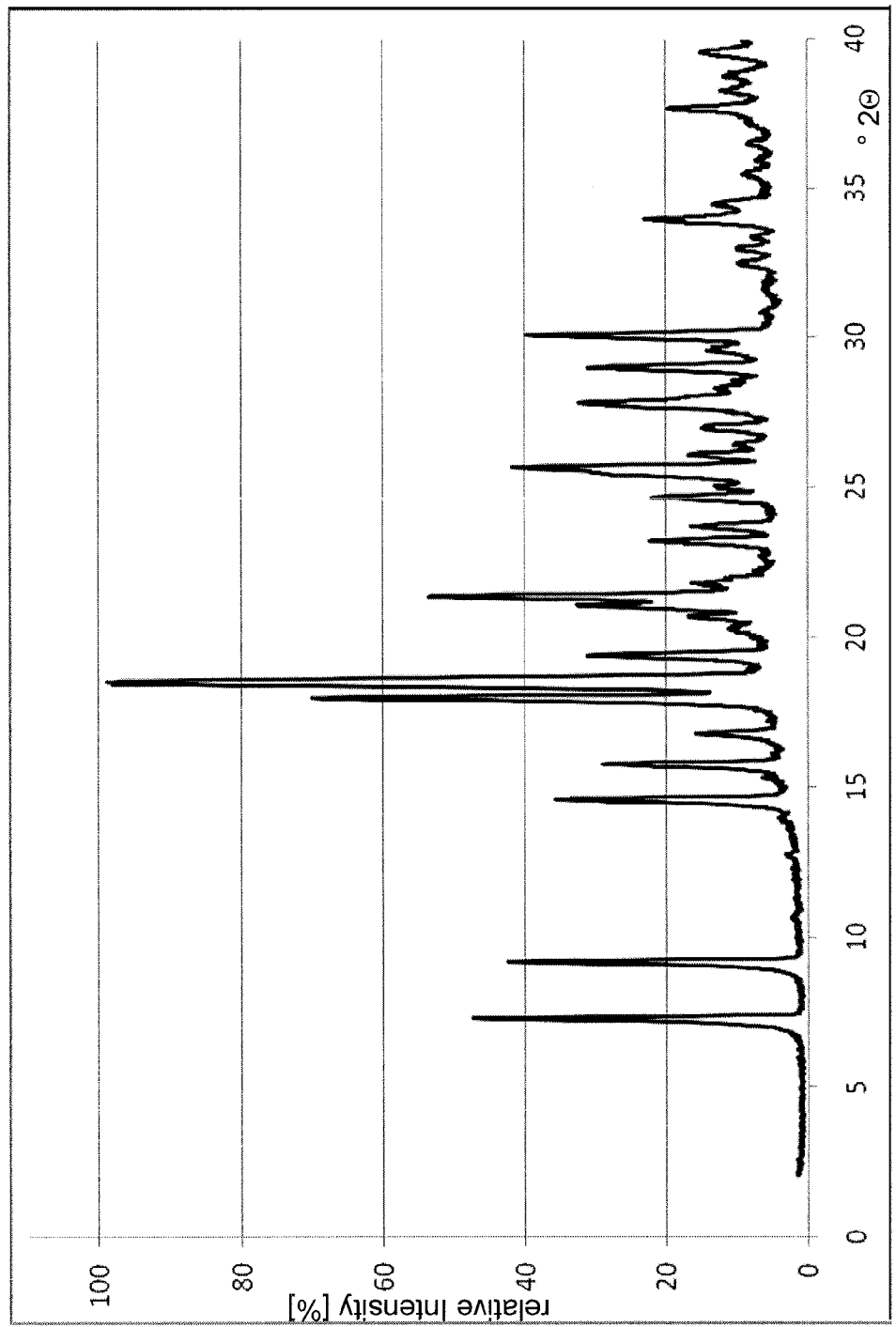
FIGS. 1a and 1b show the PXRD patterns of crystalline forms A and B.

The compound according to general formula (I) can systematically be referred to as "1,1-(3-dimethylamino-3-phenylpentamethylene)-6-fluoro-1,3,4,9-tetrahydropyrano[3,4-b]indole (trans)" or as "(1r,4r)-6'-fluoro-N,N-dimethyl-4-phenyl-4',9'-dihydro-3'H-spiro[cyclohexane-1,1'-pyrano[3,4,b]indol]-4-amine", respectively.

In the solid form according to the invention the compound according to general formula (I) is present in form of an acid addition salt of the compound according to general formula (I) and sulfuric acid. The definition of the solid form of the compound according to general formula (I) and sulfuric acid, i.e. of an acid addition salt of the compound according to general formula (I) and sulfuric acid, includes salts, solvates, co-crystals, polymorphs, amorphous forms and multi-component complex forms. The most basic functional group of the compound according to general formula (I) is its N,N-dimethylamino moiety, which thus according to the invention is preferably protonated. Methods to determine whether a chemical substance is present as a salt, co-crystalline form, crystalline form or as the free base, optionally in each case in a solvated from thereof, are known to the skilled artisan such as $^{14}$N or $^{15}$N solid state NMR, X-ray diffraction, IR, DSC, TGA, Raman, and XPS. $^1$H-NMR recorded in solution may also be used to consider the presence of protonation.

Solid forms of the compound according to general formula (I) and sulfuric acid, i.e. acid addition salts of the compound according to general formula (I) and sulfuric acid, in any stoichiometric ratio of the compound according to general formula (I) and sulfuric acid are preferably encompassed by the inventive solid forms.

In particular, solid forms of the compound according to general formula (I) and sulfuric acid, i.e. acid addition salts of the compound according to general formula (I) and sulfuric acid, are selected from the group consisting of sulfates and hemi-sulfates, i.e. from the group consisting of (1r,4r)-6'-fluoro-N,N-dimethyl-4-phenyl-4',9'-dihydro-3'H-spiro[cyclohexane-1,1'-pyrano[3,4b]indol]-4-amine sulfate and (1r,4r)-6'-fluoro-N,N-dimethyl-4-phenyl-4',9'-dihydro-3'H-spiro[cyclohexane-1,1'-pyrano[3,4b]indol]-4-amine hemi-sulfate.

For the purpose of the specification, "sulfate" in this respect preferably means that the compound according to general formula (I) is present in the solid form according to the invention in a mono-protonated, mono-cationic form together with a hydrogen sulfate anion ($HSO_4^-$) as counter-ion in a stoichiometric ratio of (1.0±0.2):1.0, even more preferably in a stoichiometric ratio of (1.0±0.1):1.0, in particular in a stoichiometric ratio of 1.0:1.0.

For the purpose of the specification, "hemi-sulfate" in this respect preferably means that the compound according to general formula (I) is present in the solid form according to the invention in a mono-protonated, mono-cationic form together with a sulfate dianion ($SO_4^{2-}$) as counter-ion in a stoichiometric ratio of (2.0±0.2):1.0, even more preferably in a stoichiometric ratio of (2.0±0.1):1.0, in particular in a stoichiometric ratio of 2.0:1.0.

Unless explicitly stated otherwise, all 2Θ values refer to a X-ray diffractogram measured using CuKα radiation having a wavelength of 1.54060 Å determined at 298 K±5 K.

Unless explicitly stated otherwise, all values in ppm refer to ppm by weight, i.e. ppmw.

One aspect of the present invention relates to a solid form of (1r,4r)-6'-fluoro-N,N-dimethyl-4-phenyl-4',9'-dihydro-3'H-spiro[cyclohexane-1,1'-pyrano[3,4b]indol]-4-amine sulfate.

Another aspect of the present invention relates to a solid form of (1r,4r)-6'-fluoro-N,N-dimethyl-4-phenyl-4',9'-dihydro-3'H-spiro[cyclohexane-1,1'-pyrano[3,4b]indol]-4-amine hemi-sulfate.

The solid form according to the invention may be a crystalline form or an amorphous form, which may be in the form of an ansolvate or in the form of a solvate.

Mixtures of crystalline forms and/or amorphous forms are also included within the scope of the present invention.

In a preferred embodiment, the solid form according to the invention is an amorphous form. Suitable methods for the preparation of amorphous forms are known to persons skilled in the art. For example, amorphous forms of or amorphous mixtures may be obtained by the following methods:
  i) precipitation from solution,
  ii) lyophilization,
  iii) spray drying,
  iv) melts extrusion,
  v) flash evaporation,
  vi) quench cooling of the melt,
  vii) grinding at ambient or liquid nitrogen temperatures, and/or
  viii) using capillary crystallization technology.

In a preferred embodiment, the solid form according to the invention is a crystalline form of (1r,4r)-6'-fluoro-N,N-dimethyl-4-phenyl-4',9'-dihydro-3'H-spiro[cyclohexane-1,1'-pyrano-[3,4b]indol]-4-amine and sulfuric acid, in particular a crystalline form of (1r,4r)-6'-fluoro-N,N-dimethyl-4-phenyl-4',9'-dihydro-3' H-spiro[cyclohexane-1,1'-pyrano-[3,4b]indol]-4-amine sulfate or a crystalline form of (1r,4r)-6'-fluoro-N,N-dimethyl-4-phenyl-4',9'-dihydro-3'H-spiro[cyclohexane-1,1'-pyrano-[3,4b]indol]-4-amine hemi-sulfate, more preferably a crystalline form of (1r,4r)-6'-fluoro-N,N-dimethyl-4-phenyl-4',9'-dihydro-3'H-spiro[cyclohexane-1,1'-pyrano-[3,4b]indol]-4-amine sulfate.

In some preferred embodiments, the crystalline form according to the invention has an X-ray diffraction peak at 9.7±1.0 (2Θ) and/or an X-ray diffraction peak at 17.7±1.0 (2Θ) and/or an X-ray diffraction peak at 18.2±1.0 (2Θ) and/or an X-ray diffraction peak at 25.7±1.0 (2Θ).

As indicated above, the uncertainty in the 2θ values is ±1.0° in 2θ. Preferably, the uncertainty in the 2θ values in each case is ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ.

More preferably, the crystalline form according to the invention has an X-ray diffraction peak at 9.7±0.7 (2Θ) and/or an X-ray diffraction peak at 17.7±0.7 (2Θ) and/or an X-ray diffraction peak at 18.2±0.7 (2Θ) and/or an X-ray diffraction peak at 25.7±0.7 (2Θ).

Even more preferably, the crystalline form according to the invention has an X-ray diffraction peak at 9.7±0.5 (2Θ) and/or an X-ray diffraction peak at 17.7±0.5 (2Θ) and/or an X-ray diffraction peak at 18.2±0.5 (2Θ) and/or an X-ray diffraction peak at 25.7±0.5 (2Θ).

Preferably, said X-ray diffraction peak(s) exhibit(s) a relative intensity of at least 20%, more preferably of at least 25%, still more preferably of at least 30%, yet more preferably of at least 40%, most preferably of at least 45% and in particular, of at least 50%.

In another preferred embodiment, the crystalline form according to the invention has:
one or more X-ray diffraction peaks (CuKα radiation) selected from the group consisting of 10±4 (2Θ), 18±4 (2Θ), 26±4 (2Θ) and 34±4 (2Θ),
preferably one or more X-ray diffraction peaks (CuKα radiation) selected from the group consisting of 10±3 (2Θ), 18±3 (2Θ), 26±3 (2Θ) and 34±3 (2Θ),
more preferably, one or more X-ray diffraction peaks (CuKα radiation) selected from the group consisting of 10±2 (2Θ), 18±2 (2Θ), 26±2 (2Θ) and 34±2 (2Θ), and
even more preferably one or more X-ray diffraction peaks (CuKα radiation) selected from the group consisting of 10±1 (2Θ), 18±1 (2Θ), 26±1 (2Θ) and 34±1 (2Θ), (2Θ),
in particular one or more X-ray diffraction peaks (CuKα radiation) selected from the group consisting of 9.7±1.0 (2Θ), 17.7±1.0 (2Θ), 18.2±1.0 (2Θ) and 25.7±1.0 (2Θ).

Preferably, the crystalline form according to the invention has one or more Raman bands at 916±5 cm$^{-1}$, 1002±5 cm$^{-1}$, 1028±5 cm$^{-1}$, 1569±5 cm$^{-1}$, 1583±5 cm$^{-1}$, 2980±5 cm$^{-1}$ and/or at 3076±5 cm$^{-1}$, preferably at least two Raman bands selected from the group consisting of 916±5 cm$^{-1}$, 1002±5 cm$^{-1}$, 1028±5 cm$^{-1}$, 1569±5 cm$^{-1}$, 1583±5 cm$^{-1}$, 2980±5 cm$^{-1}$ and 3076±5 cm$^{-1}$.

In a preferred embodiment, the crystalline form according to the invention has at least three Raman bands selected from the group consisting of 916±5 cm$^{-1}$, 1002±5 cm$^{-1}$, 1028±5 cm$^{-1}$, 1569±5 cm$^{-1}$, 1583±5 cm$^{-1}$, 2980±5 cm$^{-1}$ and 3076±5 cm$^{-1}$. In an especially preferred embodiment, the crystalline form according to the invention has at least four, even more preferably at least five, still more preferably at least six, of these bands, in particular has all seven of these bands.

In another preferred embodiment, the crystalline form according to the invention has:
one or more Raman bands at 1000±750 cm$^{-1}$, and/or at 3000±750 cm$^{-1}$,
preferably one or more Raman bands at 1000±250 cm$^{-1}$, 1500±250 cm$^{-1}$, and/or at 3000±250 cm$^{-1}$,
more preferably one or more Raman bands at 916±40 cm$^{-1}$, 1002±40 cm$^{-1}$, 1028±40 cm$^{-1}$, 1569±40 cm$^{-1}$, 1583±40 cm$^{-1}$, 2980±40 cm$^{-1}$ and/or at 3076±40 cm$^{-1}$, and
in particular one or more Raman bands at 916±5 cm$^{-1}$, 1002±5 cm$^{-1}$, 1028±5 cm$^{-1}$, 1569±5 cm$^{-1}$, 1583±5 cm$^{-1}$, 2980±5 cm$^{-1}$ and/or at 3076±5 cm$^{-1}$.

The solid form according to the invention may be an ansolvate or a solvate. Therefore, the crystalline form according to the invention may be an ansolvate or a solvate.

In a preferred embodiment, the solid form, preferably the crystalline form, is an ansolvate.

In a preferred embodiment, the ansolvate form does not contain any solvent.

In another preferred embodiment, the ansolvate form may contain up to 1.5 wt.-% of water.

In another preferred embodiment, the ansolvate form does not contain any impurities. Impurities in the sense of the present invention may be preferably understood as reagents or decomposition products thereof, which have been employed in the synthesis of the compound according to formula (I) and/or the synthesis of the inventive solid form thereof, or as decomposition or reaction products of (1r,4r)-6'-fluoro-N,N-dimethyl-4-phenyl-4',9'-dihydro-3'H-spiro[cyclohexane-1,1'-pyrano[3,4b]indol]-4-amine or sulfuric acid.

In another preferred embodiment, the solid form, preferably the crystalline form, is a solvate. Preferably, the solvate is selected from hydrates, solvates of 1,4-dioxane, solvates of pyridine, solvates from dimethyl sulfoxides, n-methylpyrrolidone, acetic acid, propionic acid, tetrahydrofurane, and toluene or mixtures thereof. More preferably, the solvate is selected from hydrates, solvates from dimethyl sulfoxides, n-methylpyrrolidone, acetic acid, or mixtures thereof. A particularly preferred solvate is a hydrate. In a preferred embodiment, the solvate form does not contain any impurities.

Another aspect of the present invention relates to a process for the production of the solid form, in particular the crystalline form according to the invention.

In a preferred embodiment, the process comprises the step of
(a-1) precipitating the sulfate or hemi-sulfate salt of (1r,4r)-6'-fluoro-N,N-dimethyl-4-phenyl-4',9'-dihydro-3'H-spiro[cyclohexane-1,1'-pyrano[3,4,b]indol]-4-amine from a solution or suspension of the free base.

For the purpose of the specification, "free base" preferably means that the compound according to general formula (I) is not present in form of a salt, particularly not in form of an acid-addition salt.

Conventional solvents known to persons skilled in the art may be used as solvents in a solution or suspension, preferably a solution, of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof. Preferred solvents are THF, DMSO, NMP, acetic acid, mixtures of acetic acid and dimethyl acetamide, mixtures of acetone and THF, mixtures of DMSO and acetic acid, and mixtures of THF and DMSO.

In an especially preferred embodiment, the organic solvent for dissolving the free base of the compound according to general formula (I) is a mixture of acetone and THF. Preferably, the ratio between acetone and THF is within the range of from 30:1 to 1:30, more preferably within the range of from 15:1 to 1:15 (volume/volume, i.e. v/v).

Step (a-1) may be carried out by the addition of sulfuric acid. In a preferred embodiment, sulfuric acid is added in form of a solution. In a preferred embodiment, the solution is a solution of sulfuric acid in an aqueous solvent, i.e. an aqueous solution of sulfuric acid.

In another preferred embodiment, the solution is a solution of sulfuric acid in an organic solvent, especially preferred are alcohols such as ethanol, isopropanol and n-butanol, and ethers such as diethylether, di-isopropylether, tetrahydrofurane, methyl-tetrahydrofurane 1,4-dioxane or carbonic acids such as acetic acid and propionic acid.

In a preferred embodiment, the sulfuric acid containing solution and the solution of the free base contain the same solvent.

In another particularly preferred embodiment, the sulfuric acid containing solution and the solution of the free base contain not the same solvent.

In a particularly preferred embodiment containing solution is an aqueous solution and the solution of the free base is an organic solvent, in which the free base is dissolved.

Preferably, the solution contains sulfuric acid in a concentration within the range of from 0.01 mol/L to 15 mol/L, more preferably within the range of from 0.02 mol/L to 12.5 mol/L, still more preferably within the range of from 0.05 mol/L to 10 mol/L, yet more preferably within the range of from 0.1 mol/L to 7.5 mol/L, most preferably within the range of from 0.2 mol/L to 10 mol/L, and in particular within the range of from 0.3 mol/L to 5 mol/L.

Preferably, the sulfuric acid is added to the solution or suspension of the free base in molar excess, in particular in order to form a sulfate salt.

In another preferred embodiment, the sulfuric acid is added to the solution or suspension of the free base in lower molar amount than the molar amount of the free base, in particular in order to form a hemi-sulfate salt.

Preferably, in the process according to the invention, step (a-1) is carried out at a temperature below or at the boiling point of the respective solvent, preferably at a temperature not higher than 100° C., more preferably not higher than 80° C., even more preferably not higher than 60° C., and in particular in a temperature range of 20-40° C.

Preferably, in the process according to the invention, the suspension or solution obtained in step (a-1) is stirred for a time period of at least 1 minute, preferably at least 2 minutes, more preferably at least 3 minutes, still more preferably at least 5 minutes, yet more preferably at least 10 minutes, most preferably at least 20 minutes, and in particular at least 30 minutes.

In a preferred embodiment, the suspension or solution obtained in step (a-1) is stirred for a time period of at least 1 hour, preferably at least 4 hours, more preferably at least 6 hours, still more preferably at least 12 hours, yet more preferably at least 18 hours, most preferably at least 1 day, and in particular at least 2 days.

In another preferred embodiment, the suspension or solution obtained in step (a-1) is stirred for a time period of at most 1 day, preferably at most 12 hours, more preferably at most 6 hours, still more preferably at most 2 hours, yet more preferably at most 60 minutes, and most preferably at most 45 minutes, and in particular at most 30 minutes.

Preferably, the process according to the invention further comprises the step
(b-1) separating, preferably filtering off the solid obtained in step (a-1).

Preferably, the process according to the invention further comprises the step
(c-1) drying of the solid obtained in step (b-1).

In a preferred embodiment, step (c-1) takes place under air, nitrogen flow or argon flow.

In another preferred embodiment, step (c-1) takes place under vacuum, more preferably at a vacuum of 0 to 900 mbar, even more preferably at a vacuum of 1 to 500 mbar, and in particular at a vacuum of 10 to 200 mbar.

Preferably, in the process according to the invention, step (c-1) takes place in a temperature range from 0 to 60° C., preferably from 10° C. to 50° C. more preferably from 20 to 40° C.

In another preferred embodiment, the process comprises the step of
(a-2) dissolving (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate in a solvent.

Conventional solvents known to persons skilled in the art may be used as solvents in a solution of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof. Preferred solvents are THF, acetic acid, NMP, DMSO, mixtures of THF and DMSO, mixtures of DMSO and acetic acid, and mixtures of acetic acid and dimethyl acetamide (DMAc).

Preferably, in the process according to the invention, step (a-2) is carried out at a temperature below or at the boiling point of the respective solvent or solvent mixture, more preferably at a temperature not higher than 100° C., more preferably not higher than 80° C., even more preferably not higher than 60° C., and in particular in a temperature range of 20-40° C.

In a preferred embodiment, the process according to the invention further comprises the step
(b-2) evaporating the solvent of the solution obtained in step (a-2).

Suitable methods for evaporating the solvent are known to persons skilled in the art. Preferably, in the process according to the invention, the solvent is evaporated in air, air flow, or inert gas flow, in particular argon or nitrogen flow. However, evaporating the solvent under vacuum, for example by means of a rotary evaporator, is also possible. Preferably, in the process according to the invention, the solvent is evaporated at room temperature.

In another preferred embodiment, the process further comprises the step of
(b-2') precipitating (1r,4r)-6'-fluoro-N,N-dimethyl-4-phenyl-4',9'-dihydro-3'H-spiro[cyclo-hexane-1,1'-pyrano[3,4,b]indol]-4-amine sulfate or hemi-sulfate from the solution obtained in step (a-2), preferably by addition of a precipitant, Suitable methods of precipitation are known to persons skilled in the art. In the process according to the invention, step (b-2') may be carried out by reducing the volume of the solution obtained in step (a-2) and/or by cooling of the solution, preferably to a temperature of at most 15° C., more preferably at most 10° C., even more preferably at most 4-8° C. and/or by cooling of the solution, preferably to a temperature of at least 10° C., more preferably at least 30° C., even more preferably at least 60° C. below the temperature according to step (a-2).

In a preferred embodiment, step (b-2') is carried out by the addition of a medium in which (1r,4r)-6'-fluoro-N,N-dimethyl-4-phenyl-4',9'-dihydro-3'H-spiro[cyclohexane-1,1'-pyrano-[3,4,b]indol]-4-amine sulfate or hemi-sulfate is only poorly soluble ("anti-solvent") to the solution obtained in step (a-2). The medium is preferably selected from the group consisting of esters such as ethyl acetate, n-propyl acetate, iso-propyl acetate, n-butyl acetate and iso-butyl acetate; alcohols such as methanol, ethanol, 1-propanol, 2-propanol; ethers such as tert-butyl methyl ether, diethyl ether and diisopropyl ether; ketones such as acetone, 2-butanone, pentan-2-one, pentan-3-one, hexan-2-one and hexan-3-one; nitriles such as acetonitril; pyridine, acetic acid and water, and DMSO. Particularly preferred are DMSO, 2-butanone (MEK), 2-propanol, and water; especially preferred are 2-butanone (MEK) and 2-propanol.

The amount of the media in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate is only poorly soluble, the precipitant or anti-solvent, is preferably selected in such a manner that upon its addition precipitation of the dissolved component begins.

The total amount of the media in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate is only poorly soluble may also be divided into several portions, preferably two or three portions. In this embodiment, the precipitation of the dissolved component preferably begins after the addition of the last portion.

The precipitation of the dissolved component preferably begins either immediately after the precipitant, preferably the total amount of the precipitant, has been added or alternatively with a delay of 2 seconds to 120 minutes. Preferably, the precipitation of the dissolved component begins within a time period of at most 90 minutes, more preferably at most 60 minutes, still more preferably at most 30 minutes, even more preferably at most 5 minutes, most preferably at most 60 seconds and in particular at most 10 seconds.

Furthermore, the amount of the media in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate, is only poorly soluble, the precipitant or anti-solvent, is preferably selected in such a manner that the dissolved component is completely precipitated or at least up to 90% of the initial amount is precipitated within a time period of at most 90 minutes, more preferably at most 80 minutes, still more preferably at most 70 minutes, and most preferably at most 60 minutes after the anti-solvent has been completely added.

Step (b-2') may also be carried out by exposing the solution obtained in step (a-2) to an atmosphere containing a solvent, in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate is only poorly soluble, i.e. by a vapour diffusion crystallization technique.

In this embodiment, dichloromethane is preferably selected as solvent in step (a-2) and the solution obtained in step (a-2) is preferably exposed to an atmosphere containing hexane.

Preferably, in the process according to the invention, after step (b-2) or respectively (b-2'), all other steps are carried out at a temperature between 40 and 0° C., preferably between 35 and 5° C., more preferably between 25 and 15° C.

Preferably, in the process according to the invention, the suspension obtained in step (b-2') is stirred for a time period of at least 1 minute, preferably at least 2 minutes, more preferably at least 3 minutes, and most preferably at least 5 minutes.

Preferably, the process according to the invention further comprises the step (c-2') separating, preferably filtering off the precipitate obtained in step (b-2').

Preferably, the process according to the invention further comprises the step (d-2') drying of the solid obtained in step (c-2').

Preferably, in the process according to the invention, step (d-2') takes place under air or inert gas flow, such as argon or nitrogen flow. However, depending on the crystalline form to be obtained evaporating the solvent at an elevated temperature, e.g. within the range of from 20° C. to 60° C., is also possible.

In still another preferred embodiment, the process comprises the step of
(a-3) suspending (1r,4r)-6'-fluoro-N,N-dimethyl-4-phenyl-4',9'-dihydro-3'H-spiro[cyclo-hexane-1,1'-pyrano[3,4,b]indol]-4-amine sulfate or hemi-sulfate in a solvent.

Conventional solvents known to persons skilled in the art may be used as solvents in a suspension of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof. Preferred solvents are alcohols such as methanol or water, particularly preferred alcohols such as methanol.

In a preferred embodiment, step (a-3) is carried out at a temperature below or at the boiling point of the respective solvent, preferably at a temperature not higher than 100° C., more preferably not higher than 90° C., still more preferably not higher than 80° C., yet more preferably not higher than 60° C., most preferably not higher than 40° C., and in particular in a temperature range of 15-35° C.

In another preferred embodiment, step (a-3) is carried out in a temperature range of 100-40° C., more preferably 90-50° C., and most preferably 85-60° C.

Preferably, in the process according to the invention, the suspension obtained in step (a-3) is stirred for a time period of at least 2 h, preferably at least 4 h, more preferably at least 8 h, still more preferably at least 12 h, yet more preferably at least 16 h, most preferably at least 24 h, and in particular at least 2 days.

Preferably, the process according to the invention further comprises the step
(b-3) separating, preferably filtering off the solid obtained in step (a-3).

Preferably, the process according to the invention further comprises the step
(c-3) drying of the solid obtained in step (b-3).

In the process according to the invention, step (c-3) may take place under air or inert gas flow, such as argon or nitrogen flow. However, drying under vacuum, more preferably at a vacuum of 0 to 900 mbar, even more preferably at a vacuum of 1 to 500 mbar, and in particular at a vacuum of 10 to 200 mbar is preferred.

Preferably, in the process according to the invention, step (c-3) takes place in a temperature range from 0 to 60° C., preferably from 10° C. to 50° C. more preferably from 20 to 40° C.

In still another preferred embodiment, the process comprises the step of
(a-4) reacting 2-(5-fluoro-1H-indol-3-yl)ethanol and 4-(dimethylamino)-4-phenylcyclohexa-none or a protected derivative thereof, optionally in the form of an acid addition salt, in a carbonic acid as reaction medium in the presence of sulfuric acid to form (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate, preferably the hydrosulfate.

A protected derivative of 4-(dimethylamino)-4-phenylcyclohexanone preferably means in the sense of the present invention a derivative of 4-(dimethylamino)-4-phenylcyclohexanone, wherein the keto-group of said compound is protected by a suitable protecting group, e.g. is present in the form of an ethylene glycol group. Reaction step (a-4) according to the present invention is an oxa-Pictet-Spengler reaction which is e.g. known from S.-Y. Chou et al., Heterocycles 2003, 60, 1095 and M. Zott et al., Tetrahedron: Asymmetry 1993, 4, 2307.

Any suitable carbonic acid can serve as reaction medium in step (a-4) according to the present invention. The reaction medium preferably serves as solvent for the starting material employed, i.e. for the compounds 2-(5-fluoro-1H-indol-3-yl)ethanol and 4-(dimethylamino)-4-phenylcyclohexanone or a protected derivative thereof, preferably also as a solvent for sulfuric acid. Preferably, the carbonic acid employed as reaction medium in step (a-4) according to the present invention is in liquid form at room temperature. Preferably, the carbonic acid employed as reaction medium in step (a-4) is selected from the group consisting of acetic acid, trifluoroacetic acid, propionic acid, lactic acid, 3-hydroxypropionic acid, butyric acid, isobutyric acid, acrylic acid and methacrylic acid or mixtures thereof. Preferably, the carbonic acid employed as reaction medium in step (a) is selected from the group consisting of acetic acid, trifluoroacetic acid, and propionic acid or mixtures thereof. Particularly preferred are acetic acid and propionic acid. Most preferred is acetic acid.

In a particularly preferred embodiment of the present invention, the carbonic acid employed as reaction medium in step (a-4) is acetic acid.

In another particularly preferred embodiment of the present invention, the carbonic acid employed as reaction medium in step (a-4) is propionic acid.

Preferably, the carbonic acid as reaction medium is employed in step (a-4) in an amount by weight that is in the range of from 5 to 60 times higher than the total amount of 4-(dimethylamino)-4-phenylcyclohexanone or a protected derivative thereof by weight. For example, in case 200 mg of each of the starting material is employed, the carbonic acid as reaction medium is employed in an amount by weight, that is in the range of from 1 g to 12 g. More preferably, the carbonic acid as reaction medium is employed in step (a-4) in an amount by weight that is in the range of from 7 to 50 times, even more preferably 10 to 45 times, still more preferably 12 to 40 times, in particular 15 to 35 times, and most preferred 20 to 30 times higher than the total amount of 4-(dimethylamino)-4-phenylcyclohexanone or a protected derivative thereof by weight.

Preferably, sulfuric acid as promoting agent is employed in step (a-4) in an amount that is in the range of from 1.05 to 2.00 equivalents, preferably of from 1.10 to 1.90 equivalents, more preferably of from 1.10 to 1.70 equivalents, even more preferably of from 1.10 to 1.50 equivalents, still more preferably of from 1.10 to 1.40 equivalents, in particular of from 1.10 to 1.30 equivalents, in each case with respect to the molar amount of either 2-(5-fluoro-1H-indol-3-yl)ethanol or 4-(dimethylamino)-4-phenylcyclohexanone or a protected derivative thereof.

Preferably, sulfuric acid employed in step (a-4) according to the process of the invention is soluble, preferably soluble at room temperature, in the reaction medium employed in step (a-4).

The reaction time of step (a-4) can vary in dependence on various parameters, such as, for example, temperature, stoichiometry, nature of the compound to be reacted with, or the nature of the reaction medium, and can be determined for the process in question by the person skilled in the art using preliminary tests. Preferably, the reaction time for performing step (a) does not exceed 24 h, more preferably does not exceed 18 h. Even more preferably, the reaction time is in the range of from 1 h to 20 h, still more preferably is in the range of from 2 h to 18, in particular is in the range of from 3 h to 16 h, most preferred is in the range of from 4 h to 10 h.

Preferably, the reaction mixture is stirred in step (a-4). The reaction temperature at which step (a-4) is performed can vary in dependence on various parameters, such as, for example, reaction time, stoichiometry, nature of the compound to be reacted with, or nature of the reaction medium and can be determined for the process in question by the person skilled in the art using preliminary tests. Preferably, the reaction temperature at which step (a-4) of the inventive process is performed, is in the range of from 20° C. to 100° C., more preferably is in the range of from 30° C. to 90° C., even more preferably is in the range of from 40° C. to 80° C., still more preferably in the range of from 40° C. to 60° C. In another preferred embodiment of the present invention, the reaction temperature at which step (a-4) of the inventive process is performed is at least 30° C., preferably at least 40° C., more preferably at least 50° C.

In a particularly preferred embodiment
  sulfuric acid is employed in step (a-4) in an amount that is in the range of from 1.10 to 1.30 equivalents with respect to the molar amount of 2-(5-fluoro-1H-indol-3-yl)ethanol or 4-(dimethylamino)-4-phenylcyclohexanone or a protected derivative thereof,
  the at least one carbonic acid as reaction medium employed in step (a) is acetic acid or propionic acid, preferably in an amount by weight that is in the range of from 5 to 60 times higher than the total amount of 4-(dimethylamino)-4-phenylcyclohexanone or a protected derivative thereof by weight.

In a very particularly preferred embodiment
  sulfuric acid is employed in step (a-4) in an amount that is in the range of from 1.10 to 1.30 equivalents with respect to the molar amount of 2-(5-fluoro-1H-indol-3-yl)ethanol or 4-(dimethylamino)-4-phenylcyclohexanone or a protected derivative thereof,
  the at least one carbonic acid as reaction medium employed in step (a) is acetic acid or propionic acid, preferably in an amount by weight that is in the range of from 5 to 60 times higher than the total amount of 4-(dimethylamino)-4-phenylcyclohexanone or a protected derivative thereof by weight,
  the reaction temperature at which step (a) is performed is in the range of from 40° C. to 80° C., preferably in the range of from 40° C. to 60° C., and
  the reaction time of step (a) is in the range of from 3 hours to 16 hours.

Preferably, the solid form of the compound according to formula (I) and sulfuric acid precipitates from the reaction mixture during the performance of step (a-4) and can be thus obtained from step (a-4) as a precipitate, preferably by filtration of the reaction mixture, i.e. by separating, preferably filtering off the precipitate.

Thus, preferably, the process according to the invention further comprises the step
(b-4) separating, preferably filtering off the solid obtained in step (a-4).

The solid obtained from step (b-4) can be optionally purified, e.g. by
(c-4) optionally performing steps (a-2) and (b-2) or (b-2') or performing steps (a-3) and (b-3).

The solid obtained from step (b-4) can be optionally further recrystallized in a manner well known to those skilled in the art, e.g. by recrystallization from a suitable solvent. Alternatively, the solid obtained can also be subjected to a chromatographic resolution.

Suitable solvents can be determined by the person skilled in the art using preliminary tests and include solvents such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; and also N-methyl-2-pyrrolidone, dimethyl acetamide, dimethyl formamide and dimethyl sulfoxide (DMSO); carbonic acids such as acetic acid and propionic acid, and mixtures thereof. Particularly preferred are acetic acid, mixtures of DMSO and acetic acid, mixtures of THF and DMSO, and mixtures of acetic acid and dimethyl acetamide. Recrystallization techniques well known to those skilled in the art e.g. include first dissolving the acid addition salt obtained from step (a) in a suitable solvent, optionally heating the mixture, followed by a precipitation of said acid addition salt, preferably by addition of another medium, or followed by evaporation off the solvent employed for dissolution.

A further aspect of the invention relates to a solid form, preferably a crystalline form of (1r,4r)-6'-fluoro-N,N-dimethyl-4-phenyl-4',9'-dihydro-3'H-spiro[cyclohexane-1,1'-pyrano-[3,4,b]indol]-4-amine sulfate or hemi-sulfate, more preferably a crystalline form of (1r,4r)-6'-fluoro-N,N-dimethyl-4-phenyl-4',9'-dihydro-3'H-spiro[cyclohexane-1,1'-pyrano[3,4,b]indol]-4-amine sulfate that is obtainable by the process as described above.

In the following, any reference to a "crystalline form" refers to a crystalline form of (1r,4r)-6'-fluoro-N,N-dimethyl-4-phenyl-4',9'-dihydro-3'H-spiro[cyclohexane-1,1'-pyrano-[3,4, b]indol]-4-amine sulfate or to a crystalline form of (1r,4r)-6'-fluoro-N,N-dimethyl-4-phenyl-4',9'-dihydro-3'H-spiro[cyclohexane-1,1'-pyrano[3,4,b]indol]-4-amine hemi-sulfate.

A further aspect of the present invention relates to a crystalline form A. Preferably, crystalline form A of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid is a (1r,4r)-6'-fluoro-N,N-dimethyl-4-phenyl-4',9'-dihydro-3'H-spiro[cyclohexane-1,1'-pyrano[3,4,b]indol]-4-amine sulfate, preferably a solvate, more preferably a hydrate, in particular a monohydrate thereof.

Preferably, the crystalline form A according to the invention has one or more X-ray diffraction peaks selected from the group consisting of 7.3±0.2 (2Θ), 9.2±0.2 (2Θ), 18.0±0.2 (2Θ), 18.5±0.2 (2Θ), 21.3±0.2 (2Θ) and 25.6±0.2 (2Θ). In some preferred embodiments, the crystalline form comprises X-ray diffraction peaks at 7.3±0.2 (2Θ), 9.2±0.2 (2Θ), 18.0±0.2 (2Θ), 18.5±0.2 (2Θ) and/or 21.3±0.2 (2Θ). In some preferred embodiments, the crystalline form comprises X-ray diffraction peaks at 18.0±0.2 (2Θ), 18.5±0.2 (2Θ) and/or 21.3±0.2 (2Θ). In some preferred embodiments, the crystalline form comprises an X-ray diffraction peak at 18.5±0.2 (2Θ).

In some preferred embodiments, crystalline form A comprises X-ray diffraction peaks at 7.3±0.2 (2Θ), 9.2±0.2 (2Θ), 18.0±0.2 (2Θ), 18.5±0.2 (2Θ), 21.3±0.2 (2Θ), 25.6±0.2 (2Θ) and optionally at 14.6±0.2 (2Θ) and 30.0±0.2 (2Θ).

The crystalline form A according to the invention may additionally have at least one X-ray diffraction peak selected from the group consisting of 15.7±0.2 (2Θ), 19.4±0.2 (2Θ), 21.0±0.2 (2Θ), 25.4±0.2 (2Θ), 27.8±0.2 (2Θ), 29.0±0.2 (2Θ), and 33.9±0.2 (2Θ).

Further, the crystalline form A according to the invention may be characterized in that as well as one or more X-ray diffraction peaks are selected from the group consisting of 7.3±0.2 (2Θ), 9.2±0.2 (2Θ), 18.0±0.2 (2Θ), 18.5±0.2 (2Θ), 21.3±0.2 (2Θ) and 25.6±0.2 (2Θ), and optionally one or more X-ray diffraction peaks selected from the group consisting of 14.6±0.2 (2Θ), 15.7±0.2 (2Θ), 19.4±0.2 (2Θ), 21.0±0.2 (2Θ), 25.4±0.2 (2Θ), 27.8±0.2 (2Θ), 29.0±0.2 (2Θ), 30.0±0.2 (2Θ) and 33.9±0.2 (2Θ); it additionally may have at least one X-ray diffraction peak selected from the group consisting of 20.7±0.2 (2Θ), 21.8±0.2 (2Θ), 23.2±0.2 (2Θ), 24.6±0.2 (2Θ), 25.0±0.2 (2Θ), 26.5±0.2 (2Θ), 27.0±0.2 (2Θ) and 29.5±0.2 (2Θ).

The crystalline form A according to the invention may further be characterized in that as well as one or more X-ray diffraction peaks selected from the group consisting of 7.3±0.2 (2Θ), 9.2±0.2 (2Θ), 18.0±0.2 (2Θ), 18.5±0.2 (2Θ), 21.3±0.2 (2Θ) and 25.6±0.2 (2Θ), and optionally one or more X-ray diffraction peaks selected from the group consisting of 14.6±0.2 (2Θ), 15.7±0.2 (2Θ), 19.4±0.2 (2Θ), 21.0±0.2 (2Θ), 25.4±0.2 (2Θ), 27.8±0.2 (2Θ), 29.0±0.2 (2Θ), 30.0±0.2 (2Θ) and 33.9±0.2 (2Θ); and further optionally one or more X-ray diffraction peak selected from the group consisting of 20.7±0.2 (2Θ), 21.8±0.2 (2Θ), 23.2±0.2 (2Θ), 24.6±0.2 (2Θ), 25.0±0.2 (2Θ), 26.5±0.2 (2Θ), 27.0±0.2 (2Θ) and 29.5±0.2 (2Θ); it additionally may have at least one X-ray diffraction peak selected from the group consisting of 16.8±0.2 (2Θ), 20.3±0.2 (2Θ), 23.7±0.2 (2Θ), 27.4±0.2 (2Θ), 28.2±0.2 (2Θ), 32.4±0.2 (2Θ), 32.9±0.2 (2Θ) and 34.4±0.2 (2Θ).

All 2Θ values refer to an X-ray diffractogram measured using CuKα radiation having a wavelength of 1.54060 Å.

In DSC analyses, the crystalline form A according to the present invention preferably exhibits multiple endothermic events, preferably with peak temperatures at 169-179° C., 205-215° C. and 231-241° C., more preferably with peak temperatures at 170-178° C., 206-214° C. and 232-240° C., even more preferably with peak temperatures at 171-177° C., 207-213° C. and 233-239° C., yet even more preferably with peak temperatures at 172-176° C., 208-212° C. and 234-238° C., and also an exothermic event with a peak temperature in the range of 237-247° C., preferably in the range of 238-246° C., more preferably in the range of 239-245° C., even more preferably in the range of 240-244° C., yet more preferably in the range of 241-243° C.

The crystalline form A according to the present invention may further be characterized in that it has one or more Raman bands selected from the group consisting of 916±2 $cm^{-1}$, 1002±2 $cm^{-1}$, 1028±2 $cm^{-1}$, 1571±2 $cm^{-1}$, 1583±2 $cm^{-1}$, 2983±2 $cm^{-1}$ and 3074±2 $cm^{-1}$.

The crystalline form A according to the present invention may further be characterized in that it has one or more Raman bands selected from the group consisting of 916±2 $cm^{-1}$, $1002\pm2$ cm$^{-1}$, $1028\pm2$ cm$^{-1}$, $1571\pm2$ cm$^{-1}$, $1583\pm2$ cm$^{-1}$, $2983\pm2$ cm$^{-1}$ and $3074\pm2$ cm$^{-1}$; and/or one or more additional Raman bands selected from the group consisting of $173\pm2$ cm$^{-1}$, $684\pm2$ cm$^{-1}$, $925\pm2$ cm$^{-1}$, $1298\pm2$ cm$^{-1}$, and $1464\pm2$ cm$^{-1}$.

The crystalline form A according to the present invention may further be characterized in that it has one or more Raman bands selected from the group consisting of $916\pm2$ cm$^{-1}$, $1002\pm2$ cm$^{-1}$, $1028\pm2$ cm$^{-1}$, $1571\pm2$ cm$^{-1}$, $1583\pm2$ cm$^{-1}$, $2983\pm2$ cm$^{-1}$, $3074\pm2$ cm$^{-1}$, $173\pm2$ cm$^{-1}$, $684\pm2$ cm$^{-1}$, $925\pm2$ cm$^{-1}$, $1298\pm2$ cm$^{-1}$, and $1464\pm2$ cm$^{-1}$.

The crystalline form A according to the present invention may further be characterized in that it has one or more additional Raman bands selected from the group consisting of $204\pm2$ cm$^{-1}$, $370\pm2$ cm$^{-1}$, $490\pm2$ cm$^{-1}$, $597\pm2$ cm$^{-1}$, $620\pm2$ cm$^{-1}$, $826\pm2$ cm$^{-1}$, $886\pm2$ cm$^{-1}$, $1115\pm2$ cm$^{-1}$, $1164\pm2$ cm$^{-1}$, $1197\pm2$ cm$^{-1}$, $1219\pm2$ cm$^{-1}$, $1265\pm2$ cm$^{-1}$, $1374\pm2$ cm$^{-1}$, $1442\pm2$ cm$^{-1}$, $2906\pm2$ cm$^{-1}$, $2925\pm2$ cm$^{-1}$ and $2957\pm2$ cm$^{-1}$.

The crystalline form A according to the present invention may further be characterized in that it has one or more additional Raman bands selected from the group consisting of $538\pm2$ cm$^{-1}$, $786\pm2$ cm$^{-1}$, $1629\pm2$ cm$^{-1}$ and $2852\pm2$ cm$^{-1}$.

Another aspect of the present invention relates to a process for the production of the crystalline form A described above.

In a preferred embodiment, the process comprises the step of
(a-1) precipitating the sulfate or hemi-sulfate salt of (1r,4r)-6'-fluoro-N,N-dimethyl-4-phenyl-4',9'-dihydro-3'H-spiro[cyclohexane-1,1'-pyrano[3,4,b]indol]-4-amine from a solution or suspension of the free base.

Conventional solvents known to persons skilled in the art may be used as solvents in a solution or suspension, preferably a solution, of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof.

Preferably, the solvent is selected from the group consisting of water, alcohols such as methanol, ethanol, n-propanol, iso-propanol and n-butanol; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; chlorinated hydrocarbons such as dichloromethane and chloroform; and mixtures thereof. Especially preferred are solvents selected from the group consisting of tetrahydrofuran, 1,4-dioxane, acetone, dichloromethane, methanol, ethanol, iso-propanol, water, and mixtures thereof, in particular THF/water, THF/acetone and acetone/water mixtures. Most preferred is a mixture of THF and acetone.

Step (a-1) may be carried out by the addition of sulfuric acid. In a preferred embodiment, the solution is a solution of sulfuric acid in an aqueous solvent, i.e. an aqueous solution of sulfuric acid.

In another preferred embodiment, the solution is a solution of sulfuric acid in an organic solvent, especially preferred are alcohols such as ethanol, isopropanol and n-butanol, and ethers such as diethylether, di-isopropylether, tetrahydrofurane, methyl-tetrahydrofurane 1,4-dioxane or carbonic acids such as acetic acid and propionic acid.

In a preferred embodiment, the sulfuric acid containing solution and the solution of the free base contain the same solvent.

In another particularly preferred embodiment, the sulfuric acid containing solution and the solution of the free base contain not the same solvent.

In a particularly preferred embodiment containing solution is an aqueous solution and the solution of the free base is an organic solvent, in which the free base is dissolved.

Preferably, a sulfuric acid containing aqueous solution is added to a solution of the free base in acetone and THF.

Preferably, the aqueous solution contains sulfuric acid in a concentration within the range of from 0.01 mol/L to 15 mol/L, more preferably within the range of from 0.02 mol/L to 12.5 mol/L, still more preferably within the range of from 0.05 mol/L to 10 mol/L, yet more preferably within the range of from 0.1 mol/L to 7.5 mol/L, most preferably within the range of from 0.2 mol/L to 10 mol/L, and in particular within the range of from 0.3 mol/L to 5 mol/L.

Preferably, the sulfuric acid is added to the solution or suspension of the free base in molar excess, in particular in order to form a sulfate salt.

Preferably, in the process according to the invention, step (a-1) is carried out at a temperature below or at the boiling point of the respective solvent, preferably at a temperature not higher than 100° C., more preferably not higher than 80° C., even more preferably not higher than 60° C., and in particular in a temperature range of 20-40° C.

Preferably, in the process of to the invention, the suspension or solution obtained in step (a-1) is stirred for a time period of at least 1 minute, preferably at least 2 minutes, more preferably at least 3 minutes, still more preferably at least 5 minutes, yet more preferably at least 10 minutes, most preferably at least 20 minutes, and in particular at least 30 minutes.

In a preferred embodiment, the suspension or solution obtained in step (a-1) is stirred for a time period of at least 1 hour, preferably at least 4 hours, more preferably at least 6 hours, still more preferably at least 12 hours, yet more preferably at least 18 hours, most preferably at least 1 day, and in particular at least 2 days.

In another preferred embodiment, the suspension or solution obtained in step (a-1) is stirred for a time period of at most 1 day, preferably at most 12 hours, more preferably at most 6 hours, still more preferably at most 2 hours, yet more preferably at most 60 minutes, and most preferably at most 45 minutes, and in particular at most 30 minutes.

Preferably, the process according to the invention further comprises the step
(b-1) separating, preferably filtering off the solid obtained in step (a-1).

Preferably, the process according to the invention further comprises the step
(c-1) drying of the solid obtained in step (b-1).

In a preferred embodiment, step (c-1) takes place under air or inert gas flow, such as argon or nitrogen flow.

In another preferred embodiment, step (c-1) takes place under vacuum, more preferably at a vacuum of 0 to 900 mbar, even more preferably at a vacuum of 1 to 500 mbar, and in particular at a vacuum of 10 to 200 mbar.

Preferably, in the process according to the invention, step (c-1) takes place in a temperature range from 0 to 60° C., preferably from 10° C. to 50° C. more preferably from 20 to 40° C.

In another preferred embodiment, the process comprises the step of
(a-2) dissolving (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate in a solvent.

Conventional solvents known to persons skilled in the art may be used as solvents in a solution of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof.

Preferably, in the process according to the invention, step (a-2) is carried out at a temperature below or at the boiling point of the respective solvent or solvent mixture, more preferably at a temperature not higher than 100° C., more preferably not higher than 80° C., even more preferably not higher than 60° C., and in particular in a temperature range of 20-40° C.

In a preferred embodiment, the process according to the invention further comprises the step
(b-2) evaporating the solvent of the solution obtained in step (a-2).

Suitable methods for evaporating the solvent are known to persons skilled in the art. Preferably, in the process according to the invention, the solvent is evaporated in air, air flow, or inert gas flow, in particular argon or nitrogen flow. However, evaporating the solvent under vacuum, for example by means of a rotary evaporator, is also possible. Preferably, in the process according to the invention, the solvent is evaporated at room temperature.

In another preferred embodiment, the process further comprises the step of
(b-2') precipitating (1r,4r)-6'-fluoro-N,N-dimethyl-4-phenyl-4',9'-dihydro-3'H-spiro[cyclo-hexane-1,1'-pyrano[3,4,b]indol]-4-amine sulfate or hemi-sulfate from the solution obtained in step (a-2).

Suitable methods of precipitation are known to persons skilled in the art. In the process according to the invention, step (b-2') may be carried out by reducing the volume of the solution obtained in step (a-2) and/or by cooling of the solution, preferably to a temperature of at most 15° C., more preferably at most 10° C., even more preferably at most 4-8° C. and/or by cooling of the solution, preferably to a temperature of at least 10° C., more preferably at least 30° C., even more preferably at least 60° C. below the temperature according to step (a-2).

In a preferred embodiment, step (b-2') is carried out by the addition of a medium in which (1r,4r)-6'-fluoro-N,N-dimethyl-4-phenyl-4',9'-dihydro-3'H-spiro[cyclohexane-1,1'-pyrano-[3,4,b]indol]-4-amine sulfate or hemi-sulfate is only poorly soluble ("anti-solvent") to the solution obtained in step (a-2). Said medium is preferably selected from the group consisting of esters such as ethyl acetate, n-propyl acetate, iso-propyl acetate, n-butyl acetate and iso-butyl acetate; alcohols such as methanol, ethanol, 1-propanol, 2-propanol; ethers such as tert-butyl methyl ether, diethyl ether and diiso-propyl ether; ketones such as acetone, 2-butanone, pentan-2-one, pentan-3-one, hexan-2-one and hexan-3-one; nitriles such as acetonitril; pyridine, acetic acid and water, and DMSO. Particularly preferred are DMSO, 2-butanone (MEK), 2-propanol, and water; especially preferred are 2-butanone (MEK) and 2-propanol.

The amount of the media in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate is only poorly soluble, the precipitant or anti-solvent, is preferably selected in such a manner that upon its addition precipitation of the dissolved component begins. The total amount of the media in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate is only poorly soluble may also be divided into several portions, preferably two or three portions. In this embodiment, the precipitation of the dissolved component preferably begins after the addition of the last portion. The precipitation of the dissolved component preferably begins either immediately after the precipitant, preferably the total amount of the precipitant, has been added or alternatively with a delay of 2 seconds to 120 minutes.

Step (b-2') may also be carried out by exposing the solution obtained in step (a-2) to an atmosphere containing a solvent, in which (1r,4r)-6'-fluoro-N,N-dimethyl-4-phenyl-4',9'-dihydro-3'H-spiro[cyclohexane-1,1'-pyrano[3,4,b]indol]-4-amine sulphate or hemi-sulfate is only poorly soluble.

Preferably, in the process according to the invention, after step (b-2) or respectively (b-2'), all other steps are carried out at a temperature between 40 and 0° C., preferably between 35 and 5° C., more preferably between 25 and 15° C.

Preferably, in the process according to the invention, the suspension obtained in step (b-2') is stirred for a time period of at least 1 minute, preferably at least 2 minutes, more preferably at least 3 minutes, and most preferably at least 5 minutes.

Preferably, the process according to the invention further comprises the step
(c-2') separating, preferably filtering off the precipitate obtained in step (b-2').

Preferably, the process according to the invention further comprises the step
(d-2') drying of the solid obtained in step (c-2').

Preferably, in the process according to the invention, step (d-2') takes place under air or inert gas flow, such as argon or nitrogen flow.

In still another preferred embodiment, the process comprises the step of
(a-3) suspending (1r,4r)-6'-fluoro-N,N-dimethyl-4-phenyl-4',9'-dihydro-3'H-spiro[cyclo-hexane-1,1'-pyrano[3,4,b]indol]-4-amine sulfate or hemi-sulfate in a solvent.

Conventional solvents known to persons skilled in the art may be used as solvents in a suspension of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO);

and mixtures thereof. Preferred solvents are alcohols such as methanol or water, particularly preferred alcohols such as methanol.

In a preferred embodiment, step (a-3) is carried out at a temperature below or at the boiling point of the respective solvent, preferably at a temperature not higher than 100° C., more preferably not higher than 90° C., still more preferably not higher than 80° C., yet more preferably not higher than 60° C., most preferably not higher than 40° C., and in particular in a temperature range of 15-35° C.

In another preferred embodiment, step (a-3) is carried out in a temperature range of 100-40° C., more preferably 90-50° C., and most preferably 85-60° C.

Preferably, in the process according to the invention, the suspension obtained in step (a-3) is stirred for a time period of at least 2 h, preferably at least 4 h, more preferably at least 8 h, still more preferably at least 12 h, yet more preferably at least 16 h, most preferably at least 24 h, and in particular at least 2 days.

Preferably, the process according to the invention further comprises the step (b-3) separating, preferably filtering off the solid obtained in step (a-3).

Preferably, the process according to the invention further comprises the step (c-3) drying of the solid obtained in step (b-3).

In the process according to the invention, step (c-3) may take place under air or inert gas flow, such as argon or nitrogen flow. However, drying under vacuum, more preferably at a vacuum of 0 to 900 mbar, even more preferably at a vacuum of 1 to 500 mbar, and in particular at a vacuum of 10 to 200 mbar is preferred.

Preferably, in the process according to the invention, step (c-3) takes place in a temperature range from 0 to 60° C., preferably from 10° C. to 50° C. more preferably from 20 to 40° C.

Most preferred is a process comprising steps (a-1) and (b-1) for the preparation of crystalline form A.

A further aspect of the invention relates to a crystalline form A that is obtainable by the process as described above.

A further aspect of the present invention relates to a crystalline form B. Preferably, crystalline form B of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid is a (1r,4r)-6'-fluoro-N,N-dimethyl-4-phenyl-4',9'-dihydro-3' H-spiro[cyclohexane-1,1'-pyrano[3,4,b]indol]-4-amine sulfate, preferably an ansolvate thereof.

Preferably, the crystalline form B according to the invention has one or more X-ray diffraction (CuKα radiation) selected from the group consisting of 10.2±0.2 (2Θ), 15.8±0.2 (2Θ), 17.5±0.2 (2Θ), 17.7±0.2 (2Θ), 18.4±0.2 (2Θ), 18.6±0.2 (2Θ), 22.8±0.2 (2Θ), and 25.9±0.2 (2Θ). In some preferred embodiments, the crystalline form comprises X-ray diffraction peaks at 15.8±0.2 (2Θ), 17.5±0.2 (2Θ), 17.7±0.2 (2Θ), 18.4±0.2 (2Θ), 18.6±0.2 (2Θ), 22.8±0.2 (2Θ), and/or 25.9±0.2 (2Θ). In some preferred embodiments, the crystalline form comprises X-ray diffraction peaks at 15.8±0.2 (2Θ), 17.5±0.2 (2Θ), 17.7±0.2 (2Θ), 18.4±0.2 (2Θ), 18.6±0.2 (2Θ) and/or 22.8±0.2 (2Θ). In some preferred embodiments, the crystalline form comprises X-ray diffraction peaks at 15.8±0.2 (2Θ), 17.5±0.2 (2Θ), 17.7±0.2 (2Θ), 18.6±0.2 (2Θ) and/or 22.8±0.2 (2Θ). In some preferred embodiments, the crystalline form comprises X-ray diffraction peaks at 17.5±0.2 (2Θ), 17.7±0.2 (2Θ), 18.6±0.2 (2Θ) and/or 22.8±0.2 (2Θ). In some preferred embodiments, the crystalline form comprises X-ray diffraction peaks at 17.5±0.2 (2Θ), 18.6±0.2 (2Θ) and/or 22.8±0.2 (2Θ). In some preferred embodiments, the crystalline form comprises X-ray diffraction peaks at 17.7±0.2 (2Θ), 18.6±0.2 (2Θ) and/or 22.8±0.2 (2Θ). In some preferred embodiments, the crystalline form comprises X-ray diffraction peaks at 17.5±0.2 (2Θ), and/or 22.8±0.2 (2Θ). In some preferred embodiments, the crystalline form comprises X-ray diffraction peaks at 17.5±0.2 (2Θ) and/or 22.8±0.2 (2Θ).

In some preferred embodiments, crystalline form B comprises one or more X-ray diffraction peaks (CuKα radiation) selected from the group consisting of 10.2±0.2 (2Θ), 15.8±0.2 (2Θ), 17.5±0.2 (2Θ), 17.7±0.2 (2Θ), 18.4±0.2 (2Θ), 18.6±0.2 (2Θ), 22.8±0.2 (2Θ), and 25.9±0.2 (2Θ), and optionally at 22.5±0.2 (2Θ), 23.1±0.2 (2Θ) and 27.9±0.2 (2Θ).

The crystalline form B according to the invention may additionally have at least one X-ray diffraction peak selected from the group consisting of 11.4±0.2 (2Θ), 14.5±0.2 (2Θ), 17.1±0.2 (2Θ), 18.9±0.2 (2Θ), 19.2±0.2 (2Θ), 26.9±0.2 (2Θ), and 27.2±0.2 (2Θ).

Further, the crystalline form B according to the invention may be characterized in that as well as one or more X-ray diffraction peaks are selected from the group consisting of 10.2±0.2 (2Θ), 15.8±0.2 (2Θ), 17.5±0.2 (2Θ), 17.7±0.2 (2Θ), 18.4±0.2 (2Θ), 18.6±0.2 (2Θ), 22.8±0.2 (2Θ), and 25.9±0.2 (2Θ), and optionally one or more X-ray diffraction peaks selected from the group consisting of 11.4±0.2 (2Θ), 14.5±0.2 (2Θ), 17.1±0.2 (2Θ), 18.9±0.2 (2Θ), 19.2±0.2 (2Θ), 22.5±0.2 (2Θ), 23.1±0.2 (2Θ), 26.9±0.2 (2Θ), 27.2±0.2 (2Θ), 27.9±0.2 (2Θ); it additionally may have at least one X-ray diffraction peak selected from the group consisting of 7.7±0.2 (2Θ), 21.0±0.2 (2Θ), 21.7±0.2 (2Θ), 25.2±0.2 (2Θ), 26.6±0.2 (2Θ), 27.4±0.2 (2Θ), 28.4±0.2 (2Θ) and 32.2±0.2 (2Θ).

The crystalline form B according to the invention may further be characterized in that as well as one or more X-ray diffraction peaks are selected from the group consisting of 10.2±0.2 (2Θ), 15.8±0.2 (2Θ), 17.5±0.2 (2Θ), 17.7±0.2 (2Θ), 18.4±0.2 (2Θ), 18.6±0.2 (2Θ), 22.8±0.2 (2Θ), and 25.9±0.2 (2Θ), and optionally one or more X-ray diffraction peaks selected from the group consisting of 11.4±0.2 (2Θ), 14.5±0.2 (2Θ), 17.1±0.2 (2Θ), 18.9±0.2 (2Θ), 19.2±0.2 (2Θ), 22.5±0.2 (2Θ), 23.1±0.2 (2Θ), 26.9±0.2 (2Θ), 27.2±0.2 (2Θ), 27.9±0.2 (2Θ); and optionally one or more X-ray diffraction peaks selected from the group consisting of 7.7±0.2 (2Θ), 21.0±0.2 (2Θ), 21.7±0.2 (2Θ), 25.2±0.2 (2Θ), 26.6±0.2 (2Θ), 27.4±0.2 (2Θ), 28.4±0.2 (2Θ) and 32.2±0.2 (2Θ); it additionally may have at least one X-ray diffraction peak selected from the group consisting of 8.8±0.2 (2Θ), 9.9±0.2 (2Θ), 13.9±0.2 (2Θ), 19.9±0.2 (2Θ), 22.0±0.2 (2Θ), 23.9±0.2 (2Θ), 26.2±0.2 (2Θ), 29.3±0.2 (2Θ), 30.6±0.2 (2Θ), 31.4±0.2 (2Θ), 33.0±0.2 (2Θ), 33.2±0.2 (2Θ), and 33.7±0.2 (2Θ).

All 2Θ values refer to an X-ray diffractogram measured using CuKα radiation having a wavelength of 1.54060 Å.

In DSC analyses, the crystalline form B according to the present invention preferably exhibits an endothermic event, with a peak temperature in the range of 247-257° C., preferably in the range of 248-256° C., more preferably in the range of 249-255° C., even more preferably in the range of 250-254° C., yet more preferably in the range of 251-253° C., and also an exothermic event with a peak temperature in the range of 250-260° C., preferably in the range of 251-259° C., more preferably in the range of 252-258° C., even more preferably in the range of 253-257° C., yet more preferably in the range of 254-256° C.

The crystalline form B according to the present invention may further be characterized in that it has one or more Raman bands selected from the group consisting of 916±2 cm$^{-1}$, 1002±2 cm$^{-1}$, 1028±2 cm$^{-1}$, 1308±2 cm$^{-1}$, 1567±2 cm$^{-1}$, 1584±2 cm$^{-1}$, 2978±2 cm$^{-1}$ and 3078±2 cm$^{-1}$.

The crystalline form B according to the present invention may further be characterized in that it has one or more Raman bands selected from the group consisting of 916±2 cm$^{-1}$, 1002±2 cm$^{-1}$, 1028±2 cm$^{-1}$, 1308±2 cm$^{-1}$, 1567±2 cm$^{-1}$, 1584±2 cm$^{-1}$, 2978±2 cm$^{-1}$ and 3078±2 cm$^{-1}$; and/or one or more additional Raman bands selected from the group consisting of 175±2 cm$^{-1}$, 686±2 cm$^{-1}$, 928±2 cm$^{-1}$, 1467±2 cm$^{-1}$, and 2985±2 cm$^{-1}$.

The crystalline form B according to the present invention may further be characterized in that it has one or more Raman bands selected from the group consisting of 916±2 cm$^{-1}$, 1002±2 cm$^{-1}$, 1028±2 cm$^{-1}$, 1308±2 cm$^{-1}$, 1567±2 cm$^{-1}$, 1584±2 cm$^{-1}$, 2978±2 cm$^{-1}$, 3078±2 cm$^{-1}$, 175±2 cm$^{-1}$, 686±2 cm$^{-1}$, 928±2 cm$^{-1}$, 1467±2 cm$^{-1}$, and 2985±2 cm$^{-1}$.

The crystalline form B according to the present invention may further be characterized in that it has one or more additional Raman bands selected from the group consisting of 187±2 cm$^{-1}$, 205±2 cm$^{-1}$, 370±2 cm$^{-1}$, 599±2 cm$^{-1}$, 621±2 cm$^{-1}$, 821±2 cm$^{-1}$, 1008±2 cm$^{-1}$, 1221±2 cm$^{-1}$, 1295±2 cm$^{-1}$, 1370±2 cm$^{-1}$, 1442±2 cm$^{-1}$, 1452±2 cm$^{-1}$, 1601±2 cm$^{-1}$, 2913±2 cm$^{-1}$, 2956±2 cm$^{-1}$, 3038±2 cm$^{-1}$ and 3059±2 cm$^{-1}$.

The crystalline form B according to the present invention may further be characterized in that it has one or more additional Raman bands selected from the group consisting of 254±2 cm$^{-1}$, 275±2 cm$^{-1}$, 396±2 cm$^{-1}$, 413±2 cm$^{-1}$, 433±2 cm$^{-1}$, 703±2 cm$^{-1}$, 886±2 cm$^{-1}$, 1050±2 cm$^{-1}$, 1113±2 cm$^{-1}$, 1133±2 cm$^{-1}$, 1167±2 cm$^{-1}$, 1201±2 cm$^{-1}$, 1266±2 cm$^{-1}$, 1625±2 cm$^{-1}$, and 2940±2 cm$^{-1}$.

Another aspect of the present invention relates to a process for the production of the crystalline form B described above.

In a preferred embodiment, the process comprises the step of (a-1) precipitating the sulfate or hemi-sulfate salt of (1r,4r)-6'-fluoro-N,N-dimethyl-4-phenyl-4',9'-dihydro-3'H-spiro[cyclohexane-1,1'-pyrano[3,4,b]indol]-4-amine from a solution or suspension of the free base.

Conventional solvents known to persons skilled in the art may be used as solvents in a solution or suspension, preferably a solution, of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof.

Step (a-1) may be carried out by the addition of sulfuric acid. In a preferred embodiment, sulfuric acid is added in form of a solution. In one preferred embodiment, the solution is a solution of sulfuric acid in an aqueous solvent, i.e. an aqueous solution of sulfuric acid. In another preferred embodiment, the solution is a solution of sulfuric acid in an organic solvent, especially preferred are alcohols such as ethanol, isopropanol and n-butanol, and ethers such as diethylether, di-isopropylether, tetrahydrofurane, methyl-tetrahydrofurane 1,4-dioxane or carbonic acids such as acetic acid and propionic acid.

In a preferred embodiment, the sulfuric acid containing solution and the solution of the free base contain the same solvent.

In another particularly preferred embodiment, the sulfuric acid containing solution and the solution of the free base contain not the same solvent.

In a particularly preferred embodiment containing solution is an aqueous solution and the solution of the free base is an organic solvent, in which the free base is dissolved.

Preferably, the solution contains sulfuric acid in a concentration within the range of from 0.01 mol/L to 15 mol/L, more preferably within the range of from 0.02 mol/L to 12.5 mol/L, still more preferably within the range of from 0.05 mol/L to 10 mol/L, yet more preferably within the range of from 0.1 mol/L to 7.5 mol/L, most preferably within the range of from 0.2 mol/L to 10 mol/L, and in particular within the range of from 0.3 mol/L to 5 mol/L.

Preferably, the sulfuric acid is added to the solution or suspension of the free base in molar excess, in particular in order to form a sulfate salt.

Preferably, in the process according to the invention, step (a-1) is carried out at a temperature below or at the boiling point of the respective solvent, preferably at a temperature not higher than 100° C., more preferably not higher than 80° C., even more preferably not higher than 60° C., and in particular in a temperature range of 20-40° C.

Preferably, in the process according to the invention, the suspension or solution obtained in step (a-1) is stirred for a time period of at least 1 minute, preferably at least 2 minutes, more preferably at least 3 minutes, still more preferably at least 5 minutes, yet more preferably at least 10 minutes, most preferably at least 20 minutes, and in particular at least 30 minutes.

In a preferred embodiment, the suspension or solution obtained in step (a-1) is stirred for a time period of at least 1 hour, preferably at least 4 hours, more preferably at least 6 hours, still more preferably at least 12 hours, yet more preferably at least 18 hours, most preferably at least 1 day, and in particular at least 2 days.

In another preferred embodiment, the suspension or solution obtained in step (a-1) is stirred for a time period of at most 1 day, preferably at most 12 hours, more preferably at most 6 hours, still more preferably at most 2 hours, yet more preferably at most 60 minutes, and most preferably at most 45 minutes, and in particular at most 30 minutes.

Preferably, the process according to the invention further comprises the step (b-1) separating, preferably filtering off the solid obtained in step (a-1).

Preferably, the process according to the invention further comprises the step (c-1) drying of the solid obtained in step (b-1).

In a preferred embodiment, step (c-1) takes place under air, nitrogen flow or argon flow.

In another preferred embodiment, step (c-1) takes place under vacuum, more preferably at a vacuum of 0 to 900 mbar, even more preferably at a vacuum of 1 to 500 mbar, and in particular at a vacuum of 10 to 200 mbar.

Preferably, in the process according to the invention, step (c-1) takes place in a temperature range from 0 to 60° C., preferably from 10° C. to 50° C. more preferably from 20 to 40° C.

In another preferred embodiment, the process comprises the step of (a-2) dissolving (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate in a solvent.

Conventional solvents known to persons skilled in the art may be used as solvents in a solution of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof.

Preferably, in the process according to the invention, step (a-2) is carried out at a temperature below or at the boiling point of the respective solvent or solvent mixture, more preferably at a temperature not higher than 100° C., more preferably not higher than 80° C., even more preferably not higher than 60° C., and in particular in a temperature range of 20-40° C.

In a preferred embodiment, the process according to the invention further comprises the step
(b-2) evaporating the solvent of the solution obtained in step (a-2).

Suitable methods for evaporating the solvent are known to persons skilled in the art. Preferably, in the process according to the invention, the solvent is evaporated in air, air flow, or inert gas flow, in particular argon or nitrogen flow. However, evaporating the solvent under vacuum, for example by means of a rotary evaporator, is also possible. Preferably, in the process according to the invention, the solvent is evaporated at room temperature.

In another preferred embodiment, the process further comprises the step of
(b-2') precipitating (1r,4r)-6'-fluoro-N,N-dimethyl-4-phenyl-4',9'-dihydro-3'H-spiro[cyclo-hexane-1,1'-pyrano[3,4,b]indol]-4-amine sulfate or hemi-sulfate from the solution obtained in step (a-2), preferably by addition of a precipitant.

Suitable methods of precipitation are known to persons skilled in the art. In the process according to the invention, step (b-2') may be carried out by reducing the volume of the solution obtained in step (a-2) and/or by cooling of the solution, preferably to a temperature of at most 15° C., more preferably at most 10° C., even more preferably at most 4-8° C. and/or by cooling of the solution, preferably to a temperature of at least 10° C., more preferably at least 30° C., even more preferably at least 60° C. below the temperature according to step (a-2).

In a preferred embodiment, step (b-2') is carried out by the addition of a medium in which (1r,4r)-6'-fluoro-N,N-dimethyl-4-phenyl-4',9'-dihydro-3' H-spiro[cyclohexane-1,1'-pyrano-[3,4,b]indol]-4-amine sulfate or hemi-sulfate is only poorly soluble ("anti-solvent") to the solution obtained in step (a-2). Said medium is preferably selected from the group consisting of esters such as ethyl acetate, n-propyl acetate, iso-propyl acetate, n-butyl acetate and iso-butyl acetate; alcohols such as methanol, ethanol, 1-propanol, 2-propanol; ethers such as tert-butyl methyl ether, diethyl ether and diisopropyl ether; ketones such as acetone, 2-butanone, pentan-2-one, pentan-3-one, hexan-2-one and hexan-3-one; nitriles such as acetonitril; pyridine, acetic acid and water, and DMSO.

The amount of the media in which (1r,4r)-6'-fluoro-N,N-dimethyl-4-phenyl-4',9'-dihydro-3'H-spiro[cyclohexane-1, 1'-pyrano[3,4,b]indol]-4-amine sulfate or hemi-sulfate is only poorly soluble, the precipitant or anti-solvent, is preferably selected in such a manner that upon its addition precipitation of the dissolved component begins. The total amount of the media in which (1r,40-6'-fluoro-N,N-dimethyl-4-phenyl-4',9'-dihydro-3'H-spiro[cyclohexane-1,1'-pyrano[3,4,b]indol]-4-amine sulfate or hemi-sulfate is only poorly soluble may also be divided into several portions, preferably two or three portions. In this embodiment, the precipitation of the dissolved component preferably begins after the addition of the last portion.

The precipitation of the dissolved component preferably begins either immediately after the precipitant, preferably the total amount of the precipitant, has been added or alternatively with a delay of 2 seconds to 120 minutes. Preferably, the precipitation of the dissolved component begins within a time period of at most 90 minutes, more preferably at most 60 minutes, still more preferably at most 30 minutes, even more preferably at most 5 minutes, most preferably at most 60 seconds and in particular at most 10 seconds.

Furthermore, the amount of the media in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate, is only poorly soluble, the precipitant or anti-solvent, is preferably selected in such a manner that the dissolved component is completely precipitated or at least up to 90% of the initial amount is precipitated within a time period of at most 90 minutes, more preferably at most 80 minutes, still more preferably at most 70 minutes, and most preferably at most 60 minutes after the anti-solvent has been completely added.

Step (b-2') may also be carried out by exposing the solution obtained in step (a-2) to an atmosphere containing a solvent, in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate is only poorly soluble, i.e. by a vapor diffusion crystallization technique.

Preferably, in the process according to the invention, after step (b-2) or respectively (b-2'), all other steps are carried out at a temperature between 40 and 0° C., preferably between 35 and 5° C., more preferably between 25 and 15° C.

Preferably, in the process according to the invention, the suspension obtained in step
(b-2') is stirred for a time period of at least 1 minute, preferably at least 2 minutes, more preferably at least 3 minutes, and most preferably at least 5 minutes.

Preferably, the process according to the invention further comprises the step
(c-2') separating, preferably filtering off the precipitate obtained in step (b-2').

Preferably, the process according to the invention further comprises the step
(d-2') drying of the solid obtained in step (c-2').

Preferably, in the process according to the invention, step (d-2') takes place under air or inert gas flow, such as argon or nitrogen flow.

In still another preferred embodiment, the process comprises the step of
(a-3) suspending (1r,4r)-6'-fluoro-N,N-dimethyl-4-phenyl-4',9'-dihydro-3' H-spiro[cyclo-hexane-1,1'-pyrano[3,4,b]indol]-4-amine sulfate or hemi-sulfate in a solvent.

Conventional solvents known to persons skilled in the art may be used as solvents in a suspension of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof. Preferred solvents are alcohols such as methanol or water, particularly preferred alcohols such as methanol. The most preferred solvent is an alcohol, preferably methanol.

In a preferred embodiment, step (a-3) is carried out at a temperature below or at the boiling point of the respective solvent, preferably at a temperature not higher than 100° C., more preferably not higher than 90° C., still more preferably not higher than 80° C., yet more preferably not higher than 60° C., most preferably not higher than 40° C., and in particular in a temperature range of 15-35° C.

In another preferred embodiment, step (a-3) is carried out in a temperature range of 100-40° C., more preferably 90-50° C., and most preferably 85-60° C.

Preferably, in the process according to the invention, the suspension obtained in step (a-3) is stirred for a time period of at least 2 h, preferably at least 4 h, more preferably at least 8 h, still more preferably at least 12 h, yet more preferably at least 16 h, most preferably at least 24 h, and in particular at least 2 days.

Preferably, the process according to the invention further comprises the step
(b-3) separating, preferably filtering off the solid obtained in step (a-3).

Preferably, the process according to the invention further comprises the step
(c-3) drying of the solid obtained in step (b-3).

In the process according to the invention, step (c-3) may take place under air or inert gas flow, such as argon or nitrogen flow. However, drying under vacuum, more preferably at a vacuum of 0 to 900 mbar, even more preferably at a vacuum of 1 to 500 mbar, and in particular at a vacuum of 10 to 200 mbar is preferred.

Preferably, in the process according to the invention, step (c-3) takes place in a temperature range from 0 to 60° C., preferably from 10° C. to 50° C. more preferably from 20 to 40° C.

In still another preferred embodiment, the process comprises the step of
(a-4) reacting 2-(5-fluoro-1H-indol-3-yl)ethanol and 4-(dimethylamino)-4-phenylcyclohexanone or a protected derivative thereof, optionally in the form of an acid addition salt, in a carbonic acid as reaction medium in the presence of sulfuric acid to form (1r,4r)-6'-fluoro-N,N-dimethyl-4-phenyl-4',9'-dihydro-3'H-spiro[cyclohexane-1,1'-pyrano-[3,4,b]indol]-4-amine sulphate or hemi-sulfate.

Any suitable carbonic acid can serve as reaction medium in step (a-4) according to the present invention. The reaction medium preferably serves as solvent for the starting material employed, i.e. for the compounds 2-(5-fluoro-1H-indol-3-yl) ethanol and 4-(dimethylamino)-4-phenylcyclohexanone or a protected derivative thereof, preferably also as a solvent for sulfuric acid. Preferably, the carbonic acid employed as reaction medium in step (a-4) according to the present invention is in liquid form at room temperature. Preferably, the carbonic acid employed as reaction medium in step (a-4) is selected from the group consisting of acetic acid, trifluoroacetic acid, propionic acid, lactic acid, 3-hydroxypropionic acid, butyric acid, isobutyric acid, acrylic acid and methacrylic acid or mixtures thereof. Preferably, the carbonic acid employed as reaction medium in step (a) is selected from the group consisting of acetic acid, trifluoroacetic acid, and propionic acid or mixtures thereof. Particularly preferred are acetic acid and propionic acid. Most preferred is acetic acid. In one particularly preferred embodiment of the present invention, the carbonic acid employed as reaction medium in step (a-4) is acetic acid. In another particularly preferred embodiment of the present invention, the carbonic acid employed as reaction medium in step (a-4) is propionic acid. Preferably, the carbonic acid as reaction medium is employed in step (a-4) in an amount by weight that is in the range of from 5 to 60 times higher than the total amount of 4-(dimethylamino)-4-phenylcyclohexanone or a protected derivative thereof by weight. For example, in case 400 mg of 4-(dimethylamino)-4-phenylcyclohexanone or a protected derivative thereof is employed, the carbonic acid as reaction medium is employed in an amount by weight, that is in the range of from 2 g to 24 g. More preferably, the carbonic acid as reaction medium is employed in step (a-4) in an amount by weight that is in the range of from 7 to 50 times, even more preferably 10 to 45 times, still more preferably 12 to 40 times, in particular 15 to 35 times, and most preferred 20 to 30 times higher than the total amount of 4-(dimethylamino)-4-phenylcyclohexanone or a protected derivative thereof by weight.

Preferably, sulfuric acid as promoting agent is employed in step (a-4) in an amount that is in the range of from 1.05 to 2.00 equivalents, preferably of from 1.10 to 1.90 equivalents, more preferably of from 1.10 to 1.70 equivalents, even more preferably of from 1.10 to 1.50 equivalents, still more preferably of from 1.10 to 1.40 equivalents, in particular of from 1.10 to 1.30 equivalents, in each case with respect to the molar amount of either 2-(5-fluoro-1H-indol-3-yl)ethanol or 4-(dimethylamino)-4-phenylcyclohexanone or a protected derivative thereof. Preferably, sulfuric acid employed in step (a-4) according to the inventive process is soluble, preferably soluble at room temperature, in the reaction medium employed in step (a-4).

The reaction time of step (a-4) can vary in dependence on various parameters, such as, for example, temperature, stoichiometry, nature of the compound to be reacted with, or the nature of the reaction medium, and can be determined for the process in question by the person skilled in the art using preliminary tests. Preferably, the reaction time for performing step (a) does not exceed 24 h, more preferably does not exceed 18 h. Even more preferably, the reaction time is in the range of from 1 h to 20 h, still more preferably is in the range of from 2 h to 18, in particular is in the range of from 3 h to 16 h, most preferred is in the range of from 4 h to 10 h.

Preferably, the reaction mixture is stirred in step (a-4).

The reaction temperature at which step (a-4) is performed can vary in dependence on various parameters, such as, for example, reaction time, stoichiometry, nature of the compound to be reacted with, or nature of the reaction medium and can be determined for the process in question by the person skilled in the art using preliminary tests. Preferably, the reaction temperature at which step (a-4) of the inventive process is performed, is in the range of from 20° C. to 100° C., more preferably is in the range of from 30° C. to 90° C., even more preferably is in the range of from 40° C. to 80° C., still more preferably in the range of from 40° C. to 60° C. In another preferred embodiment of the present invention, the reaction temperature at which step (a-4) of the inventive process is performed is at least 30° C., preferably at least 40° C., more preferably at least 50° C.

In a particularly preferred embodiment
sulfuric acid is employed in step (a-4) in an amount that is in the range of from 1.10 to 1.30 equivalents with respect to the molar amount of 2-(5-fluoro-1H-indol-3-yl)ethanol or 4-(dimethylamino)-4-phenylcyclohexanone or a protected derivative thereof, and
the at least one carbonic acid as reaction medium employed in step (a) is acetic acid or propionic acid, preferably in an amount by weight that is in the range of from 5 to 60 times higher than the total amount of 4-(dimethylamino)-4-phenylcyclohexanone or a protected derivative thereof by weight.

In a very particularly preferred embodiment
sulfuric acid is employed in step (a-4) in an amount that is in the range of from 1.10 to 1.30 equivalents with respect to the molar amount of 2-(5-fluoro-1H-indol-3-yl)ethanol or 4-(dimethylamino)-4-phenylcyclohexanone or a protected derivative thereof,
the at least one carbonic acid as reaction medium employed in step (a) is acetic acid or propionic acid, preferably in an amount by weight that is in the range of from 5 to 60 times higher than the total amount of 4-(dimethylamino)-4-phenylcyclohexanone or a protected derivative thereof by weight,
the reaction temperature at which step (a) is performed is in the range of from 40° C. to 80° C., preferably in the range of from 40° C. to 60° C., and
the reaction time of step (a) is in the range of from 3 hours to 16 hours.

Preferably, the solid form of the compound according to formula (I) and sulfuric acid precipitates from the reaction mixture during the performance of step (a-4) and can be thus obtained from step (a-4) as a precipitate, preferably by filtration of the reaction mixture, i.e. by separating, preferably filtering off the precipitate.

Thus, preferably, the process according to the invention further comprises the step
(b-4) separating, preferably filtering off the solid obtained in step (a-4).

The solid obtained from step (b-4) can be optionally purified, e.g. by
(c-4) optionally performing steps (a-2) and (b-2) or (b-2') or performing steps (a-3) and (b-3).

The solid obtained from step (b-4) can be optionally further recrystallized in a manner well known to those skilled in the art, e.g. by recrystallization from a suitable solvent. Alternatively, the solid obtained can also be subjected to a chromatographic resolution.

Suitable solvents can be determined by the person skilled in the art using preliminary tests and include solvents such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; and also N-methyl-2-pyrrolidone, dimethyl acetamide, dimethyl formamide and dimethyl sulfoxide (DMSO); carbonic acids such as acetic acid and propionic acid, and mixtures thereof. Particularly preferred are acetic acid, mixtures of DMSO and acetic acid, mixtures of THF and DMSO, and mixtures of acetic acid and dimethyl acetamide. Recrystallization techniques well known to those skilled in the art e.g. include first dissolving the acid addition salt obtained from step (a) in a suitable solvent, optionally heating the mixture, followed by a precipitation of said acid addition salt, preferably by addition of another medium, or followed by evaporation off the solvent employed for dissolution.

Particularly preferred is a process comprising steps (a-3) and (b-3) or steps (a-4) and (b-4) for the preparation of crystalline form B, especially preferred is such a process comprising steps (a-3) and (b-3).

A further aspect of the invention relates to a crystalline form B that is obtainable by the process as described above.

A further aspect of the present invention relates to a crystalline form C. Preferably, crystalline form C of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid is a (1r,4r)-6'-fluoro-N,N-dimethyl-4-phenyl-4',9'-dihydro-3'H-spiro[cyclohexane-1,1'-pyrano[3,4,b]indol]-4-amine sulfate, preferably a solvate, more preferably a N-methylpyrrolidone (NMP) solvate thereof.

The crystalline form C according to the present invention may be characterized in that it has one or more Raman bands selected from the group consisting of $917\pm2$ cm$^{-1}$, $1002\pm2$ cm$^{-1}$, $1573\pm2$ cm$^{-1}$, and $1588\pm2$ cm$^{-1}$.

The crystalline form C according to the present invention may further be characterized in that it has one or more Raman bands selected from the group consisting of $917\pm2$ cm$^{-1}$, $1002\pm2$ cm$^{-1}$, $1573\pm2$ cm$^{-1}$, and $1588\pm2$ cm$^{-1}$; and/or one or more additional Raman bands selected from the group consisting of $156\pm2$ cm$^{-1}$, $1463\pm2$ cm$^{-1}$, $2927\pm2$ cm$^{-1}$, $2948\pm2$ cm$^{-1}$, $2951\pm2$ cm$^{-1}$, $2971\pm2$ cm$^{-1}$, $3056\pm2$ cm$^{-1}$ and $3068\pm2$ cm$^{-1}$.

The crystalline form C according to the present invention may further be characterized in that it has one or more Raman bands selected from the group consisting of $917\pm2$ cm$^{-1}$, $1002\pm2$ cm$^{-1}$, $1573\pm2$ cm$^{-1}$, $1588\pm2$ cm$^{-1}$, $156\pm2$ cm$^{-1}$, $1463\pm2$ cm$^{-1}$, $2927\pm2$ cm$^{-1}$, $2948\pm2$ cm$^{-1}$, $2951\pm2$ cm$^{-1}$, $2971\pm2$ cm$^{-1}$, $3056\pm2$ cm$^{-1}$ and $3068\pm2$ cm$^{-1}$.

The crystalline form C according to the present invention may further be characterized in that it has one or more additional Raman bands selected from the group consisting of $178\pm2$ cm$^{-1}$, $205\pm2$ cm$^{-1}$, $276\pm2$ cm$^{-1}$, $370\pm2$ cm$^{-1}$, $491\pm2$ cm$^{-1}$, $598\pm2$ cm$^{-1}$, $1026\pm2$ cm$^{-1}$, $1045\pm2$ cm$^{-1}$, $1218\pm2$ cm$^{-1}$, $1308\pm2$ cm$^{-1}$, $1369\pm2$ cm$^{-1}$, $1444\pm2$ cm$^{-1}$, $1476\pm2$ cm$^{-1}$, $1488\pm2$ cm$^{-1}$, $2903\pm2$ cm$^{-1}$, $2992\pm2$ cm$^{-1}$ and $3030\pm2$ cm$^{-1}$.

The crystalline form C according to the present invention may further be characterized in that it has one or more additional Raman bands selected from the group consisting of $392\pm2$ cm$^{-1}$, $409\pm2$ cm$^{-1}$, $437\pm2$ cm$^{-1}$, $461\pm2$ cm$^{-1}$, $471\pm2$ cm$^{-1}$, $517\pm2$ cm$^{-1}$, $538\pm2$ cm$^{-1}$, $621\pm2$ cm$^{-1}$, $681\pm2$ cm$^{-1}$, $702\pm2$ cm$^{-1}$, $787\pm2$ cm$^{-1}$, $825\pm2$ cm$^{-1}$, $889\pm2$ cm$^{-1}$, $983\pm2$ cm$^{-1}$, $1118\pm2$ cm$^{-1}$, $1131\pm2$ cm$^{-1}$, $1169\pm2$ cm$^{-1}$, $1202\pm2$ cm$^{-1}$, $1232\pm2$ cm$^{-1}$, $1629\pm2$ cm$^{-1}$ and $3034\pm2$ cm$^{-1}$.

Another aspect of the present invention relates to a process for the production of the crystalline form C as described above.

In a preferred embodiment, the process comprises the step of
(a-1) precipitating the sulfate or hemi-sulfate salt of (1r,4r)-6'-fluoro-N,N-dimethyl-4-phenyl-4',9'-dihydro-3'H-spiro[cyclohexane-1,1'-pyrano[3,4,b]indol]-4-amine from a solution or suspension of the free base.

Conventional solvents known to persons skilled in the art may be used as solvents in a solution or suspension, preferably a solution, of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof. Preferred solvents are THF, DMSO, NMP, acetic acid, mixtures of acetic acid and dimethyl acetamide, mixtures of acetone and THF, mixtures of DMSO and acetic acid, and mixtures of THF and DMSO.

Step (a-1) may be carried out by the addition of sulfuric acid. In a preferred embodiment, sulfuric acid is added in form of a solution. In one preferred embodiment, the solution is a solution of sulfuric acid in an aqueous solvent, i.e. an aqueous solution of sulfuric acid. In another preferred embodiment, the solution is a solution of sulfuric acid in an organic solvent, especially preferred are alcohols such as ethanol, isopropanol and n-butanol, and ethers such as diethylether, di-isopropylether, tetrahydrofurane, methyl-tetrahydrofurane 1,4-dioxane or carbonic acids such as acetic acid and propionic acid.

In one preferred embodiment, the sulfuric acid containing solution and the solution of the free base contain the same solvent.

In another particularly preferred embodiment, the sulfuric acid containing solution and the solution of the free base contain not the same solvent.

In a particularly preferred embodiment containing solution is an aqueous solution and the solution of the free base is an organic solvent, in which the free base is dissolved.

Preferably, the solution contains sulfuric acid in a concentration within the range of from 0.01 mol/L to 15 mol/L, more preferably within the range of from 0.02 mol/L to 12.5 mol/L, still more preferably within the range of from 0.05 mol/L to 10 mol/L, yet more preferably within the range of from 0.1 mol/L to 7.5 mol/L, most preferably within the range of from 0.2 mol/L to 10 mol/L, and in particular within the range of from 0.3 mol/L to 5 mol/L. Preferably, the sulfuric acid is added to the solution or suspension of the free base in molar excess, in particular in order to form a sulfate salt.

In another preferred embodiment, the sulfuric acid is added to the solution or suspension of the free base in lower molar amount than the molar amount of the free base, in particular in order to form a hemi-sulfate salt.

Preferably, in the process according to the invention, step (a-1) is carried out at a temperature below or at the boiling point of the respective solvent, preferably at a temperature not higher than 100° C., more preferably not higher than 80° C., even more preferably not higher than 60° C., and in particular in a temperature range of 20-40° C.

Preferably, in the process according to the invention, the suspension or solution obtained in step (a-1) is stirred for a time period of at least 1 minute, preferably at least 2 minutes, more preferably at least 3 minutes, still more preferably at least 5 minutes, yet more preferably at least 10 minutes, most preferably at least 20 minutes, and in particular at least 30 minutes.

In a preferred embodiment, the suspension or solution obtained in step (a-1) is stirred for a time period of at least 1 hour, preferably at least 4 hours, more preferably at least 6 hours, still more preferably at least 12 hours, yet more preferably at least 18 hours, most preferably at least 1 day, and in particular at least 2 days.

In another preferred embodiment, the suspension or solution obtained in step (a-1) is stirred for a time period of at most 1 day, preferably at most 12 hours, more preferably at most 6 hours, still more preferably at most 2 hours, yet more preferably at most 60 minutes, and most preferably at most 45 minutes, and in particular at most 30 minutes.

Preferably, the process according to the invention further comprises the step
(b-1) separating, preferably filtering off the solid obtained in step (a-1).

Preferably, the process according to the invention further comprises the step
(c-1) drying of the solid obtained in step (b-1).

In a preferred embodiment, step (c-1) takes place under air, nitrogen flow or argon flow.

In another preferred embodiment, step (c-1) takes place under vacuum, more preferably at a vacuum of 0 to 900 mbar, even more preferably at a vacuum of 1 to 500 mbar, and in particular at a vacuum of 10 to 200 mbar.

Preferably, in the process according to the invention, step (c-1) takes place in a temperature range from 0 to 60° C., preferably from 10° C. to 50° C. more preferably from 20 to 40° C.

In another preferred embodiment, the process comprises the step of
(a-2) dissolving (1r,4r)-6'-fluoro-N,N-dimethyl-4-phenyl-4',9'-dihydro-3'H-spiro[cyclohexane-1,1'-pyrano[3,4,b]indol]-4-amine sulphate or hemi-sulfate in a solvent.

Conventional solvents known to persons skilled in the art may be used as solvents in a solution of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof. Preferred solvents are THF, acetic acid, NMP, DMSO, mixtures of THF and DMSO, mixtures of DMSO and acetic acid, and mixtures of acetic acid and dimethyl acetamide (DMAc). Particularly preferred is NMP.

Preferably, in the process according to the invention, step (a-2) is carried out at a temperature below or at the boiling point of the respective solvent or solvent mixture, more preferably at a temperature not higher than 100° C., more preferably not higher than 80° C., even more preferably not higher than 60° C., and in particular in a temperature range of 20-40° C.

In a preferred embodiment, the process according to the invention further comprises the step
(b-2) evaporating the solvent of the solution obtained in step (a-2).

Suitable methods for evaporating the solvent are known to persons skilled in the art. Preferably, in the process according to the invention, the solvent is evaporated in air, air flow, or inert gas flow, in particular argon or nitrogen flow. However, evaporating the solvent under vacuum, for example by means of a rotary evaporator, is also possible. Preferably, in the process according to the invention, the solvent is evaporated at room temperature.

In another preferred embodiment, the process further comprises the step of
(b-2') precipitating (1r,4r)-6'-fluoro-N,N-dimethyl-4-phenyl-4',9'-dihydro-3'H-spiro[cyclo-hexane-1,1'-pyrano[3,4,b]indol]-4-amine sulfate or hemi-sulfate from the solution obtained in step (a-2), preferably by addition of a precipitant, Suitable methods of precipitation are known to persons skilled in the art. In the process according to the invention, step (b-2') may be carried out by reducing the volume of the solution obtained in step (a-2) and/or by cooling of the solution, preferably to a temperature of at most 15° C., more preferably at most 10° C., even more preferably at most 4-8° C. and/or by cooling of the solution, preferably to a temperature of at least 10° C., more preferably at least 30° C., even more preferably at least 60° C. below the temperature according to step (a-2).

In a preferred embodiment, step (b-2') is carried out by the addition of a medium in which (1r,4r)-6'-fluoro-N,N-dimethyl-4-phenyl-4',9'-dihydro-3'H-spiro[cyclohexane-1,1'-pyrano-[3,4,b]indol]-4-amine sulfate or hemi-sulfate is only poorly soluble ("anti-solvent") to the solution obtained in step (a-2). Said medium is preferably selected from the group consisting of esters such as ethyl acetate, n-propyl acetate, iso-propyl acetate, n-butyl acetate and iso-butyl acetate; alcohols such as methanol, ethanol, 1-propanol, 2-propanol; ethers such as tert-butyl methyl ether, diethyl ether and diisopropyl ether; ketones such as acetone, 2-butanone, pentan-2-one, pentan-3-one, hexan-2-one and hexan-3-one; nitriles such as acetonitril; pyridine, acetic acid and water, and DMSO. Particularly preferred are DMSO, 2-butanone (MEK), 2-propanol, and water; especially preferred are 2-butanone (MEK) and 2-propanol.

The amount of the media in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate is only poorly soluble, the precipitant or anti-solvent, is preferably selected in such a manner that upon its addition precipitation of the dissolved component begins.

The total amount of the media in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate is only poorly soluble may also be divided into several portions, preferably two or three portions. In this embodiment, the precipitation of the dissolved component preferably begins after the addition of the last portion.

The precipitation of the dissolved component preferably begins either immediately after the precipitant, preferably the total amount of the precipitant, has been added or alternatively with a delay of 2 seconds to 120 minutes. Preferably, the precipitation of the dissolved component begins within a time period of at most 90 minutes, more preferably at most 60 minutes, still more preferably at most 30 minutes, even more preferably at most 5 minutes, most preferably at most 60 seconds and in particular at most 10 seconds.

Furthermore, the amount of the media in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate, is only poorly soluble, the precipitant or anti-solvent, is preferably selected in such a manner that the dissolved component is completely precipitated or at least up to 90% of the initial amount is precipitated within a time period of at most 90 minutes, more preferably at most 80 minutes, still more preferably at most 70 minutes, and most preferably at most 60 minutes after the anti-solvent has been completely added.

Step (b-2') may also be carried out by exposing the solution obtained in step (a-2) to an atmosphere containing a solvent, in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate is only poorly soluble, i.e. by a vapor diffusion crystallization technique.

In this embodiment, dichloromethane is preferably selected as solvent in step (a-2) and the solution obtained in step (a-2) is preferably exposed to an atmosphere containing hexane.

Preferably, in the process according to the invention, after step (b-2) or respectively (b-2'), all other steps are carried out at a temperature between 40 and 0° C., preferably between 35 and 5° C., more preferably between 25 and 15° C.

Preferably, in the process according to the invention, the suspension obtained in step
(b-2') is stirred for a time period of at least 1 minute, preferably at least 2 minutes, more preferably at least 3 minutes, and most preferably at least 5 minutes.

Preferably, the process according to the invention further comprises the step
(c-2') separating, preferably filtering off the precipitate obtained in step (b-2').

Preferably, the process according to the invention further comprises the step
(d-2') drying of the solid obtained in step (c-2').

Preferably, in the process according to the invention, step (d-2') takes place under air or inert gas flow, such as argon or nitrogen flow. However, depending on the crystalline form to be obtained evaporating the solvent at an elevated temperature, e.g. within the range of from 20° C. to 60° C., is also possible.

In still another preferred embodiment, the process comprises the step of
(a-3) suspending (1r,4r)-6'-fluoro-N,N-dimethyl-4-phenyl-4',9'-dihydro-3'H-spiro[cyclo-hexane-1,1'-pyrano[3,4,b]indol]-4-amine sulfate or hemi-sulfate in a solvent.

Conventional solvents known to persons skilled in the art may be used as solvents in a suspension of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof.

In one preferred embodiment, step (a-3) is carried out at a temperature below or at the boiling point of the respective solvent, preferably at a temperature not higher than 100° C., more preferably not higher than 90° C., still more preferably not higher than 80° C., yet more preferably not higher than 60° C., most preferably not higher than 40° C., and in particular in a temperature range of 15-35° C.

In another preferred embodiment, step (a-3) is carried out in a temperature range of 100-40° C., more preferably 90-50° C., and most preferably 85-60° C.

Preferably, in the process according to the invention, the suspension obtained in step
(a-3) is stirred for a time period of at least 2 h, preferably at least 4 h, more preferably at least 8 h, still more preferably at least 12 h, yet more preferably at least 16 h, most preferably at least 24 h, and in particular at least 2 days.

Preferably, the process according to the invention further comprises the step
(b-3) separating, preferably filtering off the solid obtained in step (a-3).

Preferably, the process according to the invention further comprises the step
(c-3) drying of the solid obtained in step (b-3).

In the process according to the invention, step (c-3) may take place under air or inert gas flow, such as argon or nitrogen flow. However, drying under vacuum, more preferably at a vacuum of 0 to 900 mbar, even more preferably at a vacuum of 1 to 500 mbar, and in particular at a vacuum of 10 to 200 mbar is preferred.

Preferably, in the process according to the invention, step (c-3) takes place in a temperature range from 0 to 60° C., preferably from 10° C. to 50° C. more preferably from 20 to 40° C.

Particularly preferred is a process comprising steps (a-2) and (b-2) or (b-2') for the preparation of crystalline form C.

A further aspect of the invention relates to a crystalline form C that is obtainable by the process as described above.

A further aspect of the present invention relates to a crystalline form D. Preferably, crystalline form D of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid is a (1r,4r)-6'-fluoro-N,N-dimethyl-4-phenyl-4',9'-dihydro-3'H-spiro[cyclohexane-1,1'-pyrano[3,4,b]indol]-4-amine sulfate, preferably a solvate thereof, more preferably a solvate of (1r,4r)-6'-fluoro-N,N-dimethyl-4-phenyl-4',9'-dihydro-3'H-spiro[cyclohexane-1,1'-pyrano[3,4,b]indol]-4-amine sulfate containing DMSO and water.

The crystalline form D according to the present invention may be characterized in that it has one or more Raman bands selected from the group consisting of 918±2 cm$^{-1}$, 1004±2 cm$^{-1}$, 1567±2 cm$^{-1}$, 1581±2 cm$^{-1}$ and 2977±2 cm$^{-1}$.

The crystalline form D according to the present invention may further be characterized in that it has one or more Raman bands selected from the group consisting of 918±2 cm$^{-1}$, 1004±2 cm$^{-1}$, 1567±2 cm$^{-1}$, 1581±2 cm$^{-1}$ and 2977±2 cm$^{-1}$; and/or one or more additional Raman bands selected from the group consisting of 155±2 cm$^{-1}$, 172±2 cm$^{-1}$, 966±2 cm$^{-1}$, 1310±2 cm$^{-1}$, 2990±2 cm$^{-1}$, 3057±2 cm$^{-1}$, and 3067±2 cm$^{-1}$.

The crystalline form D according to the present invention may further be characterized in that it has one or more Raman bands selected from the group consisting of 918±2 cm$^{-1}$, 1004±2 cm$^{-1}$, 1567±2 cm$^{-1}$, 1581±2 cm$^{-1}$, 2977±2 cm$^{-1}$, 155±2 cm$^{-1}$, 172±2 cm$^{-1}$, 966±2 cm$^{-1}$, 1310±2 cm$^{-1}$, 2990±2 cm$^{-1}$, 3057±2 cm$^{-1}$, and 3067±2 cm$^{-1}$.

The crystalline form D according to the present invention may further be characterized in that it has one or more additional Raman bands selected from the group consisting of 369±2 cm$^{-1}$, 392±2 cm$^{-1}$, 427±2 cm$^{-1}$, 491±2 cm$^{-1}$, 600±2 cm$^{-1}$, 619±2 cm$^{-1}$, 680±2 cm$^{-1}$, 691±2 cm$^{-1}$, 829±2 cm$^{-1}$, 982±2 cm$^{-1}$, 1047±2 cm$^{-1}$, 1106±2 cm$^{-1}$, 1199±2 cm$^{-1}$, 1217±2 cm$^{-1}$, 1374±2 cm$^{-1}$, 1462±2 cm$^{-1}$, 1598±2 cm$^{-1}$, 1630±2 cm$^{-1}$, 2929±2 cm$^{-1}$, 2941±2 cm$^{-1}$, 2948±2 cm$^{-1}$, 3032±2 cm$^{-1}$, and 3080±2 cm$^{-1}$.

The crystalline form D according to the present invention may further be characterized in that it has one or more additional Raman bands selected from the group consisting of 183±2 cm$^{-1}$, 205±2 cm$^{-1}$, 261±2 cm$^{-1}$, 277±2 cm$^{-1}$, 288±2 cm$^{-1}$, 516±2 cm$^{-1}$, 714±2 cm$^{-1}$, 1118±2 cm$^{-1}$, 1264±2 cm$^{-1}$, 1343±2 cm$^{-1}$, 1476±2 cm$^{-1}$, and 2866±2 cm$^{-1}$.

Another aspect of the present invention relates to a process for the production of the crystalline form D as described above.

In a preferred embodiment, the process comprises the step of
(a-1) precipitating the sulfate or hemi-sulfate salt of (1r,4r)-6'-fluoro-N,N-dimethyl-4-phenyl-4',9'-dihydro-3'H-spiro[cyclohexane-1,1'-pyrano[3,4,b]indol]-4-amine from a solution or suspension of the free base.

Conventional solvents known to persons skilled in the art may be used as solvents in a solution or suspension, preferably a solution, of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof. Preferred solvents are THF, DMSO, NMP, acetic acid, mixtures of acetic acid and dimethyl acetamide, mixtures of acetone and THF, mixtures of DMSO and acetic acid, and mixtures of THF and DMSO.

Step (a-1) may be carried out by the addition of sulfuric acid. In a preferred embodiment, sulfuric acid is added in form of a solution. In one preferred embodiment, the solution is a solution of sulfuric acid in an aqueous solvent, i.e. an aqueous solution of sulfuric acid.

In another preferred embodiment, the solution is a solution of sulfuric acid in an organic solvent, especially preferred are alcohols such as ethanol, isopropanol and n-butanol, and ethers such as diethylether, di-isopropylether, tetrahydrofurane, methyl-tetrahydrofurane 1,4-dioxane or carbonic acids such as acetic acid and propionic acid.

In a preferred embodiment, the sulfuric acid containing solution and the solution of the free base contain the same solvent.

In another particularly preferred embodiment, the sulfuric acid containing solution and the solution of the free base contain not the same solvent.

In a particularly preferred embodiment containing solution is an aqueous solution and the solution of the free base is an organic solvent, in which the free base is dissolved.

Preferably, the solution contains sulfuric acid in a concentration within the range of from 0.01 mol/L to 15 mol/L, more preferably within the range of from 0.02 mol/L to 12.5 mol/L, still more preferably within the range of from 0.05 mol/L to 10 mol/L, yet more preferably within the range of from 0.1 mol/L to 7.5 mol/L, most preferably within the range of from 0.2 mol/L to 10 mol/L, and in particular within the range of from 0.3 mol/L to 5 mol/L. Preferably, the sulfuric acid is added to the solution or suspension of the free base in molar excess, in particular in order to form a sulfate salt.

In another preferred embodiment, the sulfuric acid is added to the solution or suspension of the free base in lower molar amount than the molar amount of the free base, in particular in order to form a hemi-sulfate salt.

Preferably, in the process according to the invention, step (a-1) is carried out at a temperature below or at the boiling point of the respective solvent, preferably at a temperature not higher than 100° C., more preferably not higher than 80° C., even more preferably not higher than 60° C., and in particular in a temperature range of 20-40° C.

Preferably, in the process according to the invention, the suspension or solution obtained in step (a-1) is stirred for a time period of at least 1 minute, preferably at least 2 minutes, more preferably at least 3 minutes, still more preferably at least 5 minutes, yet more preferably at least 10 minutes, most preferably at least 20 minutes, and in particular at least 30 minutes.

In a preferred embodiment, the suspension or solution obtained in step (a-1) is stirred for a time period of at least 1 hour, preferably at least 4 hours, more preferably at least 6 hours, still more preferably at least 12 hours, yet more preferably at least 18 hours, most preferably at least 1 day, and in particular at least 2 days.

In another preferred embodiment, the suspension or solution obtained in step (a-1) is stirred for a time period of at most 1 day, preferably at most 12 hours, more preferably at most 6 hours, still more preferably at most 2 hours, yet more preferably at most 60 minutes, and most preferably at most 45 minutes, and in particular at most 30 minutes.

Preferably, the process according to the invention further comprises the step
(b-1) separating, preferably filtering off the solid obtained in step (a-1).

Preferably, the process according to the invention further comprises the step
(c-1) drying of the solid obtained in step (b-1).

In a preferred embodiment, step (c-1) takes place under air, nitrogen flow or argon flow.

In another preferred embodiment, step (c-1) takes place under vacuum, more preferably at a vacuum of 0 to 900 mbar, even more preferably at a vacuum of 1 to 500 mbar, and in particular at a vacuum of 10 to 200 mbar.

Preferably, in the process according to the invention, step (c-1) takes place in a temperature range from 0 to 60° C., preferably from 10° C. to 50° C. more preferably from 20 to 40° C.

In another preferred embodiment, the process comprises the step of
(a-2) dissolving (1r,4r)-6'-fluoro-N,N-dimethyl-4-phenyl-4', 9'-dihydro-3'H-spiro[cyclohexane-1,1'-pyrano[3,4,b]indol]-4-amine sulfate or hemi-sulfate in a solvent.

Conventional solvents known to persons skilled in the art may be used as solvents in a solution of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof. Preferred solvents are THF, acetic acid, NMP, DMSO, mixtures of THF and DMSO, mixtures of DMSO and acetic acid, and mixtures of acetic acid and dimethyl acetamide (DMAc). Particularly preferred is DMSO.

Preferably, in the process according to the invention, step (a-2) is carried out at a temperature below or at the boiling point of the respective solvent or solvent mixture, more preferably at a temperature not higher than 100° C., more preferably not higher than 80° C., even more preferably not higher than 60° C., and in particular in a temperature range of 20-40° C.

In a preferred embodiment, the process according to the invention further comprises the step
(b-2) evaporating the solvent of the solution obtained in step (a-2).

Suitable methods for evaporating the solvent are known to persons skilled in the art. Preferably, in the process according to the invention, the solvent is evaporated in air, air flow, or inert gas flow, in particular argon or nitrogen flow. However, evaporating the solvent under vacuum, for example by means of a rotary evaporator, is also possible.

Preferably, in the process according to the invention, the solvent is evaporated at room temperature.

In another preferred embodiment, the process further comprises the step of
(b-2') precipitating (1r,4r)-6'-fluoro-N,N-dimethyl-4-phenyl-4',9'-dihydro-3'H-spiro[cyclo-hexane-1,1'-pyrano[3,4,b]indol]-4-amine sulphate or hemi-sulfate from the solution obtained in step (a-2), preferably by addition of a precipitant, Suitable methods of precipitation are known to persons skilled in the art. In the process according to the invention, step (b-2') may be carried out by reducing the volume of the solution obtained in step (a-2) and/or by cooling of the solution, preferably to a temperature of at most 15° C., more preferably at most 10° C., even more preferably at most 4-8° C. and/or by cooling of the solution, preferably to a temperature of at least 10° C., more preferably at least 30° C., even more preferably at least 60° C. below the temperature according to step (a-2).

In a preferred embodiment, step (b-2') is carried out by the addition of a medium in which (1r,4r)-6'-fluoro-N,N-dimethyl-4-phenyl-4',9'-dihydro-3' H-spiro[cyclohexane-1,1'-pyrano-[3,4,b]indol]-4-amine sulfate or hemi-sulfate is only poorly soluble ("anti-solvent") to the solution obtained in step (a-2). Said medium is preferably selected from the group consisting of esters such as ethyl acetate, n-propyl acetate, iso-propyl acetate, n-butyl acetate and iso-butyl acetate; alcohols such as methanol, ethanol, 1-propanol, 2-propanol; ethers such as tert-butyl methyl ether, diethyl ether and diisopropyl ether; ketones such as acetone, 2-butanone, pentan-2-one, pentan-3-one, hexan-2-one and hexan-3-one; nitriles such as acetonitril; pyridine, acetic acid and water, and DMSO. Particularly preferred are DMSO, 2-butanone (MEK), 2-propanol, and water; especially preferred are 2-butanone (MEK) and 2-propanol.

The amount of the media in which (1r,4r)-6'-fluoro-N,N-dimethyl-4-phenyl-4',9'-dihydro-3'H-spiro[cyclohexane-1, 1'-pyrano[3,4,b]indol]-4-amine sulfate or hemi-sulfate is only poorly soluble, the precipitant or anti-solvent, is preferably selected in such a manner that upon its addition precipitation of the dissolved component begins. The total amount of the media in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate is only poorly soluble may also be divided into several portions, preferably two or three portions. In this embodiment, the precipitation of the dissolved component preferably begins after the addition of the last portion.

The precipitation of the dissolved component preferably begins either immediately after the precipitant, preferably the total amount of the precipitant, has been added or alternatively with a delay of 2 seconds to 120 minutes. Preferably, the precipitation of the dissolved component begins within a time period of at most 90 minutes, more preferably at most 60 minutes, still more preferably at most 30 minutes, even more preferably at most 5 minutes, most preferably at most 60 seconds and in particular at most 10 seconds.

Furthermore, the amount of the media in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate, is only poorly soluble, the precipitant or anti-solvent, is preferably selected in such a manner that the dissolved component is completely precipitated or at least up to 90% of the initial amount is precipitated within a time period of at most 90 minutes, more preferably at most 80 minutes, still more preferably at most 70 minutes, and most preferably at most 60 minutes after the anti-solvent has been completely added.

Step (b-2') may also be carried out by exposing the solution obtained in step (a-2) to an atmosphere containing a solvent, in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate is only poorly soluble, i.e. by a vapor diffusion crystallization technique.

In this embodiment, dichloromethane is preferably selected as solvent in step (a-2) and the solution obtained in step (a-2) is preferably exposed to an atmosphere containing hexane.

Preferably, in the process according to the invention, after step (b-2) or respectively (b-2'), all other steps are carried out at a temperature between 40 and 0° C., preferably between 35 and 5° C., more preferably between 25 and 15° C.

Preferably, in the process according to the invention, the suspension obtained in step (b-2') is stirred for a time period of at least 1 minute, preferably at least 2 minutes, more preferably at least 3 minutes, and most preferably at least 5 minutes.

Preferably, the process according to the invention further comprises the step
(c-2') separating, preferably filtering off the precipitate obtained in step (b-2').

Preferably, the process according to the invention further comprises the step
(d-2') drying of the solid obtained in step (c-2').

Preferably, in the process according to the invention, step (d-2') takes place under air or inert gas flow, such as argon or nitrogen flow. However, depending on the crystalline form to be obtained evaporating the solvent at an elevated temperature, e.g. within the range of from 20° C. to 60° C., is also possible.

In still another preferred embodiment, the process comprises the step of
(a-3) suspending (1r,4r)-6'-fluoro-N,N-dimethyl-4-phenyl-4',9'-dihydro-3'H-spiro[cyclo-hexane-1,1'-pyrano[3,4,b]indol]-4-amine sulfate or hemi-sulfate in a solvent.

Conventional solvents known to persons skilled in the art may be used as solvents in a suspension of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof.

In one preferred embodiment, step (a-3) is carried out at a temperature below or at the boiling point of the respective solvent, preferably at a temperature not higher than 100° C., more preferably not higher than 90° C., still more preferably not higher than 80° C., yet more preferably not higher than 60° C., most preferably not higher than 40° C., and in particular in a temperature range of 15-35° C.

In another preferred embodiment, step (a-3) is carried out in a temperature range of 100-40° C., more preferably 90-50° C., and most preferably 85-60° C.

Preferably, in the process according to the invention, the suspension obtained in step (a-3) is stirred for a time period of at least 2 h, preferably at least 4 h, more preferably at least 8 h, still more preferably at least 12 h, yet more preferably at least 16 h, most preferably at least 24 h, and in particular at least 2 days.

Preferably, the process according to the invention further comprises the step
(b-3) separating, preferably filtering off the solid obtained in step (a-3).

Preferably, the process according to the invention further comprises the step
(c-3) drying of the solid obtained in step (b-3).

In the process according to the invention, step (c-3) may take place under air or inert gas flow, such as argon or nitrogen flow. However, drying under vacuum, more preferably at a vacuum of 0 to 900 mbar, even more preferably at a vacuum of 1 to 500 mbar, and in particular at a vacuum of 10 to 200 mbar is preferred.

Preferably, in the process according to the invention, step (c-3) takes place in a temperature range from 0 to 60° C., preferably from 10° C. to 50° C. more preferably from 20 to 40° C.

Particularly preferred is a process comprising steps (a-2) and (b-2) or (b-2') for the preparation of crystalline form D.

A further aspect of the invention relates to a crystalline form D that is obtainable by the process as described above.

A further aspect of the present invention relates to a crystalline form E. Preferably, crystalline form E of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid is a (1r,4r)-6'-fluoro-N,N-dimethyl-4-phenyl-4',9'-dihydro-3'H-spiro[cyclohexane-1,1'-pyrano[3,4,b]indol]-4-amine sulfate, preferably a solvate, more preferably a DMSO solvate thereof, in particular a solvate containing three molecules of DMSO, thereof.

Preferably, the crystalline form E according to the invention has one or more X-ray diffraction peaks selected from the group consisting of 10.6±1.0 (2Θ), 15.9±1.0 (2Θ), 17.2±1.0 (2Θ), 19.5±1.0 (2Θ), 20.3±1.0 (2Θ), and 22.1±1.0 (2Θ), in a preferred embodiment measured at 298 K±5 K, in another preferred embodiment measured at 100 K±5 K, in each case using CuKα radiation having a wavelength of 1.54060 Å. As indicated, the uncertainty in the 2θ values is ±1.0° in 2θ. Preferably, the uncertainty in the 2θ values is ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ.

In some preferred embodiments, the crystalline form E comprises X-ray diffraction peaks at 10.6±1.0 (2Θ), 15.9±1.0 (2Θ), 17.2±1.0 (2Θ), 19.5±1.0 (2Θ), 20.3±1.0 (2Θ), and 22.1±1.0 (2Θ). In some preferred embodiments, the crystalline form E comprises X-ray diffraction peaks at 10.6±1.0 (2Θ), 15.9±1.0 (2Θ), 17.2±1.0 (2Θ), 19.5±1.0 (2Θ), and 20.3±1.0 (2Θ). In some preferred embodiments, the crystalline form comprises X-ray diffraction peaks at 17.2±1.0 (2Θ), 19.5±1.0 (2Θ) and/or 20.3±1.0 (2Θ). In some preferred embodiments, the crystalline form comprises an X-ray diffraction peak at 20.3±1.0 (2Θ). As indicated, the uncertainty in the 2θ values is ±1.0° in 2θ. Preferably, the uncertainty in the 2θ values is ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ. In a preferred embodiment these X-ray diffraction peaks with respect to crystalline form E refer to a measurement at 298 K±5 K, in another preferred embodiment refer, with respect to crystalline form E, to a measurement at 100 K±5 K, in each case using CuKα radiation having a wavelength of 1.54060 Å.

In some preferred embodiments, crystalline form E comprises X-ray diffraction peaks at 10.6±1.0 (2Θ), 15.9±1.0 (2Θ), 17.2±1.0 (2Θ), 19.5±1.0 (2Θ), 20.3±1.0 (2Θ), and 22.1±1.0 (2Θ), and optionally at 13.7±1.0 (2Θ) and 19.8±1.0 (2Θ). As indicated, the uncertainty in the 2θ values is ±1.0° in 2θ. Preferably, the uncertainty in the 2θ values is ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ. In a preferred embodiment these X-ray diffraction peaks with respect to crystalline form E refer to a measurement at 298 K±5 K, in another preferred embodiment refer, with respect to crystalline form E, to a measurement at 100 K±5 K, in each case using CuKα radiation having a wavelength of 1.54060 Å.

The crystalline form E according to the invention may additionally have at least one X-ray diffraction peak selected from the group consisting of 17.8±1.0 (2Θ), 19.9±1.0 (2Θ), 20.6±1.0 (2Θ), 21.9±1.0 (2Θ), 25.6±1.0 (2Θ), and 29.3±1.0 (2Θ). As indicated, the uncertainty in the 2θ values is ±1.0° in 2θ. Preferably, the uncertainty in the 2θ values is ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ. In a preferred embodiment these X-ray diffraction peaks with respect to crystalline form E refer to a measurement at 298 K±5 K, in another preferred embodiment refer, with respect to crystalline form E, to a measurement at 100 K±5 K, in each case using CuKα radiation having a wavelength of 1.54060 Å.

Further, the crystalline form E according to the invention may be characterized in that as well as one or more X-ray diffraction peaks are selected from the group consisting of 10.6±1.0 (2Θ), 15.9±1.0 (2Θ), 17.2±1.0 (2Θ), 19.5±1.0 (2Θ), 20.3±1.0 (2Θ), and 22.1±1.0 (2Θ) and optionally one or more X-ray diffraction peaks selected from the group consisting of 13.7±1.0 (2Θ), 17.8±1.0 (2Θ), 19.8±1.0 (2Θ), 19.9±1.0 (2Θ), 20.6±1.0 (2Θ), 21.9±1.0 (2Θ), 25.6±1.0 (2Θ), and 29.3±1.0 (2Θ); it additionally may have at least one X-ray diffraction peak selected from the group consisting of 9.2±1.0 (2Θ), 12.1±1.0 (2Θ), 12.8±1.0 (2Θ), 17.4±1.0 (2Θ), 18.7±1.0 (2Θ), 22.0±1.0 (2Θ), 22.2±1.0 (2Θ) and 34.4±1.0 (2Θ). As indicated, the uncertainty in the 2θ values is ±1.0° in 2θ. Preferably, the uncertainty in the 2θ values is ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ. In a preferred embodiment these X-ray diffraction peaks with respect to crystalline form E refer to a measurement at 298 K±5 K, in another preferred embodiment refer, with respect to crystalline form E, to a measurement at 100 K±5 K, in each case using CuKα radiation having a wavelength of 1.54060 Å.

Optionally, the crystalline form E according to the invention may additionally have at least one X-ray diffraction peak selected from the group consisting of 11.4±1.0 (2Θ), 12.6±1.0 (2Θ), 17.1±1.0 (2Θ), 21.0±1.0 (2Θ), 23.7±1.0 (2Θ), 25.3±1.0 (2Θ), and 26.0±1.0 (2Θ). As indicated, the uncertainty in the 2θ values is ±1.0° in 2θ. Preferably, the uncertainty in the 2θ values is ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ. In a preferred embodiment these X-ray diffraction peaks with respect to crystalline form E refer to a measurement at 298 K±5 K, in another preferred embodiment refer, with respect to crystalline form E, to a measurement at 100 K±5 K, in each case using CuKα radiation having a wavelength of 1.54060 Å.

All 2Θ values with respect to crystalline form E refer to an x-ray powder diffractogram (XRPD) obtainable using CuKα radiation having a wavelength of 1.54060 Å at 298 K (±5 K) or at 100 K (±5 K), which has been calculated from a single crystal diffractogram (SCXRD) measured using MoKα radiation having a wavelength of 0.71073 Å at 100 K (±5 K). Due to the fact that the SCXRD was determined at 100 K (±5 K), the peak positions determined by a XRPD measured at 298 K (±5 K) may differ because of temperature dependent variations of the lattice parameters of the unit cell. Therefore, the uncertainty in the 2θ values is ±1.0°, preferably ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ.

Another aspect of the present invention relates to a process for the production of the crystalline form E as described above.

In a preferred embodiment, the process comprises the step of (a-1) precipitating the sulfate or hemi-sulfate of (1r,4r)-6'-fluoro-N,N-dimethyl-4-phenyl-4',9'-dihydro-3'H-spiro[cyclohexane-1,1'-pyrano[3,4,b]indol]-4-amine from a solution or suspension of the free base.

Conventional solvents known to persons skilled in the art may be used as solvents in a solution or suspension, preferably a solution, of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof. Preferred solvents are THF, DMSO, NMP, acetic acid, mixtures of acetic acid and dimethyl acetamide, mixtures of acetone and THF, mixtures of DMSO and acetic acid, and mixtures of THF and DMSO.

Step (a-1) may be carried out by the addition of sulfuric acid. In a preferred embodiment, sulfuric acid is added in form of a solution. In one preferred embodiment, the solution is a solution of sulfuric acid in an aqueous solvent, i.e. an aqueous solution of sulfuric acid. In another preferred embodiment, the solution is a solution of sulfuric acid in an organic solvent, especially preferred are alcohols such as ethanol, isopropanol and n-butanol, and ethers such as diethylether, di-isopropylether, tetrahydrofurane, methyl-tetrahydrofurane 1,4-dioxane or carbonic acids such as acetic acid and propionic acid.

In a preferred embodiment, the sulfuric acid containing solution and the solution of the free base contain the same solvent.

In another particularly preferred embodiment, the sulfuric acid containing solution and the solution of the free base contain not the same solvent.

In a particularly preferred embodiment containing solution is an aqueous solution and the solution of the free base is an organic solvent, in which the free base is dissolved.

Preferably, the solution contains sulfuric acid in a concentration within the range of from 0.01 mol/L to 15 mol/L, more preferably within the range of from 0.02 mol/L to 12.5 mol/L, still more preferably within the range of from 0.05 mol/L to 10 mol/L, yet more preferably within the range of from 0.1 mol/L to 7.5 mol/L, most preferably within the range of from 0.2 mol/L to 10 mol/L, and in particular within the range of from 0.3 mol/L to 5 mol/L.

Preferably, the sulfuric acid is added to the solution or suspension of the free base in molar excess, in particular in order to form a sulfate salt.

Preferably, in the process according to the invention, step (a-1) is carried out at a temperature below or at the boiling point of the respective solvent, preferably at a temperature not higher than 100° C., more preferably not higher than 80° C., even more preferably not higher than 60° C., and in particular in a temperature range of 20-40° C.

Preferably, in the process according to the invention, the suspension or solution obtained in step (a-1) is stirred for a time period of at least 1 minute, preferably at least 2 minutes, more preferably at least 3 minutes, still more preferably at least 5 minutes, yet more preferably at least 10 minutes, most preferably at least 20 minutes, and in particular at least 30 minutes.

In a preferred embodiment, the suspension or solution obtained in step (a-1) is stirred for a time period of at least 1 hour, preferably at least 4 hours, more preferably at least 6 hours, still more preferably at least 12 hours, yet more preferably at least 18 hours, most preferably at least 1 day, and in particular at least 2 days.

In another preferred embodiment, the suspension or solution obtained in step (a-1) is stirred for a time period of at most 1 day, preferably at most 12 hours, more preferably at most 6 hours, still more preferably at most 2 hours, yet more preferably at most 60 minutes, and most preferably at most 45 minutes, and in particular at most 30 minutes.

Preferably, the process according to the invention further comprises the step (b-1) separating, preferably filtering off the solid obtained in step (a-1).

Preferably, the process according to the invention further comprises the step (c-1) drying of the solid obtained in step (b-1).

In a preferred embodiment, step (c-1) takes place under air, nitrogen flow or argon flow.

In another preferred embodiment, step (c-1) takes place under vacuum, more preferably at a vacuum of 0 to 900 mbar, even more preferably at a vacuum of 1 to 500 mbar, and in particular at a vacuum of 10 to 200 mbar.

Preferably, in the process according to the invention, step (c-1) takes place in a temperature range from 0 to 60° C., preferably from 10° C. to 50° C. more preferably from 20 to 40° C.

In another preferred embodiment, the process comprises the step of (a-2) dissolving (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate in a solvent.

Conventional solvents known to persons skilled in the art may be used as solvents in a solution of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof. Preferred solvents are THF, acetic acid, NMP, DMSO, mixtures of THF and DMSO, mixtures of DMSO and acetic acid, and mixtures of acetic acid and dimethyl acetamide (DMAc).

Preferably, in the process according to the invention, step (a-2) is carried out at a temperature below or at the boiling point of the respective solvent or solvent mixture, more preferably at a temperature not higher than 100° C., more preferably not higher than 80° C., even more preferably not higher than 60° C., and in particular in a temperature range of 20-40° C.

In a preferred embodiment, the process according to the invention further comprises the step (b-2) evaporating the solvent of the solution obtained in step (a-2).

Suitable methods of evaporating the solvent are known to persons skilled in the art. Preferably, in the process according to the invention, the solvent is evaporated in air, air flow, or inert gas flow, in particular argon or nitrogen flow. However, evaporating the solvent under vacuum, for example by means of a rotary evaporator, is also possible. Preferably, in the process according to the invention, the solvent is evaporated at room temperature.

In another preferred embodiment, the process further comprises the step of (b-2') precipitating (1r,4r)-6'-fluoro-N,N-dimethyl-4-phenyl-4',9'-dihydro-3'H-spiro[cyclo-hexane-1,1'-pyrano[3,4,b]indol]-4-amine sulfate or hemi-sulfate from the solution obtained in step (a-2), preferably by addition of a precipitant, Suitable methods of precipitation are known to persons skilled in the art. In the process according to the invention, step (b-2') may be carried out by reducing the volume of the solution obtained in step (a-2) and/or by cooling of the solution, preferably to a temperature of at most 15° C., more preferably at most 10° C., even more preferably at most 4-8° C. and/or by cooling of the solution, preferably to a temperature of at least 10° C., more preferably at least 30° C., even more preferably at least 60° C. below the temperature according to step (a-2).

In a preferred embodiment, step (b-2') is carried out by the addition of a medium in which (1r,4r)-6'-fluoro-N,N-dimethyl-4-phenyl-4',9'-dihydro-3' H-spiro[cyclohexane-1,1'-pyrano-[3,4,b]indol]-4-amine sulfate or hemi-sulfate is only poorly soluble ("anti-solvent") to the solution obtained in step (a-2). Said medium is preferably selected from the group consisting of esters such as ethyl acetate, n-propyl acetate, iso-propyl acetate, n-butyl acetate and iso-butyl acetate; alcohols such as methanol, ethanol, 1-propanol, 2-propanol; ethers such as tert-butyl methyl ether, diethyl ether and diisopropyl ether; ketones such as acetone, 2-butanone, pentan-2-one, pentan-3-one, hexan-2-one and hexan-3-one; nitriles such as acetonitril; pyridine, acetic acid and water, and DMSO. Particularly preferred are DMSO, 2-butanone (MEK), 2-propanol, and water; especially preferred are 2-butanone (MEK) and 2-propanol.

The amount of the media in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate is only poorly soluble, the precipitant or anti-solvent, is preferably selected in such a manner that upon its addition precipitation of the dissolved component begins.

The total amount of the media in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate is only poorly soluble may also be divided into several portions, preferably two or three portions. In this embodiment, the precipitation of the dissolved component preferably begins after the addition of the last portion.

The precipitation of the dissolved component preferably begins either immediately after the precipitant, preferably the total amount of the precipitant, has been added or alternatively with a delay of 2 seconds to 120 minutes. Preferably, the precipitation of the dissolved component begins within a time period of at most 90 minutes, more preferably at most 60 minutes, still more preferably at most 30 minutes, even more preferably at most 5 minutes, most preferably at most 60 seconds and in particular at most 10 seconds.

Furthermore, the amount of the media in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate, is only poorly soluble, the precipitant or anti-solvent, is preferably selected in such a manner that the dissolved component is completely precipitated or at least up to 90% of the initial amount is precipitated within a time period of at most 90 minutes, more preferably at most 80 minutes, still more preferably at most 70 minutes, and most preferably at most 60 minutes after the anti-solvent has been completely added.

Step (b-2') may also be carried out by exposing the solution obtained in step (a-2) to an atmosphere containing a solvent, in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate is only poorly soluble, i.e. by a vapor diffusion crystallization technique.

In this embodiment, dichloromethane is preferably selected as solvent in step (a-2) and the solution obtained in step (a-2) is preferably exposed to an atmosphere containing hexane.

Preferably, in the process according to the invention, after step (b-2) or respectively (b-2'), all other steps are carried out at a temperature between 40 and 0° C., preferably between 35 and 5° C., more preferably between 25 and 15° C.

Preferably, in the process according to the invention, the suspension obtained in step (b-2') is stirred for a time period of at least 1 minute, preferably at least 2 minutes, more preferably at least 3 minutes, and most preferably at least 5 minutes.

Preferably, the process according to the invention further comprises the step
(c-2') separating, preferably filtering off the precipitate obtained in step (b-2').

Preferably, the process according to the invention further comprises the step
(d-2') drying of the solid obtained in step (c-2').

Preferably, in the process according to the invention, step (d-2') takes place under air or inert gas flow, such as argon or nitrogen flow. However, depending on the crystalline form to be obtained evaporating the solvent at an elevated temperature, e.g. within the range of from 20° C. to 60° C., is also possible.

In still another preferred embodiment, the process comprises the step of
(a-3) suspending (1r,4r)-6'-fluoro-N,N-dimethyl-4-phenyl-4',9'-dihydro-3'H-spiro[cyclo-hexane-1,1'-pyrano[3,4,b]indol]-4-amine sulfate or hemi-sulfate in a solvent.

Conventional solvents known to persons skilled in the art may be used as solvents in a suspension of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof. Preferred solvents are alcohols such as methanol or water, particularly preferred alcohols such as methanol.

In a preferred embodiment, step (a-3) is carried out at a temperature below or at the boiling point of the respective solvent, preferably at a temperature not higher than 100° C., more preferably not higher than 90° C., still more preferably not higher than 80° C., yet more preferably not higher than 60° C., most preferably not higher than 40° C., and in particular in a temperature range of 15-35° C.

In another preferred embodiment, step (a-3) is carried out in a temperature range of 100-40° C., more preferably 90-50° C., and most preferably 85-60° C.

Preferably, in the process according to the invention, the suspension obtained in step (a-3) is stirred for a time period of at least 2 h, preferably at least 4 h, more preferably at least 8 h, still more preferably at least 12 h, yet more preferably at least 16 h, most preferably at least 24 h, and in particular at least 2 days.

Preferably, the process according to the invention further comprises the step
(b-3) separating, preferably filtering off the solid obtained in step (a-3).

Preferably, the process according to the invention further comprises the step (c-3) drying of the solid obtained in step (b-3).

In the process according to the invention, step (c-3) may take place under air or inert gas flow, such as argon or nitrogen flow. However, drying under vacuum, more preferably at a vacuum of 0 to 900 mbar, even more preferably at a vacuum of 1 to 500 mbar, and in particular at a vacuum of 10 to 200 mbar is preferred.

Preferably, in the process according to the invention, step (c-3) takes place in a temperature range from 0 to 60° C., preferably from 10° C. to 50° C. more preferably from 20 to 40° C.

In still another preferred embodiment, the process comprises the step of (a-4) reacting 2-(5-fluoro-1H-indol-3-yl)ethanol and 4-(dimethylamino)-4-phenylcyclohexanone or a protected derivative thereof, optionally in the form of an acid addition salt, in a carbonic acid as reaction medium in the presence of sulfuric acid to form (1r,4r)-6'-fluoro-N,N-dimethyl-4-phenyl-4',9'-dihydro-3'H-spiro[cyclohexane-1,1'-pyrano-[3,4,b]indol]-4-amine sulphate or hemi-sulfate.

Any suitable carbonic acid can serve as reaction medium in step (a-4) according to the present invention. The reaction medium preferably serves as solvent for the starting material employed, i.e. for the compounds 2-(5-fluoro-1H-indol-3-yl) ethanol and 4-(dimethylamino)-4-phenylcyclohexanone or a protected derivative thereof, preferably also as a solvent for sulfuric acid. Preferably, the carbonic acid employed as reaction medium in step (a-4) according to the present invention is in liquid form at room temperature. Preferably, the carbonic acid employed as reaction medium in step (a-4) is selected from the group consisting of acetic acid, trifluoroacetic acid, propionic acid, lactic acid, 3-hydroxypropionic acid, butyric acid, isobutyric acid, acrylic acid and methacrylic acid or mixtures thereof. Preferably, the carbonic acid employed as reaction medium in step (a) is selected from the group consisting of acetic acid, trifluoroacetic acid, and propionic acid or mixtures thereof. Particularly preferred are acetic acid and propionic acid. Most preferred is acetic acid. In one particularly preferred embodiment of the present invention, the carbonic acid employed as reaction medium in step (a-4) is acetic acid. In another particularly preferred embodiment of the present invention, the carbonic acid employed as reaction medium in step (a-4) is propionic acid. Preferably, the carbonic acid as reaction medium is employed in step (a-4) in an amount by weight that is in the range of from 5 to 60 times higher than the total amount of 4-(dimethylamino)-4-phenylcyclohexanone or a protected derivative thereof by weight. For example, in case 400 mg of 4-(dimethylamino)-4-phenylcyclohexanone or a protected derivative thereof is employed, the carbonic acid as reaction medium is employed in an amount by weight, that is in the range of from 2 g to 24 g. More preferably, the carbonic acid as reaction medium is employed in step (a-4) in an amount by weight that is in the range of from 7 to 50 times, even more preferably 10 to 45 times, still more preferably 12 to 40 times, in particular 15 to 35 times, and most preferred 20 to 30 times higher than the total amount of 4-(dimethylamino)-4-phenylcyclohexanone or a protected derivative thereof by weight.

Preferably, sulfuric acid as promoting agent is employed in step (a-4) in an amount that is in the range of from 1.05 to 2.00 equivalents, preferably of from 1.10 to 1.90 equivalents, more preferably of from 1.10 to 1.70 equivalents, even more preferably of from 1.10 to 1.50 equivalents, still more preferably of from 1.10 to 1.40 equivalents, in particular of from 1.10 to 1.30 equivalents, in each case with respect to the molar amount of either 2-(5-fluoro-1H-indol-3-yl)ethanol or 4-(dimethylamino)-4-phenylcyclohexanone or a protected derivative thereof.

Preferably, sulfuric acid employed in step (a-4) according to the inventive process is soluble, preferably soluble at room temperature, in the reaction medium employed in step (a-4).

The reaction time of step (a-4) can vary in dependence on various parameters, such as, for example, temperature, stoichiometry, nature of the compound to be reacted with, or the nature of the reaction medium, and can be determined for the process in question by the person skilled in the art using preliminary tests. Preferably, the reaction time for performing step (a) does not exceed 24 h, more preferably does not exceed 18 h. Even more preferably, the reaction time is in the range of from 1 h to 20 h, still more preferably is in the range of from 2 h to 18, in particular is in the range of from 3 h to 16 h, most preferred is in the range of from 4 h to 10 h.

Preferably, the reaction mixture is stirred in step (a-4).

The reaction temperature at which step (a-4) is performed can vary in dependence on various parameters, such as, for example, reaction time, stoichiometry, nature of the compound to be reacted with, or nature of the reaction medium and can be determined for the process in question by the person skilled in the art using preliminary tests. Preferably, the reaction temperature at which step (a-4) of the inventive process is performed, is in the range of from 20° C. to 100° C., more preferably is in the range of from 30° C. to 90° C., even more preferably is in the range of from 40° C. to 80° C., still more preferably in the range of from 40° C. to 60° C. In another preferred embodiment of the present invention, the reaction temperature at which step (a-4) of the inventive process is performed is at least 30° C., preferably at least 40° C., more preferably at least 50° C.

In a particularly preferred embodiment
  sulfuric acid is employed in step (a-4) in an amount that is in the range of from 1.10 to 1.30 equivalents with respect to the molar amount of 2-(5-fluoro-1H-indol-3-yl)ethanol or 4-(dimethylamino)-4-phenylcyclohexanone or a protected derivative thereof, and
  the at least one carbonic acid as reaction medium employed in step (a) is acetic acid or propionic acid, preferably in an amount by weight that is in the range of from 5 to 60 times higher than the total amount of 4-(dimethylamino)-4-phenylcyclohexanone or a protected derivative thereof by weight.

In a very particularly preferred embodiment
  sulfuric acid is employed in step (a-4) in an amount that is in the range of from 1.10 to 1.30 equivalents with respect to the molar amount of 2-(5-fluoro-1H-indol-3-yl)ethanol or 4-(dimethylamino)-4-phenylcyclohexanone or a protected derivative thereof,
  the at least one carbonic acid as reaction medium employed in step (a) is acetic acid or propionic acid, preferably in an amount by weight that is in the range of from 5 to 60 times higher than the total amount of 4-(dimethylamino)-4-phenylcyclohexanone or a protected derivative thereof by weight,
  the reaction temperature at which step (a) is performed is in the range of from 40° C. to 80° C., preferably in the range of from 40° C. to 60° C., and
  the reaction time of step (a) is in the range of from 3 hours to 16 hours.

Preferably, the solid form of the compound according to formula (I) and sulfuric acid precipitates from the reaction mixture during the performance of step (a-4) and can be thus obtained from step (a-4) as a precipitate, preferably by filtration of the reaction mixture, i.e. by separating, preferably filtering off the precipitate.

Thus, preferably, the process according to the invention further comprises the step (b-4) separating, preferably filtering off the solid obtained in step (a-4).

The solid obtained from step (b-4) can be optionally purified, e.g. by (c-4) optionally performing steps (a-2) and (b-2) or (b-2') or performing steps (a-3) and (b-3).

The solid obtained from step (b-4) can be optionally further recrystallized in a manner well known to those skilled in the art, e.g. by recrystallization from a suitable solvent. Alternatively, the solid obtained can also be subjected to a chromatographic resolution.

Suitable solvents can be determined by the person skilled in the art using preliminary tests and include solvents such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; and also N-methyl-2-pyrrolidone, dimethyl acetamide, dimethyl formamide and dimethyl sulfoxide (DMSO); carbonic acids such as acetic acid and propionic acid, and mixtures thereof. Particularly preferred are acetic acid, mixtures of DMSO and acetic acid, mixtures of THF and DMSO, and mixtures of acetic acid and dimethyl acetamide. Recrystallization techniques well known to those skilled in the art e.g. include first dissolving the acid addition salt obtained from step (a) in a suitable solvent, optionally heating the mixture, followed by a precipitation of said acid addition salt, preferably by addition of another medium, or followed by evaporation off the solvent employed for dissolution.

Particularly preferred is a process comprising steps (a-2) and (b-2) or (b-2') or steps (a-4) and (b-4) for the preparation of crystalline form E, especially preferred is such a process comprising steps (a-3) and (b-3) or (b-2').

A further aspect of the invention relates to a crystalline form E that is obtainable by the process as described above.

A further aspect of the present invention relates to a crystalline form F. Preferably, crystalline form F of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid is a (1r,4r)-6'-fluoro-N,N-dimethyl-4-phenyl-4',9'-dihydro-3'H-spiro[cyclohexane-1,1'-pyrano[3,4,b]indol]-4-amine hemi-sulfate, preferably a solvate thereof, more preferably an acetic acid solvate thereof, in particular a solvate containing two molecules of acetic acid, thereof.

Preferably, the crystalline form F according to the invention has one or more X-ray diffraction peaks selected from the group consisting of 10.2±1.0 (2Θ), 11.6±1.0 (2Θ), 16.0±1.0 (2Θ), 18.3±1.0 (2Θ), 19.3±1.0 (2Θ), and 24.5±1.0 (2Θ), in a preferred embodiment measured at 298 K±5 K, in another preferred embodiment measured at 100 K±5 K, in each case using CuKα radiation having a wavelength of 1.54060 Å. As indicated, the uncertainty in the 2θ values is ±1.0° in 2θ. Preferably, the uncertainty in the 2θ values is ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ.

In some preferred embodiments, the crystalline form F comprises X-ray diffraction peaks at 10.2±1.0 (2Θ), 11.6±1.0 (2Θ), 16.0±1.0 (2Θ), 18.3±1.0 (2Θ), and 19.3±1.0 (2Θ), and 24.5±1.0 (2Θ). In some preferred embodiments, the crystalline form comprises X-ray diffraction peaks at 10.2±1.0 (2Θ), 11.6±1.0 (2Θ), 16.0±1.0 (2Θ), 18.3±1.0 (2Θ), and 19.3±1.0 (2Θ). In some preferred embodiments, the crystalline form comprises X-ray diffraction peaks at 10.2±1.0 (2Θ), 16.0±1.0 (2Θ) and 19.3±1.0 (2Θ). In some preferred embodiments, the crystalline form comprises an X-ray diffraction peak at 19.3±1.0 (2Θ). As indicated, the uncertainty in the 2θ values is ±1.0° in 2θ. Preferably, the uncertainty in the 2θ values is ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ. In a preferred embodiment these X-ray diffraction peaks with respect to crystalline form F refer to a measurement at 298 K±5 K, in another preferred embodiment refer, with respect to crystalline form F, to a measurement at 100 K±5 K, in each case using CuKα radiation having a wavelength of 1.54060 Å.

In some preferred embodiments, crystalline form F comprises X-ray diffraction peaks at 10.2±1.0 (2Θ), 11.6±1.0 (2Θ), 16.0±1.0 (2Θ), 18.3±1.0 (2Θ), and 19.3±1.0 (2Θ), and 24.5±1.0 (2Θ) and optionally at 12.4±1.0 (2Θ) and 19.5±1.0 (2Θ). As indicated, the uncertainty in the 2θ values is ±1.0° in 2θ. Preferably, the uncertainty in the 2θ values is ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ. In a preferred embodiment these X-ray diffraction peaks with respect to crystalline form F refer to a measurement at 298 K±5 K, in another preferred embodiment refer, with respect to crystalline form F, to a measurement at 100 K±5 K, in each case using CuKα radiation having a wavelength of 1.54060 Å.

The crystalline form F according to the invention may additionally have at least one X-ray diffraction peak selected from the group consisting of 12.0±1.0 (2Θ), 12.4±1.0 (2Θ), 18.6±1.0 (2Θ), 19.5±1.0 (2Θ), 21.6±1.0 (2Θ), and 24.7±1.0 (2Θ). As indicated, the uncertainty in the 2θ values is ±1.0° in 2θ. Preferably, the uncertainty in the 2θ values is ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ. In a preferred embodiment these X-ray diffraction peaks with respect to crystalline form F refer to a measurement at 298 K±5 K, in another preferred embodiment refer, with respect to crystalline form F, to a measurement at 100 K±5 K, in each case using CuKα radiation having a wavelength of 1.54060 Å.

Further, the crystalline form F according to the invention may be characterized in that as well as one or more X-ray diffraction peaks are selected from the group consisting of 10.2±1.0 (2Θ), 11.6±1.0 (2Θ), 16.0±1.0 (2Θ), 18.3±1.0 (2Θ), and 19.3±1.0 (2Θ), and 24.5±1.0 (2Θ) and optionally one or more X-ray diffraction peaks selected from the group consisting of 12.0±1.0 (2Θ), 12.4±1.0 (2Θ), 18.6±1.0 (2Θ), 19.5±1.0 (2Θ), 21.6±1.0 (2Θ), and 24.7±1.0 (2Θ), it additionally may have at least one X-ray diffraction peak selected from the group consisting of 9.5±1.0 (2Θ), 10.4±1.0 (2Θ), 22.0±1.0 (2Θ), 23.3±1.0 (2Θ), 23.6±1.0 (2Θ), 24.6±1.0 (2Θ), 26.8±1.0 (2Θ) and 28.8±1.0 (2Θ). As indicated, the uncertainty in the 2θ values is ±1.0° in 2θ. Preferably, the uncertainty in the 2θ values is ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ. In a preferred embodiment these X-ray diffraction peaks with respect to crystalline form F refer to a measurement at 298 K±5 K, in another preferred embodiment refer, with respect to crystalline form F, to a measurement at 100 K±5 K, in each case using CuKα radiation having a wavelength of 1.54060 Å.

Optionally, the crystalline form F according to the invention may additionally have at least one X-ray diffraction peak selected from the group consisting of 22.6±1.0 (2Θ), 27.5±1.0 (2Θ), 30.4±1.0 (2Θ), 38.1±1.0 (2Θ), and 39.0±1.0 (2Θ). As indicated, the uncertainty in the 2θ values is ±1.0° in 2θ. Preferably, the uncertainty in the 2θ values is ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ. In a preferred embodiment these X-ray diffraction peaks with respect to crystalline form F refer to a measurement at 298 K±5 K, in another preferred embodiment refer, with respect to crystalline form F, to a measurement at 100 K±5 K, in each case using CuKα radiation having a wavelength of 1.54060 Å.

All 2Θ values with respect to crystalline form F refer to an x-ray powder diffractogram (XRPD) obtainable using CuKα radiation having a wavelength of 1.54060 Å at 298 K (±5 K) or at 100 K (±5 K), which has been calculated from a single crystal diffractogram (SCXRD) measured using MoKα radiation having a wavelength of 0.71073 Å at 100 K (±5 K). Due to the fact that the SCXRD was determined at 100 K (±5 K), the peak positions determined by a XRPD measured at 298 K (±5 K) may differ because of temperature dependent variations of the lattice parameters of the unit cell. Therefore, the uncertainty in the 2θ values is ±1.0°, preferably ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ.

Another aspect of the present invention relates to a process for the production of the crystalline form F as described above.

In a preferred embodiment, the process comprises the step of (a-1) precipitating the sulphate or hemi-sulfate salt of (1r,4r)-6'-fluoro-N,N-dimethyl-4-phenyl-4',9'-dihydro-3'H-spiro [cyclohexane-1,1'-pyrano[3,4,b]indol]-4-amine from a solution or suspension of the free base.

Conventional solvents known to persons skilled in the art may be used as solvents in a solution or suspension, preferably a solution, of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof. Preferred solvents are THF, DMSO, NMP, acetic acid, mixtures of acetic acid and dimethyl acetamide, mixtures of acetone and THF, mixtures of DMSO and acetic acid, and mixtures of THF and DMSO.

In an especially preferred embodiment, the organic solvent for dissolving the free base of the compound according to general formula (I) is a mixture of acetone and THF. Preferably, the ratio between acetone and THF is within the range of from 15:1 to 1:15, more preferably within the range of from 12:1 to 1:12 (volume/volume).

Step (a-1) may be carried out by the addition of sulfuric acid. In a preferred embodiment, sulfuric acid is added in form of a solution. In one preferred embodiment, the solution is a solution of sulfuric acid in an aqueous solvent, i.e. an aqueous solution of sulfuric acid. In another preferred embodiment, the solution is a solution of sulfuric acid in an organic solvent, especially preferred are alcohols such as ethanol, isopropanol and n-butanol, and ethers such as diethylether, di-isopropylether, tetrahydrofurane, methyl-tetrahydrofurane 1,4-dioxane or carbonic acids such as acetic acid and propionic acid.

In a preferred embodiment, the sulfuric acid containing solution and the solution of the free base contain the same solvent.

In another particularly preferred embodiment, the sulfuric acid containing solution and the solution of the free base contain not the same solvent.

In a particularly preferred embodiment containing solution is an aqueous solution and the solution of the free base is an organic solvent, in which the free base is dissolved.

Preferably, the solution contains sulfuric acid in a concentration within the range of from 0.01 mol/L to 15 mol/L, more preferably within the range of from 0.02 mol/L to 12.5 mol/L, still more preferably within the range of from 0.05 mol/L to 10 mol/L, yet more preferably within the range of from 0.1 mol/L to 7.5 mol/L, most preferably within the range of from 0.2 mol/L to 10 mol/L, and in particular within the range of from 0.3 mol/L to 5 mol/L.

Preferably, in the process according to the invention, step (a-1) is carried out at a temperature below or at the boiling point of the respective solvent, preferably at a temperature not higher than 100° C., more preferably not higher than 80° C., even more preferably not higher than 60° C., and in particular in a temperature range of 20-40° C.

Preferably, in the process according to the invention, the suspension or solution obtained in step (a-1) is stirred for a time period of at least 1 minute, preferably at least 2 minutes, more preferably at least 3 minutes, still more preferably at least 5 minutes, yet more preferably at least 10 minutes, most preferably at least 20 minutes, and in particular at least 30 minutes.

In a preferred embodiment, the suspension or solution obtained in step (a-1) is stirred for a time period of at least 1 hour, preferably at least 4 hours, more preferably at least 6 hours, still more preferably at least 12 hours, yet more preferably at least 18 hours, most preferably at least 1 day, and in particular at least 2 days.

In another preferred embodiment, the suspension or solution obtained in step (a-1) is stirred for a time period of at most 1 day, preferably at most 12 hours, more preferably at most 6 hours, still more preferably at most 2 hours, yet more preferably at most 60 minutes, and most preferably at most 45 minutes, and in particular at most 30 minutes.

Preferably, the process according to the invention further comprises the step (b-1) separating, preferably filtering off the solid obtained in step (a-1).

Preferably, the process according to the invention further comprises the step (c-1) drying of the solid obtained in step (b-1).

In a preferred embodiment, step (c-1) takes place under air, nitrogen flow or argon flow.

In another preferred embodiment, step (c-1) takes place under vacuum, more preferably at a vacuum of 0 to 900 mbar, even more preferably at a vacuum of 1 to 500 mbar, and in particular at a vacuum of 10 to 200 mbar.

Preferably, in the process according to the invention, step (c-1) takes place in a temperature range from 0 to 60° C., preferably from 10° C. to 50° C. more preferably from 20 to 40° C.

In another preferred embodiment, the process comprises the step of (a-2) dissolving (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate in a solvent.

Conventional solvents known to persons skilled in the art may be used as solvents in a solution of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof. Preferred solvents are THF, acetic acid, NMP, DMSO, mixtures of THF and DMSO, mixtures of DMSO and acetic acid, and mixtures of acetic acid and dimethyl acetamide (DMAc).

Preferably, in the process according to the invention, step (a-2) is carried out at a temperature below or at the boiling point of the respective solvent or solvent mixture, more preferably at a temperature not higher than 100° C., more preferably not higher than 80° C., even more preferably not higher than 60° C., and in particular in a temperature range of 20-40° C.

In a preferred embodiment, the process according to the invention further comprises the step (b-2) evaporating the solvent of the solution obtained in step (a-2).

Suitable methods for evaporating the solvent are known to persons skilled in the art. Preferably, in the process according to the invention, the solvent is evaporated in air, air flow, or inert gas flow, in particular argon or nitrogen flow. However, evaporating the solvent under vacuum, for example by means of a rotary evaporator, is also possible.

Preferably, in the process according to the invention, the solvent is evaporated at room temperature.

In another preferred embodiment, the process further comprises the step of (b-2') precipitating (1r,4r)-6'-fluoro-N,N-dimethyl-4-phenyl-4',9'-dihydro-3'H-spiro[cyclo-hexane-1,1'-pyrano[3,4,b]indol]-4-amine sulfate or hemi-sulfate from the solution obtained in step (a-2), preferably by addition of a precipitant, Suitable methods of precipitation are known to persons skilled in the art. In the process according to the invention, step (b-2') may be carried out by reducing the volume of the solution obtained in step (a-2) and/or by cooling of the solution, preferably to a temperature of at most 15° C., more preferably at most 10° C., even more preferably at most 4-8° C. and/or by cooling of the solution, preferably to a temperature of at least 10° C., more preferably at least 30° C., even more preferably at least 60° C. below the temperature according to step (a-2).

In a preferred embodiment, step (b-2') is carried out by the addition of a medium in which (1r,4r)-6'-fluoro-N,N-dimethyl-4-phenyl-4',9'-dihydro-3'H-spiro[cyclohexane-1,1'-pyrano-[3,4,b]indol]-4-amine sulfate or hemi-sulfate is only poorly soluble ("anti-solvent") to the solution obtained in step (a-2). Said medium is preferably selected from the group consisting of esters such as ethyl acetate, n-propyl acetate, iso-propyl acetate, n-butyl acetate and iso-butyl acetate; alcohols such as methanol, ethanol, 1-propanol, 2-propanol; ethers such as tert-butyl methyl ether, diethyl ether and diisopropyl ether; ketones such as acetone, 2-butanone, pentan-2-one, pentan-3-one, hexan-2-one and hexan-3-one; nitriles such as acetonitril; pyridine, acetic acid and water, and DMSO. Particularly preferred are DMSO, 2-butanone (MEK), 2-propanol, and water; especially preferred are 2-butanone (MEK) and 2-propanol.

The amount of the media in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate is only poorly soluble, the precipitant or anti-solvent, is preferably selected in such a manner that upon its addition precipitation of the dissolved component begins.

The total amount of the media in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate is only poorly soluble may also be divided into several portions, preferably two or three portions. In this embodiment, the precipitation of the dissolved component preferably begins after the addition of the last portion.

The precipitation of the dissolved component preferably begins either immediately after the precipitant, preferably the total amount of the precipitant, has been added or alternatively with a delay of 2 seconds to 120 minutes. Preferably, the precipitation of the dissolved component begins within a time period of at most 90 minutes, more preferably at most 60 minutes, still more preferably at most 30 minutes, even more preferably at most 5 minutes, most preferably at most 60 seconds and in particular at most 10 seconds.

Furthermore, the amount of the media in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate, is only poorly soluble, the precipitant or anti-solvent, is preferably selected in such a manner that the dissolved component is completely precipitated or at least up to 90% of the initial amount is precipitated within a time period of at most 90 minutes, more preferably at most 80 minutes, still more preferably at most 70 minutes, and most preferably at most 60 minutes after the anti-solvent has been completely added.

Step (b-2') may also be carried out by exposing the solution obtained in step (a-2) to an atmosphere containing a solvent, in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate is only poorly soluble, i.e. by a vapor diffusion crystallization technique.

In this embodiment, dichloromethane is preferably selected as solvent in step (a-2) and the solution obtained in step (a-2) is preferably exposed to an atmosphere containing hexane.

Preferably, in the process according to the invention, after step (b-2) or respectively (b-2'), all other steps are carried out at a temperature between 40 and 0° C., preferably between 35 and 5° C., more preferably between 25 and 15° C.

Preferably, in the process according to the invention, the suspension obtained in step (b-2') is stirred for a time period of at least 1 minute, preferably at least 2 minutes, more preferably at least 3 minutes, and most preferably at least 5 minutes.

Preferably, the process according to the invention further comprises the step (c-2') separating, preferably filtering off the precipitate obtained in step (b-2').

Preferably, the process according to the invention further comprises the step (d-2') drying of the solid obtained in step (c-2').

Preferably, in the process according to the invention, step (d-2') takes place under air or inert gas flow, such as argon or nitrogen flow. However, depending on the crystalline form to be obtained evaporating the solvent at an elevated temperature, e.g. within the range of from 20° C. to 60° C., is also possible.

In still another preferred embodiment, the process comprises the step of (a-3) suspending (1r,4r)-6'-fluoro-N,N-dimethyl-4-phenyl-4',9'-dihydro-3'H-spiro[cyclo-hexane-1,1'-pyrano[3,4,b]indol]-4-amine sulfate or hemi-sulfate in a solvent.

Conventional solvents known to persons skilled in the art may be used as solvents in a suspension of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof. Preferred solvents are alcohols such as methanol or water, particularly preferred alcohols such as methanol.

In a preferred embodiment, step (a-3) is carried out at a temperature below or at the boiling point of the respective solvent, preferably at a temperature not higher than 100° C., more preferably not higher than 90° C., still more preferably not higher than 80° C., yet more preferably not higher than 60° C., most preferably not higher than 40° C., and in particular in a temperature range of 15-35° C.

In another preferred embodiment, step (a-3) is carried out in a temperature range of 100-40° C., more preferably 90-50° C., and most preferably 85-60° C.

Preferably, in the process according to the invention, the suspension obtained in step (a-3) is stirred for a time period of at least 2 hours, preferably at least 4 hours, more preferably at least 8 h, still more preferably at least 12 hours, yet more preferably at least 16 hours, most preferably at least 24 hours, and in particular at least 2 days.

Preferably, the process according to the invention further comprises the step (b-3) separating, preferably filtering off the solid obtained in step (a-3).

Preferably, the process according to the invention further comprises the step (c-3) drying of the solid obtained in step (b-3).

In the process according to the invention, step (c-3) may take place under air or inert gas flow, such as argon or nitrogen flow. However, drying under vacuum, more preferably at a vacuum of 0 to 900 mbar, even more preferably at a vacuum of 1 to 500 mbar, and in particular at a vacuum of 10 to 200 mbar is preferred.

Preferably, in the process according to the invention, step (c-3) takes place in a temperature range from 0 to 60° C., preferably from 10° C. to 50° C. more preferably from 20 to 40° C.

In still another preferred embodiment, the process comprises the step of (a-4) reacting 2-(5-fluoro-1H-indol-3-yl)ethanol and 4-(dimethylamino)-4-phenylcyclohexanone or a protected derivative thereof, optionally in the form of an acid addition salt, in a carbonic acid as reaction medium in the presence of sulfuric acid to form (1r,4r)-6'-fluoro-N,N-dimethyl-4-phenyl-4',9'-dihydro-3'H-spiro[cyclohexane-1,1'-pyrano-[3,4,b]indol]-4-amine sulfate or hemi-sulfate.

A protected derivative of 4-(dimethylamino)-4-phenylcyclohexanone preferably means in the sense of the present invention a derivative of 4-(dimethylamino)-4-phenylcyclohexanone, wherein the keto-group of said compound is protected by a suitable protecting group, e.g. is present in the form of an ethylene glycol group. Reaction step (a-4) according to the present invention is an oxa-Pictet-Spengler reaction which is e.g. known from S.-Y. Chou et al., Heterocycles 2003, 60, 1095 and M. Zott et al., Tetrahedron: Asymmetry 1993, 4, 2307.

Any suitable carbonic acid can serve as reaction medium in step (a-4) according to the present invention. The reaction medium preferably serves as solvent for the starting material employed, i.e. for the compounds 2-(5-fluoro-1H-indol-3-yl)ethanol and 4-(dimethylamino)-4-phenylcyclohexanone or a protected derivative thereof, preferably also as a solvent for sulfuric acid.

Preferably, the carbonic acid employed as reaction medium in step (a-4) according to the present invention is in liquid form at room temperature.

Preferably, the carbonic acid employed as reaction medium in step (a-4) is selected from the group consisting of acetic acid, trifluoroacetic acid, propionic acid, lactic acid, 3-hydroxypropionic acid, butyric acid, isobutyric acid, acrylic acid and methacrylic acid or mixtures thereof. Preferably, the carbonic acid employed as reaction medium in step (a) is selected from the group consisting of acetic acid, trifluoroacetic acid, and propionic acid or mixtures thereof. Particularly preferred are acetic acid and propionic acid. Most preferred is acetic acid.

In a particularly preferred embodiment of the present invention, the carbonic acid employed as reaction medium in step (a-4) is acetic acid.

In another particularly preferred embodiment of the present invention, the carbonic acid employed as reaction medium in step (a-4) is propionic acid.

Preferably, the carbonic acid as reaction medium is employed in step (a-4) in an amount by weight that is in the range of from 5 to 60 times higher than the total amount of 4-(dimethylamino)-4-phenylcyclohexanone or a protected derivative thereof by weight. For example, in case 400 mg of each of 4-(dimethylamino)-4-phenylcyclohexanone or a protected derivative thereof is employed, the carbonic acid as reaction medium is employed in an amount by weight, that is in the range of from 2 g to 24 g. More preferably, the carbonic acid as reaction medium is employed in step (a-4) in an amount by weight that is in the range of from 7 to 50 times, even more preferably 10 to 45 times, still more preferably 12 to 40 times, in particular 15 to 35 times, and most preferred 20 to 30 times higher than the total amount of 4-(dimethylamino)-4-phenylcyclohexanone or a protected derivative thereof by weight.

Preferably, sulfuric acid as promoting agent is employed in step (a-4) in an amount that is in the range of from 1.05 to 2.00 equivalents, preferably of from 1.10 to 1.90 equivalents, more preferably of from 1.10 to 1.70 equivalents, even more preferably of from 1.10 to 1.50 equivalents, still more preferably of from 1.10 to 1.40 equivalents, in particular of from 1.10 to 1.30 equivalents, in each case with respect to the molar amount of either 2-(5-fluoro-1H-indol-3-yl)ethanol or 4-(dimethylamino)-4-phenylcyclohexanone or a protected derivative thereof.

Preferably, sulfuric acid employed in step (a-4) according to the process of the invention is soluble, preferably soluble at room temperature, in the reaction medium employed in step (a-4).

The reaction time of step (a-4) can vary in dependence on various parameters, such as, for example, temperature, stoichiometry, nature of the compound to be reacted with, or the nature of the reaction medium, and can be determined for the process in question by the person skilled in the art using preliminary tests. Preferably, the reaction time for performing step (a) does not exceed 24 h, more preferably does not exceed 18 h. Even more preferably, the reaction time is in the range of from 1 h to 20 h, still more preferably is in the range of from 2 hours to 18 hours, in particular is in the range of from 3 hours to 16 hours, most preferred is in the range of from 4 hours to 10 hours.

Preferably, stirring of the reaction mixture is performed in step (a-4).

The reaction temperature at which step (a-4) is performed can vary in dependence on various parameters, such as, for example, reaction time, stoichiometry, nature of the compound to be reacted with, or nature of the reaction medium and can be determined for the process in question by the person skilled in the art using preliminary tests. Preferably, the reaction temperature at which step (a-4) of the inventive process is performed, is in the range of from 20° C. to 100° C., more preferably is in the range of from 30° C. to 90° C., even more preferably is in the range of from 40° C. to 80° C., still more preferably in the range of from 40° C. to 60° C. In another preferred embodiment of the present invention, the reaction temperature at which step (a-4) of the inventive process is performed is at least 30° C., preferably at least 40° C., more preferably at least 50° C.

In a particularly preferred embodiment
sulfuric acid is employed in step (a-4) in an amount that is in the range of from 1.10 to 1.30 equivalents with respect to the molar amount of 2-(5-fluoro-1H-indol-3-yl)ethanol or 4-(dimethylamino)-4-phenylcyclohexanone or a protected derivative thereof, and
the at least one carbonic acid as reaction medium employed in step (a) is acetic acid or propionic acid, preferably in an amount by weight that is in the range of from 5 to 60 times higher than the total amount of 4-(dimethylamino)-4-phenylcyclohexanone or a protected derivative thereof by weight.

In a very particularly preferred embodiment
sulfuric acid is employed in step (a-4) in an amount that is in the range of from 1.10 to 1.30 equivalents with respect to the molar amount of 2-(5-fluoro-1H-indol-3-yl)ethanol or 4-(dimethylamino)-4-phenylcyclohexanone or a protected derivative thereof,
the at least one carbonic acid as reaction medium employed in step (a) is acetic acid or propionic acid, preferably in an amount by weight that is in the range of from 5 to 60 times higher than the total amount of 4-(dimethylamino)-4-phenylcyclohexanone or a protected derivative thereof by weight,
the reaction temperature at which step (a) is performed is in the range of from 40° C. to 80° C., preferably in the range of from 40° C. to 60° C., and
the reaction time of step (a) is in the range of from 3 hours to 16 hours.

Preferably, the solid form of the compound according to formula (I) and sulfuric acid precipitates from the reaction mixture during the performance of step (a-4) and can be thus obtained from step (a-4) as a precipitate, preferably by filtration of the reaction mixture, i.e. by separating, preferably filtering out the precipitate.

Thus, preferably, the process according to the invention further comprises the step
(b-4) separating, preferably filtering off the solid obtained in step (a-4).

The solid obtained from step (b-4) can be optionally purified, e.g. by
(c-4) optionally performing steps (a-2) and (b-2) or (b-2') or performing steps (a-3) and (b-3).

The solid obtained from step (b-4) can be optionally further recrystallized in a manner well known to those skilled in the art, e.g. by recrystallization from a suitable solvent. Alternatively, the solid obtained can also be subjected to a chromatographic resolution.

Suitable solvents can be determined by persons skilled in the art using preliminary tests and include solvents such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; and also N-methyl-2-pyrrolidone, dimethyl acetamide, dimethyl formamide and dimethyl sulfoxide (DMSO); carbonic acids such as acetic acid and propionic acid, and mixtures thereof. Particularly preferred are acetic acid, mixtures of DMSO and acetic acid, mixtures of THF and DMSO, and mixtures of acetic acid and dimethyl acetamide. Recrystallization techniques well known to those skilled in the art e.g. include first dissolving the acid addition salt obtained from step (a) in a suitable solvent, optionally heating the mixture, followed by a precipitation of said acid addition salt, preferably by addition of another medium, or followed by evaporation off the solvent employed for dissolution.

Particularly preferred is a process comprising steps (a-1) and (b-1) steps (a-4) and (b-4) for the preparation of crystalline form F, especially preferred is such a process comprising steps (a-1) and (b-1).

A further aspect of the invention relates to a crystalline form F that is obtainable by the process as described above.

A further aspect of the present invention relates to a crystalline form G. Preferably, crystalline form G of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid is a (1r,4r)-6'-fluoro-N,N-dimethyl-4-phenyl-4',9'-dihydro-3'H-spiro[cyclohexane-1,1'-pyrano[3,4,b]indol]-4-amine sulfate, preferably an ansolvate thereof.

Preferably, the crystalline form G according to the invention has one or more X-ray diffraction peaks selected from the group consisting of 10.3±1.0 (2Θ), 16.0±1.0 (2Θ), 17.9±1.0 (2Θ), 18.8±1.0 (2Θ), 23.0±1.0 (2Θ), and 26.2±1.0 (2Θ), in a preferred embodiment measured at 298 K±5 K, in another preferred embodiment measured at 100 K±5 K, in each case using CuKα radiation having a wavelength of 1.54060 Å. As indicated, the uncertainty in the 2θ values is ±1.0° in 2θ. Preferably, the uncertainty in the 2θ values is ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ.

In some preferred embodiments, the crystalline form G comprises X-ray diffraction peaks at 10.3±1.0 (2Θ), 16.0±1.0 (2Θ), 17.9±1.0 (2Θ), 18.8±1.0 (2Θ), 23.0±1.0 (2Θ), and 26.2±1.0 (2Θ). In some preferred embodiments, the crystalline form comprises X-ray diffraction peaks at 10.3±1.0 (2Θ), 16.0±1.0 (2Θ), 17.9±1.0 (2Θ), 18.8±1.0 (2Θ), and 23.0±1.0 (2Θ). In some preferred embodiments, the crystalline form comprises X-ray diffraction peaks at 16.0±1.0 (2Θ), 17.9±1.0 (2Θ) and 18.8±1.0 (2Θ). In some preferred embodiments, the crystalline form comprises an X-ray diffraction peak at 18.8±1.0 (2Θ). As indicated, the uncertainty in the 2θ values is ±1.0° in 2θ. Preferably, the uncertainty in the 2θ values is ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ. In a preferred embodiment these X-ray diffraction peaks with respect to crystalline form G refer to a measurement at 298 K±5 K, in another preferred embodiment refer, with respect to crystalline form G, to a measurement at 100 K±5 K, in each case using CuKα radiation having a wavelength of 1.54060 Å.

In some preferred embodiments, crystalline form G comprises X-ray diffraction peaks at 10.3±1.0 (2Θ), 16.0±1.0 (2Θ), 17.9±1.0 (2Θ), 18.8±1.0 (2Θ), 23.0±1.0 (2Θ), and 26.2±1.0 (2Θ) and optionally at 14.6±1.0 (2Θ) and 19.0±1.0 (2Θ). As indicated, the uncertainty in the 2θ values is ±1.0° in 2θ. Preferably, the uncertainty in the 2θ values is ±0.9°, more preferably ±0.8°, even more preferably ±0.7°, still more preferably ±0.6°, yet more preferably ±0.5°, still more preferably ±0.4°, particularly ±0.3°, most preferably ±0.2°, in 26. In a preferred embodiment these X-ray diffraction peaks with respect to crystalline form G refer to a measurement at 298 K±5 K, in another preferred embodiment refer, with respect to crystalline form G, to a measurement at 100 K±5 K, in each case using CuKα radiation having a wavelength of 1.54060 Å.

The crystalline form G according to the invention may additionally have at least one X-ray diffraction peak selected from the group consisting of 14.6±1.0 (2Θ), 17.7±1.0 (2Θ), 18.6±1.0 (2Θ), 19.0±1.0 (2Θ), 22.8±1.0 (2Θ), and 23.1±1.0 (2Θ). As indicated, the uncertainty in the 2θ values is ±1.0° in 2θ. Preferably, the uncertainty in the 2θ values is ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ. In a preferred embodiment these X-ray diffraction peaks with respect to crystalline form G refer to a measurement at 298 K±5 K, in another preferred embodiment refer, with respect to crystalline form G, to a measurement at 100 K±5 K, in each case using CuKα radiation having a wavelength of 1.54060 Å.

Further, the crystalline form G according to the invention may be characterized in that as well as one or more X-ray diffraction peaks are selected from the group consisting of 10.3±1.0 (2Θ), 16.0±1.0 (2Θ), 17.9±1.0 (2Θ), 18.8±1.0 (2Θ), 23.0±1.0 (2Θ), and 26.2±1.0 (2Θ) and optionally one or more X-ray diffraction peaks selected from the group consisting of 14.6±1.0 (2Θ), 17.7±1.0 (2Θ), 18.6±1.0 (2Θ), 19.0±1.0 (2Θ), 22.8±1.0 (2Θ), and 23.1±1.0 (2Θ), it additionally may have at least one X-ray diffraction peak selected from the group consisting of 18.9±1.0 (2Θ), 21.2±1.0 (2Θ), 22.0±1.0 (2Θ), 22.9±1.0 (2Θ), 23.3±1.0 (2Θ), 27.4±1.0 (2Θ), 28.2±1.0 (2Θ) and 29.6±1.0 (2Θ). As indicated, the uncertainty in the 2θ values is ±1.0° in 2θ. Preferably, the uncertainty in the 2θ values is ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ. In a preferred embodiment these X-ray diffraction peaks with respect to crystalline form G refer to a measurement at 298 K±5 K, in another preferred embodiment refer, with respect to crystalline form G, to a measurement at 100 K±5 K, in each case using CuKα radiation having a wavelength of 1.54060 Å.

Optionally, the crystalline form G according to the invention may additionally have at least one X-ray diffraction peak selected from the group consisting of 12.9±1.0 (2Θ), 17.4±1.0 (2Θ), 23.4±1.0 (2Θ), 28.5±1.0 (2Θ), and 28.9±1.0 (2Θ). As indicated, the uncertainty in the 2θ values is ±1.0° in 2θ. Preferably, the uncertainty in the 2θ values is ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ. In a preferred embodiment these X-ray diffraction peaks with respect to crystalline form G refer to a measurement at 298 K±5 K, in another preferred embodiment refer, with respect to crystalline form G, to a measurement at 100 K±5 K, in each case using CuKα radiation having a wavelength of 1.54060 Å.

All 2Θ values with respect to crystalline form G refer to an x-ray powder diffractogram (XRPD) obtainable using CuKα radiation having a wavelength of 1.54060 Å at 298 K (±5 K) or at 100 K (±5 K), which has been calculated from a single crystal diffractogram (SCXRD) measured using MoKα radiation having a wavelength of 0.71073 Å at 100 K (±5 K). Due to the fact that the SCXRD was determined at 100 K (±5 K), the peak positions determined by a XRPD measured at 298 K (±5 K) may differ because of temperature dependent variations of the lattice parameters of the unit cell. Therefore, the uncertainty in the 2θ values is ±1.0°, preferably ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ.

Another aspect of the present invention relates to a process for the production of the crystalline form G as described above.

In a preferred embodiment, the process comprises the step of (a-1) precipitating the sulfate or hemi-sulfate salt of (1r,4r)-6'-fluoro-N,N-dimethyl-4-phenyl-4',9'-dihydro-3'H-spiro[cyclohexane-1,1'-pyrano[3,4,b]indol]-4-amine from a solution or suspension of the free base.

For the purpose of the specification, "free base" preferably means that the compound according to general formula (I) is not present in form of a salt, particularly not in form of an acid-addition salt.

Conventional solvents known to persons skilled in the art may be used as solvents in a solution or suspension, preferably a solution, of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof. Preferred solvents are THF, DMSO, NMP, acetic acid, mixtures of acetic acid and dimethyl acetamide, mixtures of acetone and THF, mixtures of DMSO and acetic acid, and mixtures of THF and DMSO.

In an especially preferred embodiment, the organic solvent for dissolving the free base of the compound according to general formula (I) is a mixture of acetone and THF. Preferably, the ratio between acetone and THF is within the range of from 15:1 to 1:15, more preferably within the range of from 12:1 to 1:12 (volume/volume).

Step (a-1) may be carried out by the addition of sulfuric acid. In a preferred embodiment, sulfuric acid is added in form of a solution. In one preferred embodiment, the solution is a solution of sulfuric acid in an aqueous solvent, i.e. an aqueous solution of sulfuric acid. In another preferred embodiment, the solution is a solution of sulfuric acid in an organic solvent, especially preferred are alcohols such as ethanol, isopropanol and n-butanol, and ethers such as diethylether, di-isopropylether, tetrahydrofurane, methyl-tetrahydrofurane 1,4-dioxane or carbonic acids such as acetic acid and propionic acid.

In a preferred embodiment, the sulfuric acid containing solution and the solution of the free base contain the same solvent.

In another particularly preferred embodiment, the sulfuric acid containing solution and the solution of the free base contain not the same solvent.

In a particularly preferred embodiment containing solution is an aqueous solution and the solution of the free base is an organic solvent, in which the free base is dissolved.

Preferably, the solution contains sulfuric acid in a concentration within the range of from 0.01 mol/L to 15 mol/L, more preferably within the range of from 0.02 mol/L to 12.5 mol/L, still more preferably within the range of from 0.05 mol/L to 10 mol/L, yet more preferably within the range of from 0.1 mol/L to 7.5 mol/L, most preferably within the range of from 0.2 mol/L to 10 mol/L, and in particular within the range of from 0.3 mol/L to 5 mol/L.

Preferably, the sulfuric acid is added to the solution or suspension of the free base in molar excess, in particular in order to form a sulfate salt.

In another preferred embodiment, the sulfuric acid is added to the solution or suspension of the free base in lower molar amount than the molar amount of the free base, in particular in order to form a hemi-sulfate salt.

Preferably, in the process according to the invention, step (a-1) is carried out at a temperature below or at the boiling point of the respective solvent, preferably at a temperature not higher than 100° C., more preferably not higher than 80° C., even more preferably not higher than 60° C., and in particular in a temperature range of 20-40° C.

Preferably, in the process according to the invention, the suspension or solution obtained in step (a-1) is stirred for a time period of at least 1 minute, preferably at least 2 minutes, more preferably at least 3 minutes, still more preferably at least 5 minutes, yet more preferably at least 10 minutes, most preferably at least 20 minutes, and in particular at least 30 minutes.

In a preferred embodiment, the suspension or solution obtained in step (a-1) is stirred for a time period of at least 1 hour, preferably at least 4 hours, more preferably at least 6 hours, still more preferably at least 12 hours, yet more preferably at least 18 hours, most preferably at least 1 day, and in particular at least 2 days.

In another preferred embodiment, the suspension or solution obtained in step (a-1) is stirred for a time period of at most 1 day, preferably at most 12 hours, more preferably at most 6 hours, still more preferably at most 2 hours, yet more preferably at most 60 minutes, and most preferably at most 45 minutes, and in particular at most 30 minutes.

Preferably, the process according to the invention further comprises the step (b-1) separating, preferably filtering off the solid obtained in step (a-1).

Preferably, the process according to the invention further comprises the step (c-1) drying of the solid obtained in step (b-1).

In a preferred embodiment, step (c-1) takes place under air, nitrogen flow or argon flow.

In another preferred embodiment, step (c-1) takes place under vacuum, more preferably at a vacuum of 0 to 900 mbar, even more preferably at a vacuum of 1 to 500 mbar, and in particular at a vacuum of 10 to 200 mbar.

Preferably, in the process according to the invention, step (c-1) takes place in a temperature range from 0 to 60° C., preferably from 10° C. to 50° C. more preferably from 20 to 40° C.

In another preferred embodiment, the process comprises the step of (a-2) dissolving (1r,4r)-6'-fluoro-N,N-dimethyl-4-phenyl-4', 9'-dihydro-3'H-spiro[cyclohexane-1,1'-pyrano[3,4,b]indol]-4-amine sulfate or hemi-sulfate in a solvent.

Conventional solvents known to persons skilled in the art may be used as solvents in a solution of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof. Preferred solvents are THF, acetic acid, NMP, DMSO, mixtures of THF and DMSO, mixtures of DMSO and acetic acid, and mixtures of acetic acid and dimethyl acetamide (DMAc).

Preferably, in the process according to the invention, step (a-2) is carried out at a temperature below or at the boiling point of the respective solvent or solvent mixture, more preferably at a temperature not higher than 100° C., more preferably not higher than 80° C., even more preferably not higher than 60° C., and in particular in a temperature range of 20-40° C.

In a preferred embodiment, the process according to the invention further comprises the step
(b-2) evaporating the solvent of the solution obtained in step (a-2).

Suitable methods for evaporating the solvent are known to persons skilled in the art. Preferably, in the process according to the invention, the solvent is evaporated in air, air flow, or inert gas flow, in particular argon or nitrogen flow. However, evaporating the solvent under vacuum, for example by means of a rotary evaporator, is also possible. Preferably, in the process according to the invention, the solvent is evaporated at room temperature.

In another preferred embodiment, the process further comprises the step of
(b-2') precipitating (1r,4r)-6'-fluoro-N,N-dimethyl-4-phenyl-4',9'-dihydro-3'H-spiro[cyclo-hexane-1,1'-pyrano[3,4,b]indol]-4-amine sulfate or hemi-sulfate from the solution obtained in step (a-2), preferably by addition of a precipitant, Suitable methods of precipitation are known to persons skilled in the art. In the process according to the invention, step (b-2') may be carried out by reducing the volume of the solution obtained in step (a-2) and/or by cooling of the solution, preferably to a temperature of at most 15° C., more preferably at most 10° C., even more preferably at most 4-8° C. and/or by cooling of the solution, preferably to a temperature of at least 10° C., more preferably at least 30° C., even more preferably at least 60° C. below the temperature according to step (a-2).

In a preferred embodiment, step (b-2') is carried out by the addition of a medium in which (1r,4r)-6'-fluoro-N,N-dimethyl-4-phenyl-4',9'-dihydro-3' H-spiro[cyclohexane-1,1'-pyrano-[3,4,b]indol]-4-amine sulfate or hemi-sulfate is only poorly soluble ("anti-solvent") to the solution obtained in step (a-2). Said medium is preferably selected from the group consisting of esters such as ethyl acetate, n-propyl acetate, iso-propyl acetate, n-butyl acetate and iso-butyl acetate; alcohols such as methanol, ethanol, 1-propanol, 2-propanol; ethers such as tert-butyl methyl ether, diethyl ether and diisopropyl ether; ketones such as acetone, 2-butanone, pentan-2-one, pentan-3-one, hexan-2-one and hexan-3-one; nitriles such as acetonitril; pyridine, acetic acid and water, and DMSO. Particularly preferred are DMSO, 2-butanone (MEK), 2-propanol, and water; especially preferred are 2-butanone (MEK) and 2-propanol.

The amount of the media in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate is only poorly soluble, the precipitant or anti-solvent, is preferably selected in such a manner that upon its addition precipitation of the dissolved component begins. The total amount of the media in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate is only poorly soluble may also be divided into several portions, preferably two or three portions. In this embodiment, the precipitation of the dissolved component preferably begins after the addition of the last portion.

The precipitation of the dissolved component preferably begins either immediately after the precipitant, preferably the total amount of the precipitant, has been added or alternatively with a delay of 2 seconds to 120 minutes. Preferably, the precipitation of the dissolved component begins within a time period of at most 90 minutes, more preferably at most 60 minutes, still more preferably at most 30 minutes, even more preferably at most 5 minutes, most preferably at most 60 seconds and in particular at most 10 seconds.

Furthermore, the amount of the media in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate, is only poorly soluble, the precipitant or anti-solvent, is preferably selected in such a manner that the dissolved component is completely precipitated or at least up to 90% of the initial amount is precipitated within a time period of at most 90 minutes, more preferably at most 80 minutes, still more preferably at most 70 minutes, and most preferably at most 60 minutes after the anti-solvent has been completely added.

Step (b-2') may also be carried out by exposing the solution obtained in step (a-2) to an atmosphere containing a solvent, in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate is only poorly soluble, i.e. by a vapor diffusion crystallization technique.

In this embodiment, dichloromethane is preferably selected as solvent in step (a-2) and the solution obtained in step (a-2) is preferably exposed to an atmosphere containing hexane.

Preferably, in the process according to the invention, after step (b-2) or respectively (b-2'), all other steps are carried out at a temperature between 40 and 0° C., preferably between 35 and 5° C., more preferably between 25 and 15° C.

Preferably, in the process according to the invention, the suspension obtained in step (b-2') is stirred for a time period of at least 1 minute, preferably at least 2 minutes, more preferably at least 3 minutes, and most preferably at least 5 minutes.

Preferably, the process according to the invention further comprises the step
(c-2') separating, preferably filtering off the precipitate obtained in step (b-2').

Preferably, the process according to the invention further comprises the step
(d-2') drying of the solid obtained in step (c-2').

Preferably, in the process according to the invention, step (d-2') takes place under air or inert gas flow, such as argon or nitrogen flow. However, depending on the crystalline form to be obtained evaporating the solvent at an elevated temperature, e.g. within the range of from 20° C. to 60° C., is also possible.

In still another preferred embodiment, the process comprises the step of
(a-3) suspending (1r,4r)-6'-fluoro-N,N-dimethyl-4-phenyl-4',9'-dihydro-3'H-spiro[cyclo-hexane-1,1'-pyrano[3,4,b]indol]-4-amine sulfate or hemi-sulfate in a solvent.

Conventional solvents known to persons skilled in the art may be used as solvents in a suspension of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof. Preferred solvents are alcohols such as methanol or water, particularly preferred alcohols such as methanol.

In a preferred embodiment, step (a-3) is carried out at a temperature below or at the boiling point of the respective solvent, preferably at a temperature not higher than 100° C., more preferably not higher than 90° C., still more preferably not higher than 80° C., yet more preferably not higher than 60° C., most preferably not higher than 40° C., and in particular in a temperature range of 15-35° C.

In another preferred embodiment, step (a-3) is carried out in a temperature range of 100-40° C., more preferably 90-50° C., and most preferably 85-60° C.

Preferably, in the process according to the invention, the suspension obtained in step (a-3) is stirred for a time period of at least 2 h, preferably at least 4 hours, more preferably at least 8 hours, still more preferably at least 12 hours, yet more preferably at least 16 hours, most preferably at least 24 hours, and in particular at least 2 days.

Preferably, the process according to the invention further comprises the step
(b-3) separating, preferably filtering off the solid obtained in step (a-3).

Preferably, the process according to the invention further comprises the step
(c-3) drying of the solid obtained in step (b-3).

In the process according to the invention, step (c-3) may take place under air or inert gas flow, such as argon or nitrogen flow. However, drying under vacuum, more preferably at a vacuum of 0 to 900 mbar, even more preferably at a vacuum of 1 to 500 mbar, and in particular at a vacuum of 10 to 200 mbar is preferred.

Preferably, in the process according to the invention, step (c-3) takes place in a temperature range from 0 to 60° C., preferably from 10° C. to 50° C. more preferably from 20 to 40° C.

In still another preferred embodiment, the process comprises the step of
(a-4) reacting 2-(5-fluoro-1H-indol-3-yl)ethanol and 4-(dimethylamino)-4-phenylcyclohexanone or a protected derivative thereof, optionally in the form of an acid addition salt, in a carbonic acid as reaction medium in the presence of sulfuric acid to form (1r,4r)-6'-fluoro-N,N-dimethyl-4-phenyl-4',9'-dihydro-3'H-spiro[cyclohexane-1,1'-pyrano-[3,4,b]indol]-4-amine sulfate or hemi-sulfate.

A protected derivative of 4-(dimethylamino)-4-phenylcyclohexanone preferably means in the sense of the present invention a derivative of 4-(dimethylamino)-4-phenylcyclohexanone, wherein the keto-group of said compound is protected by a suitable protecting group, e.g. is present in the form of an ethylene glycol group. Reaction step (a-4) according to the present invention is an oxa-Pictet-Spengler reaction which is e.g. known from S.-Y. Chou et al., Heterocycles 2003, 60, 1095 and M. Zott et al., Tetrahedron: Asymmetry 1993, 4, 2307.

Any suitable carbonic acid can serve as reaction medium in step (a-4) according to the present invention. The reaction medium preferably serves as solvent for the starting material employed, i.e. for the compounds 2-(5-fluoro-1H-indol-3-yl)ethanol and 4-(dimethylamino)-4-phenylcyclohexanone or a protected derivative thereof, preferably also as a solvent for sulfuric acid. Preferably, the carbonic acid employed as reaction medium in step (a-4) according to the present invention is in liquid form at room temperature. Preferably, the carbonic acid employed as reaction medium in step (a-4) is selected from the group consisting of acetic acid, trifluoroacetic acid, propionic acid, lactic acid, 3-hydroxypropionic acid, butyric acid, isobutyric acid, acrylic acid and methacrylic acid or mixtures thereof. Preferably, the carbonic acid employed as reaction medium in step (a) is selected from the group consisting of acetic acid, trifluoroacetic acid, and propionic acid or mixtures thereof. Particularly preferred are acetic acid and propionic acid. Most preferred is acetic acid. In one particularly preferred embodiment of the present invention, the carbonic acid employed as reaction medium in step (a-4) is acetic acid. In another particularly preferred embodiment of the present invention, the carbonic acid employed as reaction medium in step (a-4) is propionic acid. Preferably, the carbonic acid as reaction medium is employed in step (a-4) in an amount by weight that is in the range of from 5 to 60 times higher than the total amount of starting material by weight. For example, in case 400 mg of 4-(dimethylamino)-4-phenylcyclohexanone or a protected derivative thereof is are employed, the carbonic acid as reaction medium is employed in an amount by weight, that is in the range of from 2 g to 24 g. More preferably, the carbonic acid as reaction medium is employed in step (a-4) in an amount by weight that is in the range of from 7 to 50 times, even more preferably 10 to 45 times, still more preferably 12 to 40 times, in particular 15 to 35 times, and most preferred 20 to 30 times higher than the total amount of 4-(dimethylamino)-4-phenylcyclohexanone or a protected derivative thereof by weight.

Preferably, sulfuric acid as promoting agent is employed in step (a-4) in an amount that is in the range of from 1.05 to 2.00 equivalents, preferably of from 1.10 to 1.90 equivalents, more preferably of from 1.10 to 1.70 equivalents, even more preferably of from 1.10 to 1.50 equivalents, still more preferably of from 1.10 to 1.40 equivalents, in particular of from 1.10 to 1.30 equivalents, in each case with respect to the molar amount of either 2-(5-fluoro-1H-indol-3-yl)ethanol or 4-(dimethylamino)-4-phenylcyclohexanone or a protected derivative thereof.

Preferably, sulfuric acid employed in step (a-4) according to the inventive process is soluble, preferably soluble at room temperature, in the reaction medium employed in step (a-4).

The reaction time of step (a-4) can vary in dependence on various parameters, such as, for example, temperature, stoichiometry, nature of the compound to be reacted with, or the nature of the reaction medium, and can be determined for the process in question by the person skilled in the art using preliminary tests. Preferably, the reaction time for performing step (a) does not exceed 24 hours, more preferably does not exceed 18 hours. Even more preferably, the reaction time is in the range of from 1 hour to 20 hours, still more preferably is in the range of from 2 hours to 18 hours, in particular is in the range of from 3 hours to 16 hours, most preferred is in the range of from 4 h to 10 hours.

Preferably, of the reaction mixture is stirred in step (a-4).

The reaction temperature at which step (a-4) is performed can vary in dependence on various parameters, such as, for example, reaction time, stoichiometry, nature of the compound to be reacted with, or nature of the reaction medium and can be determined for the process in question by the person skilled in the art using preliminary tests. Preferably, the reaction temperature at which step (a-4) of the inventive process is performed, is in the range of from 20° C. to 100° C., more preferably is in the range of from 30° C. to 90° C., even more preferably is in the range of from 40° C. to 80° C., still more preferably in the range of from 40° C. to 60° C. In another preferred embodiment of the present invention, the reaction temperature at which step (a-4) of the inventive process is performed is at least 30° C., preferably at least 40° C., more preferably at least 50° C.

In a particularly preferred embodiment
sulfuric acid is employed in step (a-4) in an amount that is in the range of from 1.10 to 1.30 equivalents with respect to the molar amount of 2-(5-fluoro-1H-indol-3-yl)ethanol or 4-(dimethylamino)-4-phenylcyclohexanone or a protected derivative thereof, and
the at least one carbonic acid as reaction medium employed in step (a) is acetic acid or propionic acid, preferably in an amount by weight that is in the range of from 5 to 60 times higher than the total amount of 4-(dimethylamino)-4-phenylcyclohexanone or a protected derivative thereof by weight.

In a very particularly preferred embodiment
sulfuric acid is employed in step (a-4) in an amount that is in the range of from 1.10 to 1.30 equivalents with respect to the molar amount of 2-(5-fluoro-1H-indol-3-yl)ethanol or 4-(dimethylamino)-4-phenylcyclohexanone or a protected derivative thereof,
the at least one carbonic acid as reaction medium employed in step (a) is acetic acid or propionic acid, preferably in an amount by weight that is in the range of from 5 to 60 times higher than the total amount of 4-(dimethylamino)-4-phenylcyclohexanone or a protected derivative thereof by weight,
the reaction temperature at which step (a) is performed is in the range of from 40° C. to 80° C., preferably in the range of from 40° C. to 60° C., and
the reaction time of step (a) is in the range of from 3 hours to 16 hours.

Preferably, the solid form of the compound according to formula (I) and sulfuric acid precipitates from the reaction mixture during the performance of step (a-4) and can be thus obtained from step (a-4) as a precipitate, preferably by filtration of the reaction mixture, i.e. by separating, preferably filtering off the precipitate.

Thus, preferably, the process according to the invention further comprises the step
(b-4) separating, preferably filtering off the solid obtained in step (a-4).

The solid obtained from step (b-4) can be optionally purified, e.g. by
(c-4) optionally performing steps (a-2) and (b-2) or (b-2') or performing steps (a-3) and (b-3).

The solid obtained from step (b-4) can be optionally further recrystallized in a manner well known to those skilled in the art, e.g. by recrystallization from a suitable solvent. Alternatively, the solid obtained can also be subjected to a chromatographic resolution.

Suitable solvents can be determined by the person skilled in the art using preliminary tests and include solvents such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; and also N-methyl-2-pyrrolidone, dimethyl acetamide, dimethyl formamide and dimethyl sulfoxide (DMSO); carbonic acids such as acetic acid and propionic acid, and mixtures thereof. Particularly preferred are acetic acid, mixtures of DMSO and acetic acid, mixtures of THF and DMSO, and mixtures of acetic acid and dimethyl acetamide. Recrystallization techniques well known to those skilled in the art e.g. include first dissolving the acid addition salt obtained from step (a) in a suitable solvent, optionally heating the mixture, followed by a precipitation of said acid addition salt, preferably by addition of another medium, or followed by evaporation off the solvent employed for dissolution.

Particularly preferred is a process comprising steps (a-1) and (b-1) steps (a-4) and (b-4) for the preparation of crystalline form G, especially preferred is such a process comprising steps (a-1) and (b-1).

A further aspect of the invention relates to a crystalline form G that is obtainable by the process as described above.

In preferred embodiment of the present invention, crystalline forms E, F and G are characterized by XRPD peaks calculated as Cu—Kα reflections at 298 K±5 K on the basis of single crystal Mo—Kα measurements at 100 K±5 K.

A further aspect of the present invention relates to a crystalline form H. Preferably, crystalline form H of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid is a (1r,4r)-6'-fluoro-N,N-dimethyl-4-phenyl-4',9'-dihydro-3'H-spiro[cyclohexane-1,1'-pyrano[3,4,b]indol]-4-amine hemi-sulfate, preferably a solvate thereof, more preferably a hydrate thereof.

The crystalline form H according to the present invention may be characterized in that it has one or more Raman bands selected from the group consisting of $917\pm2$ $cm^{-1}$, $1003\pm2$ $cm^{-1}$, $1572\pm2$ $cm^{-1}$, and $1586\pm2$ $cm^{-1}$.

The crystalline form H according to the present invention may further be characterized in that it has one or more Raman bands selected from the group consisting of $917\pm2$ $cm^{-1}$, $1003\pm2$ $cm^{-1}$, $1572\pm2$ $cm^{-1}$, and $1586\pm2$ $cm^{-1}$ and/or one or more additional Raman bands selected from the group consisting of $162\pm2$ $cm^{-1}$, $175\pm2$ $cm^{-1}$, $1028\pm2$ $cm^{-1}$, and $1038\pm2$ $cm^{-1}$.

The crystalline form H according to the present invention may further be characterized in that it has one or more Raman bands selected from the group consisting of $926\pm2$ $cm^{-1}$, $1116\pm2$ $cm^{-1}$, $1165\pm2$ $cm^{-1}$, $1200\pm2$ $cm^{-1}$, $1220\pm2$ $cm^{-1}$, $1265\pm2$ $cm^{-1}$, $1311\pm2$ $cm^{-1}$, $1360\pm2$ $cm^{-1}$, $1374\pm2$ $cm^{-1}$, $1443\pm2$ $cm^{-1}$, and $1466\pm2$ $cm^{-1}$.

The crystalline form H according to the present invention may further be characterized in that it has one or more additional Raman bands selected from the group consisting of $370\pm2$ $cm^{-1}$, $396\pm2$ $cm^{-1}$, $415\pm2$ $cm^{-1}$, $430\pm2$ $cm^{-1}$, $439\pm2$ $cm^{-1}$, $450\pm2$ $cm^{-1}$, $458\pm2$ $cm^{-1}$, $472\pm2$ $cm^{-1}$, $490\pm2$ $cm^{-1}$, $518\pm2$ $cm^{-1}$, $538\pm2$ $cm^{-1}$, $597\pm2$ $cm^{-1}$, $621\pm2$ $cm^{-1}$, $628\pm2$ $cm^{-1}$, $685\pm2$ $cm^{-1}$, $708\pm2$ $cm^{-1}$, $826\pm2$ $cm^{-1}$, and $888\pm2$ $cm^{-1}$.

The crystalline form H according to the present invention may further be characterized in that it has one or more additional Raman bands selected from the group consisting of $213\pm2$ $cm^{-1}$, $238\pm2$ $cm^{-1}$, $257\pm2$ $cm^{-1}$, $284\pm2$ $cm^{-1}$, $341\pm2$ $cm^{-1}$, $353\pm2$ $cm^{-1}$, $566\pm2$ $cm^{-1}$, and $982\pm2$ $cm^{-1}$.

A further aspect of the present invention relates to a crystalline form I. Preferably, crystalline form I of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid is a (1r,4r)-6'-fluoro-N,N-dimethyl-4-phenyl-4',9'-dihydro-3'H-spiro[cyclohexane-1,1'-pyrano[3,4,b]indol]-4-amine hemi-sulfate, preferably a solvate thereof, more preferably a toluene solvate thereof.

The crystalline form I according to the present invention may be characterized in that it has one or more Raman bands selected from the group consisting of 916±2 cm$^{-1}$, 1003±2 cm$^{-1}$, 1570±2 cm$^{-1}$, and 1582±2 cm$^{-1}$.

The crystalline form I according to the present invention may further be characterized in that it has one or more Raman bands selected from the group consisting of 916±2 cm$^{-1}$, 1003±2 cm$^{-1}$, 1570±2 cm$^{-1}$, and 1582±2 cm$^{-1}$ and/or one or more additional Raman bands selected from the group consisting of 169±2 cm$^{-1}$, 368±2 cm$^{-1}$, 397±2 cm$^{-1}$, and 434±2 cm$^{-1}$.

The crystalline form I according to the present invention may further be characterized in that it has one or more Raman bands selected from the group consisting of 187±2 cm$^{-1}$, 207±2 cm$^{-1}$, 259±2 cm$^{-1}$, 451±2 cm$^{-1}$, 491±2 cm$^{-1}$, 680±2 cm$^{-1}$, 923±2 cm$^{-1}$, 1031±2 cm$^{-1}$, 1037±2 cm$^{-1}$, 1201±2 cm$^{-1}$, 1296±2 cm$^{-1}$, and 1311±2 cm$^{-1}$.

The crystalline form I according to the present invention may further be characterized in that it has one or more additional Raman bands selected from the group consisting of 1478±2 cm$^{-1}$, 1466±2 cm$^{-1}$, 1459±2 cm$^{-1}$, 1454±2 cm$^{-1}$, 1443±2 cm$^{-1}$, 1375±2 cm$^{-1}$, 1358±2 cm$^{-1}$, 1339±2 cm$^{-1}$, 1264±2 cm$^{-1}$, 1157±2 cm$^{-1}$, 1113±2 cm$^{-1}$, 1057±2 cm$^{-1}$, 986±2 cm$^{-1}$, 824±2 cm$^{-1}$, 788±2 cm$^{-1}$, 633±2 cm$^{-1}$, 621±2 cm$^{-1}$, and 604±2 cm$^{-1}$.

The crystalline form I according to the present invention may further be characterized in that it has one or more additional Raman bands selected from the group consisting of 598±2 and 539±2 cm$^{-1}$.

A further aspect of the present invention relates to a crystalline form J. Preferably, crystalline form J of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid is a (1r,4r)-6'-fluoro-N,N-dimethyl-4-phenyl-4',9'-dihydro-3'H-spiro[cyclohexane-1,1'-pyrano[3,4,b]indol]-4-amine hemi-sulfate, preferably a solvate thereof, more preferably a THF solvate thereof.

The crystalline form J according to the present invention may be characterized in that it has one or more Raman bands selected from the group consisting of 916±2 cm$^{-1}$, 1003±2 cm$^{-1}$, 1572±2 cm$^{-1}$, and 1585±2 cm$^{-1}$.

The crystalline form J according to the present invention may further be characterized in that it has one or more Raman bands selected from the group consisting of 916±2 cm$^{-1}$, 1003±2 cm$^{-1}$, 1572±2 cm$^{-1}$, and 1585±2 cm$^{-1}$ and/or one or more additional Raman bands selected from the group consisting of 175±2 cm$^{-1}$, 258±2 cm$^{-1}$, 371±2 cm$^{-1}$, and 441±2 cm$^{-1}$.

The crystalline form J according to the present invention may further be characterized in that it has one or more Raman bands selected from the group consisting of 207±2 cm$^{-1}$, 415±2 cm$^{-1}$, 489±2 cm$^{-1}$, 519±2 cm$^{-1}$, 539±2 cm$^{-1}$, 598±2 cm$^{-1}$, 621±2 cm$^{-1}$, 685±2 cm$^{-1}$, 708±2 cm$^{-1}$, 825±2 cm$^{-1}$, 888±2 cm$^{-1}$, 1029±2 cm$^{-1}$, and 1037±2 cm$^{-1}$.

The crystalline form J according to the present invention may further be characterized in that it has one or more additional Raman bands selected from the group consisting of 1466±2 cm$^{-1}$, 1443±2 cm$^{-1}$, 1376±2 cm$^{-1}$, 1342±2 cm$^{-1}$, 1321±2 cm$^{-1}$, 1310±2 cm$^{-1}$, 1299±2 cm$^{-1}$, 1266±2 cm$^{-1}$, 1225±2 cm$^{-1}$, 1219±2 cm$^{-1}$, 1207±2 cm$^{-1}$, 1166±2 cm$^{-1}$, 1135±2 cm$^{-1}$, 1116±2 cm$^{-1}$, 1083±2 cm$^{-1}$, 1071±2 cm$^{-1}$, 1046±2 cm$^{-1}$, and 983±2 cm$^{-1}$.

The crystalline form J according to the present invention may further be characterized in that it has one or more additional Raman bands selected from the group consisting of 949±2 cm$^{-1}$, 925±2 cm$^{-1}$ and 787±2 cm$^{-1}$.

A further aspect of the present invention relates to a crystalline form K. Preferably, crystalline form K of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid is a (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate, more preferably a sulfate, even preferably a THF solvate and/or hydrate thereof.

The crystalline form K according to the present invention may be characterized in that it has one or more Raman bands selected from the group consisting of 918±2 cm$^{-1}$, 1004±2 cm$^{-1}$, 1568±2 cm$^{-1}$, and 1583±2 cm$^{-1}$.

The crystalline form K according to the present invention may further be characterized in that it has one or more Raman bands selected from the group consisting of 918±2 cm$^{-1}$, 1004±2 cm$^{-1}$, 1568±2 cm$^{-1}$, and 1583±2 cm$^{-1}$ and/or one or more additional Raman bands selected from the group consisting of 170±2 cm$^{-1}$, 257±2 cm$^{-1}$, 396±2 cm$^{-1}$, and 489±2 cm$^{-1}$.

The crystalline form K according to the present invention may further be characterized in that it has one or more Raman bands selected from the group consisting of 155±2 cm$^{-1}$, 207±2 cm$^{-1}$, 369±2 cm$^{-1}$, 433±2 cm$^{-1}$, 455±2 cm$^{-1}$, 514±2 cm$^{-1}$, 537±2 cm$^{-1}$, 566±2 cm$^{-1}$, 599±2 cm$^{-1}$, 621±2 cm$^{-1}$, 630±2 cm$^{-1}$, 680±2 cm$^{-1}$, and 717±2 cm$^{-1}$.

The crystalline form K according to the present invention may further be characterized in that it has one or more additional Raman bands selected from the group consisting of 1629±2 cm$^{-1}$, 1465±2 cm$^{-1}$, 1438±2 cm$^{-1}$, 1371±2 cm$^{-1}$, 1342±2 cm$^{-1}$, 1315±2 cm$^{-1}$, 1295±2 cm$^{-1}$, 1267±2 cm$^{-1}$, 1219±2 cm$^{-1}$, 1199±2 cm$^{-1}$, 1115±2 cm$^{-1}$, 1076±2 cm$^{-1}$, 1051±2 cm$^{-1}$, 1030±2 cm$^{-1}$, 982±2 cm$^{-1}$, 889±2 cm$^{-1}$, 829±2 cm$^{-1}$, and 787±2 cm$^{-1}$.

Further aspects of the present invention relates to a process for the production of the crystalline forms H, I, J and K, in each case independently of one another, as described above.

In a preferred embodiment, the process comprises the step of (a-1) precipitating the sulfate or hemi-sulfate salt of (1r,4r)-6'-fluoro-N,N-dimethyl-4-phenyl-4',9'-dihydro-3'H-spiro[cyclohexane-1,1'-pyrano[3,4,b]indol]-4-amine from a solution or suspension of the free base.

Conventional solvents known to persons skilled in the art may be used as solvents in a solution or suspension, preferably a solution, of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof. Preferred solvents are THF, DMSO, NMP, acetic acid, mixtures of acetic acid and dimethyl acetamide, mixtures of acetone and THF, mixtures of DMSO and acetic acid, and mixtures of THF and DMSO.

In an especially preferred embodiment, the organic solvent for dissolving the free base of the compound according to general formula (I) is a mixture of acetone and THF. Preferably, the ratio between acetone and THF is within the range of from 15:1 to 1:15, more preferably within the range of from 12:1 to 1:12 (volume/volume).

Step (a-1) may be carried out by the addition of sulfuric acid. In a preferred embodiment, sulfuric acid is added in form of a solution. In one preferred embodiment, the solution is a solution of sulfuric acid in an aqueous solvent, i.e. an aqueous solution of sulfuric acid. In another preferred embodiment, the solution is a solution of sulfuric acid in an organic solvent, especially preferred are alcohols such as ethanol, isopropanol and n-butanol, and ethers such as diethylether, di-isopropylether, tetrahydrofurane, methyl-tetrahydrofurane 1,4-dioxane or carbonic acids such as acetic acid and propionic acid.

In a preferred embodiment, the sulfuric acid containing solution and the solution of the free base contain the same solvent.

In another particularly preferred embodiment, the sulfuric acid containing solution and the solution of the free base contain not the same solvent.

In a particularly preferred embodiment containing solution is an aqueous solution and the solution of the free base is an organic solvent, in which the free base is dissolved.

Preferably, the solution contains sulfuric acid in a concentration within the range of from 0.01 mol/L to 15 mol/L, more preferably within the range of from 0.02 mol/L to 12.5 mol/L, still more preferably within the range of from 0.05 mol/L to 10 mol/L, yet more preferably within the range of from 0.1 mol/L to 7.5 mol/L, most preferably within the range of from 0.2 mol/L to 10 mol/L, and in particular within the range of from 0.3 mol/L to 5 mol/L. Preferably, the sulfuric acid is added to the solution or suspension of the free base in molar excess, in particular in order to form a sulfate salt.

In another preferred embodiment, the sulfuric acid is added to the solution or suspension of the free base in lower molar amount than the molar amount of the free base, in particular in order to form a hemi-sulfate salt.

Preferably, in the process according to the invention, step (a-1) is carried out at a temperature below or at the boiling point of the respective solvent, preferably at a temperature not higher than 100° C., more preferably not higher than 80° C., even more preferably not higher than 60° C., and in particular in a temperature range of 20-40° C.

Preferably, in the process according to the invention, the suspension or solution obtained in step (a-1) is stirred for a time period of at least 1 minute, preferably at least 2 minutes, more preferably at least 3 minutes, still more preferably at least 5 minutes, yet more preferably at least 10 minutes, most preferably at least 20 minutes, and in particular at least 30 minutes.

In a preferred embodiment, the suspension or solution obtained in step (a-1) is stirred for a time period of at least 1 hour, preferably at least 4 hours, more preferably at least 6 hours, still more preferably at least 12 hours, yet more preferably at least 18 hours, most preferably at least 1 day, and in particular at least 2 days.

In another preferred embodiment, the suspension or solution obtained in step (a-1) is stirred for a time period of at most 1 day, preferably at most 12 hours, more preferably at most 6 hours, still more preferably at most 2 hours, yet more preferably at most 60 minutes, and most preferably at most 45 minutes, and in particular at most 30 minutes.

Preferably, the process according to the invention further comprises the step
(b-1) separating, preferably filtering out the solid obtained in step (a-1).

Preferably, the process according to the invention further comprises the step
(c-1) drying of the solid obtained in step (b-1).

In a preferred embodiment, step (c-1) takes place under air, nitrogen flow or argon flow.

In another preferred embodiment, step (c-1) takes place under vacuum, more preferably at a vacuum of 0 to 900 mbar, even more preferably at a vacuum of 1 to 500 mbar, and in particular at a vacuum of 10 to 200 mbar.

Preferably, in the process according to the invention, step (c-1) takes place in a temperature range from 0 to 60° C., preferably from 10° C. to 50° C. more preferably from 20 to 40° C.

In another preferred embodiment, the process comprises the step of
(a-2) dissolving (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate in a solvent.

Conventional solvents known to persons skilled in the art may be used as solvents in a solution of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof. Preferred solvents are THF, acetic acid, NMP, DMSO, mixtures of THF and DMSO, mixtures of DMSO and acetic acid, and mixtures of acetic acid and dimethyl acetamide (DMAc).

Preferably, in the process according to the invention, step (a-2) is carried out at a temperature below or at the boiling point of the respective solvent or solvent mixture, more preferably at a temperature not higher than 100° C., more preferably not higher than 80° C., even more preferably not higher than 60° C., and in particular in a temperature range of 20-40° C.

In a preferred embodiment, the process according to the invention further comprises the step
(b-2) evaporating the solvent of the solution obtained in step (a-2).

Suitable methods for evaporating the solvent are known to persons skilled in the art. Preferably, in the process according to the invention, the solvent is evaporated in air, air flow, or inert gas flow, in particular argon or nitrogen flow. However, evaporating the solvent under vacuum, for example by means of a rotary evaporator, is also possible. Preferably, in the process according to the invention, the solvent is evaporated at room temperature.

In another preferred embodiment, the process further comprises the step of
(b-2') precipitating (1r,4r)-6'-fluoro-N,N-dimethyl-4-phenyl-4',9'-dihydro-3'H-spiro[cyclo-hexane-1,1'-pyrano[3,4,b]indol]-4-amine sulfate or hemi-sulfate from the solution obtained in step (a-2), preferably by addition of a precipitant, Suitable methods of precipitation are known to persons skilled in the art. In the process according to the invention, step (b-2') may be carried out by reducing the volume of the solution obtained in step (a-2) and/or by cooling of the solution, preferably to a temperature of at most 15° C., more preferably at most 10° C., even more preferably at most 4-8° C. and/or by cooling of the solution, preferably to a temperature of at least 10° C., more preferably at least 30° C., even more preferably at least 60° C. below the temperature according to step (a-2).

In a preferred embodiment, step (b-2') is carried out by the addition of a medium in which (1r,4r)-6'-fluoro-N,N-dimethyl-4-phenyl-4',9'-dihydro-3' H-spiro[cyclohexane-1,1'-pyrano-[3,4,b]indol]-4-amine sulfate or hemi-sulfate is only poorly soluble ("anti-solvent") to the solution obtained in step (a-2). Said medium is preferably selected from the group consisting of esters such as ethyl acetate, n-propyl acetate, iso-propyl acetate, n-butyl acetate and iso-butyl acetate; alcohols such as methanol, ethanol, 1-propanol, 2-propanol; ethers such as tert-butyl methyl ether, diethyl ether and diisopropyl ether; ketones such as acetone, 2-butanone, pentan-2-one, pentan-3-one, hexan-2-one and hexan-3-one; nitriles such as acetonitril; pyridine, acetic acid and water, and DMSO. Particularly preferred are DMSO, 2-butanone (MEK), 2-propanol, and water; especially preferred are 2-butanone (MEK) and 2-propanol.

The amount of the media in which (1r,4r)-6'-fluoro-N,N-dimethyl-4-phenyl-4',9'-dihydro-3'H-spiro[cyclohexane-1, 1'-pyrano[3,4,b]indol]-4-amine sulfate or hemi-sulfate is only poorly soluble, the precipitant or anti-solvent, is preferably selected in such a manner that upon its addition precipitation of the dissolved component begins. The total amount of the media in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate is only poorly soluble may also be divided into several portions, preferably two or three portions. In this embodiment, the precipitation of the dissolved component preferably begins after the addition of the last portion.

The precipitation of the dissolved component preferably begins either immediately after the precipitant, preferably the total amount of the precipitant, has been added or alternatively with a delay of 2 seconds to 120 minutes. Preferably, the precipitation of the dissolved component begins within a time period of at most 90 minutes, more preferably at most 60 minutes, still more preferably at most 30 minutes, even more preferably at most 5 minutes, most preferably at most 60 seconds and in particular at most 10 seconds.

Furthermore, the amount of the media in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate, is only poorly soluble, the precipitant or anti-solvent, is preferably selected in such a manner that the dissolved component is completely precipitated or at least up to 90% of the initial amount is precipitated within a time period of at most 90 minutes, more preferably at most 80 minutes, still more preferably at most 70 minutes, and most preferably at most 60 minutes after the anti-solvent has been completely added.

Step (b-2') may also be carried out by exposing the solution obtained in step (a-2) to an atmosphere containing a solvent, in which (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate is only poorly soluble, i.e. by a vapor diffusion crystallization technique.

In this embodiment, dichloromethane is preferably selected as solvent in step (a-2) and the solution obtained in step (a-2) is preferably exposed to an atmosphere containing hexane.

Preferably, in the process according to the invention, after step (b-2) or respectively (b-2'), all other steps are carried out at a temperature between 40 and 0° C., preferably between 35 and 5° C., more preferably between 25 and 15° C.

Preferably, in the process according to the invention, the suspension obtained in step (b-2') is stirred for a time period of at least 1 minute, preferably at least 2 minutes, more preferably at least 3 minutes, and most preferably at least 5 minutes.

Preferably, the process according to the invention further comprises the step
(c-2') separating, preferably filtering off the precipitate obtained in step (b-2').

Preferably, the process according to the invention further comprises the step
(d-2') drying of the solid obtained in step (c-2').

Preferably, in the process according to the invention, step (d-2') takes place under air or inert gas flow, such as argon or nitrogen flow. However, depending on the crystalline form to be obtained evaporating the solvent at an elevated temperature, e.g. within the range of from 20° C. to 60° C., is also possible.

In still another preferred embodiment, the process comprises the step of
(a-3) suspending (1r,4r)-6'-fluoro-N,N-dimethyl-4-phenyl-4',9'-dihydro-3'H-spiro[cyclo-hexane-1,1'-pyrano[3,4,b]indol]-4-amine sulfate or hemi-sulfate in a solvent.

Conventional solvents known to persons skilled in the art may be used as solvents in a suspension of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran (THF), diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; carbonic acids such as acetic acid and propionic acid; and also N-methyl-2-pyrrolidone (NMP), dimethyl acetamide, dimethyl formamide (DMF) and dimethyl sulfoxide (DMSO); and mixtures thereof. Preferred solvents are alcohols such as methanol or water, particularly preferred alcohols such as methanol.

In one preferred embodiment, step (a-3) is carried out at a temperature below or at the boiling point of the respective solvent, preferably at a temperature not higher than 100° C., more preferably not higher than 90° C., still more preferably not higher than 80° C., yet more preferably not higher than 60° C., most preferably not higher than 40° C., and in particular in a temperature range of 15-35° C. In another preferred embodiment, step (a-3) is carried out in a temperature range of 100-40° C., more preferably 90-50° C., and most preferably 85-60° C.

Preferably, in the process according to the invention, the suspension obtained in step (a-3) is stirred for a time period of at least 2 h, preferably at least 4 h, more preferably at least 8 hours, still more preferably at least 12 hours, yet more preferably at least 16 hours, most preferably at least 24 hours, and in particular at least 2 days.

Preferably, the process according to the invention further comprises the step
(b-3) separating, preferably filtering off the solid obtained in step (a-3).

Preferably, the process according to the invention further comprises the step (c-3) drying of the solid obtained in step (b-3).

In the process according to the invention, step (c-3) may take place under air or inert gas flow, such as argon or nitrogen flow. However, drying under vacuum, more preferably at a vacuum of 0 to 900 mbar, even more preferably at a vacuum of 1 to 500 mbar, and in particular at a vacuum of 10 to 200 mbar is preferred.

Preferably, in the process according to the invention, step (c-3) takes place in a temperature range from 0 to 60° C., preferably from 10° C. to 50° C. more preferably from 20 to 40° C.

Further aspects of the invention relate to a crystalline forms H, I, J and K that are independently of one another obtainable by the process as described above.

A further aspect of the present invention relates to a crystalline form which is obtained by a process comprising the steps of (a-1) precipitating the sulfate or hemi-sulfate salt of (1r,4r)-6'-fluoro-N,N-dimethyl-4-phenyl-4',9'-dihydro-3'H-spiro[cyclohexane-1,1'-pyrano[3,4,b]indol]-4-amine from a solution or suspension of the free base; and (b-1) separating, preferably filtering off the solid;

wherein the free base is dissolved or suspended in a solvent or solvent mixture selected from the group consisting of acetone, 2-butanone, a mixture of ethanol and THF, ethyl acetate, THF, 1,4-dioxane, 1-butanol, a mixture of acetone and $H_2O$, and a mixture of THF and $H_2O$, or (a-2) dissolving (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate in a solvent; and (b-2) evaporating the solvent from the solution, or (b-2') precipitating (1r,4r)-6'-fluoro-N,N-dimethyl-4-phenyl-4',9'-dihydro-3'H-spiro-[cyclohexane-1,1'-pyrano[3,4,b]indol]-4-amine sulfate or hemi-sulfate from the solution;

wherein the solvent is selected from the group consisting of 2-propanol, 2-butanone, iso-butyl acetate, TBME, ethanol, 1-butanol, toluene and $H_2O$, or (a-3) suspending (1r,4r)-6'-fluoro-N,N-dimethyl-4-phenyl-4',9'-dihydro-3'H-spiro-[cyclohexane-1,1'-pyrano[3,4,b]indol]-4-amine sulfate or hemi-sulfate in a solvent, and stirring the resulting suspension; and (b-3) separating, preferably filtering off the solid;

wherein the solvent is selected from the group consisting of 2-propanol, 2-butanone, iso-butyl acetate, TBME, ethanol, 1-butanol, toluene and $H_2O$.

In some embodiments, the solid forms of the present invention make it possible to obtain (1r,4r)-6'-fluoro-N,N-dimethyl-4-phenyl-4',9'-dihydro-3'H-spiro[cyclohexane-1,1'-pyrano[3,4,b]indol]-4-amine in form of the sulfate or hemi-sulfate salt with high yields and purity. These forms are further distinguished in that they have fundamentally different properties, which may provide advantages.

In some embodiments, the solid forms of the present invention are characterized by higher ease-of-handling and allow for more precise (or even exact) metering of the active ingredient.

In some embodiments, it has been surprisingly found that (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate is capable of forming an ansolvate form (crystalline forms B and G), a hydrate (crystalline form A) and different solvates with organic solvents and/or water (crystalline forms C, D, E and F).

In some embodiments, it has been surprisingly found that (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate is capable of forming different solvates with organic solvents and/or water (crystalline forms H, I, J and K).

In some embodiments, it has been surprisingly found that some crystalline forms or mixtures thereof are obtained by crystallization techniques with short equilibration times. In some embodiments, it has been surprisingly found that crystalline form A represents the most dominant form obtainable by these fast crystallization techniques as long as the presence of water and/or moisture has not been prevented.

Further, it has been found that crystalline form B is not hygroscopic. In some embodiments, it has been found that crystalline form B may be obtained from crystalline form A by treating crystalline form A in an alcohol such as methanol.

In some embodiments, it has been found that some crystalline forms such as crystalline form B can be obtained by slower crystallization techniques. In some embodiments, it has surprisingly been found that crystalline form A may be converted into other crystalline forms such as crystalline forms B, C and D by these slower crystallization techniques.

Mixtures of the crystalline forms A, B, C, D, E, F, G, H, I, J and K, preferably mixtures of two or three of these crystalline forms, are also included within the scope of the present invention.

In a preferred embodiment, the crystalline form according to the invention is subsequently converted into an amorphous form.

Another aspect of the invention relates to a composition comprising a mixture of at least two solid, preferably crystalline forms as described herein; or a mixture of at least one solid, preferably crystalline form as described herein with an amorphous form; or a mixture of at least one solid, preferably crystalline form as described herein with a solid, preferably crystalline form of (1r,4r)-6'-fluoro-N,N-dimethyl-4-phenyl-4',9'-dihydro-3'H-spiro[cyclo-hexane-1,1'-pyrano[3,4,b]indol]-4-amine (free base) in any mixing ratio.

In a preferred embodiment, the pharmaceutical composition according to the invention additionally comprises a solid, preferably crystalline form of (1r,4r)-6'-fluoro-N,N-dimethyl-4-phenyl-4',9'-dihydro-3'H-spiro[cyclohexane-1,1'-pyrano[3,4,b]indol]-4-amine (free base). Thus, according to this embodiment, the pharmaceutical composition comprises a mixture of both, the solid, preferably crystalline form of (1r,4r)-6'-fluoro-N,N-dimethyl-4-phenyl-4',9'-dihydro-3'H-spiro[cyclohexane-1,1'-pyrano[3,4,b]indol]-4-amine (free base), as well as a sulfuric acid salt thereof, preferably the hydrogen sulfate salt, as described herein.

Preferably, the total content of the sulfuric acid salt of (1r,4r)-6'-fluoro-N,N-dimethyl-4-phenyl-4',9'-dihydro-3'H-spiro[cyclohexane-1,1'-pyrano[3,4,b]indol]-4-amine, preferably the hydrogen sulfate salt, is at most 2000 ppm, more preferably at most 1000 ppm, still more preferably at most 750 ppm, yet more preferably at most 500 ppm, even more preferably at most 250 ppm, most preferably at most 100 ppm, and in particular at most 50 ppm, relative to the total amount (1r,4r)-6'-fluoro-N,N-dimethyl-4-phenyl-4',9'-dihydro-3'H-spiro-[cyclohexane-1,1'-pyrano[3,4,b]indol]-4-amine (free base+salts).

Preferably, the total content of the sulfuric acid salt of (1r,4r)-6'-fluoro-N,N-dimethyl-4-phenyl-4',9'-dihydro-3'H-spiro[cyclohexane-1,1'-pyrano[3,4,b]indol]-4-amine, preferably the hydrogen sulfate salt, is within the range of from 1 ppm to 500 ppm, more preferably 4 ppm to 440 ppm, still more preferably 7 ppm to 380 ppm, yet more preferably 10 ppm to 300 ppm, even more preferably 13 ppm to 220 ppm, most preferably 17 ppm to 140 ppm, and in particular 20 ppm to 60 ppm, relative to the total amount (1r,4r)-6'-fluoro-N,N-dimethyl-4-phenyl-4',9'-dihydro-3'H-spiro[cyclohexane-1,1'-pyrano[3,4,b]indol]-4-amine (free base+salts).

Suitable methods for determining the content of the sulfuric acid salt of (1r,4r)-6'-fluoro-N,N-dimethyl-4-phenyl-4',9'-dihydro-3'H-spiro[cyclohexane-1,1'-pyrano[3,4,b]indol]-4-amine are known to those skilled in the art and include e.g. XRPD, elemental analysis, Raman spectroscopy, infrared spectroscopy, chromatographic methods, NMR spectroscopy, thermal analysis, electrophoresis, atom absorption spectroscopy, energy dispersive X-ray spectroscopy thermal methods comprise, among others, e.g. DSC, TGA, modulated temperature DSC, high-speed DSC, melting point, hot-stage XRPD, hot-stage microscopy, heat of solution, microthermal analysis, calorimetry, micro-calorimetry.

In another aspect the present invention relates to a solid form, in particular a crystalline form and/or an amorphous form and/or a mixture of at least two solid, preferably crystalline forms as described herein and/or a mixture of at least one solid, preferably crystalline form as described herein with an amorphous form and/or a mixture of at least one solid, preferably crystalline form as described herein with the crystalline form of (1r,4r)-6'-fluoro-N,N-dimethyl-4-phenyl-4',9'-dihydro-3'H-spiro[cyclohexane-1,1'-pyrano[3,4,b]indol]-4-amine (free base) as described herein for use in the treatment of pain.

In another aspect the present invention relates to methods of treating pain, comprising administering a solid form as described herein to a patient in need thereof (for example, a patient who has been diagnosed with a pain disorder).

In another aspect the present invention relates to methods of treating pain, comprising administering a pharmaceutical composition that comprises a solid form as described herein to a patient in need thereof (for example, a patient who has been diagnosed with a pain disorder).

The term pain as used herein preferably includes but is not limited to pain selected from the group consisting of inflammatory pain, postoperative pain, neuropathic pain, diabetic neuropathic pain, acute pain, chronic pain, visceral pain, migraine pain and cancer pain.

In some preferred embodiments, the solid form, in particular the crystalline form and/or the amorphous form according to the invention is for use in the treatment of acute, visceral, neuropathic or chronic pain (cf. WO 2008/040481).

In another aspect the present invention relates to a pharmaceutical composition comprising a solid form, in particular a crystalline form and/or an amorphous form as described herein and optionally one or more suitable additives and/or adjuvants such as described below.

In some preferred embodiments, the pharmaceutical composition comprises between about 0.001% by weight and about 40% by weight of one or more of the solid forms, in particular crystalline forms and/or amorphous forms described herein. In some preferred embodiments, the pharmaceutical composition comprises between about 0.001% by weight and about 20% by weight of one or more of the solid forms, in particular crystalline forms and/or amorphous forms described herein. In some preferred embodiments, the pharmaceutical composition comprises between about 0.001% by weight and about 10% by weight of one or more of the solid forms, in particular crystalline forms and/or amorphous forms described herein. In some preferred embodiments, the pharmaceutical composition comprises between about 0.001% by weight and about 5% by weight of one or more of the solid forms, in particular crystalline forms and/or amorphous forms described herein. In some preferred embodiments, the pharmaceutical composition comprises between about 0.001% by weight and about 1% by weight of one or more of the solid forms, in particular crystalline forms and/or amorphous forms described herein. In some preferred embodiments, the pharmaceutical composition comprises between about 0.01% by weight and about 1% by weight of one or more of the solid forms, in particular crystalline forms and/or amorphous forms described herein.

Preferably said pharmaceutical composition may be used for the treatment of pain.

In still another aspect the present invention relates to a medicament comprising a solid form, in particular a crystalline form and/or an amorphous form as described herein. In yet another aspect the present invention relates to a medicament comprising the pharmaceutical composition as described herein. In a preferred embodiment, the medicament is a solid drug form. The medicament is preferably manufactured for oral administration. However, other forms of administration are also possible, e.g. for buccal, sublingual, transmucosal, rectal, intralumbal, intraperitoneal, transdermal, intravenous, intramuscular, intragluteal, intracutaneous and subcutaneous application.

Depending on the configuration, the medicament (dosage form) preferably contains suitable additives and/or adjuvants. Suitable additives and/or adjuvants in the sense of the invention are all substances known to persons skilled in the art for the formation of galenic formulations. The choice of these adjuvants and also the quantities to be used are dependent on how the medication is to be administered, i.e. orally, intravenously, intraperitoneally, intradermally, intramuscularly, intranasally, buccally or locally.

In some preferred embodiments, the dosage form comprises 40±35 µg, more preferably 40±30 µg, still more preferably 40±25 µg, yet more preferably 40±20 µg, even more preferably 40±15 µg, most preferably 40±10 µg, and in particular 40±5 µg of one or more of the crystalline forms described herein. In some other preferred embodiments, the dosage form comprises 400±375 µg or 400±350 µg, more preferably 400±300 µg, still more preferably 400±250 µg, yet more preferably 400±200 µg, even more preferably 400±150 µg, most preferably 40±100 µg, and in particular 400±50 µg of one or more of the crystalline forms described herein.

Preparations suitable for oral administration are those in the form of tablets, chewable tablets, lozenges, capsules, granules, drops, liquids or syrups, and those suitable for parenteral, topical and inhalatory administration are solutions, suspensions, easily reconstituted dry preparations and sprays. A further possibility is suppositories for rectal administration. The application in a depot in dissolved form, a patch or a plaster, possibly with the addition of agents promoting skin penetration, are examples of suitable percutaneous forms of application.

Examples of adjuvants and additives for oral forms of application are disintegrants, lubricants, binders, fillers, mould release agents, possibly solvents, flavourings, sugar, in particular carriers, diluents, colouring agents, antioxidants etc.

Waxes or fatty acid esters, amongst others, can be used for suppositories and carrier substances, preservatives, suspension aids etc. can be used for parenteral forms of application.

Adjuvants can be, for example: water, ethanol, 2-propanol, glycerine, ethylene glycol, propylene glycol, polyethylene glycol, polypropylene glycol, glucose, fructose, lactose, saccharose, dextrose, molasses, starch, modified starch, gelatine, sorbitol, inositol, mannitol, microcrystalline cellulose, methyl cellulose, carboxymethyl-cellulose, cellulose acetate, shellac, cetyl alcohol, polyvinylpyrrolidone, paraffins, waxes, natural and synthetic rubbers, acacia gum, alginates, dextran, saturated and unsaturated fatty acids, stearic acid, magnesium stearate, zinc stearate, glyceryl stearate, sodium lauryl sulphate, edible oils, sesame oil, coconut oil, peanut oil, soybean oil, lecithin, sodium lactate, polyoxyethylene and propylene fatty acid esters, sorbitane fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulphate, zinc sulphate, calcium sulphate, potash, calcium phosphate, dicalcium phosphate, potassium bromide, potassium iodide, talc, kaolin, pectin, crospovidon, agar and bentonite.

The production of these medicaments and pharmaceutical compositions is conducted using means, devices, methods and processes that are well known in the art of pharmaceutical technology, as described, for example, in "*Remington's Pharmaceutical Sciences*", A. R. Gennaro, 17th ed., Mack Publishing Company, Easton, Pa. (1985), in particular in part 8, chapters 76 to 93.

Thus, for example, for a solid formulation such as a tablet, the active substance of the drug can be granulated with a pharmaceutical carrier substance, e.g. conventional tablet constituents such as cornstarch, lactose, saccharose, sorbitol, talc, magnesium stearate, dicalcium phosphate or pharmaceutically acceptable rubbers, and pharmaceutical diluents such as water, for example, in order to form a solid composition that contains the active substance in a homogenous dispersion. Homogenous dispersion is understood here to mean that the active substances are uniformly dispersed throughout the composition, so that this can be readily divided into identically effective standard dosage forms such as tablets, capsules, lozenges. The solid composition is then divided into standard dosage forms. The tablets or pills can also be coated or otherwise compounded to prepare a slow release dosage form. Suitable coating agents include polymeric acids and mixtures of polymeric acids with materials such as shellac, cetyl alcohol and/or cellulose acetate, for example.

In one embodiment of the present invention the solid form, in particular the crystalline form and/or the amorphous forms described herein is present in immediate release form.

In another embodiment of the present invention the solid form, in particular the crystalline form and/or the amorphous form as described herein is at least partially present in controlled-release form. In particular, the active ingredient can be released slowly from preparations that can be applied orally, rectally or percutaneously.

The medicament can preferably be manufactured for administration once daily, twice daily (bid), or three times daily, the once daily or twice daily administration (bid) being preferred.

The term controlled release as used herein refers to any type of release other than immediate release such as delayed release, sustained release, slow release, extended release and the like. These terms are well known to any person skilled in the art as are the means, devices, methods and processes for obtaining such type of release.

In another embodiment of the present invention
- the medicament is manufactured for oral administration; and/or
- the medicament is a solid and/or compressed and/or film-coated drug form; and/or
- the medicament releases the solid form, in particular the crystalline form and/or the amorphous form as described herein slowly from a matrix; and/or
- the medicament contains the solid form, in particular the crystalline form and/or the amorphous form in a quantity of 0.001 to 99.999% by wt., more preferred 0.1 to 99.9% by wt., still more preferred 1.0 to 99.0% by wt., even more preferred 2.5 to 80% by wt., most preferred 5.0 to 50% by wt. and in particular 7.5 to 40% by wt., based on the total weight of the medicament; and/or
- the medicament contains a pharmaceutically compatible carrier and/or pharmaceutically compatible adjuvants; and/or
- the medicament has a total mass in the range of 25 to 2000 mg, more preferred 50 to 1800 mg, still more preferred 60 to 1600 mg, more preferred 70 to 1400 mg, most preferred 80 to 1200 mg and in particular 100 to 1000 mg; and/or
- the medicament is selected from the group comprising tablets, capsules, pellets and granules.

The medicament can be provided as a simple tablet and as a coated tablet (e.g. as film-coated tablet or lozenge). The tablets are usually round and biconvex, but oblong forms are also possible. Granules, spheres, pellets or microcapsules, which are contained in sachets or capsules or are compressed to form disintegrating tablets, are also possible.

In yet another one of its aspects, the present invention relates to the use of the solid form, in particular the crystalline form and/or the amorphous form as described herein for the production of a medicament. Preferably said medicament is suitable for the treatment of pain.

In still another one of its aspects, the present invention relates to the use of the solid form, in particular the crystalline form and/or the amorphous form as described herein for the treatment of pain.

Furthermore, the present invention relates to a method for treating pain in a patient, preferably in a mammal, which comprises administering an effective amount of a solid form, in particular a crystalline form and/or an amorphous form as described herein to a patient.

EXAMPLES

The following examples serve to explain the invention in more detail, but should not be interpreted as restrictive. The following abbreviations are used in the examples:

iBuOAc iso-butyl acetate
1BuOH n-butanol (1-butanol)
DMSO dimethylsulfoxid
EA elemental analysis
EtOAc ethyl acetate
EtOH ethanol
h hour(s)
IPE diisopropyl ether
MeCN acetonitril
MEK 2-butanone
MeOH methanol
min minute(s)
NMP N-methyl-2-pyrrolidone
1PrOH n-propanol (1-propanol)
2PrOH iso-propanol (2-propanol)
r.h. relative humidity
RT or r.t. room temperature, preferably 20-25° C.
sec seconds
TBME tert-butyl methyl ether
THF tetrahydrofuran
NMR nuclear magnetic resonance spectroscopy
PXRD powder x-ray diffraction
XRPD x-ray powder diffraction
SCXRD single crystal x-ray diffraction FT Raman Fourier-Transform Raman spectroscopy
TG-FTIR thermogravimetry coupled with Fourier-Transform infrared spectroscopy
DSC differential scanning calorimetry
DVS dynamic vapour sorption Unless otherwise specified, solvent mixtures are always volume/volume.

Synthesis of (1r,4r)-6'-fluoro-N,N-dimethyl-4-phenyl-4',9'-dihydro-3'H-spiro[cyclohexane-1,1'-pyrano[3,4,b]indol]-4-amine Alternative 1

(4-(dimethylamino)-4-phenylcyclohexanone (3 g, 13.82 mmol), 2-(5-fluoro-1H-indol-3-yl)ethanol (2.47 g, 13.82 mmol) and 150 mL dichloromethane were charged to a flask at 0° C. A solution of trifluoromethane sulfonic acid trimethylsilylester (3 mL, 15.5 mmol) in 3 mL dichloromethane were added quickly. The reaction mixture changed color to violet and the temperature rose to 10° C. The reaction mixture was cooled in an ice bath and stirred for 20 min. Meanwhile a solid precipitated. The ice bath was removed and the reaction mixture was stirred for 3 to 3.5 hours at room temperature. Subsequently 50 mL of NaOH (1N) were added and the reaction mixture was stirred further 10 min. The colour changed to yellow and a solid precipitated. In order to complete the precipitation the reaction mixture (two liquid phases) was stirred for further 20 min while cooled in an ice bath. Eventually the solid was filtered off. The resulting solid (4.2 g) was subsequently recrystallized in 800 mL 2-propanol. Yield: 3.5 g.

To enhance the yield, the liquid (water and dichloromethane) filtrate was separated. The aqueous solution with extracted 3 times with 20 mL dichloromethane. The organic phases were united and dried with $MgSO_4$ and subsequently the solvent was stripped off until dryness. The resulting solid (1.7 g) was subsequently recrystallized under reflux in 800 mL 2-Propanol.

Alternative 2

23.65 g (0.132 mol) of 2-(5-fluoro-1H-indol-3-yl)ethanol and 28.68 g (0.132 mol) of (4-(dimethylamino)-4-phenylcyclohexanone are dissolved in 717 ml of acetic acid. The mixture is warmed up to 45-50° C. under stirring. At 45-50° C. 8.44 ml (0.158 mol) of sulfuric acid are added over a period of 20-30 seconds. The resulting solid is stirred for 4-16 h at 50-60° C. The mixture is cooled to 20° C., filtered off and washed subsequently with each 72 ml of acetic acid and isopropanol. The solid is suspended in 550 ml of isopropanol and 42 ml of diethylamine are added. The resulting suspension is stirred at room temperature for 17-20 h. The solid is filtered off and washed with 144 ml of isopropanol. 450 ml of dimethyl sulfoxide (DMSO) are added to dissolve the solid at 80-87° C. Then 1200 ml of isopropanol are added and the mixture is cooled to room temperature. The resulting solid is filtered off after 3-24 h and washed with 200 ml of isopropanol. The solid is suspended in 250 ml of ethyl acetate and stirred at 55-70° C. for 10-24 h. The solid is filtered off and dried in vacuum. Yield: 50-60%.

Alternatively, instead of sulfuric acid, another mono- or diprotic acid such as trifluoromethane sulphonic acid may be employed.

Synthesis of Crystalline Form A

Alternative 1

150 mg (1r,4r)-6'-fluoro-N,N-dimethyl-4-phenyl-4',9'-dihydro-3'H-spiro[cyclohexane-1,1'-pyrano[3,4,b]indol]-4-amine were dissolved in 25 mL acetone and 1 mL THF. 0.8 mL of sulfuric acid (0.5 M in $H_2O$) was added. The salt precipitated out after short time of stirring. The resulting suspension was stirred for 1 day at RT. The resulting solids were filtered off and dried in air. A crystalline solid of crystalline form A was obtained and characterized by NMR, PXRD, FT Raman, TG-FTIR, DSC and elemental analysis (cf. Section "Analysis").

By addition of 2 mL of TBME to 30 mg of crystalline form A, stirring the resulting suspension for 5 days at RT and separating, preferably filtering off the resulting solid and drying said solid in air, crystalline form A is still obtained as characterized by FT Raman and TG-FTIR (cf. Section "Analysis").

Alternative 2

205 mg (1r,4r)-6'-fluoro-N,N-dimethyl-4-phenyl-4',9'-dihydro-3'H-spiro[cyclohexane-1,1'-pyrano[3,4,b]indol]-4-amine were dissolved in 34 mL acetone and 1.4 mL THF. 1.1 mL of sulfuric acid (0.5 M in $H_2O$) was added. The salt precipitated out after short time of stirring. The resulting suspension was stirred for 4 days at RT. The precipitate was filtered off and dried in air. A crystalline solid of crystalline form A was obtained and characterized by FT Raman (cf. Section "Analysis").

Synthesis of Crystalline Form B

Alternative 1

150 mg (1r,4r)-6'-fluoro-N,N-dimethyl-4-phenyl-4',9'-dihydro-3'H-spiro[cyclohexane-1,1'-pyrano[3,4,b]indol]-4-amine were dissolved in 25 mL acetone and 2 mL THF. 0.8 mL of sulfuric acid (0.5 M in $H_2O$) was added. The salt precipitated out after short time of stirring. The resulting suspension was stirred for 3 days at RT. The precipitate was filtered off and dried in air. 2 mL of MeOH was added to the obtained solid. The resulting suspension was stirred at RT for 3 days. The resulting solid was filtered off and dried in air. A crystalline solid of crystalline form B was obtained and characterized by NMR, PXRD, FT Raman and TG-FTIR (cf. Section "Analysis").

Alternative 2

2 mL of MeOH were added to 30 mg of crystalline form A. The suspension was stirred for 5 days at RT. The resulting solids were filtered off and dried in air. A crystalline solid of crystalline form B was obtained and characterized by NMR, PXRD, FT Raman, TG-FTIR, DSC, elemental analysis and DVS (cf. Section "Analysis").

Synthesis of Crystalline Form C

Alternative 1

100 mg (1r,4r)-6'-fluoro-N,N-dimethyl-4-phenyl-4',9'-dihydro-3'H-spiro[cyclohexane-1,1'-pyrano[3,4,b]indol]-4-amine were dissolved in 8 mL THF. 0.5 mL of sulfuric acid (0.5 M in $H_2O$) was added. The resulting suspension was stirred at 50° C. for 1 h, for 3 days at RT, 6 h at 50° C. and over night at RT. The resulting solid was filtered off and then dissolved in 4 mL of hot NMP (120° C.-130° C.). The resulting solution was cooled to RT over night. The resulting precipitate was filtered off and dried in air. A crystalline solid of crystalline form C was obtained and characterized by FT Raman and NMR (cf. Section "Analysis").

Alternative 2

20 mg of crystalline form A were dissolved in 2 mL NMP. The solution was stored in a saturated atmosphere of MEK. The resulting precipitate was filtered off and dried in air. A crystalline solid of crystalline form C was obtained and characterized by FT Raman and TG-FTIR (cf. Section "Analysis").

Alternative 3

20 mg of crystalline form A were dissolved in 2 mL NMP. The solution was stored in a saturated atmosphere of 2-propanol. The resulting precipitate was filtered off and dried in air. A crystalline solid of crystalline form C was obtained. A crystalline solid of crystalline form C was obtained and characterized by FT Raman (cf. Section "Analysis").

Synthesis of Crystalline Form D 100 mg (1r,4r)-6'-fluoro-N,N-dimethyl-4-phenyl-4',9'-dihydro-3'H-spiro[cyclohexane-1,1'-pyrano[3,4,b]indol]-4-amine were dissolved in 18 mL acetone and 2 mL THF. 0.5 mL of sulfuric acid (0.5 M in $H_2O$) was added. The resulting suspension was stirred for 1 h at 50° C., 3 days at RT, 6 h at 50° C. and over night at RT. The solid was filtered off and dissolved in 8 mL of hot DMSO (120° C.-130° C.). The resulting solution was cooled to RT over night. The resulting precipitate was filtered off and dried in air. A crystalline solid of crystalline form D was obtained and characterized by FT Raman and TG-FTIR (cf. Section "Analysis").

Synthesis of Crystalline Form E 23.65 g (0.132 mol) of 2-(5-fluoro-1H-indol-3-yl)ethanol and 28.68 g (0.132 mol) of (4-(dimethylamino)-4-phenylcyclohexanone are dissolved in 717 ml of acetic acid. The mixture is warmed up to 45-50° C. under stirring. At 45-50° C. 8.44 ml (0.158 mol) of sulfuric acid are added over a period of 20-30 seconds. The resulting solid is stirred for 4-16 h at 50-60° C. The mixture is cooled to 20° and filtered off. 2 g of the obtained solid was dissolved in 65 ml THF/DMSO and the resulting solution was filtered and stored over air overnight. The resulting crystals were filtered off and the mother liquor was left for more than 48 h over air. The resulting single crystals were filtered of and single crystal structure analysis (SCXRD) was performed (yield: roughly 130 mg). From the SCXRD data the corresponding PXRD pattern was calculated (cf. Section "Analysis").

Synthesis of Crystalline Form F 5 g of (1r,4r)-6'-fluoro-N,N-dimethyl-4-phenyl-4',9'-dihydro-3'H-spiro[cyclohexane-1,1'-pyrano-[3,4,b]indol]-4-amine were dissolved in 500 ml of acetic acid at 60° C. and 1.25 equivalents of sulfuric acid were added. After 16 h the resulting solid was filtered off and dissolved in 400 ml of acetic acid and 150 ml dimethyl acetamide (DMAc) at 95° C. The resulting solution was allowed to cool down to room temperature without stirring. The resulting crystals were analyzed by single crystal analysis (SCXRD). From the SCXRD data the corresponding PXRD pattern was calculated (cf. Section "Analysis").

Synthesis of Crystalline Form G 5 g of (1r,4r)-6'-fluoro-N,N-dimethyl-4-phenyl-4',9'-dihydro-3'H-spiro[cyclohexane-1,1'-pyrano-[3,4,b]indol]-4-amine were dissolved in 500 ml of acetic acid at 60° C. and 1.25 equivalents of sulfuric acid were added. After 16 h the resulting solid was filtered off and 1.5 g of the resulting wet solid was dissolved in 800 ml of acetic acid at 90° C. 10 ml of DMSO were added and the resulting solution was allowed to cool down to room temperature without stirring. The resulting crystals were analyzed by single crystal analysis (SCXRD). From the SCXRD data the corresponding PXRD pattern was calculated (cf. Section "Analysis").

Synthesis of Crystalline Form H 0.05 ml to 0.1 ml of $H_2O$ were added to crystalline form K in the well of a microtiter plate (MTP). The MTP was shaken at RT on an Eppendorf Thermo-Mixer for 3-4 days. For safety reasons the solvents were evaporated under nitrogen flow before the obtained crystalline solid was characterized by FT Raman (cf. Section "Analysis").

Synthesis of Crystalline Form I

A stock solution of (1r,4r)-6'-fluoro-N,N-dimethyl-4-phenyl-4',9'-dihydro-3'H-spiro[cyclohexane-1,1'-pyrano[3,4,b]indol]-4-amine in 5 ml acetone (16.8 mg/ml) was prepared (solution A). A second stock solution (10 ml) of sulfuric acid in $H_2O$ was prepared having a concentration of 0.5 mol/l (solution B). 197.3 µl of solution A containing 1.0 mg (1r,4r)-6'-fluoro-N,N-dimethyl-4-phenyl-4',9'-dihydro-3'H-spiro[cyclohexane-1,1'-pyrano-[3,4,b]indol]-4-amine and 2.7 µl of solution B containing 0.1 mg sulfuric acid were mixed in a well of a microtiter plate resulting in a solution having a total volume of 200 µl. Crystallization was performed by evaporation of the solvents at RT under nitrogen flow (0.4 ml/min.) 0.05 ml to 0.1 ml of toluene were added to the obtained solid in the well of a microtiter plate (MTP). The MTP was shaken at RT on an Eppendorf Thermo-Mixer for 3-4 days. For safety reasons the solvents were evaporated under nitrogen flow before the obtained crystalline solid was characterized by FT Raman (cf. Section "Analysis").

Synthesis of Crystalline Form J

A stock solution of (1r,4r)-6'-fluoro-N,N-dimethyl-4-phenyl-4',9'-dihydro-3'H-spiro[cyclohexane-1,1'-pyrano[3,4,b]indol]-4-amine in 5 ml THF (16.8 mg/ml) was prepared (solution A). A second stock solution (10 ml) of sulfuric acid in $H_2O$ was prepared having a concentration of 0.5 mol/l (solution B). 191.5 µl of solution A containing 3.2 mg (1r,4r)-6'-fluoro-N,N-dimethyl-4-phenyl-4',9'-dihydro-3' H-spiro[cyclohexane-1,1'-pyrano[3,4,b]indol]-4-amine and 8.5 µl of solution B containing 0.4 mg sulfuric acid were mixed in a well of a microtiter plate resulting in a solution having a total volume of 200 µl. Crystallization was performed by evaporation of the solvents at RT under nitrogen flow (0.4 ml/min.) The resulting solid was characterized by FT Raman (cf. Section "Analysis").

Synthesis of Crystalline Form K

A stock solution of (1r,4r)-6'-fluoro-N,N-dimethyl-4-phenyl-4',9'-dihydro-3'H-spiro[cyclohexane-1,1'-pyrano[3,4,b]indol]-4-amine in 5 ml THF (16.8 mg/ml) was prepared (solution A). A second stock solution (10 ml) of sulfuric acid in $H_2O$ was prepared having a concentration of 0.5 mol/l (solution B). 183.7 µl of solution A containing 3.1 mg (1r,4r)-6'-fluoro-N,N-dimethyl-4-phenyl-4',9'-dihydro-3'H-spiro[cyclohexane-1,1'-pyrano[3,4,b]indol]-4-amine and 16.3 µl of solution B containing 0.8 mg sulfuric acid were mixed in a well of a microtiter plate resulting in a solution having a total volume of 200 µl. Crystallization was performed by evaporation of the solvents at RT under nitrogen flow (0.4 ml/min.) The resulting solid was characterized by FT Raman (cf. Section "Analysis").

Synthesis of a Crystalline Form L 20 mg of crystalline form A were dissolved in 2 mL DMSO. The solution was stored in a saturated atmosphere of MEK. The resulting precipitate was filtered off and dried in air. A crystalline solid of crystalline form L was obtained.

Synthesis of a Crystalline Form M 20 mg of crystalline form A were dissolved in 2 mL DMSO. The solution was stored in a saturated atmosphere of 2-propanol. The resulting precipitate was filtered off and dried in air. A crystalline solid of crystalline form M was obtained.

Synthesis of Further Crystalline Forms by Quick-Screen Experiments

Method 1

A stock solution of (1r,4r)-6'-fluoro-N,N-dimethyl-4-phenyl-4',9'-dihydro-3'H-spiro[cyclohexane-1,1'-pyrano[3,4,b]indol]-4-amine in a solvent was prepared (solution A). A second stock solution of sulfuric acid in $H_2O$ was prepared having a concentration of 0.5 mol/l (solution B). A solution A containing (1r,4r)-6'-fluoro-N,N-dimethyl-4-phenyl-4',9'-dihydro-3'H-spiro[cyclohexane-1,1'-pyrano[3,4,b]indol]-4-amine and a solution B containing sulfuric acid were mixed in a well of a microtiter plate resulting in a solution having a total volume of 200 µl. Crystallization was performed by evaporation of the solvents at RT under nitrogen flow (0.4 ml/min.) A molar ratio of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid of (2.0±0.2):1.0 was employed:

Method 2

As described for Method 1: however, a molar ratio of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid of (1.0±0.2):1.0 was employed.

In all experiments crystalline forms were obtained. The samples obtained were characterized by Raman Microscopy using a Renishaw System 1000, stabilized diode laser 785 nm excitation, NIR enhanced Peltier cooled CCD camera as detector. Measurements were carried out with a 50× or a long working distance 20× objective (Measurement range: 2000-100 $cm^{-1}$). The Raman spectra were classified to Raman classes using the software "Peak compare".

The results from these experiments are depicted in the following Table M1:

TABLE M1

| Experiment no. | Solvent | Raman class of crystalline sample obtained according to method 1 | Raman class of crystalline sample obtained according to method 2 |
|---|---|---|---|
| E1 | S1: acetone | 20 | 20 |
| E2 | S2: ethanol/THF | 20 | 20 |
| E3 | S3: ethyl acetate | 20 | 20 |
| E4 | S4: THF | 71 | 20 |
| E5 | S5: 1,4-dioxane | + | + |
| E6 | S6: 1-butanol | 15 | 15 |
| E7 | S7: acetone/$H_2O$ | 56 | 20 |
| E8 | S8: THF/$H_2O$ | 20 | 20 |

Method 3

To the samples obtained from method 1 was added a solvent in the well of a microtiter plate (MTP). The MTP was shaken at RT on an Eppendorf Thermo-Mixer for 3-4 days. For safety reasons the solvents were evaporated under nitrogen flow before the obtained crystalline solid was characterized by Raman Microscopy.

Method 4

To the samples obtained from method 2 was added a solvent in the well of a microtiter plate (MTP). The MTP was shaken at RT on an Eppendorf Thermo-Mixer for 3-4 days. For safety reasons the solvents were evaporated under nitrogen flow before the obtained crystalline solid was characterized by Raman Microscopy.

In all experiments crystalline forms were obtained. The samples obtained were characterized by Raman Microscopy using a Renishaw System 1000, stabilized diode laser 785 nm excitation, NIR enhanced Peltier cooled CCD camera as detector. Measurements were carried out with a 50× or a long working distance 20× objective (Measurement range: 2000-100 $cm^{-1}$). The Raman spectra were classified to Raman classes using the software "Peak compare". The results from these experiments are depicted in the following Table M2:

TABLE M2

| Experiment no. | Sample used in methods 3 and 4 which is obtained from experiment no. | Solvent | Raman class of crystalline sample obtained according to method 3 | Raman class of crystalline sample obtained according to method 4 |
|---|---|---|---|---|
| E9 | E1 | S9: 2-propanol | 15 | 20 |
| E10 | E2 | S10: 2-butanone | 15 and 20 | 40 |
| E11 | E3 | S11: iso butyl acetate | 20 | + |
| E12 | E4 | S12: TBME | 15 | 20 |
| E13 | E5 | S13: ethanol | 2 | + |

TABLE M2-continued

| Experiment no. | Sample used in methods 3 and 4 which is obtained from experiment no. | Solvent | Raman class of crystalline sample obtained according to method 3 | Raman class of crystalline sample obtained according to method 4 |
|---|---|---|---|---|
| E14 | E6 | S14: 1-butanol | 15 | 15 and 44 |
| E15 | E7 | S15: toluene | 25 and 70 | + |
| E16 | E8 | S16: H$_2$O | 55 | 20 |

Analysis

A. NMR

The $^1$H-NMR spectra of the crystalline forms complied with the structure of (1r,4r)-6'-fluoro-N,N-dimethyl-4-phenyl-4',9'-dihydro-3'H-spiro[cyclohexane-1,1'-pyrano[3,4,b]indol]-4-amine sulfate or hemi-sulfate. The $^1$H-NMR spectra show peak shifts compared to the spectrum of the free base, also indicating the salt formation.

B. Elemental Analysis (EA)

Crystalline Form A

The result of the elemental composition analysis is given in Table B1. It confirms the salt formation.

TABLE B1

| Element | Found | Calculated* |
|---|---|---|
| C | 57.78 | 58.28 |
| H | 6.19 | 6.32 |
| N | 5.52 | 5.66 |
| O | 19.51 | 19.41 |
| F | 3.89 | 3.84 |
| S | 6.40 | 6.48 |

*Calculated for C$_{24}$H$_{27}$FN$_2$O•H$_2$SO$_4$•H$_2$O

Crystalline Form B

The result of the elemental composition analysis is given in Table B2. It confirms the salt formation.

TABLE B2

| Element | Found | Calculated* |
|---|---|---|
| C | 58.5 | 60.49 |
| H | 6.3 | 6.13 |
| N | 6.4 | 5.88 |
| O | 16.9 | 16.79 |
| F | 3.8 | 3.99 |
| S | 5.5 | 6.73 |

*Calculated for C$_{24}$H$_{27}$FN$_2$O•H$_2$SO$_4$

C. XRPD (X-Ray Powder Diffraction)

The term PXRD may be used as a synonym for XRPD.

C.1 Measurements

Figure 1B:
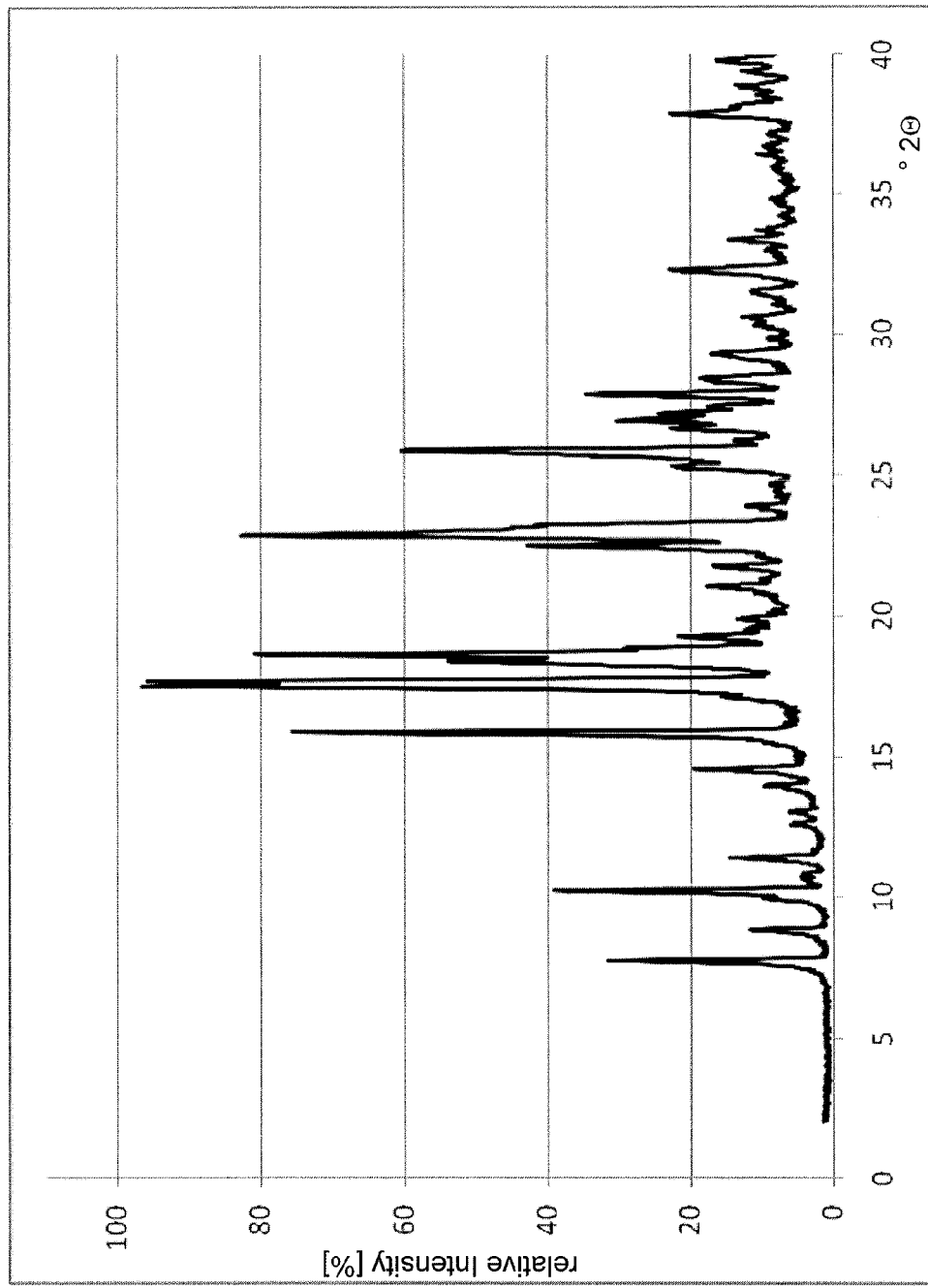

XRPD analyses were carried out in transmission geometry with a Philips X'pert PW 3040 X-ray powder diffractometer, monochromatised CuKα radiation being used by means of a germanium monochrystal at 298 K±5 K. d-distances were calculated from the 2θ values, the wavelength of 1.54060 Å being taken as basis. The d-value analysis was performed with the software EVA version 10, 0, 0, 0. The CuKα$_2$ was removed by the software and only lines up to 35° 2θ were listed. In general, the 2θ values have an error rate of ±0.2° in 2θ. The experimental error in the d-distance values is therefore dependent on the location of the peak. d-distance values can be calculated from 2θ values using Bragg's law. The samples were measured without any special treatment other than the application of slight pressure to get a flat surface. An ambient air atmosphere was used. To avoid contamination of the equipment, the samples were sealed with capton foil. FIG. 1a shows the PXRD pattern of crystalline form A. FIG. 1b shows the PXRD pattern of crystalline form B.

Crystalline Form A

FIG. 1a shows the PXRD pattern of crystalline form A. Table C1 shows the peak list for crystalline form A. The uncertainty in the 2θ values is ±0.2° in 2θ; rel. I is the relative intensity of the respective peaks. Maximum relative intensity is 100.

TABLE C1

| 2θ | d value Å | Intensity Cps | rel. I % |
|---|---|---|---|
| 7.27 | 12.2 | 590 | 47 |
| 9.16 | 9.6 | 556 | 44 |
| 12.71 | 7.0 | 38.1 | 3 |
| 14.58 | 6.1 | 470 | 37 |
| 15.74 | 5.62 | 390 | 31 |
| 16.76 | 5.29 | 207 | 16 |
| 17.96 | 4.93 | 891 | 71 |
| 18.50 | 4.79 | 1258 | 100 |
| 19.39 | 4.57 | 405 | 32 |
| 20.29 | 4.37 | 149 | 12 |
| 20.68 | 4.29 | 223 | 18 |
| 21.04 | 4.22 | 434 | 35 |
| 21.35 | 4.16 | 692 | 55 |
| 21.78 | 4.08 | 203 | 16 |
| 23.19 | 3.83 | 300 | 24 |
| 23.67 | 3.76 | 214 | 17 |
| 24.64 | 3.61 | 291 | 23 |
| 24.97 | 3.56 | 172 | 14 |
| 25.43 | 3.50 | 375 | 30 |
| 25.62 | 3.47 | 553 | 44 |
| 26.05 | 3.42 | 218 | 17 |
| 26.39 | 3.37 | 136 | 11 |
| 26.96 | 3.30 | 196 | 16 |
| 27.78 | 3.21 | 423 | 34 |
| 28.25 | 3.16 | 159 | 13 |
| 28.98 | 3.08 | 410 | 33 |
| 29.54 | 3.02 | 190 | 15 |
| 30.05 | 2.97 | 510 | 41 |
| 32.44 | 2.76 | 133 | 11 |
| 32.94 | 2.72 | 130 | 10 |
| 33.32 | 2.69 | 105 | 8 |
| 33.90 | 2.64 | 286 | 23 |
| 34.42 | 2.60 | 169 | 13 |

Crystalline Form B

FIG. 1b shows the PXRD pattern of crystalline form B. Table C2 shows the peak list for crystalline form B. The uncertainty in the 2θ values is ±0.2° in 2θ; rel. I is the relative intensity of the respective peaks. Maximum relative intensity is 100.

TABLE C2

| 2θ | d value Å | Intensity Cps | rel. I % |
|---|---|---|---|
| 7.72 | 11.4 | 365 | 33 |
| 8.81 | 10.0 | 131 | 12 |
| 9.95 | 8.9 | 114 | 10 |
| 10.23 | 8.6 | 443 | 40 |
| 10.62 | 8.3 | 44.4 | 4 |
| 10.80 | 8.2 | 47 | 4 |
| 11.40 | 7.8 | 168 | 15 |
| 12.60 | 7.0 | 70 | 6 |
| 13.04 | 6.8 | 74.3 | 7 |
| 13.95 | 6.3 | 121 | 11 |
| 14.54 | 6.1 | 223 | 20 |
| 15.85 | 5.59 | 848 | 77 |
| 17.10 | 5.18 | 175 | 16 |

TABLE C2-continued

| 2θ | d value Å | Intensity Cps | rel. I % |
|---|---|---|---|
| 17.52 | 5.06 | 1097 | 100 |
| 17.67 | 5.02 | 1090 | 99 |
| 18.37 | 4.83 | 633 | 58 |
| 18.62 | 4.76 | 928 | 85 |
| 18.85 | 4.70 | 327 | 30 |
| 19.23 | 4.61 | 250 | 23 |
| 19.86 | 4.47 | 156 | 14 |
| 21.02 | 4.22 | 199 | 18 |
| 21.74 | 4.09 | 205 | 19 |
| 22.08 | 4.02 | 129 | 12 |
| 22.46 | 3.96 | 518 | 47 |
| 22.84 | 3.89 | 980 | 90 |
| 23.15 | 3.84 | 509 | 46 |
| 23.88 | 3.72 | 154 | 14 |
| 25.27 | 3.52 | 256 | 23 |
| 25.87 | 3.44 | 721 | 66 |
| 26.21 | 3.40 | 163 | 15 |
| 26.64 | 3.34 | 271 | 25 |
| 26.95 | 3.31 | 368 | 34 |
| 27.18 | 3.28 | 302 | 28 |
| 27.43 | 3.25 | 211 | 19 |
| 27.86 | 3.20 | 420 | 38 |
| 28.43 | 3.14 | 215 | 20 |
| 29.31 | 3.04 | 204 | 19 |
| 29.85 | 2.99 | 105 | 10 |
| 30.58 | 2.92 | 134 | 12 |
| 31.45 | 2.84 | 121 | 11 |
| 32.26 | 2.77 | 260 | 24 |
| 32.99 | 2.71 | 113 | 10 |
| 33.25 | 2.68 | 170 | 16 |
| 33.69 | 2.66 | 123 | 11 |

C.2 Calculations

Figure 3A:
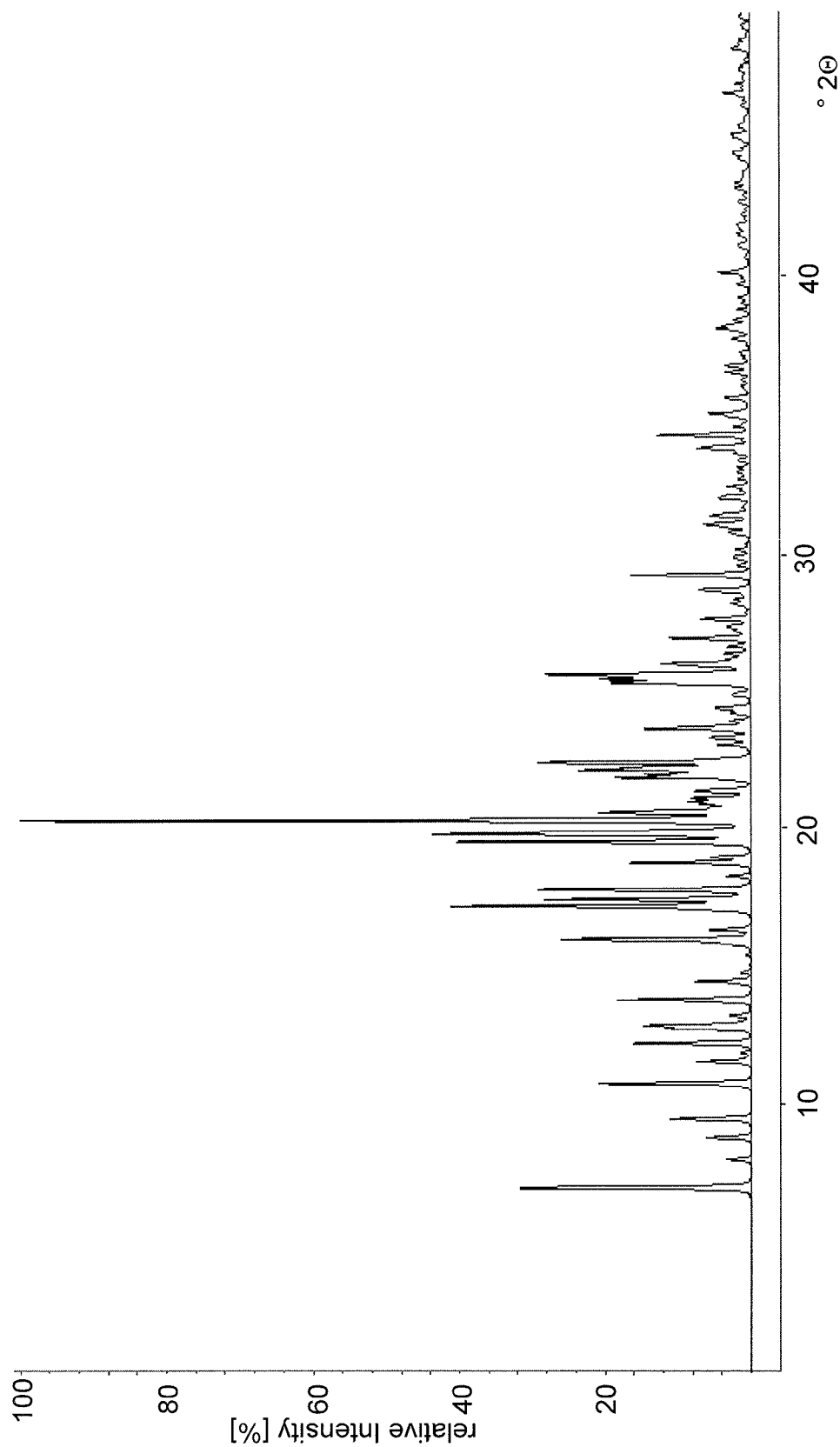
Figure 3B:
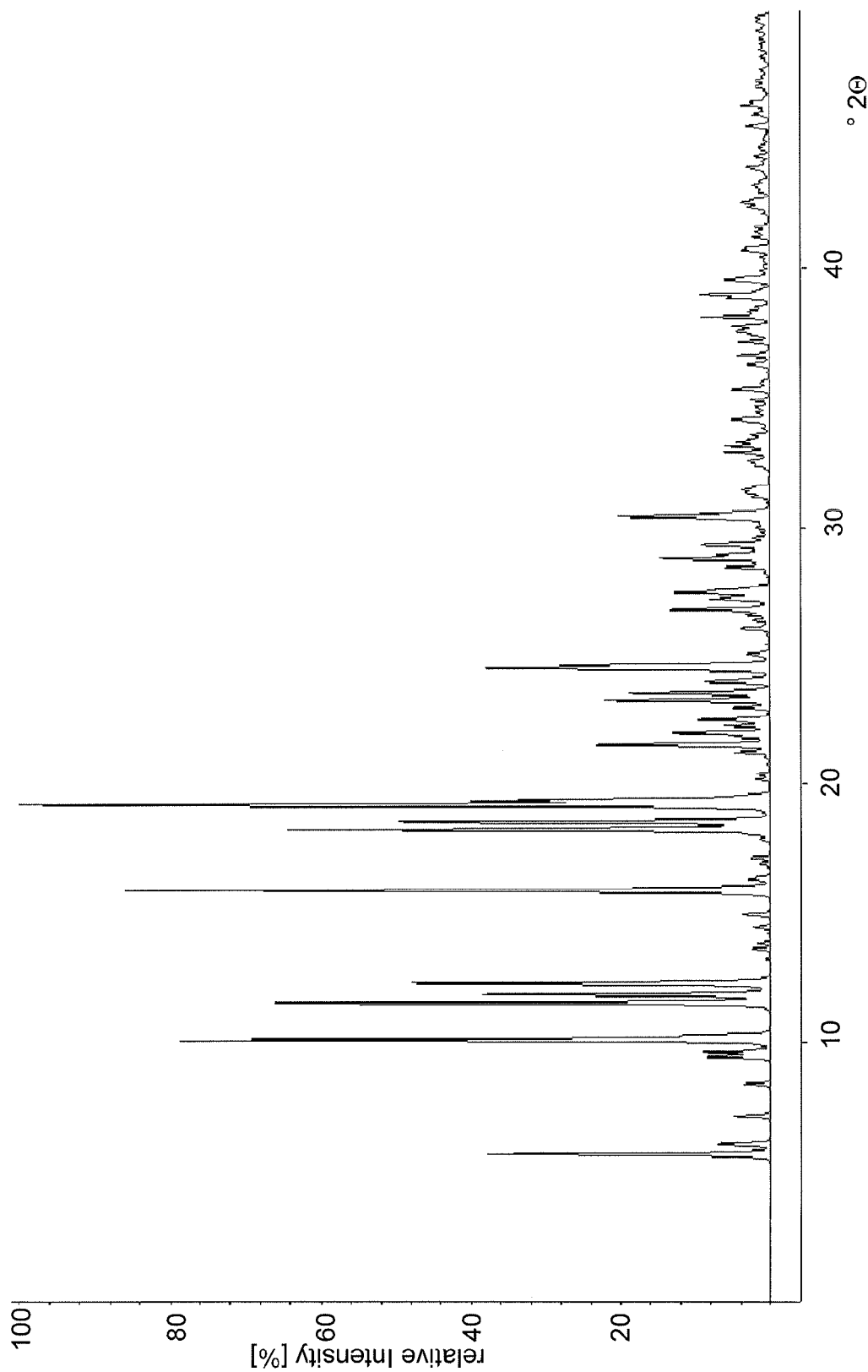

The peak tables and graphical representations of the diffractograms were produced on basis of the single crystal data using the programm WinXPow (THEO 1.11, version PKS__2.01) of the company STOE. FIG. 3a shows the PXRD pattern of crystalline form E calculated based on the parameters determined in the corresponding SCXRD experiment. FIG. 3b shows the PXRD pattern of crystalline form F calculated based on the parameters determined in the corresponding SCXRD experiment. FIG. 3c shows the PXRD pattern of crystalline form G calculated based on the parameters determined in the corresponding SCXRD experiment. The parameters that were used for the calculations of the PXRD diffractograms (FIGS. 3a-c) are given in the following table C3:

TABLE C3

| Parameter | crystalline form E single crystal obtained as described before ("synthesis of crystalline form E") | crystalline form F single crystal obtained as described before ("synthesis of crystalline form F") | crystalline form G single crystal obtained as described before ("synthesis of crystalline form G") |
|---|---|---|---|
| Formula | $C_{24}H_{27}FN_2O \cdot H_2SO_4 \cdot 3DMSO$ $(C_6H_{18}O_3S_3)$ | $C_{48}H_{54}F_2N_4O_2 \cdot H_2SO_4 \cdot 2CH_3COOH$ $(C_4H_8O_4)$ | $C_{24}H_{27}FN_2O \cdot H_2SO_4$ |
| Laue Symmetry | Monoclinic 2/m (b) | Triclinic-1 | Triclinic-1 |
| Lattice Type | Primitive | Primitive | Primitive |
| Molecular weight | 711.03 | 975.26 | 476.61 |
| Z | 4.0 | 2.0 | 2.0 |
| Space Group | P 21/c | P-1 | P-1 |
| Radiation | Cu (1.540598) | Cu (1.540598) | Cu (1.540598) |
| Generate Full Pattern | Yes (box checked) | Yes (box checked) | Yes (box checked) |
| 2Theta (Min, Max) | 0.1, 50.0 | 0.1, 50.0 | 0.1, 50.0 |
| Cell Parameters A | 13.401 | 10.549 | 9.756 |
| Cell Parameters B | 16.622 | 15.012 | 10.602 |
| Cell Parameters C | 15.839 | 15.837 | 12.164 |
| Cell Parameters Alpha | 90.0 | 74.131 | 98.559 |
| Cell Parameters Beta | 105.797 | 86.480 | 105.991 |
| Cell Parameters Gamma | 90.0 | 80.662 | 105.867 |
| Geometry | Transmission | Transmission | Transmission |
| Monochromator | Germanium | Germanium | Germanium |
| Profile Function | Pearson | Pearson | Pearson |
| Mu * T | 0.0 | 0.0 | 0.0 |
| Pearson Exponent | 2.0 | 2.0 | 2.0 |
| 2Theta (Min, Max, Step) | 0.1, 50.0, 0.02 | 0.1, 50.0, 0.02 | 0.1, 50.0, 0.02 |
| Halfwidth | 0.1, 0.0 | 0.1, 0.0 | 0.1, 0.0 |
| Max. Intensity | 100000.0 | 100000.0 | 100000.0 |
| Generate Alpha2 Peaks | No (box not checked) | No (box not checked) | No (box not checked) |
| Constant Sample Area | No (box not checked) | No (box not checked) | No (box not checked) |

Crystalline Form E

FIG. 3a shows the PXRD pattern of crystalline form E calculated based on the parameters determined in the corresponding SCXRD experiment. Table C4 shows the calculated peak list obtained by the computer program WinXPow for crystalline form E. The uncertainty in the 2θ values is ±1.0°, preferably ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ; rel. I is the relative intensity of the respective peaks. Maximum relative intensity is 100.

TABLE C4

| d value Å | 2θ | rel. I % |
|---|---|---|
| 9.46 | 9.34 | 11 |
| 8.31 | 10.64 | 21 |
| 7.74 | 11.43 | 8 |
| 7.30 | 12.12 | 16 |
| 6.99 | 12.66 | 10 |
| 6.93 | 12.77 | 14 |
| 6.45 | 13.72 | 18 |
| 6.15 | 14.39 | 8 |
| 5.56 | 15.94 | 25 |
| 5.18 | 17.11 | 11 |
| 5.16 | 17.16 | 35 |
| 5.09 | 17.39 | 13 |
| 5.09 | 17.41 | 15 |
| 5.00 | 17.74 | 12 |
| 4.99 | 17.75 | 18 |
| 4.73 | 18.74 | 17 |
| 4.55 | 19.51 | 41 |
| 4.48 | 19.80 | 40 |
| 4.46 | 19.89 | 22 |
| 4.37 | 20.30 | 100 |
| 4.31 | 20.57 | 18 |
| 4.30 | 20.65 | 8 |
| 4.23 | 21.00 | 7 |
| 4.06 | 21.87 | 17 |
| 4.04 | 22.00 | 12 |
| 4.01 | 22.15 | 21 |
| 3.99 | 22.25 | 14 |
| 3.96 | 22.44 | 27 |
| 3.76 | 23.65 | 9 |
| 3.51 | 25.36 | 16 |
| 3.49 | 25.48 | 17 |
| 3.47 | 25.65 | 20 |
| 3.46 | 25.70 | 9 |
| 3.42 | 26.06 | 11 |
| 3.05 | 29.29 | 15 |
| 2.60 | 34.42 | 9 |

Crystalline Form F

FIG. 3b shows the PXRD pattern of crystalline form F calculated based on the parameters determined in the corresponding SCXRD experiment. Table C5 shows the calculated peak list obtained by the computer program WinXPow for crystalline form F. The uncertainty in the 2θ values is ±1.0°, preferably ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ; rel. I is the relative intensity of the respective peaks. Maximum relative intensity is 100.

TABLE C5

| d value Å | 2θ | rel. I % |
|---|---|---|
| 12.16 | 7.26 | 5 |
| 9.25 | 9.55 | 9 |
| 9.09 | 9.72 | 9 |
| 8.67 | 10.20 | 80 |
| 8.52 | 10.37 | 8 |
| 7.62 | 11.61 | 69 |
| 7.40 | 11.95 | 40 |
| 7.14 | 12.39 | 50 |
| 5.54 | 15.98 | 87 |
| 4.83 | 18.35 | 67 |
| 4.76 | 18.64 | 50 |
| 4.60 | 19.30 | 100 |
| 4.56 | 19.46 | 34 |
| 4.11 | 21.61 | 19 |
| 4.03 | 22.06 | 13 |
| 3.98 | 22.34 | 6 |
| 3.93 | 22.60 | 8 |

TABLE C5-continued

| d value Å | 2θ | rel. I % |
|---|---|---|
| 3.86 | 23.03 | 5 |
| 3.81 | 23.32 | 15 |
| 3.81 | 23.33 | 7 |
| 3.77 | 23.59 | 18 |
| 3.70 | 24.03 | 6 |
| 3.63 | 24.54 | 25 |
| 3.62 | 24.59 | 16 |
| 3.61 | 24.66 | 19 |
| 3.32 | 26.82 | 11 |
| 3.27 | 27.22 | 7 |
| 3.24 | 27.48 | 12 |
| 3.10 | 28.78 | 14 |
| 3.05 | 29.29 | 6 |
| 3.04 | 29.37 | 7 |
| 2.94 | 30.40 | 18 |
| 2.92 | 30.55 | 8 |
| 2.72 | 32.90 | 6 |
| 2.36 | 38.14 | 8 |
| 2.31 | 39.02 | 8 |

Crystalline Form G

FIG. 3c shows the PXRD pattern of crystalline form G calculated based on the parameters determined in the corresponding SCXRD experiment. Table C6 shows the calculated peak list obtained by the computer program WinXPow for crystalline form G. The uncertainty in the 2θ values is ±1.0°, preferably ±0.9°, more preferably ±0.8°, even more preferably ±0.7°, still more preferably ±0.6°, yet more preferably ±0.5°, still yet more preferably ±0.4°, particularly ±0.3°, most preferably ±0.2°, in 2θ; rel. I is the relative intensity of the respective peaks. Maximum relative intensity is 100.

TABLE C6

| d value Å | 2θ | rel. I % |
|---|---|---|
| 8.55 | 10.33 | 16 |
| 8.05 | 10.98 | 4 |
| 6.92 | 12.79 | 5 |
| 6.26 | 14.13 | 5 |
| 6.05 | 14.64 | 10 |
| 5.53 | 16.00 | 21 |
| 5.10 | 17.39 | 4 |
| 5.00 | 17.72 | 16 |
| 4.95 | 17.92 | 29 |
| 4.75 | 18.66 | 14 |
| 4.71 | 18.81 | 100 |
| 4.68 | 18.93 | 8 |
| 4.65 | 19.05 | 13 |
| 4.19 | 21.21 | 8 |
| 4.03 | 22.06 | 8 |
| 3.91 | 22.75 | 11 |
| 3.88 | 22.93 | 8 |
| 3.86 | 23.03 | 13 |
| 3.84 | 23.11 | 11 |
| 3.81 | 23.30 | 9 |
| 3.80 | 23.40 | 9 |
| 3.40 | 26.23 | 9 |
| 3.25 | 27.42 | 10 |
| 3.16 | 28.26 | 7 |
| 3.12 | 28.55 | 6 |
| 3.08 | 28.93 | 7 |
| 3.01 | 29.66 | 7 |

D. SCXRD (Single Crystal X-Ray Diffraction)

SCXRD analyses of crystalline forms E, F and G were carried out with a Bruker D8-goniometer with SMART APEX CCD area detector at 100 K (±5 K) using MoKα radiation (wavelength of 0.71073 Å, Incoatec microsource, multilayer optics).

SCXRD analysis showed that in crystalline form E (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid are present in the form of a DMSO solvate sulfate salt of (1r,4r)-6'-fluoro-N,N-dimethyl-4-phenyl-4',9'-dihydro-3'H-spiro[cyclohexane-1,1'-pyrano[3,4,b]indol]-4-amine, i.e. a crystalline form of (1r,4r)-6'-fluoro-N,N-dimethyl-4-phenyl-4',9'-dihydro-3'H-spiro[cyclohexane-1,1'-pyrano[3,4,b]indol]-4-amine sulfate containing three DMSO molecules.

SCXRD analysis showed that in crystalline form F (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid are present in the form of a acetic acid solvate hemisulfate salt of (1r,4r)-6'-fluoro-N,N-dimethyl-4-phenyl-4',9'-dihydro-3'H-spiro[cyclohexane-1,1'-pyrano[3,4,b]indol]-4-amine, i.e. a crystalline form of (1r,4r)-6'-fluoro-N,N-dimethyl-4-phenyl-4',9'-dihydro-3'H-spiro[cyclohexane-1,1'-pyrano[3,4,b]indol]-4-amine hemi-sulfate containing two acetic acid molecules.

SCXRD analysis showed that in crystalline form G (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid are present in the form of an ansolvate sulfate salt of (1r,4r)-6'-fluoro-N,N-dimethyl-4-phenyl-4',9'-dihydro-3'H-spiro[cyclohexane-1,1'-pyrano[3,4,b]indol]-4-amine, i.e. a crystalline form of (1r,4r)-6'-fluoro-N,N-dimethyl-4-phenyl-4',9'-dihydro-3'H-spiro[cyclohexane-1,1'-pyrano-[3,4,b]indol]-4-amine sulfate not containing any solvent.

E. FT Raman Spectroscopy (Fourier-Transform Raman Spectroscopy)

FT Raman spectra were recorded on a Bruker RFS100 Raman spectrometer (Nd-YAG 100 mW laser, excitation 1064 nm, laser power 100 mW, Ge detector, 64 scans, 25-3500 $cm^{-1}$, resolution 2 $cm^{-1}$).

Figure 2A:
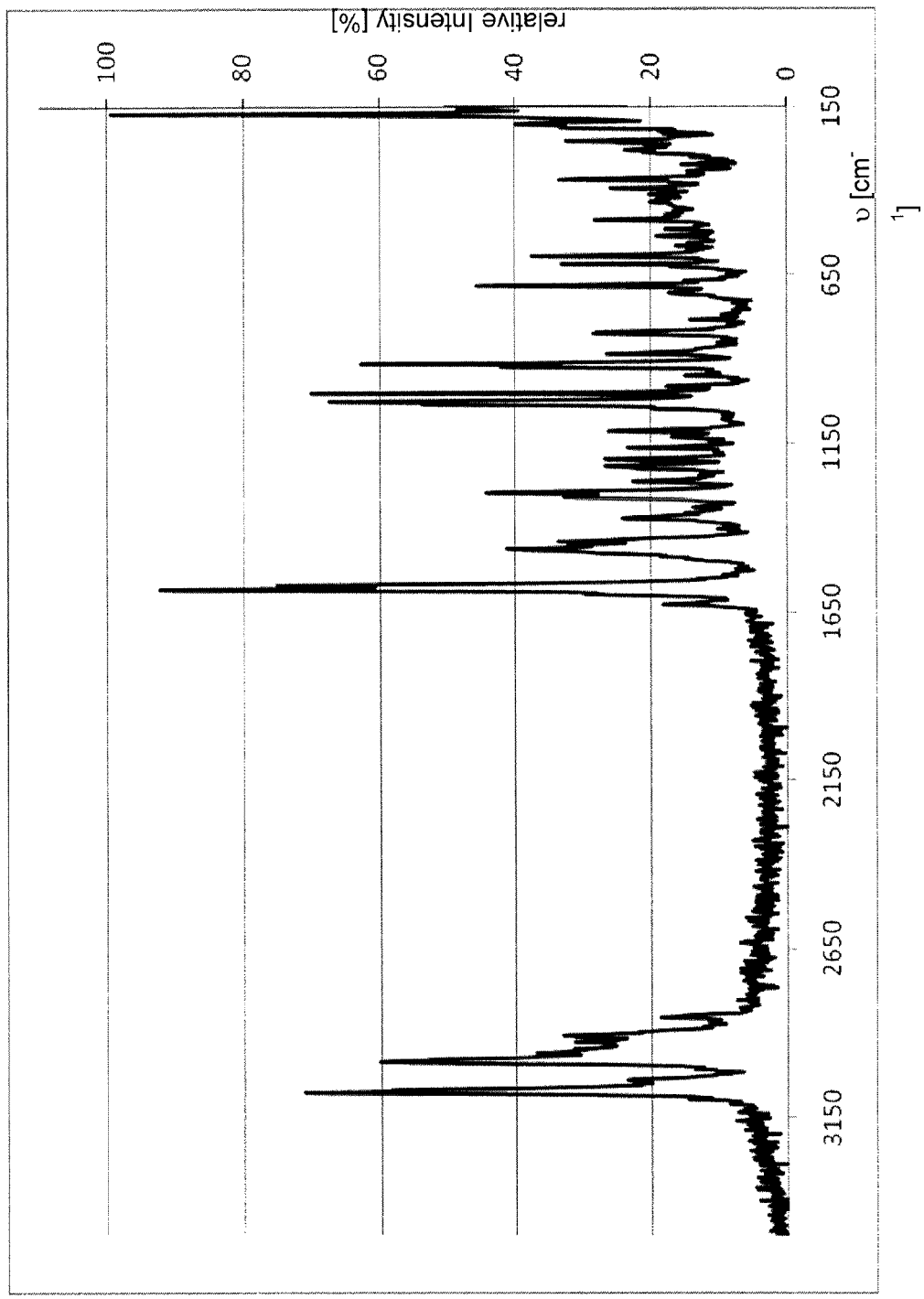
FIGS. 2a-h (FIG. 2a-h) show the Raman spectra of crystalline forms A, B, C, D, H, I, J and K, respectively.
Figure 2B:
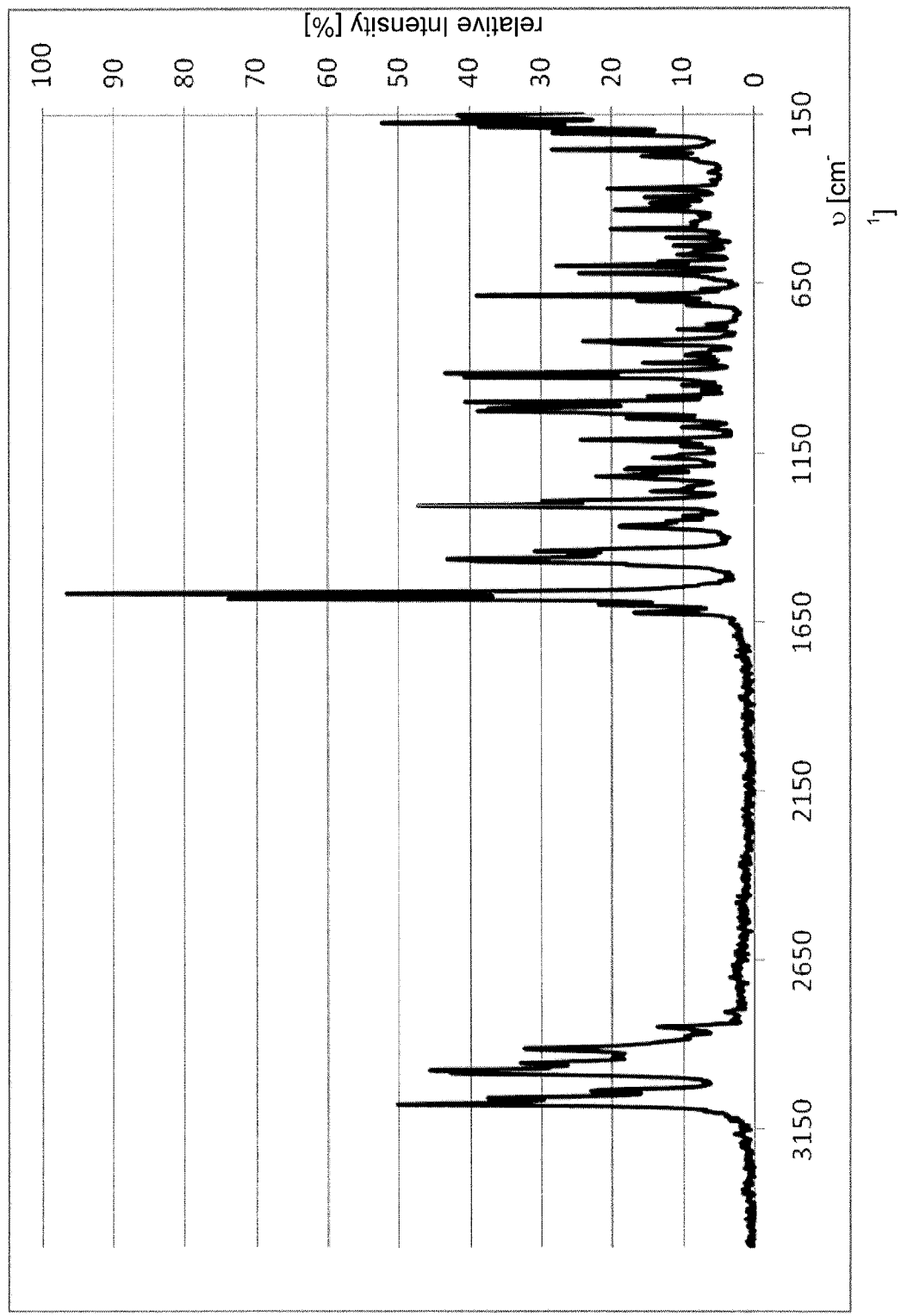
Figure 2C:
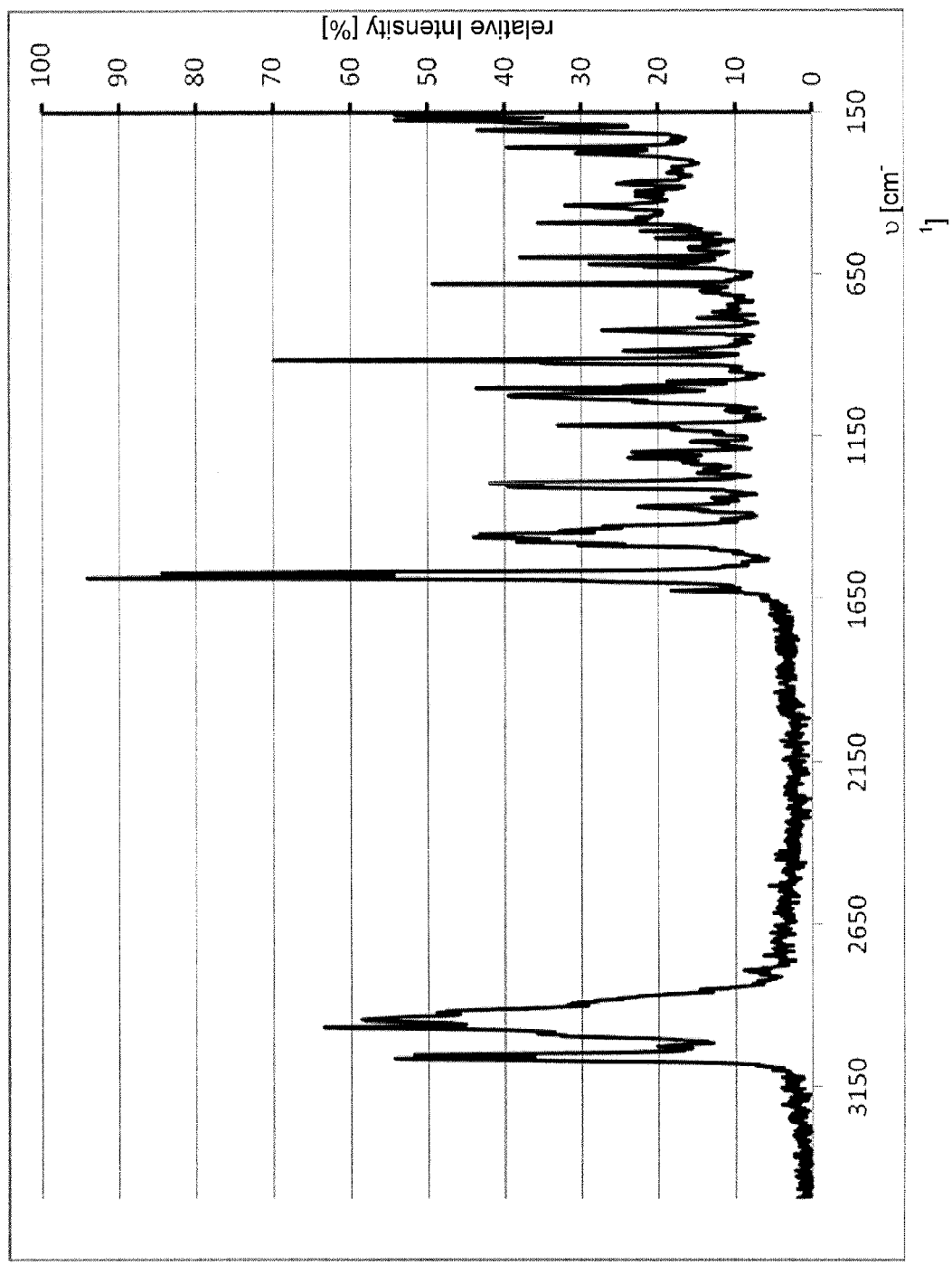
Figure 2D:
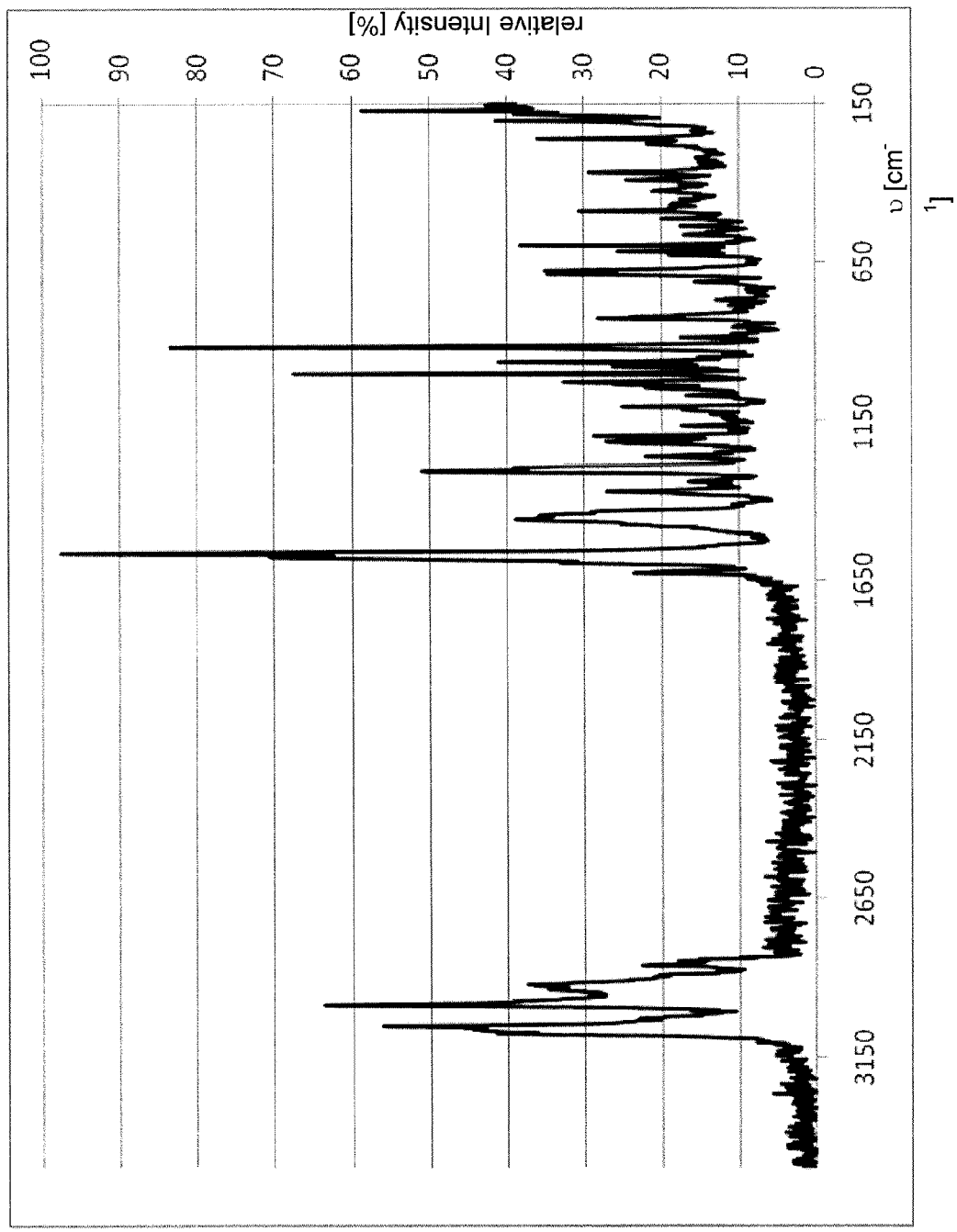
Figure 2E:
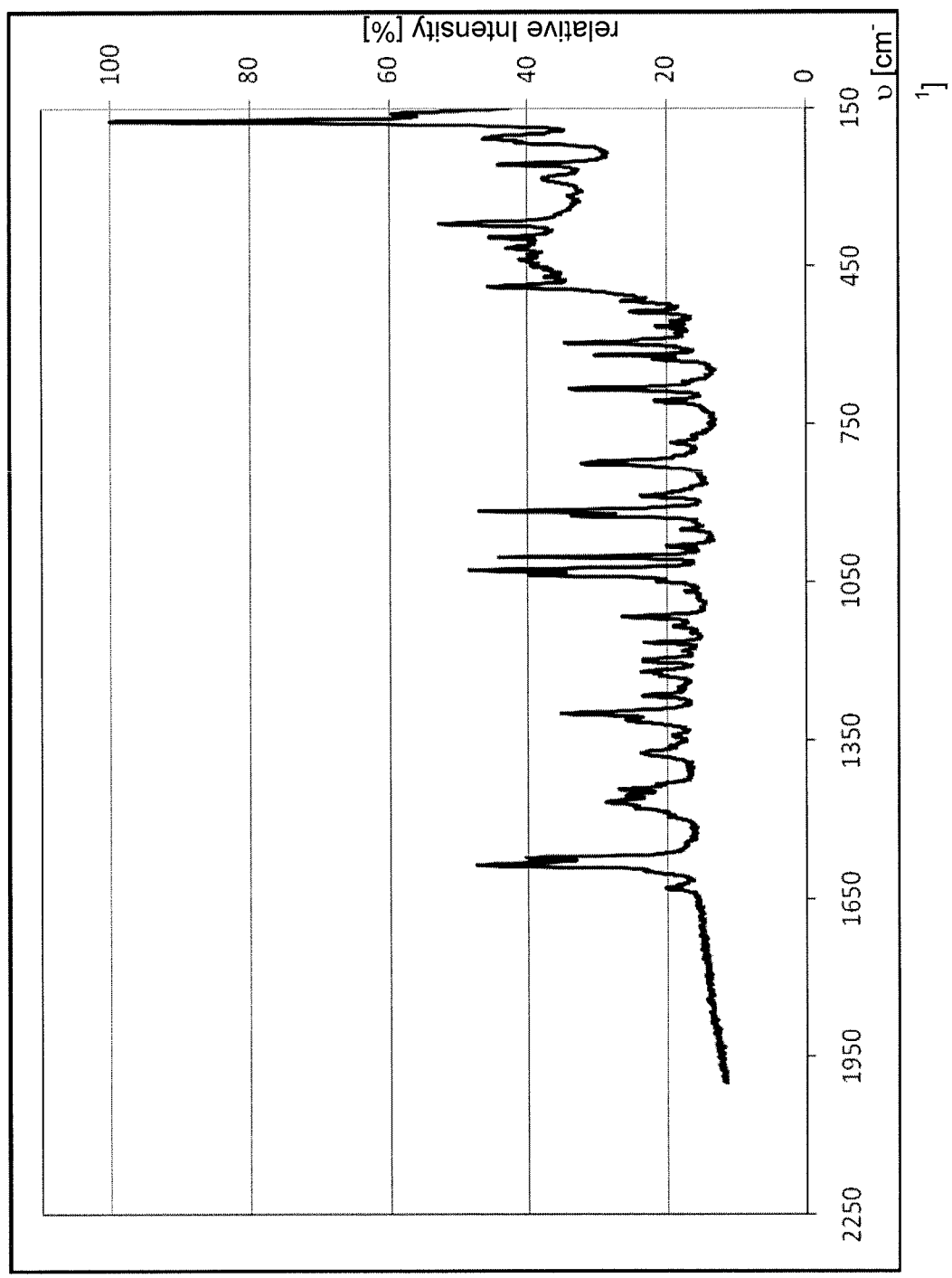
Figure 2F:
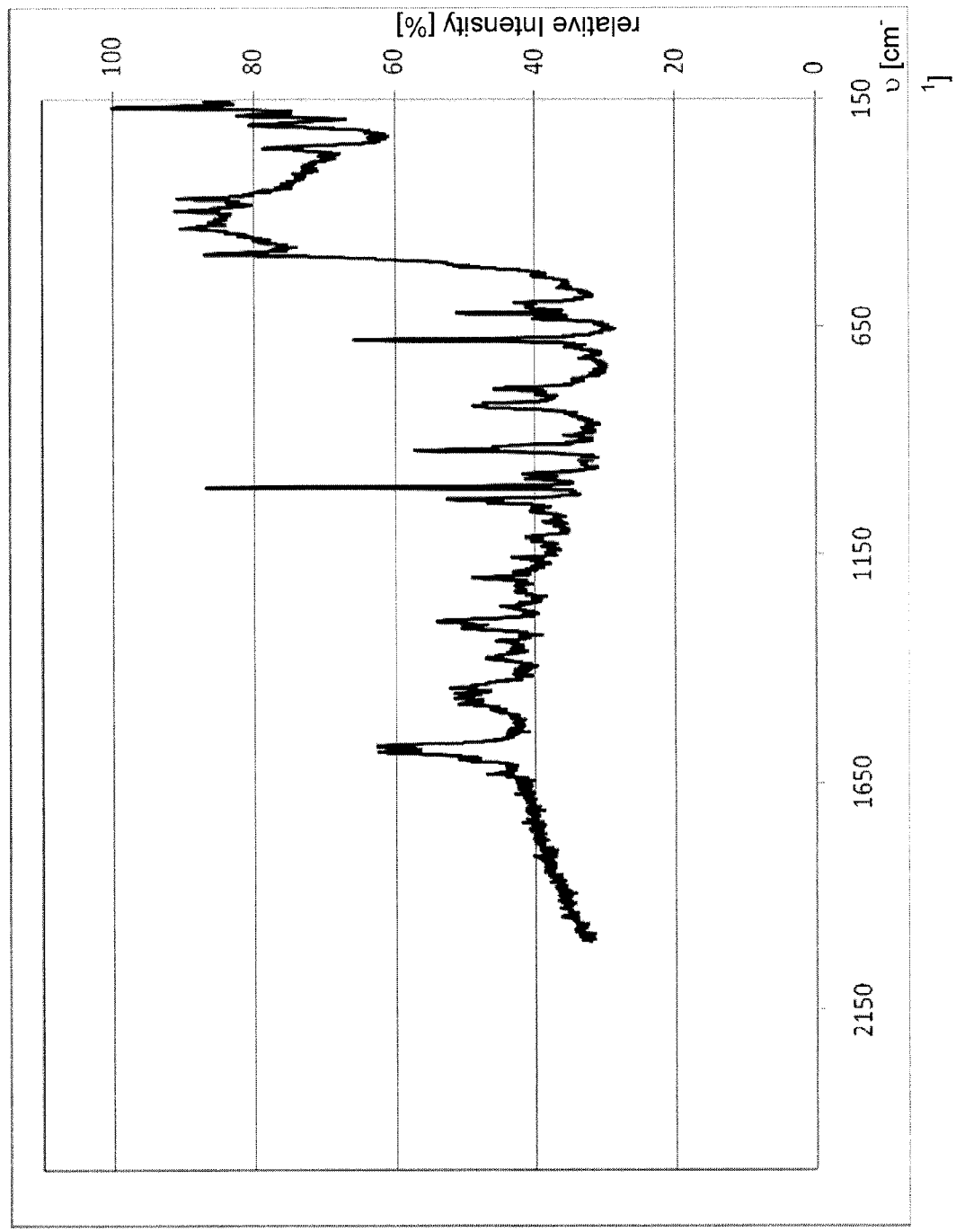
Figure 2G:
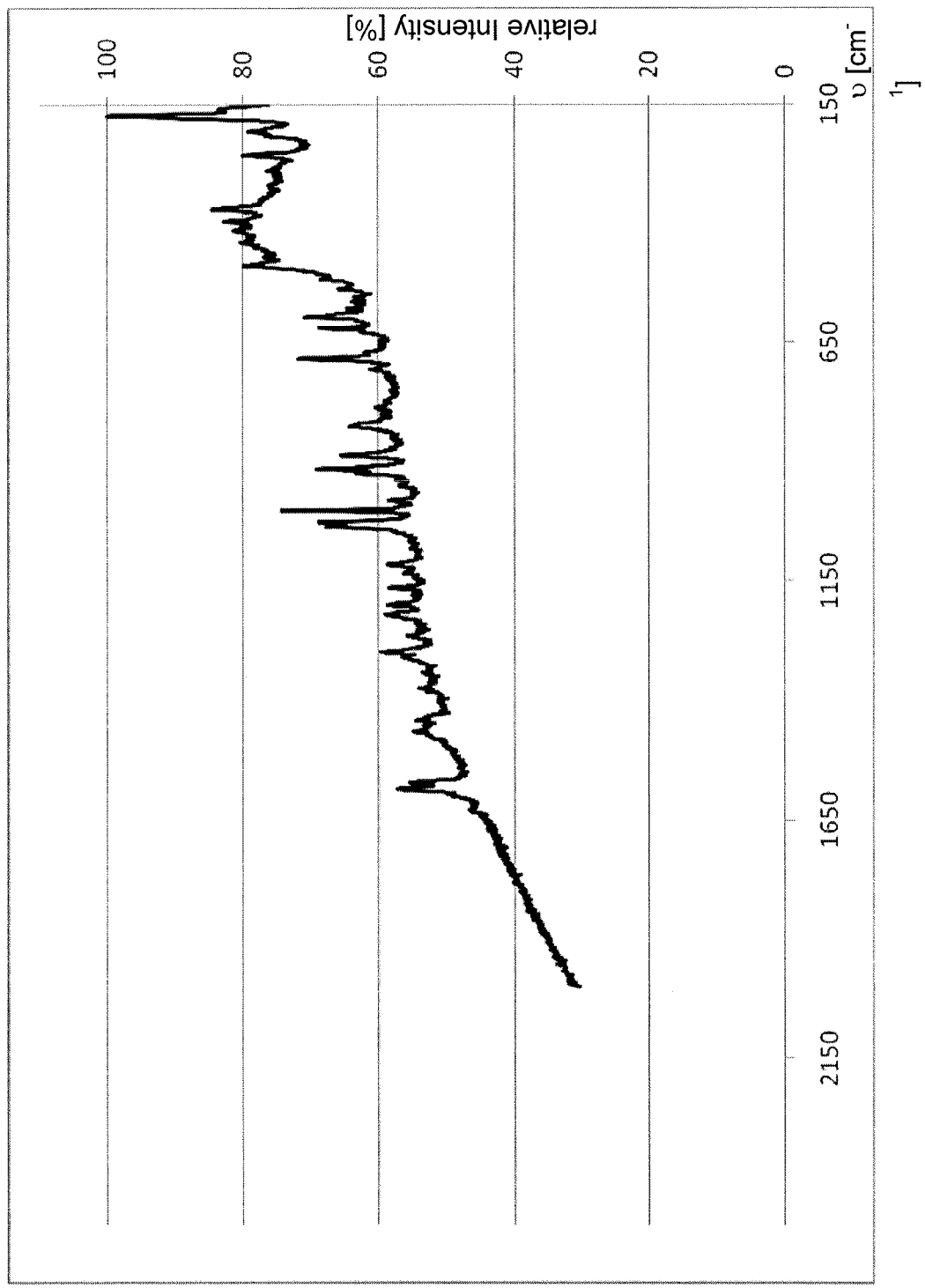
Figure 2H:
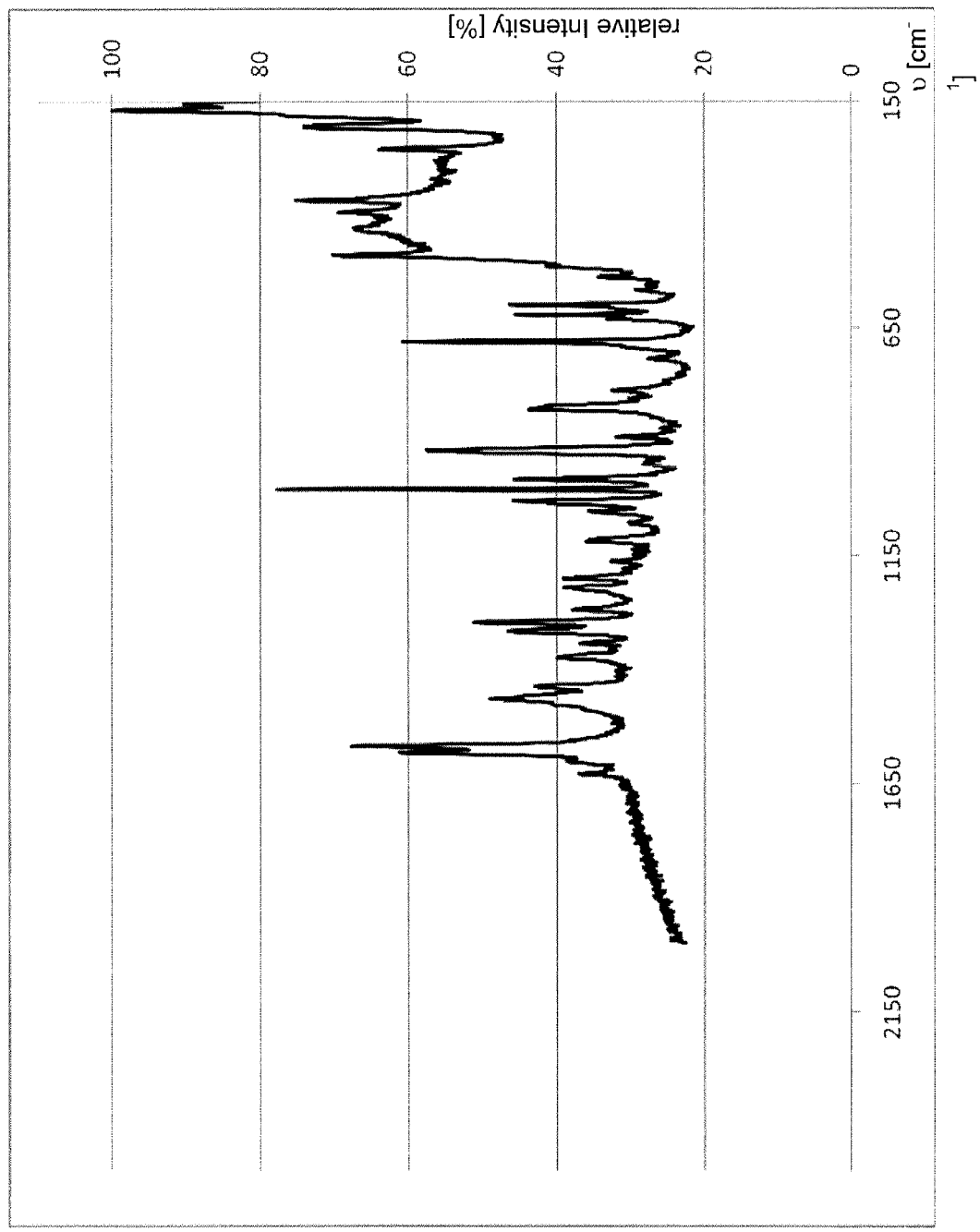

FIG. 2a shows the Raman spectrum of crystalline form A.
FIG. 2b shows the Raman spectrum of crystalline form B.
FIG. 2c shows the Raman spectrum of crystalline form C.
FIG. 2d shows the Raman spectrum of crystalline form D.
FIG. 2e shows the Raman spectrum of crystalline form H.
FIG. 2f shows the Raman spectrum of crystalline form I.
FIG. 2g shows the Raman spectrum of crystalline form J.
FIG. 2h shows the Raman spectrum of crystalline form K.

Raman peak tables were generated using the software OPUS, version 3.1, build: 3, 0, 17 (20010216). The sensitivity of the peak picking function was chosen in a way that most of the peaks were found (typically between 0.5% to 3%). Features which were accidentally attributed to peaks and which were obviously noise, were removed by hand. Peaks are listed in a spectral region between 3200 $cm^{-1}$ and 150 $cm^{-1}$. For the intensity classification, the absolute intensity was used and the most intense peak was scaled to about 100%. The classification is as follow: very strong (vs): I>80%; strong (s): 80%≥I>60%; medium (m): 60%≥I>40%; weak (w): 40%≥I>20%; and very weak (vw): 20%≥I.

Crystalline Form A 3074 (s); 2983 (s); 2957 (w); 2925 (w); 2906 (w); 2852 (vw); 1629 (vw); 1583 (vs); 1571 (s); 1464 (m); 1442 (w); 1374 (w); 1298 (m); 1265 (w); 1219 (w); 1197 (w); 1164 (w); 1115 (w); 1028 (s); 1002 (s); 925 (m); 916 (s); 886 (w); 826 (w); 786 (vw); 684 (m); 620 (w); 597 (w); 538 (vw); 490 (w); 370 (w); 204 (w); 173 (vs).

Crystalline Form B 3078 (m); 3059 (w); 3038 (w); 2985 (m); 2978 (m); 2956 (w); 2940 (vw); 2913 (w); 1625 (vw); 1601 (w); 1584 (s); 1567 (vs); 1467 (m); 1452 (w); 1442 (w); 1370 (w); 1308 (m); 1295 (w); 1266 (vw); 1221 (w); 1201 (w); 1167 (w); 1133 (vw); 1113 (w); 1050 (vw); 1028 (w); 1008 (w); 1002 (m); 928 (m); 916 (m); 886 (vw); 821 (w); 703 (vw); 686 (m); 621 (w); 599 (w); 433 (vw); 413 (vw); 396 (vw); 370 (w); 275 (vw); 254 (w); 205 (w); 187 (w), 175 (m).

Crystalline Form C 3068 (m); 3056 (m); 3034 (vw); 3030 (vw); 2992 (w); 2971 (s); 2951 (m); 2948 (m); 2927 (m); 2903 (w); 1629 (vw); 1588 (vs); 1573 (vs); 1488 (w); 1476 (w); 1463 (m); 1444 (w); 1369 (w); 1308 (w); 1232 (vw); 1218 (w); 1202 (vw); 1169 (vw); 1131 (vw); 1118 (w); 1045 (w); 1026 (w); 1004 (w); 983 (vw); 917 (s); 889 (w); 825 (w); 787 (vw); 702 (vw); 681 (m); 621 (w); 598 (w); 538 (vw); 517 (vw); 491 (w); 471 (vw); 461 (vw); 437 (w); 409 (vw); 392 (vw); 370 (w); 276 (w); 205 (w); 178 (w), 156 (m).

Crystalline Form D 3080 (w); 3067 (m); 3057 (m); 3032 (w); 2990 (s); 2977 (m); 2948 (w); 2941 (w); 2929 (w); 2866 (vw); 1630 (w); 1598 (w); 1581 (s); 1567 (vs); 1476 (vw); 1462 (w); 1374 (w); 1343 (vw); 1310 (m); 1264 (vw); 1217 (w); 1199 (w); 1118 (vw); 1106 (w); 1047 (w); 1002 (s); 982 (w); 966 (m); 918 (vs); 829 (w); 714 (vw); 691 (w); 680 (w); 619 (w); 600 (w); 516 (vw); 491 (w); 427 (w); 392 (w); 369 (w); 288 (vw); 277 (vw); 261 (w); 205 (m); 183 (w), 172 (m), 155 (m).

Crystalline Form H 1586 (m); 1572 (m); 1466 (w); 1443 (w); 1374 (w); 1360 (w); 1311 (w); 1299 (w); 1265 (w); 1220 (w); 1200 (w); 1165 (w); 1116 (w); 1038 (m); 1028 (w); 1003 (m); 982 (vw); 926 (w); 917 (m); 888 (w); 826 (w); 708 (w); 685 (w); 628 (w); 621 (w); 597 (w); 566 (vw); 538 (w); 518 (w); 490 (m); 472 (w); 458 (w); 450 (m); 439 (m); 430 (m); 415 (m); 396 (m); 370 (m); 353 (w); 341 (w); 284 (w); 257 (m); 238 (w); 213 (m); 175 (vs); 162 (s).

Crystalline Form I 1582 (s); 1570 (s); 1478 (s); 1466 (s); 1459 (s); 1454 (s); 1443 (s); 1375 (m); 1358 (m); 1339 (m); 1311 (s); 1296 (s); 1264 (m); 1201 (s); 1157 (m); 1113 (m); 1057 (m); 1037 (s); 1031 (s); 1003 (vs); 986 (m); 923 (s); 916 (m); 824 (m); 788 (m); 680 (s); 633 (m); 621 (m); 604 (m); 598 (m); 539 (w), 491 (s); 451 (s); 434 (vs); 397 (vs); 368 (vs); 259 (s); 207 (s); 187 (s); 169 (vs).

Crystalline Form J 1585 (m); 1572 (m); 1466 (m); 1443 (m); 1376 (m); 1342 (m); 1321 (m); 1310 (m); 1299 (s); 1266 (m); 1225 (m); 1219 (m); 1207 (m); 1166 (m); 1135 (m); 1116 (m); 1083 (m); 1071 (m); 1046 (m); 1037 (s); 1029 (s); 1003 (s); 983 (m); 949 (m); 925 (m); 916 (s); 888 (s); 825 (s); 787 (m); 708 (s); 685 (s); 621 (s); 598 (s); 539 (s); 519 (s); 489 (s); 441 (s); 415 (s); 371 (vs); 257 (vs); 207 (s); 175 (vs).

Crystalline Form K 1629 (w); 1583 (s); 1568 (s); 1465 (m); 1438 (m); 1371 (w); 1342 (w); 1315 (m); 1295 (m); 1267 (w); 1219 (w); 1199 (w); 1115 (w); 1076 (w); 1051 (w); 1030 (m); 1004 (s); 982 (m); 918 (m); 889 (w); 829 (m); 787 (w); 717 (w); 680 (s); 630 (w); 621 (m); 599 (m); 566 (w); 537 (w); 514 (m); 489 (s); 455 (m); 433 (s); 396 (s); 369 (s); 257 (s); 207 (s); 170 (vs); 155 (vs).

F. DSC (Differential Scanning Calorimetry)

Differential Scanning calorimetry (DSC): device reference Perkin Elmer DSC 7. Unless otherwise specified, the samples were weighed in a sealed gold crucible. The measurement took place in a nitrogen flow in a temperature range from −50° C. up to 350° C. with a heating rate of 10° C./min. The temperatures specified in relation to DSC analyses are, unless otherwise specified, the temperatures of the peak maxima.

In the following Table F, "ΔH" means "specific heat", and "peak" means that a thermal event was observed at the temperature with the given peak temperature.

TABLE F

| | DSC |
|---|---|
| Crystalline form A | step at 130.1° C., $\Delta C_p$ = 0.4 J/g ° C.<br>multiple endothermic events at 174.0° C., 209.8° C. and 236.3° C.<br>peak at 241.6° C., $\Delta H$ = −30 J/g |
| Crystalline form B | endothermic peak at 251.9° C., $\Delta H$ = 57 J/g<br>exothermic peak at 254.4° C., $\Delta H$ = −82 J/g |

G. TG-FTIR (Thermogravimetry Coupled with Fourier-Transform Infrared Spectroscopy)

Thermogravimetric analysis coupled with Fourier transform infrared spectra (TG-FTIR) were recorded with a Netzsch Thermo-Microwaage TG 209 and a Bruker FT-IR spectrometer Vector 22 (aluminium crucible (open or with micro-aperture), nitrogen atmosphere, heating rate 10° C./min, 25 up to 350° C.).

TG-FTIR analyses performed with a sample of crystalline form A showed a weight loss of 4.43% within the temperature range from RT to 225° C., which is attributable to a weight loss of water indicating that crystalline form A does contain water as an enclosed solvent, i.e. based on these measurements crystalline form A is a hydrate.

TG-FTIR analyses performed with a sample of crystalline form B showed a weight loss of about 0.3% within the temperature range from RT to 250° C., indicating that crystalline form B does not contain any enclosed solvent (i.e. is an ansolvate, in particular an anhydrate).

TG-FTIR analyses performed with a sample of crystalline form C showed a weight loss of 17.2% within the temperature range from RT to 250° C., which is attributable to a weight loss of NMP indicating that crystalline form C does contain NMP as an enclosed solvent, i.e. based on these measurements crystalline form A is a solvate.

TG-FTIR analyses performed with samples of crystalline form D showed a weight loss of 18.3% within the temperature range from RT to 250° C. The weight loss is attributable to a weight loss of DMSO and water indicating that crystalline form D does contain DMSO and water as an enclosed solvent, i.e. based on these measurements crystalline form A is a solvate.

H. Dynamic Vapour Sorption (DVS)

Crystalline Form B

Crystalline form B was characterized by dynamic vapour sorption (DVS) using a Projekt Messtechnik SPS 11-100n multi sample vapour sorption analyzer. For the DVS analysis, each sample was placed in an Al crucible and allowed to equilibrate at 50% r.h. (relative humidity) before starting a pre-defined humidity program during which the change in weight of the sample is determined.

Although hygroscopicity was measured in a slightly different manner, it was classified according to the European Pharmacopoeia as follows: very hygroscopic (vh): increase of the mass≥15%; hygroscopic (h): increase of the mass is less than 15% and equal or greater than 2%; slightly hygroscopic (sh): increase of the mass is less than 2% and equal or greater than 0.2%; not hygroscopic (nh): increase of the mass is less than 0.2%; deliquescent (d): sufficient water is absorbed to form a liquid.

DVS with two cycles was performed on a sample of crystalline form B according to the following program: 2 h at 50% r.h.; 50% r.h.→0% r.h. (10%/h); 5 h at 0% r.h.; 0→95% r.h. (5%/h); 3 h at 95% r.h.; 95→50% (10%/h), and 2 h at 50% r.h.

The DVS showed two reversible cycles with no significant mass changes ($\Delta m$<0.2%), i.e. the sample was found to be not hygroscopic (nh).

Another sample of crystalline form B was stored at RT and 85% r.h. for 24 h for hygroscopicity testing. The sample was found to be not hygroscopic (nh) ($\Delta m$=0.10%).

Crystalline Form A

A sample of crystalline form A (4.57 mg) was stored at RT and 80% r.h. for 24 h for hygroscopicity testing. The weight after storage was determined to be 4.85 mg. The sample was found to be hygroscopic (h) ($\Delta m$=6.10%).

I. Solubility in Water

The aqueous solubility was determined in bidest $H_2O$ from saturated solutions (24 h equilibration time, RT). The concentration was measured by HPLC and the pH of the saturated solutions was determined.

TABLE I

| | solubility [mg/L] | resulting pH |
|---|---|---|
| free base | <0.30 | 8.4 |
| sulfate (crystalline form A) | 1.03 | 2.0 |
| sulfate (crystalline form B) | 1.20 | 2.7 |

It becomes evident from the solubility data in Table I that formation of both the sulfate salt in crystalline forms A and B improves the aqueous solubility of the compound.

J. Physical and Chemical Stability

In this experiment the physical and chemical stability of (1r,4r)-6'-fluoro-N,N-dimethyl-4-phenyl-4',9'-dihydro-3'H-spiro[cyclohexane-1,1'-pyrano[3,4,b]indol]-4-amine sulfate (in the form of crystalline form B) was compared to that of the free base.

The stability tests were performed under two conditions. The samples were stored for four weeks at 75% r.h. at 40° C. in open vials and one week at 80° C. in closed vials. The purity was determined by HPLC. The results are summarized in Table J.

TABLE J

| | Ref. | 4 weeks at 40° C., 75% r.h. | | 1 week at 80° C. | |
|---|---|---|---|---|---|
| | Purity [area %] | Purity [area %] | PXRD | Purity [area %] | PXRD |
| free base | 99.7 | 99.5 | new peaks and peak shifts | 99.7 | new peaks and peak shifts |
| sulfate (crystalline form B) | 100.0 | 99.7 | no change | 99.8 | no change |

The sulfate salt showed no significant degradation after stability testing, whereas the free base showed clearly changes.

K. Single Crystal Diffraction

Measurements were realized using MoKα-radiation ($\lambda$=0.71073 Å, Incoatec Microsource) and a Bruker AXS D8-Goniometer equipped with a SMART APEX-CCD detector at 100 K. Crystal data of crystalline forms E, F and G are summarized in the following tables K1-K15.

Crystalline Form E

TABLE K1

Crystal data and structure refinement for crystalline from E.

| | |
|---|---|
| Empirical formula | $C_{30}H_{47}FN_2O_8S_4$ |
| Formula weight | 710.94 |
| Temperature | 100(2) K |
| Wavelength | .71073 Å |

TABLE K1-continued

Crystal data and structure refinement for crystalline from E.

| | |
|---|---|
| Crystal system | Monoclinic |
| Space group | P 2₁/c |
| Unit cell dimensions | a = 13.401(4) Å alpha = 90 deg. |
| | b = 16.622(5) Å beta = 105.797(7) deg. |
| | c = 15.839(5) Å gamma = 90 deg. |
| Volume | 3394.9(18) Å³ |
| Z | 4 |
| Density (calculated) | 1.391 Mg/m³ |
| Absorption coefficient | 0.336 mm⁻¹ |
| F(000) | 1512 |
| Crystal size | 0.20 × 0.20 × 0.15 mm |
| Theta range for data collection | 1.81 to 26.54 deg. |
| Index ranges | −16 ≤ h ≤ 15, −20 ≤ k ≤ 17, |
| | −18 ≤ l ≤ 19 |
| Reflections collected | 24958 |
| Independent reflections | 7034 [R(int) = 0.0702] |
| Absorption correction | Semi-empirical from equivalents |
| Max. and min. transmission | 0.951 and 0.936 |
| Refinement method | Full-matrix least-squares on F² |
| Data/restraints/parameters | 7034/5/414 |
| Goodness-of-fit on F² | 1.108 |
| Final R indices [I > 2sigma(I)] | R1 = 0.0752, wR2 = 0.1904 |
| R indices (all data) | R1 = 0.1024, wR2 = 0.2106 |
| Largest diff. peak and hole | 1.134 and −1.007 e · Å⁻³ |

TABLE K2

Atomic coordinates (×10⁴) (i.e. (×10^4)) and equivalent isotropic displacement parameters (² × 10³) (i.e. (^2 × 10^3)) for crystalline from E. U(eq) is defined as one third of the trace of the orthogonalized Uij tensor.

| | x | y | z | U(eq) |
|---|---|---|---|---|
| S(1) | 7837(1) | 6403(1) | 3437(1) | 21(1) |
| O(1) | 8140(2) | 5684(2) | 3970(2) | 33(1) |
| O(2) | 8491(2) | 6514(2) | 2866(2) | 38(1) |
| O(3) | 6749(2) | 6421(2) | 3023(2) | 45(1) |
| O(4) | 8091(2) | 7129(2) | 4081(2) | 35(1) |
| S(2) | 2991(1) | 2330(1) | 4135(1) | 30(1) |
| O(5) | 3263(2) | 2649(2) | 5070(2) | 39(1) |
| C(1) | 4150(4) | 2345(4) | 3847(4) | 72(2) |
| C(2) | 2854(5) | 1278(3) | 4211(3) | 61(2) |
| S(3A) | 4115(2) | 4593(2) | 2337(2) | 32(1) |
| O(6A) | 4430(6) | 4372(6) | 3303(5) | 35(2) |
| C(3) | 3833(5) | 3668(4) | 1802(4) | 79(2) |
| C(4) | 5127(4) | 4930(4) | 2120(4) | 63(2) |
| S(3B) | 4756(4) | 3976(3) | 2533(4) | 32(1) |
| O(6B) | 4594(6) | 4112(7) | 3447(5) | 39(2) |
| S(3C) | 4040(3) | 4475(2) | 2570(3) | 32(1) |
| S(4A) | 6693(2) | 1275(2) | 5177(2) | 60(1) |
| O(7A) | 5950(6) | 640(5) | 5086(5) | 106(3) |
| C(5) | 7205(5) | 1477(4) | 6283(4) | 63(2) |
| C(6) | 7840(6) | 896(5) | 5057(5) | 86(2) |
| S(4B) | 7303(8) | 1621(6) | 5394(6) | 60(1) |
| S(4C) | 6713(8) | 836(7) | 5430(7) | 60(1) |
| O(7B) | 6050(9) | 1492(7) | 4659(8) | 40(4) |
| F(1) | 11329(3) | 4113(2) | 605(2) | 42(1) |
| O(8) | 8817(2) | 2712(1) | 4176(2) | 23(1) |
| N(1) | 9191(2) | 4586(2) | 3026(2) | 21(1) |
| N(2) | 7397(2) | 4926(2) | 5222(2) | 19(1) |
| C(7) | 10794(3) | 4251(2) | 1214(3) | 29(1) |
| C(8) | 10642(3) | 3619(2) | 1724(2) | 25(1) |
| C(9) | 10080(3) | 3791(2) | 2328(2) | 21(1) |
| C(10) | 9706(3) | 4582(2) | 2384(2) | 21(1) |
| C(11) | 9233(3) | 3821(2) | 3370(2) | 20(1) |
| C(12) | 8729(3) | 3578(2) | 4067(2) | 20(1) |
| C(13) | 9802(3) | 2387(2) | 4155(2) | 25(1) |
| C(14) | 9962(3) | 2464(2) | 3245(2) | 24(1) |
| C(15) | 9772(3) | 3319(2) | 2970(2) | 20(1) |
| C(16) | 9232(3) | 3997(2) | 4943(2) | 20(1) |
| C(17) | 8687(3) | 3798(2) | 5642(2) | 19(1) |
| C(18) | 7520(3) | 4006(2) | 5377(2) | 19(1) |
| C(19) | 7979(3) | 5429(2) | 5980(2) | 24(1) |
| C(20) | 6305(3) | 5220(2) | 4935(2) | 24(1) |

TABLE K2-continued

Atomic coordinates (×10⁴) (i.e. (×10^4)) and equivalent isotropic displacement parameters (² × 10³) (i.e. (^2 × 10^3)) for crystalline from E. U(eq) is defined as one third of the trace of the orthogonalized Uij tensor.

| | x | y | z | U(eq) |
|---|---|---|---|---|
| C(21) | 7026(3) | 3573(2) | 4495(2) | 21(1) |
| C(22) | 7572(3) | 3749(2) | 3778(2) | 21(1) |
| C(23) | 7000(3) | 3756(2) | 6076(2) | 20(1) |
| C(24) | 7548(3) | 3713(2) | 6956(2) | 25(1) |
| C(25) | 7098(3) | 3431(2) | 7593(3) | 31(1) |
| C(26) | 6069(3) | 3212(2) | 7359(3) | 30(1) |
| C(27) | 5494(3) | 3267(2) | 6493(3) | 28(1) |
| C(28) | 5950(3) | 3531(2) | 5857(2) | 25(1) |
| C(29) | 9871(3) | 5205(2) | 1851(2) | 25(1) |
| O(30) | 10426(3) | 5028(2) | 1260(3) | 29(1) |

TABLE K3-A

Bond lengths [Å] and angles [deg] for crystalline from E.

| bond lengths [Å] and angles [deg] | | bond lengths [Å] and angles [deg] | |
|---|---|---|---|
| S(1)—O(3) | 1.427(3) | C(8)—H(8) | .9500 |
| S(1)—O(2) | 1.432(3) | C(9)—C(10) | 1.418(5) |
| S(1)—O(1) | 1.456(3) | C(9)—C(15) | 1.432(5) |
| S(1)—O(4) | 1.557(3) | C(10)—C(29) | 1.391(5) |
| O(4)—H(4O) | .833(19) | C(11)—C(15) | 1.367(5) |
| S(2)—O(5) | 1.520(3) | C(11)—C(12) | 1.498(5) |
| S(2)—C(1) | 1.734(5) | C(12)—C(22) | 1.519(5) |
| S(2)—C(2) | 1.766(5) | C(12)—C(16) | 1.534(5) |
| C(1)—H(1A) | .9800 | C(13)—C(14) | 1.520(5) |
| C(1)—H(1B) | .9800 | C(13)—H(13A) | .9900 |
| C(1)—H(1C) | .9800 | C(13)—H(13B) | .9900 |
| C(2)—H(2A) | .9800 | C(14)—C(15) | 1.487(5) |
| C(2)—H(2B) | .9800 | C(14)—H(14A) | .9900 |
| C(2)—H(2C) | .9800 | C(14)—H(14B) | .9900 |
| S(3A)—O(6A) | 1.517(9) | C(16)—C(17) | 1.520(5) |
| S(3A)—C(4) | 1.590(7) | C(16)—H(16A) | .9900 |
| S(3A)—C(3) | 1.747(7) | C(16)—H(16B) | .9900 |
| C(3)—H(3A) | .9800 | C(17)—C(18) | 1.543(5) |
| C(3)—H(3B) | .9800 | C(17)—H(17A) | .9900 |
| C(3)—H(3C) | .9800 | C(17)—H(17B) | .9900 |
| C(4)—H(4A) | .9800 | C(18)—C(23) | 1.519(5) |
| C(4)—H(4B) | .9800 | C(18)—C(21) | 1.550(5) |
| C(4)—H(4C) | .9800 | C(19)—H(19A) | .9800 |
| S(3B)—O(6B) | 1.540(9) | C(19)—H(19B) | .9800 |
| S(4A)—O(7A) | 1.430(8) | C(19)—H(19C) | .9800 |
| S(4A)—C(6) | 1.720(8) | C(20)—H(20A) | .9800 |
| S(4A)—C(5) | 1.731(6) | C(20)—H(20B) | .9800 |
| C(5)—H(5A) | .9800 | C(20)—H(20C) | .9800 |
| C(5)—H(5B) | .9800 | C(21)—C(22) | 1.537(5) |
| C(5)—H(5C) | .9800 | C(21)—H(21A) | .9900 |
| C(6)—H(6A) | .9800 | C(21)—H(21B) | .9900 |
| C(6)—H(6B) | .9800 | C(22)—H(22A) | .9900 |
| C(6)—H(6C) | .9800 | C(22)—H(22B) | .9900 |
| S(4C)—O(7B) | 1.696(17) | C(23)—C(24) | 1.390(5) |
| F(1)—C(7) | 1.368(4) | C(23)—C(28) | 1.404(5) |
| O(8)—C(13) | 1.435(4) | C(24)—C(25) | 1.390(5) |
| O(8)—C(12) | 1.450(4) | C(24)—H(24) | .9500 |
| N(1)—C(10) | 1.376(5) | C(25)—C(26) | 1.376(6) |
| N(1)—C(11) | 1.379(4) | C(25)—H(25) | .9500 |
| N(1)—H(1N) | .879(19) | C(26)—C(27) | 1.382(6) |
| N(2)—C(20) | 1.491(4) | C(26)—H(26) | .9500 |
| N(2)—C(19) | 1.495(4) | C(27)—C(28) | 1.384(5) |
| N(2)—C(18) | 1.552(4) | C(27)—H(27) | .9500 |
| N(2)—H(2N) | .893(19) | C(28)—H(28) | .9500 |
| C(7)—C(8) | 1.374(5) | C(29)—C(30) | 1.378(5) |
| C(7)—C(30) | 1.391(5) | C(29)—H(29) | .9500 |
| C(8)—C(9) | 1.399(5) | C(30)—H(30) | .9500 |

TABLE K3-B (Table K3-A continued) Bond lengths [Å] and angles [deg] for crystalline from E.

| | bond lengths [Å] and angles [deg] | | bond lengths [Å] and angles [deg] |
|---|---|---|---|
| O(3)—S(1)—O(2) | 115.63(19) | H(14A)—C(14)—H(14B) | 108.5 |
| O(3)—S(1)—O(1) | 111.80(19) | C(11)—C(15)—C(9) | 106.6(3) |
| O(2)—S(1)—O(1) | 110.52(17) | C(11)—C(15)—C(14) | 121.1(3) |
| O(3)—S(1)—O(4) | 107.37(18) | C(9)—C(15)—C(14) | 132.2(3) |
| O(2)—S(1)—O(4) | 104.53(17) | C(17)—C(16)—C(12) | 112.3(3) |
| O(1)—S(1)—O(4) | 106.25(17) | C(17)—C(16)—H(16A) | 109.1 |
| S(1)—O(4)—H(4O) | 113(4) | C(12)—C(16)—H(16A) | 109.1 |
| O(5)—S(2)—C(1) | 104.9(2) | C(17)—C(16)—H(16B) | 109.1 |
| O(5)—S(2)—C(2) | 106.3(2) | C(12)—C(16)—H(16B) | 109.1 |
| C(1)—S(2)—C(2) | 98.6(3) | H(16A)—C(16)—H(16B) | 107.9 |
| S(2)—C(1)—H(1A) | 109.5 | C(16)—C(17)—C(18) | 113.9(3) |
| S(2)—C(1)—H(1B) | 109.5 | C(16)—C(17)—H(17A) | 108.8 |
| H(1A)—C(1)—H(1B) | 109.5 | C(18)—C(17)—H(17A) | 108.8 |
| S(2)—C(1)—H(1C) | 109.5 | C(16)—C(17)—H(17B) | 108.8 |
| H(1A)—C(1)—H(1C) | 109.5 | C(18)—C(17)—H(17B) | 108.8 |
| H(1B)—C(1)—H(1C) | 109.5 | H(17A)-C(17)-H(17B) | 107.7 |
| S(2)—C(2)—H(2A) | 109.5 | C(23)—C(18)—C(17) | 111.9(3) |
| S(2)—C(2)—H(2B) | 109.5 | C(23)—C(18)—C(21) | 111.2(3) |
| H(2A)—C(2)—H(2B) | 109.5 | C(17)—C(18)—C(21) | 107.1(3) |
| S(2)—C(2)—H(2C) | 109.5 | C(23)—C(18)—N(2) | 109.5(3) |
| H(2A)—C(2)—H(2C) | 109.5 | C(17)—C(18)—N(2) | 108.7(3) |
| H(2B)—C(2)—H(2C) | 109.5 | C(21)—C(18)—N(2) | 108.3(3) |
| O(6A)—S(3A)—C(4) | 106.5(4) | N(2)—C(19)—H(19A) | 109.5 |
| O(6A)—S(3A)—C(3) | 103.9(5) | N(2)—C(19)—H(19B) | 109.5 |
| C(4)—S(3A)—C(3) | 106.8(4) | H(19A)—C(19)—H(19B) | 109.5 |
| O(7A)—S(4A)—C(6) | 109.7(4) | N(2)—C(19)—H(19C) | 109.5 |
| O(7A)—S(4A)—C(5) | 108.6(4) | H(19A)—C(19)—H(19C) | 109.5 |
| C(6)—S(4A)—C(5) | 93.6(3) | H(19B)—C(19)—H(19C) | 109.5 |
| C(13)—O(8)—C(12) | 114.7(3) | N(2)—C(20)—H(20A) | 109.5 |
| C(10)—N(1)—C(11) | 108.2(3) | N(2)—C(20)—H(20B) | 109.5 |
| C(10)—N(1)—H(1N) | 124(3) | H(20A)—C(20)—H(20B) | 109.5 |
| C(11)—N(1)—H(1N) | 128(3) | N(2)—C(20)—H(20C) | 109.5 |
| C(20)—N(2)—C(19) | 108.4(3) | H(20A)—C(20)—H(20C) | 109.5 |
| C(20)—N(2)—C(18) | 115.1(3) | H(20B)—C(20)—H(20C) | 109.5 |
| C(19)—N(2)—C(18) | 114.5(3) | C(22)—C(21)—C(18) | 113.9(3) |
| C(20)—N(2)—H(2N) | 107(3) | C(22)—C(21)—H(21A) | 108.8 |
| C(19)—N(2)—H(2N) | 101(3) | C(18)—C(21)—H(21A) | 108.8 |
| C(18)—N(2)—H(2N) | 109(3) | C(22)—C(21)—H(21B) | 108.8 |
| F(1)—C(7)—C(8) | 118.4(3) | C(18)—C(21)—H(21B) | 108.8 |
| F(1)—C(7)—C(30) | 117.0(3) | H(21A)—C(21)—H(21B) | 107.7 |
| C(8)—C(7)—C(30) | 124.6(4) | C(12)—C(22)—C(21) | 113.2(3) |
| C(7)—C(8)—C(9) | 116.0(3) | C(12)—C(22)—H(22A) | 108.9 |
| C(7)—C(8)—H(8) | 122.0 | C(21)—C(22)—H(22A) | 108.9 |
| C(9)—C(8)—H(8) | 122.0 | C(12)—C(22)—H(22B) | 108.9 |
| C(8)—C(9)—C(10) | 119.9(3) | C(21)—C(22)—H(22B) | 108.9 |
| C(8)—C(9)—C(15) | 133.3(3) | H(22A)—C(22)—H(22B) | 107.8 |
| C(10)—C(9)—C(15) | 106.8(3) | C(24)—C(23)—C(28) | 117.1(3) |
| N(1)—C(10)—C(29) | 129.8(3) | C(24)—C(23)—C(18) | 121.5(3) |
| N(1)—C(10)—C(9) | 107.9(3) | C(28)—C(23)—C(18) | 121.4(3) |
| C(29)—C(10)—C(9) | 122.3(3) | C(23)—C(24)—C(25) | 122.0(4) |
| C(15)—C(11)—N(1) | 110.5(3) | C(23)—C(24)—H(24) | 119.0 |
| C(15)—C(11)—C(12) | 125.3(3) | C(25)—C(24)—H(24) | 119.0 |
| N(1)—C(11)—C(12) | 124.2(3) | C(26)—C(25)—C(24) | 119.7(4) |
| O(8)—C(12)—C(11) | 108.5(3) | C(26)—C(25)—H(25) | 120.2 |
| O(8)—C(12)—C(22) | 105.4(3) | C(24)—C(25)—H(25) | 120.2 |
| C(11)—C(12)—C(22) | 110.9(3) | C(25)—C(26)—C(27) | 119.8(4) |
| O(8)—C(12)—C(16) | 110.0(3) | C(25)—C(26)—H(26) | 120.1 |
| C(11)—C(12)—C(16) | 111.6(3) | C(27)—C(26)—H(26) | 120.1 |
| C(22)—C(12)—C(16) | 110.4(3) | C(26)—C(27)—C(28) | 120.4(4) |
| O(8)—C(13)—C(14) | 111.0(3) | C(26)—C(27)—H(27) | 119.8 |
| O(8)—C(13)—H(13A) | 109.4 | C(28)—C(27)—H(27) | 119.8 |
| C(14)—C(13)—H(13A) | 109.4 | C(27)—C(28)—C(23) | 121.0(3) |
| O(8)—C(13)—H(13B) | 109.4 | C(27)—C(28)—H(28) | 119.5 |
| C(14)—C(13)—H(13B) | 109.4 | C(23)—C(28)—H(28) | 119.5 |
| H(13A)—C(13)—H(13B) | 108.0 | C(30)—C(29)—C(10) | 117.3(3) |
| C(15)—C(14)—C(13) | 107.6(3) | C(30)—C(29)—H(29) | 121.4 |
| C(15)—C(14)—H(14A) | 110.2 | C(10)—C(29)—H(29) | 121.4 |
| C(13)—C(14)—H(14A) | 110.2 | C(29)—C(30)—C(7) | 119.9(4) |
| C(15)—C(14)—H(14B) | 110.2 | C(29)—C(30)—H(30) | 120.1 |
| C(13)—C(14)—H(14B) | 110.2 | C(7)—C(30)—H(30) | 120.1 |

Symmetry Transformations Used to Generate Equivalent Atoms:

TABLE K4

Hydrogen coordinates (×10$^4$) (i.e. (×10^4)) and isotropic displacement parameters ($^2$ × 10$^3$) (i.e. (^2 × 10^3)) for crystalline form E.

| | x | y | z | U(eq) |
|---|---|---|---|---|
| H(4O) | 7720(3) | 7150(3) | 4420(3) | 58(17) |
| H(1A) | 4366 | 2904 | 3805 | 109 |
| H(1B) | 4055 | 2079 | 3278 | 109 |
| H(1C) | 4685 | 2062 | 4294 | 109 |
| H(2A) | 3497 | 1051 | 4588 | 91 |
| H(2B) | 2711 | 1040 | 3624 | 91 |
| H(2C) | 2279 | 1160 | 4463 | 91 |
| H(3A) | 4464 | 3339 | 1926 | 118 |
| H(3B) | 3576 | 3757 | 1168 | 118 |
| H(3C) | 3303 | 3388 | 2012 | 118 |
| H(4A) | 5360 | 5419 | 2463 | 94 |
| H(4B) | 4969 | 5056 | 1493 | 94 |
| H(4C) | 5676 | 4523 | 2269 | 94 |
| H(5A) | 6656 | 1679 | 6528 | 95 |
| H(5B) | 7753 | 1883 | 6358 | 95 |
| H(5C) | 7497 | 982 | 6589 | 95 |
| H(6A) | 8091 | 470 | 5490 | 129 |
| H(6B) | 8357 | 1328 | 5147 | 129 |
| H(6C) | 7727 | 675 | 4465 | 129 |
| H(1N) | 8900(3) | 5014(19) | 3180(3) | 46(14) |
| H(2N) | 7700(3) | 5070(2) | 4810(2) | 34(12) |
| H(8) | 10904 | 3096 | 1670 | 30 |
| H(13A) | 9837 | 1812 | 4326 | 30 |
| H(13B) | 10363 | 2676 | 4584 | 30 |
| H(14A) | 10678 | 2308 | 3257 | 29 |
| H(14B) | 9474 | 2109 | 2827 | 29 |
| H(16A) | 9967 | 3831 | 5152 | 24 |
| H(16B) | 9215 | 4586 | 4850 | 24 |
| H(17A) | 9030 | 4095 | 6185 | 23 |
| H(17B) | 8768 | 3216 | 5776 | 23 |
| H(19A) | 7868 | 5999 | 5829 | 37 |
| H(19B) | 8720 | 5305 | 6114 | 37 |
| H(19C) | 7729 | 5311 | 6494 | 37 |
| H(20A) | 5989 | 5175 | 5423 | 36 |
| H(20B) | 5911 | 4894 | 4441 | 36 |
| H(20C) | 6298 | 5784 | 4753 | 36 |
| H(21A) | 7040 | 2986 | 4601 | 25 |
| H(21B) | 6291 | 3739 | 4280 | 25 |
| H(22A) | 7250 | 3417 | 3256 | 25 |
| H(22B) | 7463 | 4321 | 3604 | 25 |
| H(24) | 8253 | 3881 | 7128 | 30 |
| H(25) | 7498 | 3391 | 8187 | 38 |
| H(26) | 5755 | 3022 | 7792 | 36 |
| H(27) | 4781 | 3123 | 6333 | 34 |
| H(28) | 5547 | 3561 | 5263 | 30 |
| H(29) | 9611 | 5731 | 1893 | 30 |
| H(30) | 10559 | 5436 | 884 | 35 |

TABLE K5

Anisotropic displacement parameters ($^2$ × 10$^3$) (i.e. (^2 × 10^3)) for crystalline form E. The anisotropic displacement factor exponent takes the form: $-2\pi^2 [h^2 a^{*2} U_{11} + \ldots + 2 h k a^* b^* U_{12}]$.

| | U11 | U22 | U33 | U23 | U13 | U12 |
|---|---|---|---|---|---|---|
| S(1) | 26(1) | 18(1) | 20(1) | 1(1) | 10(1) | 2(1) |
| O(1) | 43(2) | 22(2) | 40(2) | 11(1) | 22(1) | 9(1) |
| O(2) | 54(2) | 33(2) | 37(2) | 2(1) | 31(1) | 0(1) |
| O(3) | 30(2) | 64(2) | 36(2) | −9(2) | −2(1) | 8(2) |
| O(4) | 44(2) | 25(2) | 44(2) | −12(2) | 26(1) | −8(1) |
| S(2) | 33(1) | 32(1) | 25(1) | −5(1) | 7(1) | 5(1) |
| O(5) | 40(2) | 50(2) | 31(2) | −17(1) | 17(1) | −3(1) |
| C(1) | 63(3) | 117(5) | 53(3) | −45(3) | 43(3) | −39(3) |
| C(2) | 111(5) | 40(3) | 31(3) | −4(2) | 20(3) | −26(3) |
| F(1) | 62(2) | 31(1) | 48(2) | −2(1) | 42(1) | 2(1) |
| O(8) | 25(1) | 15(1) | 30(1) | 2(1) | 11(1) | 1(1) |
| N(1) | 26(2) | 14(1) | 24(2) | −1(1) | 12(1) | 3(1) |

TABLE K5-continued

Anisotropic displacement parameters ($^2$ × 10$^3$) (i.e. (^2 × 10^3)) for crystalline form E. The anisotropic displacement factor exponent takes the form: $-2\pi^2 [h^2 a^{*2} U_{11} + \ldots + 2 h k a^* b^* U_{12}]$.

| | U11 | U22 | U33 | U23 | U13 | U12 |
|---|---|---|---|---|---|---|
| N(2) | 22(2) | 17(2) | 19(2) | 2(1) | 7(1) | 0(1) |
| C(7) | 37(2) | 26(2) | 31(2) | −5(2) | 21(2) | −1(2) |
| C(8) | 28(2) | 20(2) | 30(2) | −4(2) | 13(2) | 2(2) |
| C(9) | 25(2) | 17(2) | 23(2) | −3(1) | 9(1) | −1(1) |
| C(10) | 23(2) | 17(2) | 24(2) | −2(1) | 7(1) | −1(1) |
| C(11) | 21(2) | 17(2) | 22(2) | −1(1) | 7(1) | 1(1) |
| C(12) | 24(2) | 16(2) | 22(2) | 2(1) | 10(1) | 0(1) |
| C(13) | 28(2) | 16(2) | 33(2) | 5(2) | 12(2) | 4(2) |
| C(14) | 25(2) | 17(2) | 33(2) | −2(2) | 13(2) | 1(1) |
| C(15) | 20(2) | 19(2) | 23(2) | −2(1) | 6(1) | 2(1) |
| C(16) | 18(2) | 19(2) | 22(2) | −1(1) | 6(1) | 0(1) |
| C(17) | 20(2) | 16(2) | 22(2) | 0(1) | 7(1) | 1(1) |
| C(18) | 21(2) | 16(2) | 20(2) | 3(1) | 6(1) | 2(1) |
| C(19) | 27(2) | 18(2) | 27(2) | −4(1) | 5(2) | −2(2) |
| C(20) | 22(2) | 24(2) | 26(2) | 2(2) | 6(2) | 4(2) |
| C(21) | 20(2) | 20(2) | 22(2) | 0(1) | 7(1) | 0(1) |
| C(22) | 21(2) | 20(2) | 22(2) | −2(1) | 5(1) | −1(1) |
| C(23) | 22(2) | 15(2) | 23(2) | 2(1) | 7(1) | 2(1) |
| C(24) | 24(2) | 28(2) | 24(2) | 3(2) | 5(2) | 4(2) |
| C(25) | 32(2) | 39(2) | 24(2) | 6(2) | 10(2) | 3(2) |
| C(26) | 32(2) | 32(2) | 33(2) | 8(2) | 21(2) | 3(2) |
| C(27) | 23(2) | 30(2) | 36(2) | 5(2) | 14(2) | 0(2) |
| C(28) | 25(2) | 24(2) | 26(2) | 4(2) | 7(2) | 2(2) |
| C(29) | 32(2) | 16(2) | 29(2) | −2(2) | 13(2) | 1(2) |
| C(30) | 38(2) | 24(2) | 29(2) | −1(2) | 18(2) | −6(2) |

Crystalline Form F

TABLE K6

Crystal data and structure refinement for crystalline form F.

| | |
|---|---|
| Empirical formula | $C_{52}H_{64}F_2N_4O_{10}S$ |
| Formula weight | 975.13 |
| Temperature | 100(2) K |
| Wavelength | .71073 Å |
| Crystal system | Triclinic |
| Space group | P-1 |
| Unit cell dimensions | a = 10.549(5) Å alpha = 74.131(8) deg. |
| | b = 15.012(7) Å beta = 86.480(9) deg. |
| | c = 15.837(8) Å gamma = 80.662(8) deg. |
| Volume | 2380(2) Å$^3$ |
| Z | 2 |
| Density (calculated) | 1.361 Mg/m$^3$ |
| Absorption coefficient | 0.141 mm$^{-1}$ |
| F(000) | 1036 |
| Crystal size | 0.24 × 0.18 × 0.08 mm |
| Theta range for data collection | 1.43 to 30.77 deg. |
| Index ranges | −15 ≤ h ≤ 14, −21 ≤ k ≤ 21, −22 ≤ l ≤ 15 |
| Reflections collected | 24212 |
| Independent reflections | 13421 [R(int) = 0.0627] |
| Absorption correction | Semi-empirical from equivalents |
| Max. and min. transmission | 0.989 and 0.967 |
| Refinement method | Full-matrix least-squares on F$^2$ |
| Data/restraints/parameters | 13421/33/650 |
| Goodness-of-fit on F$^2$ | 1.033 |
| Final R indices [I > 2sigma(I)] | R1 = 0.0688, wR2 = 0.1638 |
| R indices (all data) | R1 = 0.1039, wR2 = 0.1899 |
| Largest diff. peak and hole | 0.690 and −0.552 e · Å$^{-3}$ |

TABLE K7

Atomic coordinates (×10⁴) (i.e. (×10^4)) and equivalent isotropic displacement parameters (Å² × 10³) (i.e. (Å^2 × 10^3)) for crystalline form F. U(eq) is defined as one third of the trace of the orthogonalized Uij tensor.

| | x | y | z | U(eq) |
|---|---|---|---|---|
| S(1) | 2479(1) | 36(1) | 7266(1) | 21(1) |
| O(1) | 2664(2) | −985(1) | 7597(1) | 25(1) |
| O(2) | 3516(2) | 403(1) | 7601(1) | 27(1) |
| O(3) | 2558(2) | 326(1) | 6308(1) | 46(1) |
| O(4) | 1237(2) | 419(1) | 7569(2) | 51(1) |
| F(1) | 576(1) | 3068(1) | 4360(1) | 25(1) |
| O(5) | 6992(1) | 4316(1) | 2203(1) | 16(1) |
| N(1) | 5303(2) | 2255(1) | 2941(1) | 15(1) |
| N(2) | 9532(2) | 1735(1) | 1599(1) | 16(1) |
| C(1) | 1763(2) | 2831(2) | 4013(1) | 18(1) |
| C(2) | 2507(2) | 3517(2) | 3701(1) | 16(1) |
| C(3) | 3711(2) | 3265(1) | 3342(1) | 14(1) |
| C(4) | 4102(2) | 2321(1) | 3325(1) | 14(1) |
| C(5) | 5671(2) | 3130(1) | 2718(1) | 13(1) |
| C(6) | 6915(2) | 3345(1) | 2279(1) | 13(1) |
| C(7) | 5825(2) | 4950(1) | 1972(1) | 16(1) |
| C(8) | 4837(2) | 4783(1) | 2712(1) | 16(1) |
| C(9) | 4727(2) | 3762(1) | 2947(1) | 14(1) |
| C(10) | 7058(2) | 3170(1) | 1367(1) | 14(1) |
| C(11) | 8355(2) | 3354(1) | 942(1) | 15(1) |
| C(12) | 9517(2) | 2792(1) | 1490(1) | 13(1) |
| C(13) | 9500(3) | 1477(2) | 756(1) | 26(1) |
| C(14) | 10616(2) | 1121(2) | 2136(2) | 21(1) |
| C(15) | 9337(2) | 2968(1) | 2402(1) | 13(1) |
| C(16) | 8049(2) | 2791(1) | 2844(1) | 14(1) |
| C(17) | 10773(2) | 3090(1) | 1045(1) | 14(1) |
| C(18) | 11825(2) | 3064(2) | 1538(2) | 20(1) |
| C(19) | 12935(2) | 3390(2) | 1145(2) | 23(1) |
| C(20) | 13009(2) | 3758(2) | 249(2) | 21(1) |
| C(21) | 11976(2) | 3782(2) | −256(2) | 21(1) |
| C(22) | 10877(2) | 3451(2) | 138(1) | 18(1) |
| C(23) | 3312(2) | 1642(1) | 3649(1) | 16(1) |
| C(24) | 2123(2) | 1906(2) | 4001(1) | 19(1) |
| F(2) | −4343(1) | 2934(1) | 9435(1) | 30(1) |
| O(6) | 2057(1) | 4088(1) | 7199(1) | 16(1) |
| N(3) | 296(2) | 2066(1) | 7929(1) | 16(1) |
| N(4) | 4796(2) | 1665(1) | 6444(1) | 16(1) |
| C(25) | −3183(2) | 2686(2) | 9073(2) | 21(1) |
| C(26) | −2414(2) | 3360(2) | 8751(1) | 18(1) |
| C(27) | −1234(2) | 3092(1) | 8372(1) | 15(1) |
| C(28) | −888(2) | 2148(2) | 8335(1) | 16(1) |
| C(29) | 697(2) | 2930(1) | 7709(1) | 14(1) |
| C(30) | 1945(2) | 3128(1) | 7261(1) | 14(1) |
| C(31) | 908(2) | 4741(1) | 6979(1) | 17(1) |
| C(32) | −70(2) | 4585(1) | 7728(1) | 16(1) |
| C(33) | −204(2) | 3570(1) | 7961(1) | 14(1) |
| C(34) | 2107(2) | 2956(1) | 6349(1) | 15(1) |
| C(35) | 3372(2) | 3224(1) | 5917(1) | 15(1) |
| C(36) | 4582(2) | 2712(1) | 6435(1) | 13(1) |
| C(37) | 4713(3) | 1499(2) | 5559(2) | 25(1) |
| C(38) | 6027(2) | 1134(2) | 6846(2) | 30(1) |
| C(39) | 4370(2) | 2778(1) | 7388(1) | 14(1) |
| C(40) | 3082(2) | 2553(1) | 7813(1) | 14(1) |
| C(41) | 5769(2) | 3141(1) | 6017(1) | 14(1) |
| C(42) | 5854(2) | 3554(2) | 5113(1) | 17(1) |
| C(43) | 6912(2) | 3958(2) | 4738(1) | 20(1) |
| C(44) | 7918(2) | 3964(2) | 5255(2) | 20(1) |
| C(45) | 7852(2) | 3561(2) | 6148(2) | 19(1) |
| C(46) | 6789(2) | 3158(2) | 6526(1) | 17(1) |
| C(47) | −1693(2) | 1484(2) | 8665(2) | 20(1) |
| C(48) | −2860(2) | 1762(2) | 9039(2) | 22(1) |
| O(7) | 9556(2) | 916(1) | 4158(1) | 25(1) |
| O(8) | 7776(2) | 531(1) | 4899(1) | 33(1) |
| C(49) | 8869(2) | 876(1) | 4800(2) | 24(1) |
| C(50) | 9140(3) | 1224(2) | 5563(2) | 32(1) |
| O(9) | 5406(2) | 588(2) | 899(1) | 45(1) |
| O(10A) | 3487(4) | 233(4) | 1381(3) | 44(2) |
| O(10B) | 3752(5) | 862(4) | 1685(3) | 68(3) |
| C(51) | 4170(3) | 772(2) | 928(2) | 57(1) |
| C(52) | 3594(3) | 1271(2) | 58(2) | 46(1) |

TABLE K8-A

Bond lengths [Å] and angles [deg] for crystalline form F.

| bond lengths [Å] and angles [deg] | | bond lengths [Å] and angles [deg] | | bond lengths [Å] and angles [deg] | |
|---|---|---|---|---|---|
| S(1)—O(4) | 1.451(2) | C(15)—H(15B) | .9900 | C(35)—C(36) | 1.536(3) |
| S(1)—O(3) | 1.461(2) | C(16)—H(16A) | .9900 | C(35)—H(35A) | .9900 |
| S(1)—O(1) | 1.4630(17) | C(16)—H(16B) | .9900 | C(35)—H(35B) | .9900 |
| S(1)—O(2) | 1.4861(18) | C(17)—C(18) | 1.385(3) | C(36)—C(41) | 1.533(3) |
| F(1)—C(1) | 1.369(2) | C(17)—C(22) | 1.395(3) | C(36)—C(39) | 1.539(3) |
| O(5)—C(7) | 1.429(2) | C(18)—C(19) | 1.388(3) | C(37)—H(37A) | .9800 |
| O(5)—C(6) | 1.444(2) | C(18)—H(18) | .9500 | C(37)—H(37B) | .9800 |
| N(1)—C(4) | 1.372(3) | C(19)—C(20) | 1.377(3) | C(37)—H(37C) | .9800 |
| N(1)—C(5) | 1.377(2) | C(19)—H(19) | .9500 | C(38)—H(38A) | .9800 |
| N(1)—H(1N) | .8800 | C(20)—C(21) | 1.381(3) | C(38)—H(38B) | .9800 |
| N(2)—C(13) | 1.492(3) | C(20)—H(20) | .9500 | C(38)—H(38C) | .9800 |
| N(2)—C(14) | 1.492(3) | C(21)—C(22) | 1.381(3) | C(39)—C(40) | 1.525(3) |
| N(2)—C(12) | 1.546(3) | C(21)—H(21) | .9500 | C(39)—H(39A) | .9900 |
| N(2)—H(2N) | .91(2) | C(22)—H(22) | .9500 | C(39)—H(39B) | .9900 |
| C(1)—C(2) | 1.363(3) | C(23)—C(24) | 1.383(3) | C(40)—H(40A) | .9900 |
| C(1)—C(24) | 1.385(3) | C(23)—H(23) | .9500 | C(40)—H(40B) | .9900 |
| C(2)—C(3) | 1.396(3) | C(24)—H(24) | .9500 | C(41)—C(46) | 1.391(3) |
| C(2)—H(2) | .9500 | F(2)—C(25) | 1.360(3) | C(41)—C(42) | 1.400(3) |
| C(3)—C(4) | 1.418(3) | O(6)—C(31) | 1.425(2) | C(42)—C(43) | 1.380(3) |
| C(3)—C(9) | 1.421(3) | O(6)—C(30) | 1.442(2) | C(42)—H(42) | .9500 |
| C(4)—C(23) | 1.391(3) | N(3)—C(28) | 1.372(3) | C(43)—C(44) | 1.382(3) |
| C(5)—C(9) | 1.364(3) | N(3)—C(29) | 1.376(3) | C(43)—H(43) | .9500 |
| C(5)—C(6) | 1.487(3) | N(3)—H(3N) | .8800 | C(44)—C(45) | 1.380(3) |
| C(6)—C(16) | 1.525(3) | N(4)—C(38) | 1.489(3) | C(44)—H(44) | .9500 |
| C(6)—C(10) | 1.531(3) | N(4)—C(37) | 1.499(3) | C(45)—C(46) | 1.386(3) |
| C(7)—C(8) | 1.516(3) | N(4)—C(36) | 1.548(3) | C(45)—H(45) | .9500 |

TABLE K8-A-continued

Bond lengths [Å] and angles [deg] for crystalline form F.

| bond lengths [Å] and angles [deg] | | bond lengths [Å] and angles [deg] | | bond lengths [Å] and angles [deg] | |
|---|---|---|---|---|---|
| C(7)—H(7A) | .9900 | N(4)—H(4N) | .94(2) | C(46)—H(46) | .9500 |
| C(7)—H(7B) | .9900 | C(25)—C(26) | 1.370(3) | C(47)—C(48) | 1.386(3) |
| C(8)—C(9) | 1.496(3) | C(25)—C(48) | 1.388(3) | C(47)—H(47) | .9500 |
| C(8)—H(8A) | .9900 | C(26)—C(27) | 1.396(3) | C(48)—H(48) | .9500 |
| C(8)—H(8B) | .9900 | C(26)—H(26) | .9500 | O(7)—C(49) | 1.205(3) |
| C(10)—C(11) | 1.519(3) | C(27)—C(28) | 1.421(3) | O(8)—C(49) | 1.322(3) |
| C(10)—H(10A) | .9900 | C(27)—C(33) | 1.425(3) | O(8)—H(8O) | .80(3) |
| C(10)—H(10B) | .9900 | C(28)—C(47) | 1.387(3) | C(49)—C(50) | 1.501(4) |
| C(11)—C(12) | 1.537(3) | C(29)—C(33) | 1.361(3) | C(50)—H(50A) | .9800 |
| C(11)—H(11A) | .9900 | C(29)—C(30) | 1.490(3) | C(50)—H(50B) | .9800 |
| C(11)—H(11B) | .9900 | C(30)—C(40) | 1.525(3) | C(50)—H(50C) | .9800 |
| C(12)—C(15) | 1.534(3) | C(30)—C(34) | 1.530(3) | O(9)—C(51) | 1.289(3) |
| C(12)—C(17) | 1.535(3) | C(31)—C(32) | 1.518(3) | O(9)—H(9O) | .87(3) |
| C(13)—H(13A) | .9800 | C(31)—H(31A) | .9900 | O(10A)—C(51) | 1.224(3) |
| C(13)—H(13B) | .9800 | C(31)—H(31B) | .9900 | O(10B)—C(51) | 1.286(4) |
| C(13)—H(13C) | .9800 | C(32)—C(33) | 1.493(3) | C(51)—C(52) | 1.489(4) |
| C(14)—H(14A) | .9800 | C(32)—H(32A) | .9900 | C(52)—H(52A) | .9800 |
| C(14)—H(14B) | .9800 | C(32)—H(32B) | .9900 | C(52)—H(52B) | .9800 |
| C(14)—H(14C) | .9800 | C(34)—C(35) | 1.524(3) | C(52)—H(52C) | .9800 |
| C(15)—C(16) | 1.519(3) | C(34)—H(34A) | .9900 | | |
| C(15)—H(15A) | .9900 | C(34)—H(34B) | .9900 | | |

TABLE K8-B (Table K8-A continued) Bond lengths [Å] and angles [deg] for crystalline form F.

| bond lengths [Å] and angles [deg] | | bond lengths [Å] and angles [deg] | |
|---|---|---|---|
| O(4)—S(1)—O(3) | 110.14(14) | C(36)—N(4)—H(4N) | 107.9(15) |
| O(4)—S(1)—O(1) | 109.17(11) | F(2)—C(25)—C(26) | 118.4(2) |
| O(3)—S(1)—O(1) | 111.09(11) | F(2)—C(25)—C(48) | 117.6(2) |
| O(4)—S(1)—O(2) | 109.83(12) | C(26)—C(25)—C(48) | 124.0(2) |
| O(3)—S(1)—O(2) | 107.53(10) | C(25)—C(26)—C(27) | 117.4(2) |
| O(1)—S(1)—O(2) | 109.05(10) | C(25)—C(26)—H(26) | 121.3 |
| C(7)—O(5)—C(6) | 115.34(15) | C(27)—C(26)—H(26) | 121.3 |
| C(4)—N(1)—C(5) | 108.17(17) | C(26)—C(27)—C(28) | 119.3(2) |
| C(4)—N(1)—H(1N) | 125.9 | C(26)—C(27)—C(33) | 134.4(2) |
| C(5)—N(1)—H(1N) | 125.9 | C(28)—C(27)—C(33) | 106.32(19) |
| C(13)—N(2)—C(14) | 109.19(18) | N(3)—C(28)—C(47) | 130.2(2) |
| C(13)—N(2)—C(12) | 114.30(16) | N(3)—C(28)—C(27) | 108.08(18) |
| C(14)—N(2)—C(12) | 113.82(16) | C(47)—C(28)—C(27) | 121.7(2) |
| C(13)—N(2)—H(2N) | 101.9(15) | C(33)—C(29)—N(3) | 110.37(19) |
| C(14)—N(2)—H(2N) | 106.7(15) | C(33)—C(29)—C(30) | 125.21(19) |
| C(12)—N(2)—H(2N) | 110.0(15) | N(3)—C(29)—C(30) | 124.42(18) |
| C(2)—C(1)—F(1) | 118.2(2) | O(6)—C(30)—C(29) | 108.05(16) |
| C(2)—C(1)—C(24) | 124.4(2) | O(6)—C(30)—C(40) | 104.64(16) |
| F(1)—C(1)—C(24) | 117.42(19) | C(29)—C(30)—C(40) | 111.51(17) |
| C(1)—C(2)—C(3) | 117.5(2) | O(6)—C(30)—C(34) | 109.85(16) |
| C(1)—C(2)—H(2) | 121.3 | C(29)—C(30)—C(34) | 114.22(17) |
| C(3)—C(2)—H(2) | 121.3 | C(40)—C(30)—C(34) | 108.14(17) |
| C(2)—C(3)—C(4) | 119.16(19) | O(6)—C(31)—C(32) | 110.69(17) |
| C(2)—C(3)—C(9) | 134.2(2) | O(6)—C(31)—H(31A) | 109.5 |
| C(4)—C(3)—C(9) | 106.58(19) | C(32)—C(31)—H(31A) | 109.5 |
| N(1)—C(4)—C(23) | 130.42(19) | O(6)—C(31)—H(31B) | 109.5 |
| N(1)—C(4)—C(3) | 108.01(18) | C(32)—C(31)—H(31B) | 109.5 |
| C(23)—C(4)—C(3) | 121.6(2) | H(31A)—C(31)—H(31B) | 108.1 |
| C(9)—C(5)—N(1) | 110.20(19) | C(33)—C(32)—C(31) | 106.63(17) |
| C(9)—C(5)—C(6) | 125.57(18) | C(33)—C(32)—H(32A) | 110.4 |
| N(1)—C(5)—C(6) | 124.23(18) | C(31)—C(32)—H(32A) | 110.4 |
| O(5)—C(6)—C(5) | 108.28(16) | C(33)—C(32)—H(32B) | 110.4 |
| O(5)—C(6)—C(16) | 105.03(16) | C(31)—C(32)—H(32B) | 110.4 |
| C(5)—C(6)—C(16) | 111.25(17) | H(32A)—C(32)—H(32B) | 108.6 |
| O(5)—C(6)—C(10) | 109.52(16) | C(29)—C(33)—C(27) | 107.10(19) |
| C(5)—C(6)—C(10) | 112.42(17) | C(29)—C(33)—C(32) | 121.6(2) |
| C(16)—C(6)—C(10) | 110.05(17) | C(27)—C(33)—C(32) | 131.09(19) |
| O(5)—C(7)—C(8) | 110.80(17) | C(35)—C(34)—C(30) | 110.91(17) |
| O(5)—C(7)—H(7A) | 109.5 | C(35)—C(34)—H(34A) | 109.5 |
| C(8)—C(7)—H(7A) | 109.5 | C(30)—C(34)—H(34A) | 109.5 |
| O(5)—C(7)—H(7B) | 109.5 | C(35)—C(34)—H(34B) | 109.5 |
| C(8)—C(7)—H(7B) | 109.5 | C(30)—C(34)—H(34B) | 109.5 |

TABLE K8-B-continued (Table K8-A continued) Bond lengths [Å] and angles [deg] for crystalline form F.

| bond lengths [Å] and angles [deg] | | bond lengths [Å] and angles [deg] | |
|---|---|---|---|
| H(7A)—C(7)—H(7B) | 108.1 | H(34A)—C(34)—H(34B) | 108.0 |
| C(9)—C(8)—C(7) | 106.84(17) | C(34)—C(35)—C(36) | 115.20(17) |
| C(9)—C(8)—H(8A) | 110.4 | C(34)—C(35)—H(35A) | 108.5 |
| C(7)—C(8)—H(8A) | 110.4 | C(36)—C(35)—H(35A) | 108.5 |
| C(9)—C(8)—H(8B) | 110.4 | C(34)—C(35)—H(35B) | 108.5 |
| C(7)—C(8)—H(8B) | 110.4 | C(36)—C(35)—H(35B) | 108.5 |
| H(8A)—C(8)—H(8B) | 108.6 | H(35A)—C(35)—H(35B) | 107.5 |
| C(5)—C(9)—C(3) | 107.04(18) | C(41)—C(36)—C(35) | 110.66(17) |
| C(5)—C(9)—C(8) | 121.08(19) | C(41)—C(36)—C(39) | 111.04(16) |
| C(3)—C(9)—C(8) | 131.68(19) | C(35)—C(36)—C(39) | 108.16(17) |
| C(11)—C(10)—C(6) | 111.82(17) | C(41)—C(36)—N(4) | 108.60(16) |
| C(11)—C(10)—H(10A) | 109.3 | C(35)—C(36)—N(4) | 109.94(16) |
| C(6)—C(10)—H(10A) | 109.3 | C(39)—C(36)—N(4) | 108.41(15) |
| C(11)—C(10)—H(10B) | 109.3 | N(4)—C(37)—H(37A) | 109.5 |
| C(6)—C(10)—H(10B) | 109.3 | N(4)—C(37)—H(37B) | 109.5 |
| H(10A)—C(10)—H(10B) | 107.9 | H(37A)—C(37)—H(37B) | 109.5 |
| C(10)—C(11)—C(12) | 114.62(17) | N(4)—C(37)—H(37C) | 109.5 |
| C(10)—C(11)—H(11A) | 108.6 | H(37A)—C(37)—H(37C) | 109.5 |
| C(12)—C(11)—H(11A) | 108.6 | H(37B)—C(37)—H(37C) | 109.5 |
| C(10)—C(11)—H(11B) | 108.6 | N(4)—C(38)—H(38A) | 109.5 |
| C(12)—C(11)—H(11B) | 108.6 | N(4)—C(38)—H(38B) | 109.5 |
| H(11A)—C(11)—H(11B) | 107.6 | H(38A)—C(38)—H(38B) | 109.5 |
| C(15)—C(12)—C(17) | 111.29(17) | N(4)—C(38)—H(38C) | 109.5 |
| C(15)—C(12)—C(11) | 107.34(17) | H(38A)—C(38)—H(38C) | 109.5 |
| C(17)—C(12)—C(11) | 110.61(17) | H(38B)—C(38)—H(38C) | 109.5 |
| C(15)—C(12)—N(2) | 108.13(16) | C(40)—C(39)—C(36) | 115.74(17) |
| C(17)—C(12)—N(2) | 110.00(16) | C(40)—C(39)—H(39A) | 108.3 |
| C(11)—C(12)—N(2) | 109.39(16) | C(36)—C(39)—H(39A) | 108.3 |
| N(2)—C(13)—H(13A) | 109.5 | C(40)—C(39)—H(39B) | 108.3 |
| N(2)—C(13)—H(13B) | 109.5 | C(36)—C(39)—H(39B) | 108.3 |
| H(13A)—C(13)—H(13B) | 109.5 | H(39A)—C(39)—H(39B) | 107.4 |
| N(2)—C(13)—H(13C) | 109.5 | C(39)—C(40)—C(30) | 112.51(17) |
| H(13A)—C(13)—H(13C) | 109.5 | C(39)—C(40)—H(40A) | 109.1 |
| H(13B)—C(13)—H(13C) | 109.5 | C(30)—C(40)—H(40A) | 109.1 |
| N(2)—C(14)—H(14A) | 109.5 | C(39)—C(40)—H(40B) | 109.1 |
| N(2)—C(14)—H(14B) | 109.5 | C(30)—C(40)—H(40B) | 109.1 |
| H(14A)—C(14)—H(14B) | 109.5 | H(40A)—C(40)—H(40B) | 107.8 |
| N(2)—C(14)—H(14C) | 109.5 | C(46)—C(41)—C(42) | 117.4(2) |
| H(14A)—C(14)—H(14C) | 109.5 | C(46)—C(41)—C(36) | 121.13(19) |
| H(14B)—C(14)—H(14C) | 109.5 | C(42)—C(41)—C(36) | 121.40(18) |
| C(16)—C(15)—C(12) | 114.48(17) | C(43)—C(42)—C(41) | 121.4(2) |
| C(16)—C(15)—H(15A) | 108.6 | C(43)—C(42)—H(42) | 119.3 |
| C(12)—C(15)—H(15A) | 108.6 | C(41)—C(42)—H(42) | 119.3 |
| C(16)—C(15)—H(15B) | 108.6 | C(42)—C(43)—C(44) | 120.3(2) |
| C(12)—C(15)—H(15B) | 108.6 | C(42)—C(43)—H(43) | 119.9 |
| H(15A)—C(15)—H(15B) | 107.6 | C(44)—C(43)—H(43) | 119.9 |
| C(15)—C(16)—C(6) | 112.66(17) | C(45)—C(44)—C(43) | 119.2(2) |
| C(15)—C(16)—H(16A) | 109.1 | C(45)—C(44)—H(44) | 120.4 |
| C(6)—C(16)—H(16A) | 109.1 | C(43)—C(44)—H(44) | 120.4 |
| C(15)—C(16)—H(16B) | 109.1 | C(44)—C(45)—C(46) | 120.6(2) |
| C(6)—C(16)—H(16B) | 109.1 | C(44)—C(45)—H(45) | 119.7 |
| H(16A)—C(16)—H(16B) | 107.8 | C(46)—C(45)—H(45) | 119.7 |
| C(18)—C(17)—C(22) | 117.3(2) | C(45)—C(46)—C(41) | 121.1(2) |
| C(18)—C(17)—C(12) | 120.97(19) | C(45)—C(46)—H(46) | 119.5 |
| C(22)—C(17)—C(12) | 121.63(19) | C(41)—C(46)—H(46) | 119.5 |
| C(17)—C(18)—C(19) | 121.3(2) | C(48)—C(47)—C(28) | 118.3(2) |
| C(17)—C(18)—H(18) | 119.3 | C(48)—C(47)—H(47) | 120.9 |
| C(19)—C(18)—H(18) | 119.3 | C(28)—C(47)—H(47) | 120.9 |
| C(20)—C(19)—C(18) | 120.4(2) | C(47)—C(48)—C(25) | 119.3(2) |
| C(20)—C(19)—H(19) | 119.8 | C(47)—C(48)—H(48) | 120.3 |
| C(18)—C(19)—H(19) | 119.8 | C(25)—C(48)—H(48) | 120.3 |
| C(19)—C(20)—C(21) | 119.2(2) | C(49)—O(8)—H(8O) | 99(2) |
| C(19)—C(20)—H(20) | 120.4 | O(7)—C(49)—O(8) | 123.2(2) |
| C(21)—C(20)—H(20) | 120.4 | O(7)—C(49)—C(50) | 124.1(2) |
| C(20)—C(21)—C(22) | 120.2(2) | O(8)—C(49)—C(50) | 112.7(2) |
| C(20)—C(21)—H(21) | 119.9 | C(49)—C(50)—H(50A) | 109.5 |
| C(22)—C(21)—H(21) | 119.9 | C(49)—C(50)—H(50B) | 109.5 |
| C(21)—C(22)—C(17) | 121.6(2) | H(50A)—C(50)—H(50B) | 109.5 |
| C(21)—C(22)—H(22) | 119.2 | C(49)—C(50)—H(50C) | 109.5 |
| C(17)—C(22)—H(22) | 119.2 | H(50A)—C(50)—H(50C) | 109.5 |
| C(24)—C(23)—C(4) | 118.4(2) | H(50B)—C(50)—H(50C) | 109.5 |
| C(24)—C(23)—H(23) | 120.8 | C(51)—O(9)—H(9O) | 115(2) |
| C(4)—C(23)—H(23) | 120.8 | O(10A)—C(51)—O(10B) | 59.4(3) |
| C(23)—C(24)—C(1) | 119.0(2) | O(10A)—C(51)—O(9) | 123.6(3) |
| C(23)—C(24)—H(24) | 120.5 | O(10B)—C(51)—O(9) | 111.7(4) |

TABLE K8-B-continued (Table K8-A continued) Bond lengths [Å] and angles [deg] for crystalline form F.

| | bond lengths [Å] and angles [deg] | | bond lengths [Å] and angles [deg] |
|---|---|---|---|
| C(1)—C(24)—H(24) | 120.5 | O(10A)—C(51)—C(52) | 111.9(3) |
| C(31)—O(6)—C(30) | 115.37(16) | O(10B)—C(51)—C(52) | 127.3(3) |
| C(28)—N(3)—C(29) | 108.12(18) | O(9)—C(51)—C(52) | 113.5(2) |
| C(28)—N(3)—H(3N) | 125.9 | C(51)—C(52)—H(52A) | 109.5 |
| C(29)—N(3)—H(3N) | 125.9 | C(51)—C(52)—H(52B) | 109.5 |
| C(38)—N(4)—C(37) | 108.36(19) | H(52A)—C(52)—H(52B) | 109.5 |
| C(38)—N(4)—C(36) | 113.69(17) | C(51)—C(52)—H(52C) | 109.5 |
| C(37)—N(4)—C(36) | 114.14(16) | H(52A)—C(52)—H(52C) | 109.5 |
| C(38)—N(4)—H(4N) | 104.1(14) | H(52B)—C(52)—H(52C) | 109.5 |
| C(37)—N(4)—H(4N) | 108.1(15) | | |

Symmetry Transformations Used to Generate Equivalent Atoms:

TABLE K9

Hydrogen coordinates ($\times 10^4$) (i.e. ($\times 10^{\wedge}4$)) and isotropic displacement parameters ($^2 \times 10^3$) (i.e. ($^2 \times 10^{\wedge}3$)) for crystalline form F.

| | x | y | z | U(eq) |
|---|---|---|---|---|
| H(1N) | 5760 | 1742 | 2852 | 18 |
| H(2N) | 8790(2) | 1555(16) | 1872(15) | 19 |
| H(2) | 2219 | 4142 | 3726 | 19 |
| H(7A) | 5479 | 4865 | 1436 | 19 |
| H(7B) | 6001 | 5602 | 1841 | 19 |
| H(8A) | 5116 | 4954 | 3225 | 19 |
| H(8B) | 3997 | 5166 | 2520 | 19 |
| H(10A) | 6958 | 2513 | 1419 | 17 |
| H(10B) | 6367 | 3583 | 987 | 17 |
| H(11A) | 8402 | 4030 | 828 | 18 |
| H(11B) | 8413 | 3205 | 368 | 18 |
| H(13A) | 10262 | 1641 | 398 | 38 |
| H(13B) | 8725 | 1819 | 437 | 38 |
| H(13C) | 9492 | 802 | 880 | 38 |
| H(14A) | 10505 | 464 | 2243 | 31 |
| H(14B) | 10625 | 1276 | 2697 | 31 |
| H(14C) | 11431 | 1221 | 1818 | 31 |
| H(15A) | 10029 | 2561 | 2785 | 16 |
| H(15B) | 9436 | 3627 | 2348 | 16 |
| H(16A) | 7992 | 2963 | 3408 | 17 |
| H(16B) | 7996 | 2114 | 2978 | 17 |
| H(18) | 11786 | 2819 | 2158 | 24 |
| H(19) | 13647 | 3359 | 1497 | 28 |
| H(20) | 13762 | 3992 | −18 | 25 |
| H(21) | 12020 | 4028 | −875 | 25 |
| H(22) | 10176 | 3469 | −219 | 22 |
| H(23) | 3582 | 1012 | 3631 | 20 |
| H(24) | 1562 | 1459 | 4230 | 23 |
| H(3N) | 725 | 1551 | 7827 | 19 |
| H(4N) | 4160(2) | 1376(16) | 6813(16) | 19 |
| H(26) | −2673 | 3986 | 8784 | 22 |
| H(31A) | 542 | 4669 | 6445 | 21 |
| H(31B) | 1109 | 5387 | 6851 | 21 |
| H(32A) | 228 | 4748 | 8240 | 20 |
| H(32B) | −906 | 4979 | 7544 | 20 |
| H(34A) | 2088 | 2286 | 6401 | 18 |
| H(34B) | 1384 | 3330 | 5977 | 18 |
| H(35A) | 3346 | 3907 | 5824 | 18 |
| H(35B) | 3445 | 3099 | 5333 | 18 |
| H(37A) | 5344 | 1816 | 5157 | 38 |
| H(37B) | 3848 | 1748 | 5329 | 38 |
| H(37C) | 4893 | 825 | 5612 | 38 |
| H(38A) | 6040 | 464 | 6916 | 44 |
| H(38B) | 6103 | 1242 | 7423 | 44 |
| H(38C) | 6748 | 1347 | 6466 | 44 |
| H(39A) | 5063 | 2344 | 7751 | 17 |
| H(39B) | 4457 | 3420 | 7402 | 17 |
| H(40A) | 3010 | 2678 | 8397 | 17 |
| H(40B) | 3049 | 1879 | 7900 | 17 |
| H(42) | 5169 | 3557 | 4749 | 21 |
| H(43) | 6949 | 4232 | 4122 | 24 |
| H(44) | 8647 | 4242 | 4998 | 24 |
| H(45) | 8541 | 3560 | 6507 | 23 |
| H(46) | 6757 | 2889 | 7142 | 21 |
| H(47) | −1450 | 855 | 8636 | 24 |
| H(48) | −3434 | 1324 | 9270 | 26 |
| H(8O) | 7810(3) | 360(2) | 4460(2) | 40 |
| H(50A) | 10057 | 1269 | 5563 | 48 |
| H(50B) | 8907 | 787 | 6112 | 48 |
| H(50C) | 8633 | 1844 | 5513 | 48 |
| H(9O) | 5770(3) | 330(2) | 1400(2) | 54 |
| H(52A) | 3599 | 825 | −294 | 69 |
| H(52B) | 4097 | 1763 | −248 | 69 |
| H(52C) | 2708 | 1554 | 143 | 69 |

TABLE K10

Anisotropic displacement parameters ($^2 \times 10^3$) (i.e. ($^{\wedge}2 \times 10^{\wedge}3$) for crystalline form F. The anisotropic displacement factor exponent takes the form: $-2\pi^2$ [$h^2 a^{*2} U11 + \ldots + 2 h k a^* b^* U12$].

| | U11 | U22 | U33 | U23 | U13 | U12 |
|---|---|---|---|---|---|---|
| S(1) | 19(1) | 13(1) | 32(1) | −7(1) | 4(1) | −5(1) |
| O(1) | 19(1) | 14(1) | 41(1) | −6(1) | 2(1) | −4(1) |
| O(2) | 33(1) | 22(1) | 29(1) | −5(1) | −1(1) | −15(1) |
| O(3) | 59(2) | 47(1) | 34(1) | 3(1) | −8(1) | −33(1) |
| O(4) | 27(1) | 22(1) | 107(2) | −31(1) | 20(1) | −3(1) |
| F(1) | 13(1) | 35(1) | 26(1) | −10(1) | 8(1) | −3(1) |
| O(5) | 15(1) | 11(1) | 22(1) | −6(1) | 2(1) | −3(1) |
| N(1) | 12(1) | 13(1) | 21(1) | −6(1) | 3(1) | −2(1) |
| N(2) | 15(1) | 14(1) | 20(1) | −7(1) | 1(1) | −2(1) |
| C(1) | 8(1) | 30(1) | 15(1) | −6(1) | 2(1) | −2(1) |
| C(2) | 14(1) | 19(1) | 13(1) | −6(1) | 0(1) | 0(1) |
| C(3) | 14(1) | 15(1) | 14(1) | −4(1) | −2(1) | −1(1) |
| C(4) | 12(1) | 17(1) | 15(1) | −6(1) | 0(1) | −3(1) |
| C(5) | 11(1) | 13(1) | 15(1) | −4(1) | −1(1) | −3(1) |
| C(6) | 12(1) | 11(1) | 16(1) | −5(1) | 2(1) | −3(1) |
| C(7) | 15(1) | 13(1) | 19(1) | −4(1) | 0(1) | −2(1) |
| C(8) | 16(1) | 12(1) | 18(1) | −4(1) | 1(1) | −2(1) |
| C(9) | 14(1) | 14(1) | 14(1) | −4(1) | −1(1) | −2(1) |
| C(10) | 13(1) | 15(1) | 15(1) | −4(1) | −1(1) | −4(1) |
| C(11) | 14(1) | 18(1) | 13(1) | −4(1) | 1(1) | −2(1) |
| C(12) | 13(1) | 12(1) | 15(1) | −6(1) | 1(1) | −4(1) |
| C(13) | 33(2) | 23(1) | 26(1) | −14(1) | −3(1) | −4(1) |
| C(14) | 17(1) | 15(1) | 28(1) | −4(1) | −2(1) | 0(1) |
| C(15) | 11(1) | 15(1) | 14(1) | −5(1) | 1(1) | −3(1) |
| C(16) | 14(1) | 15(1) | 14(1) | −5(1) | 2(1) | −4(1) |
| C(17) | 14(1) | 14(1) | 17(1) | −7(1) | 2(1) | −2(1) |
| C(18) | 17(1) | 27(1) | 16(1) | −6(1) | 2(1) | −6(1) |
| C(19) | 16(1) | 34(1) | 20(1) | −6(1) | 1(1) | −10(1) |

TABLE K10-continued

Anisotropic displacement parameters ($Å^2 \times 10^3$) (i.e. ($Å^2 \times 10^3$) for crystalline form F. The anisotropic displacement factor exponent takes the form: $-2\pi^2$ [$h^2 a^{*2}$ U11 + ... + 2 h k $a^* b^*$ U12].

| | U11 | U22 | U33 | U23 | U13 | U12 |
|---|---|---|---|---|---|---|
| C(20) | 16(1) | 27(1) | 21(1) | −7(1) | 6(1) | −7(1) |
| C(21) | 19(1) | 24(1) | 17(1) | −3(1) | 4(1) | −3(1) |
| C(22) | 14(1) | 24(1) | 17(1) | −7(1) | 0(1) | −3(1) |
| C(23) | 18(1) | 16(1) | 16(1) | −4(1) | 1(1) | −5(1) |
| C(24) | 15(1) | 24(1) | 18(1) | −3(1) | 0(1) | −8(1) |
| F(2) | 16(1) | 41(1) | 33(1) | −14(1) | 10(1) | −2(1) |
| O(6) | 15(1) | 12(1) | 24(1) | −8(1) | 1(1) | −2(1) |
| N(3) | 13(1) | 14(1) | 23(1) | −8(1) | 4(1) | −2(1) |
| N(4) | 16(1) | 14(1) | 19(1) | −6(1) | 2(1) | −4(1) |
| C(25) | 9(1) | 34(1) | 19(1) | −9(1) | 3(1) | −1(1) |
| C(26) | 15(1) | 23(1) | 15(1) | −6(1) | −1(1) | 1(1) |
| C(27) | 14(1) | 17(1) | 13(1) | −6(1) | −2(1) | 0(1) |
| C(28) | 13(1) | 20(1) | 16(1) | −6(1) | 2(1) | −2(1) |
| C(29) | 14(1) | 15(1) | 16(1) | −4(1) | −1(1) | −5(1) |
| C(30) | 14(1) | 12(1) | 16(1) | −5(1) | 1(1) | −2(1) |
| C(31) | 18(1) | 14(1) | 20(1) | −5(1) | −1(1) | 1(1) |
| C(32) | 17(1) | 14(1) | 19(1) | −6(1) | −1(1) | −1(1) |
| C(33) | 14(1) | 16(1) | 14(1) | −7(1) | −1(1) | −2(1) |
| C(34) | 12(1) | 18(1) | 16(1) | −6(1) | 0(1) | −2(1) |
| C(35) | 16(1) | 16(1) | 13(1) | −5(1) | 1(1) | −2(1) |
| C(36) | 14(1) | 11(1) | 14(1) | −5(1) | 0(1) | −2(1) |
| C(37) | 34(2) | 23(1) | 25(1) | −16(1) | 9(1) | −10(1) |
| C(38) | 23(1) | 16(1) | 48(2) | −9(1) | −7(1) | 4(1) |
| C(39) | 12(1) | 16(1) | 15(1) | −4(1) | 1(1) | −3(1) |
| C(40) | 15(1) | 14(1) | 14(1) | −5(1) | 1(1) | −1(1) |
| C(41) | 14(1) | 13(1) | 15(1) | −6(1) | 3(1) | −2(1) |
| C(42) | 16(1) | 21(1) | 17(1) | −7(1) | 0(1) | −3(1) |
| C(43) | 21(1) | 21(1) | 16(1) | −3(1) | 4(1) | −5(1) |
| C(44) | 18(1) | 20(1) | 23(1) | −5(1) | 3(1) | −7(1) |
| C(45) | 17(1) | 24(1) | 19(1) | −8(1) | 1(1) | −6(1) |
| C(46) | 17(1) | 19(1) | 17(1) | −6(1) | −1(1) | −4(1) |
| C(47) | 17(1) | 20(1) | 25(1) | −7(1) | 1(1) | −4(1) |
| C(48) | 16(1) | 31(1) | 20(1) | −6(1) | 2(1) | −7(1) |
| O(7) | 21(1) | 29(1) | 24(1) | −4(1) | 3(1) | −5(1) |
| O(8) | 22(1) | 40(1) | 38(1) | −12(1) | 7(1) | −9(1) |
| C(49) | 17(1) | 18(1) | 32(1) | −1(1) | 1(1) | 0(1) |
| C(50) | 31(2) | 33(1) | 36(2) | −17(1) | 10(1) | −8(1) |
| O(9) | 28(1) | 68(2) | 31(1) | −2(1) | 2(1) | −9(1) |
| O(10A) | 32(2) | 50(3) | 40(3) | 12(2) | −1(2) | −18(2) |
| O(10B) | 50(3) | 78(5) | 38(3) | 20(3) | 21(2) | 31(3) |
| C(51) | 31(2) | 50(2) | 56(2) | 28(2) | 21(2) | 14(1) |
| C(52) | 28(2) | 40(2) | 61(2) | 1(1) | −3(1) | 0(1) |

Crystalline Form G

TABLE K11

Crystal data and structure refinement for crystalline form G.

| | |
|---|---|
| Empirical formula | $C_{24}H_{29}FN_2O_5S$ |
| Formula weight | 476.55 |
| Temperature | 100(2) K |
| Wavelength | .71073 Å |
| Crystal system | Triclinic |
| Space group | P-1 |
| Unit cell dimensions | a = 9.756(6) Å alpha = 98.559(15) deg. |
| | b = 10.602(6) Å beta = 105.991(14) deg. |
| | c = 12.164(7) Å gamma = 105.867(13) deg. |
| Volume | 1128.7(11) Å$^3$ |
| Z | 2 |
| Density (calculated) | 1.402 Mg/m$^3$ |
| Absorption coefficient | 0.191 mm$^{-1}$ |
| F(000) | 504 |
| Crystal size | 0.20 × 0.04 × 0.02 mm |
| Theta range for data collection | 1.80 to 25.27 deg. |
| Index ranges | −11 <= h <= 10, −12 <= k <= 12, 0 <= l <= 14 |
| Reflections collected | 21344 |
| Independent reflections | 4653 [R(int) = 0.1194] |
| Absorption correction | Semi-empirical from equivalents |
| Max. and min. transmission | 0.996 and 0.963 |

TABLE K11-continued

Crystal data and structure refinement for crystalline form G.

| | |
|---|---|
| Refinement method | Full-matrix least-squares on F$^2$ |
| Data/restraints/parameters | 4653/0/309 |
| Goodness-of-fit on F$^2$ | 1.013 |
| Final R indices [I > 2sigma(I)] | R1 = 0.0887, wR2 = 0.1864 |
| R indices (all data) | R1 = 0.2039, wR2 = 0.2309 |
| Largest diff. peak and hole | 0.417 and −0.515 e · Å$^{-3}$ |

TABLE K12

Atomic coordinates (×10$^4$) (i.e. (×10$^4$)) and equivalent isotropic displacement parameters ($Å^2 \times 10^3$) (i.e. ($Å^2 \times 10^3$)) for crystalline form G. U(eq) is defined as one third of the trace of the orthogonalized Uij tensor.

| | x | y | z | U(eq) |
|---|---|---|---|---|
| F(1) | −1684(4) | 5807(3) | −5541(3) | 43(1) |
| O(5) | 1965(4) | 8121(4) | 1201(3) | 26(1) |
| N(1) | 1824(6) | 9537(5) | −1421(4) | 26(1) |
| N(2) | 4749(5) | 12669(5) | 2326(4) | 22(1) |
| C(1) | −806(7) | 6774(6) | −4530(5) | 31(2) |
| C(2) | −646(7) | 6410(6) | −3485(5) | 28(2) |
| C(3) | 268(6) | 7429(6) | −2446(5) | 22(1) |
| C(4) | 977(6) | 8742(6) | −2547(5) | 21(1) |
| C(5) | 1619(6) | 8742(6) | −627(5) | 22(1) |
| C(6) | 2327(6) | 9247(6) | 681(5) | 23(2) |
| C(7) | 443(6) | 7191(6) | 671(5) | 30(2) |
| C(8) | 211(7) | 6429(6) | −561(5) | 28(2) |
| C(9) | 683(7) | 7468(6) | −1233(5) | 25(2) |
| C(10) | 1778(7) | 10349(6) | 1180(5) | 24(2) |
| C(11) | 2560(6) | 10937(6) | 2499(5) | 22(1) |
| C(12) | 4298(6) | 11460(6) | 2893(5) | 21(1) |
| C(13) | 6364(6) | 13115(6) | 2363(5) | 30(2) |
| C(14) | 4391(7) | 13884(6) | 2806(6) | 36(2) |
| C(15) | 4806(6) | 10321(6) | 2393(5) | 24(2) |
| C(16) | 4053(6) | 9749(6) | 1071(5) | 22(1) |
| C(17) | 5030(7) | 11969(6) | 4213(5) | 26(2) |
| C(18) | 4207(7) | 12301(6) | 4934(5) | 25(2) |
| C(19) | 4839(7) | 12731(6) | 6140(5) | 27(2) |
| C(20) | 6344(7) | 12881(6) | 6685(5) | 29(2) |
| C(21) | 7168(7) | 12550(6) | 6012(6) | 34(2) |
| C(22) | 6531(7) | 12091(6) | 4796(5) | 31(2) |
| C(23) | 764(7) | 9059(6) | −3635(5) | 25(2) |
| C(24) | −139(7) | 8067(6) | −4638(5) | 28(2) |
| S(1) | 3487(2) | 13182(2) | −1021(1) | 27(1) |
| O(1) | 2914(5) | 14338(4) | −657(4) | 41(1) |
| O(2) | 3628(5) | 12448(4) | −111(3) | 32(1) |
| O(3) | 5002(5) | 13842(4) | −1108(4) | 39(1) |
| O(4) | 2433(5) | 12352(4) | −2133(3) | 35(1) |

TABLE K13-A

Bond lengths [Å] and angles [deg] for crystalline form G.

| bond lengths [Å] and angles [deg] | | bond lengths [Å] and angles [deg] | |
|---|---|---|---|
| F(1)—C(1) | 1.364(7) | C(12)—C(17) | 1.510(8) |
| O(5)—C(6) | 1.438(6) | C(12)—C(15) | 1.532(8) |
| O(5)—C(7) | 1.440(6) | C(13)—H(13A) | .9800 |
| N(1)—C(4) | 1.386(7) | C(13)—H(13B) | .9800 |
| N(1)—C(5) | 1.393(7) | C(13)—H(13C) | .9800 |
| N(1)—H(1N) | .97(7) | C(14)—H(14A) | .9800 |
| N(2)—C(14) | 1.503(7) | C(14)—H(14B) | .9800 |
| N(2)—C(13) | 1.502(7) | C(14)—H(14C) | .9800 |
| N(2)—C(12) | 1.559(7) | C(15)—C(16) | 1.520(7) |
| N(2)—H(2N) | 1.03(6) | C(15)—H(15A) | .9900 |
| C(1)—C(2) | 1.364(8) | C(15)—H(15B) | .9900 |
| C(1)—C(24) | 1.390(8) | C(16)—H(16A) | .9900 |
| C(2)—C(3) | 1.416(8) | C(16)—H(16B) | .9900 |

TABLE K13-A-continued

Bond lengths [Å] and angles [deg] for crystalline form G.

| | bond lengths [Å] and angles [deg] | | bond lengths [Å] and angles [deg] |
|---|---|---|---|
| C(2)—H(2) | .9500 | C(17)—C(22) | 1.401(8) |
| C(3)—C(9) | 1.410(8) | C(17)—C(18) | 1.410(8) |
| C(3)—C(4) | 1.415(8) | C(18)—C(19) | 1.374(8) |
| C(4)—C(23) | 1.388(8) | C(18)—H(18) | .9500 |
| C(5)—C(9) | 1.364(8) | C(19)—C(20) | 1.388(8) |
| C(5)—C(6) | 1.494(8) | C(19)—H(19) | .9500 |
| C(6)—C(10) | 1.527(8) | C(20)—C(21) | 1.368(8) |
| C(6)—C(16) | 1.529(8) | C(20)—H(20) | .9500 |
| C(7)—C(8) | 1.517(8) | C(21)—C(22) | 1.388(8) |
| C(7)—H(7A) | .9900 | C(21)—H(21) | .9500 |
| C(7)—H(7B) | .9900 | C(22)—H(22) | .9500 |
| C(8)—C(9) | 1.514(8) | C(23)—C(24) | 1.375(8) |
| C(8)—H(8A) | .9900 | C(23)—H(23) | .9500 |
| C(8)—H(8B) | .9900 | C(24)—H(24) | .9500 |
| C(10)—C(11) | 1.520(7) | S(1)—O(4) | 1.431(4) |
| C(10)—H(10A) | .9900 | S(1)—O(2) | 1.442(4) |
| C(10)—H(10B) | .9900 | S(1)—O(3) | 1.492(4) |
| C(11)—C(12) | 1.541(8) | S(1)—O(1) | 1.536(4) |
| C(11)—H(11A) | .9900 | O(1)—H(1) | .8400 |
| C(11)—H(11B) | .9900 | | |

TABLE K13-B (Table K13-A continued) Bond lengths [Å] and angles [deg] for crystalline form G.

| | bond lengths [Å] and angles [deg] | | bond lengths [Å] and angles [deg] |
|---|---|---|---|
| C(6)—O(5)—C(7) | 115.4(4) | C(15)—C(12)—C(11) | 107.7(5) |
| C(4)—N(1)—C(5) | 107.8(5) | C(17)—C(12)—N(2) | 107.9(4) |
| C(4)—N(1)—H(1N) | 119(4) | C(15)—C(12)—N(2) | 109.1(4) |
| C(5)—N(1)—H(1N) | 133(4) | C(11)—C(12)—N(2) | 106.8(4) |
| C(14)—N(2)—C(13) | 108.7(5) | N(2)—C(13)—H(13A) | 109.5 |
| C(14)—N(2)—C(12) | 113.9(4) | N(2)—C(13)—H(13B) | 109.5 |
| C(13)—N(2)—C(12) | 115.1(4) | H(13A)—C(13)—H(13B) | 109.5 |
| C(14)—N(2)—H(2N) | 104(3) | N(2)—C(13)—H(13C) | 109.5 |
| C(13)—N(2)—H(2N) | 101(4) | H(13A)—C(13)—H(13C) | 109.5 |
| C(12)—N(2)—H(2N) | 113(3) | H(13B)—C(13)—H(13C) | 109.5 |
| F(1)—C(1)—C(2) | 118.0(6) | N(2)—C(14)—H(14A) | 109.5 |
| F(1)—C(1)—C(24) | 117.6(5) | N(2)—C(14)—H(14B) | 109.5 |
| C(2)—C(1)—C(24) | 124.5(6) | H(14A)—C(14)—H(14B) | 109.5 |
| C(1)—C(2)—C(3) | 117.0(6) | N(2)—C(14)—H(14C) | 109.5 |
| C(1)—C(2)—H(2) | 121.5 | H(14A)—C(14)—H(14C) | 109.5 |
| C(3)—C(2)—H(2) | 121.5 | H(14B)—C(14)—H(14C) | 109.5 |
| C(9)—C(3)—C(4) | 106.9(5) | C(16)—C(15)—C(12) | 113.8(5) |
| C(9)—C(3)—C(2) | 134.2(6) | C(16)—C(15)—H(15A) | 108.8 |
| C(4)—C(3)—C(2) | 118.9(5) | C(12)—C(15)—H(15A) | 108.8 |
| N(1)—C(4)—C(23) | 130.6(6) | C(16)—C(15)—H(15B) | 108.8 |
| N(1)—C(4)—C(3) | 107.8(5) | C(12)—C(15)—H(15B) | 108.8 |
| C(23)—C(4)—C(3) | 121.5(6) | H(15A)—C(15)—H(15B) | 107.7 |
| C(9)—C(5)—N(1) | 109.3(5) | C(15)—C(16)—C(6) | 113.4(5) |
| C(9)—C(5)—C(6) | 126.7(5) | C(15)—C(16)—H(16A) | 108.9 |
| N(1)—C(5)—C(6) | 124.0(5) | C(6)—C(16)—H(16A) | 108.9 |
| O(5)—C(6)—C(5) | 108.1(4) | C(15)—C(16)—H(16B) | 108.9 |
| O(5)—C(6)—C(10) | 109.5(5) | C(6)—C(16)—H(16B) | 108.9 |
| C(5)—C(6)—C(10) | 112.5(5) | H(16A)—C(16)—H(16B) | 107.7 |
| O(5)—C(6)—C(16) | 104.3(4) | C(22)—C(17)—C(18) | 116.2(5) |
| C(5)—C(6)—C(16) | 112.2(5) | C(22)—C(17)—C(12) | 122.5(6) |
| C(10)—C(6)—C(16) | 109.9(5) | C(18)—C(17)—C(12) | 121.2(6) |
| O(5)—C(7)—C(8) | 110.3(5) | C(19)—C(18)—C(17) | 122.2(6) |
| O(5)—C(7)—H(7A) | 109.6 | C(19)—C(18)—H(18) | 118.9 |
| C(8)—C(7)—H(7A) | 109.6 | C(17)—C(18)—H(18) | 118.9 |
| O(5)—C(7)—H(7B) | 109.6 | C(18)—C(19)—C(20) | 120.1(6) |
| C(8)—C(7)—H(7B) | 109.6 | C(18)—C(19)—H(19) | 120.0 |
| H(7A)—C(7)—H(7B) | 108.1 | C(20)—C(19)—H(19) | 120.0 |
| C(9)—C(8)—C(7) | 107.4(5) | C(21)—C(20)—C(19) | 119.2(6) |
| C(9)—C(8)—H(8A) | 110.2 | C(21)—C(20)—H(20) | 120.4 |
| C(7)—C(8)—H(8A) | 110.2 | C(19)—C(20)—H(20) | 120.4 |
| C(9)—C(8)—H(8B) | 110.2 | C(20)—C(21)—C(22) | 121.1(6) |
| C(7)—C(8)—H(8B) | 110.2 | C(20)—C(21)—H(21) | 119.4 |
| H(8A)—C(8)—H(8B) | 108.5 | C(22)—C(21)—H(21) | 119.4 |
| C(5)—C(9)—C(3) | 108.2(5) | C(21)—C(22)—C(17) | 121.2(6) |
| C(5)—C(9)—C(8) | 119.5(5) | C(21)—C(22)—H(22) | 119.4 |
| C(3)—C(9)—C(8) | 132.3(5) | C(17)—C(22)—H(22) | 119.4 |
| C(11)—C(10)—C(6) | 113.2(5) | C(24)—C(23)—C(4) | 119.1(6) |
| C(11)—C(10)—H(10A) | 108.9 | C(24)—C(23)—H(23) | 120.4 |
| C(6)—C(10)—H(10A) | 108.9 | C(4)—C(23)—H(23) | 120.4 |
| C(11)—C(10)—H(10B) | 108.9 | C(23)—C(24)—C(1) | 118.9(6) |
| C(6)—C(10)—H(10B) | 108.9 | C(23)—C(24)—H(24) | 120.6 |
| H(10A)—C(10)—H(10B) | 107.7 | C(1)—C(24)—H(24) | 120.6 |

TABLE K13-B-continued (Table K13-A continued) Bond lengths [Å] and angles [deg] for crystalline form G.

| | bond lengths [Å] and angles [deg] | | bond lengths [Å] and angles [deg] |
|---|---|---|---|
| C(10)—C(11)—C(12) | 114.7(5) | O(4)—S(1)—O(2) | 112.4(3) |
| C(10)—C(11)—H(11A) | 108.6 | O(4)—S(1)—O(3) | 111.8(3) |
| C(12)—C(11)—H(11A) | 108.6 | O(2)—S(1)—O(3) | 110.2(3) |
| C(10)—C(11)—H(11B) | 108.6 | O(4)—S(1)—O(1) | 107.8(3) |
| C(12)—C(11)—H(11B) | 108.6 | O(2)—S(1)—O(1) | 108.5(3) |
| H(11A)—C(11)—H(11B) | 107.6 | O(3)—S(1)—O(1) | 105.9(3) |
| C(17)—C(12)—C(15) | 112.2(5) | S(1)—O(1)—H(1) | 109.5 |
| C(17)—C(12)—C(11) | 112.9(5) | | |

Symmetry Transformations Used to Generate Equivalent Atoms:

TABLE K14

Hydrogen coordinates (×10$^4$) and isotropic displacement parameters ($\text{Å}^2 \times 10^3$) (i.e. ($\text{Å}^2 \times 10^{\wedge}3$)) for crystalline form G.

| | x | y | z | U(eq) |
|---|---|---|---|---|
| H(1N) | 2340(8) | 10490(7) | −1320(6) | 80(3) |
| H(2N) | 4180(7) | 12430(6) | 1440(5) | 50(2) |
| H(2) | −1127 | 5512 | −3455 | 33 |
| H(7A) | −280 | 7695 | 632 | 36 |
| H(7B) | 248 | 6542 | 1162 | 36 |
| H(8A) | 831 | 5827 | −523 | 33 |
| H(8B) | −864 | 5870 | −958 | 33 |
| H(10A) | 1952 | 11085 | 769 | 29 |
| H(10B) | 676 | 9968 | 1019 | 29 |
| H(11A) | 2243 | 10233 | 2914 | 26 |
| H(11B) | 2211 | 11691 | 2746 | 26 |
| H(13A) | 6537 | 13857 | 1969 | 45 |
| H(13B) | 6573 | 12355 | 1958 | 45 |
| H(13C) | 7035 | 13424 | 3185 | 45 |
| H(14A) | 5097 | 14328 | 3607 | 53 |
| H(14B) | 3356 | 13600 | 2825 | 53 |
| H(14C) | 4487 | 14519 | 2300 | 53 |
| H(15A) | 5914 | 10668 | 2573 | 29 |
| H(15B) | 4581 | 9581 | 2795 | 29 |
| H(16A) | 4395 | 8990 | 824 | 26 |
| H(16B) | 4384 | 10457 | 663 | 26 |
| H(18) | 3182 | 12225 | 4574 | 30 |
| H(19) | 4245 | 12926 | 6600 | 33 |
| H(20) | 6796 | 13209 | 7516 | 35 |
| H(21) | 8194 | 12636 | 6384 | 41 |
| H(22) | 7124 | 11856 | 4350 | 37 |
| H(23) | 1236 | 9949 | −3686 | 30 |
| H(24) | −303 | 8261 | −5392 | 34 |
| H(1) | 3514 | 14838 | −3 | 61 |

TABLE K15

Anisotropic displacement parameters ($\text{Å}^2 \times 10^3$) (i.e. ($\text{Å}^2 \times 10^{\wedge}3$)) for crystalline form G. The anisotropic displacement factor exponent takes the form: −2 pi$^2$ [h$^2$ a*$^2$ U11 + ... + 2 h k a* b* U12].

| | U11 | U22 | U33 | U23 | U13 | U12 |
|---|---|---|---|---|---|---|
| F(1) | 45(3) | 43(2) | 27(2) | −4(2) | 3(2) | 7(2) |
| O(5) | 18(3) | 27(2) | 34(3) | 12(2) | 10(2) | 3(2) |
| N(1) | 24(3) | 28(3) | 29(3) | 13(3) | 13(3) | 9(3) |
| N(2) | 11(3) | 28(3) | 26(3) | 5(2) | 10(2) | 3(2) |
| C(1) | 18(4) | 37(4) | 29(4) | −1(3) | 0(3) | 8(3) |
| C(2) | 23(4) | 26(4) | 37(4) | 10(3) | 13(3) | 7(3) |
| C(3) | 10(3) | 26(4) | 25(4) | 1(3) | 3(3) | 3(3) |
| C(4) | 13(3) | 26(4) | 23(4) | 0(3) | 5(3) | 8(3) |
| C(5) | 13(3) | 27(4) | 38(4) | 14(3) | 16(3) | 11(3) |
| C(6) | 17(4) | 25(4) | 27(4) | 9(3) | 12(3) | 1(3) |
| C(7) | 15(4) | 27(4) | 37(4) | 5(3) | 6(3) | −5(3) |
| C(8) | 15(4) | 22(4) | 39(4) | 7(3) | 5(3) | 1(3) |
| C(9) | 18(4) | 22(4) | 29(4) | −4(3) | 4(3) | 4(3) |

TABLE K15-continued

Anisotropic displacement parameters ($\text{Å}^2 \times 10^3$) (i.e. ($\text{Å}^2 \times 10^{\wedge}3$)) for crystalline form G. The anisotropic displacement factor exponent takes the form: −2 pi$^2$ [h$^2$ a*$^2$ U11 + ... + 2 h k a* b* U12].

| | U11 | U22 | U33 | U23 | U13 | U12 |
|---|---|---|---|---|---|---|
| C(10) | 16(4) | 27(4) | 30(4) | 6(3) | 12(3) | 4(3) |
| C(11) | 17(4) | 28(4) | 28(4) | 15(3) | 13(3) | 9(3) |
| C(12) | 20(4) | 26(3) | 21(3) | 8(3) | 10(3) | 11(3) |
| C(13) | 16(4) | 40(4) | 34(4) | 11(3) | 14(3) | 3(3) |
| C(14) | 39(5) | 31(4) | 48(4) | 8(3) | 26(4) | 19(3) |
| C(15) | 11(3) | 31(4) | 30(4) | 4(3) | 6(3) | 10(3) |
| C(16) | 15(3) | 23(3) | 25(4) | −4(3) | 9(3) | 4(3) |
| C(17) | 27(4) | 22(3) | 26(4) | 8(3) | 9(3) | 3(3) |
| C(18) | 27(4) | 26(3) | 27(4) | 8(3) | 16(3) | 11(3) |
| C(19) | 28(4) | 28(4) | 32(4) | 9(3) | 17(3) | 9(3) |
| C(20) | 36(4) | 28(4) | 18(4) | 4(3) | 5(3) | 9(3) |
| C(21) | 26(4) | 31(4) | 38(4) | 3(3) | 4(3) | 6(3) |
| C(22) | 26(4) | 34(4) | 31(4) | 3(3) | 11(3) | 12(3) |
| C(23) | 23(4) | 33(4) | 28(4) | 11(3) | 12(3) | 17(3) |
| C(24) | 20(4) | 38(4) | 25(4) | 5(3) | 3(3) | 10(3) |
| S(1) | 24(1) | 26(1) | 31(1) | 5(1) | 14(1) | 4(1) |
| O(1) | 31(3) | 33(3) | 50(3) | −1(2) | 8(2) | 10(2) |
| O(2) | 36(3) | 34(3) | 28(2) | 14(2) | 12(2) | 7(2) |
| O(3) | 24(3) | 46(3) | 41(3) | 8(2) | 19(2) | −4(2) |
| O(4) | 31(3) | 37(3) | 25(3) | 2(2) | 6(2) | −1(2) |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A solid form of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid.

2. The solid form according to claim 1, which is a solid form of (1r,4r)-6'-fluoro-N,N-dimethyl-4-phenyl-4',9'-dihydro-3'H-spiro[cyclohexane-1,1'-pyrano[3,4,b]indol]-4-amine sulfate or (1r,4r)-6'-fluoro-N,N-dimethyl-4-phenyl-4',9'-dihydro-3'H-spiro[cyclohexane-1,1'-pyrano[3,4,b]indol]-4-amine hemi-sulfate.

3. The solid form according to claim 1, which is an amorphous form.

4. The solid form according to claim 1, which is a crystalline form.

5. The crystalline form according to claim 4, which has:
at least one CuKα radiation X-ray diffraction peak selected from the group consisting of 9.7±1.0 (2Θ), 17.7±1.0 (2Θ), 18.2±1.0 (2Θ) and 25.7±1.0 (2Θ); and/or
at least one Raman band selected from the group consisting of 916±5 cm$^{-1}$, 1002±5 cm$^{-1}$, 1028±5 cm$^{-1}$, 1569±5 cm$^{-1}$, 1583±5 cm$^{-1}$, 2980±5 cm$^{-1}$ and 3076±5 cm$^{-1}$.

6. The crystalline form according to claim 4, which is an ansolvate.

7. The crystalline form according to claim 4 which is a solvate.

8. The crystalline form according to claim 4, which has:
A: one or more CuKα radiation X-ray diffraction peaks selected from the group consisting of 7.3±0.2 (2Θ), 9.2±0.2 (2Θ), 18.0±0.2 (2Θ), 18.5±0.2 (2Θ), 21.3±0.2 (2Θ) and 25.6±0.2 (2Θ); and/or
one or more Raman bands selected from the group consisting of 916±2 cm$^{-1}$, 1002±2 cm$^{-1}$, 1028±2 cm$^{-1}$, 1571±2 cm$^{-1}$, 1583±2 cm$^{-1}$, 2983±2 cm$^{-1}$ and 3074±2 cm$^{-1}$;
or
B: one or more CuKα radiation X-ray diffraction peaks selected from the group consisting of 10.2±0.2 (2Θ), 15.8±0.2 (2Θ), 17.5±0.2 (2Θ), 17.7±0.2 (2Θ), 18.4±0.2 (2Θ), 18.6±0.2 (2Θ), 22.8±0.2 (2Θ), and 25.9±0.2 (2Θ), and/or one or more Raman bands selected from the group consisting of 916±2 cm$^{-1}$, 1002±2 cm$^{-1}$, 1028±2 cm$^{-1}$, 1308±2 cm$^{-1}$, 1567±2 cm$^{-1}$, 1584±2 cm$^{-1}$, 2978±2 cm$^{-1}$ and 3078±2 cm$^{-1}$;
or
C: one or more Raman bands selected from the group consisting of 917±2 cm$^{-1}$, 1002±2 cm$^{-1}$, 1573±2 cm$^{-1}$, and 1588±2 cm$^{-1}$;
or
D: one or more Raman bands selected from the group consisting of 918±2 cm$^{-1}$, 1004±2 cm$^{-1}$, 1567±2 cm$^{-1}$, 1581±2 cm$^{-1}$ and 2977±2 cm$^{-1}$;
or
E: one or more CuKα radiation X-ray diffraction peaks selected from the group consisting of 10.6±1.0 (2Θ), 15.9±1.0 (2Θ), 17.2±1.0 (2Θ), 19.5±1.0 (2Θ), 20.3±1.0 (2Θ), and 22.1±1.0 (2Θ);
or
F: one or more CuKα radiation X-ray diffraction peaks selected from the group consisting of 10.2±1.0 (2Θ), 11.6±1.0 (2Θ), 16.0±1.0 (2Θ), 18.3±1.0 (2Θ), 19.3±1.0 (2Θ), and 24.5±1.0 (2Θ);
or
G: one or more CuKα radiation X-ray diffraction peaks selected from the group consisting of 10.3±1.0 (2Θ), 16.0±1.0 (2Θ), 17.9±1.0 (2Θ), 18.8±1.0 (2Θ), 23.0±1.0 (2Θ), and 26.2±1.0 (2Θ);
or
H: one or more Raman bands selected from the group consisting of 917±2 cm$^{-1}$, 1003±2 cm$^{-1}$, 1572±2 cm$^{-1}$, and 1586±2 cm$^{-1}$;
or
I: one or more Raman bands selected from the group consisting of 916±2 cm$^{-1}$, 1003±2 cm$^{-1}$, 1570±2 cm$^{-1}$, and 1582±2 cm$^{-1}$;
or
J: one or more Raman bands selected from the group consisting of 916±2 cm$^{-1}$, 1003±2 cm$^{-1}$, 1572±2 cm$^{-1}$ and 1585±2 cm$^{-1}$;
or
K: one or more Raman bands selected from the group consisting of 918±2 cm$^{-1}$, 1004±2 cm$^{-1}$, 1568±2 cm$^{-1}$, and 1583±2 cm$^{-1}$.

9. The crystalline form according to claim 8, which:
A: in DSC analysis exhibits multiple endothermic events and an exothermic event with a peak temperature in the range of 237-247° C.;
or
B: in DSC analysis exhibits an endothermic event with a peak temperature in the range of 247-257° C. and an exothermic event with a peak temperature in the range of 250-260° C.

10. A pharmaceutical composition comprising at least one solid form according to claim 1.

11. A pharmaceutical composition comprising at least one crystalline form according to claim 4.

12. The pharmaceutical composition according to claim 10, which additionally comprises a solid form of the free base of (1r,4r)-6'-fluoro-N,N-dimethyl-4-phenyl-4',9'-dihydro-3'H-spiro[cyclohexane-1,1'-pyran [3,4,b]indol]-4-amine.

13. A process for obtaining a solid form of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid according to claim 1, comprising:
(a-1) precipitating the sulfate or hemi-sulfate salt of (1r,4r)-6'-fluoro-N,N-dimethyl-4-phenyl-4',9'-dihydro-3'H-spiro[cyclohexane-1,1'-pyrano[3,4,b]indol]-4-amine from a solution or suspension of the free base; and
(b-1) separating the solid;
or
(a-2) dissolving (1r,4r)-6'-fluoro-N,N-dimethyl-4-phenyl-4',9'-dihydro-3'H-spiro-[cyclohexane-1,1'-pyrano[3,4,b]indol]-4-amine sulfate or hemi-sulfate in a solvent; and
(b-2) evaporating the solvent from the solution, or
(b-2') precipitating (1r,4r)-6'-fluoro-N,N-dimethyl-4-phenyl-4',9'-dihydro-3'H-spiro-[cyclohexane-1,1'-pyrano[3,4,b]indol]-4-amine sulfate or hemi-sulfate from the solution;
or
(a-3) suspending (1r,4r)-6'-fluoro-N,N-dimethyl-4-phenyl-4',9'-dihydro-3'H-spiro-[cyclohexane-1,1'-pyrano[3,4,b]indol]-4-amine sulfate or hemi-sulfate in a solvent, and stirring the resulting suspension; and
(b-3) separating the solid;
or
(a-4) reacting 2-(5-fluoro-1H-indol-3-yl)ethanol and 4-(dimethylamino)-4-phenylcyclohexanone or a protected derivative thereof, optionally in the form of an acid addition salt, in a carbonic acid as reaction medium in the presence of sulfuric acid to form (1r,4r)-6'-fluoro-N,N-dimethyl-4-phenyl-4',9'-dihydro-3'H-spiro-[cyclohexane-1,1'-pyrano[3,4,b]indol]-4-amine sulfate or hemi-sulfate;
(b-4) separating the precipitated solid; and
(c-4) optionally performing steps (a-2) and (b-2) or (b-2') or performing steps (a-3) and (b-3).

14. A crystalline form A of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid according to claim 4, having a CuKα radiation X-ray powder diffraction pattern comprising characteristic peaks at 7.3±0.2 (2Θ), 9.2±0.2 (2Θ), 18.0±0.2 (2Θ), 18.5±0.2 (2Θ), 21.3±0.2 (2Θ), and 25.6±0.2 (2Θ).

15. A crystalline form A of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid according to claim

14, having a CuKα radiation X-ray powder diffraction pattern further comprising characteristic peaks at 14.6±0.2 (2Θ) and 30.0±0.2 (2Θ).

16. A crystalline form B of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid according to claim 4, having a CuKα radiation X-ray powder diffraction pattern comprising characteristic peaks at 10.2±0.2 (2Θ), 15.8±0.2 (2Θ), 17.5±0.2 (2Θ), 17.7±0.2 (2Θ), 18.4±0.2 (2Θ), 18.6±0.2 (2Θ), 22.8±0.2 (2Θ), and 25.9±0.2 (2Θ).

17. A crystalline form B of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid according to claim 16, having a CuKα radiation X-ray powder diffraction pattern further comprising characteristic peaks at 7.7±0.2 (2Θ) and 23.1±0.2 (2Θ).

18. A crystalline form E of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid according to claim 4, having a CuKα radiation X-ray powder diffraction pattern comprising characteristic peaks at 10.6±1.0 (2Θ), 15.9±1.0 (2Θ), 17.2±1.0 (2Θ), 19.5±1.0 (2Θ), 20.3±1.0 (2Θ), and 22.1±1.0 (2Θ).

19. A crystalline form E of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid according to claim 18, having a CuKα radiation X-ray powder diffraction pattern further comprising characteristic peaks at 13.7±1.0 (2Θ) and 19.8±1.0 (2Θ).

20. A crystalline form F of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid according to claim 4, having a CuKα radiation X-ray powder diffraction pattern comprising characteristic peaks at 10.2±1.0 (2Θ), 11.6±1.0 (2Θ), 16.0±1.0 (2Θ), 18.3±1.0 (2Θ), 19.3±1.0 (2Θ), and 24.5±1.0 (2Θ).

21. A crystalline form F of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid according to claim 20, having a CuKα radiation X-ray powder diffraction pattern further comprising characteristic peaks at 12.4±1.0 (2Θ) and 19.5±1.0 (2Θ).

22. A crystalline form G of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid according to claim 4, having a CuKα radiation X-ray powder diffraction pattern comprising characteristic peaks at 10.3±1.0 (2Θ), 16.0±1.0 (2Θ), 17.9±1.0 (2Θ), 18.8±1.0 (2Θ), 23.0±1.0 (2Θ), and 26.2±1.0 (2Θ).

23. A crystalline form G of (1r,4r)-6'-fluoro-N,N-dimethyl-4-phenyl-4',9'-dihydro-3'H-spiro[cyclohexane-1,1'-pyrano[3,4,b]indol]-4-amine and sulfuric acid according to claim 22, having a CuKα radiation X-ray powder diffraction pattern further comprising characteristic peaks at 14.6±1.0 (2Θ) and 19.0±1.0 (2Θ).

24. A pharmaceutical composition according to claim 11, comprising between about 0.001% by weight and about 20% by weight of a crystalline form of (1r,4r)-6'-fluoro-N,N-dimethyl-4-phenyl-4',9'-dihydro-3'H-spiro[cyclohexane-1,1'-pyran [3,4,b]indol]-4-amine and sulfuric acid selected from the group consisting of crystalline form A, crystalline form B, crystalline form E, crystalline form F, and crystalline form G.

* * * * *